US012807736B2

(12) United States Patent
Skolaut et al.

(10) Patent No.: US 12,807,736 B2
(45) Date of Patent: Nov. 24, 2026

(54) FC-REGION VARIANTS WITH MODIFIED FCRN- AND MAINTAINED PROTEIN A-BINDING PROPERTIES

(71) Applicant: Hoffmann-La Roche Inc., Little Falls, NJ (US)

(72) Inventors: Alexander Skolaut, Penzberg (DE); Tilman Schlothauer, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 404 days.

(21) Appl. No.: 15/947,424

(22) Filed: Apr. 6, 2018

(65) Prior Publication Data

US 2019/0016828 A1 Jan. 17, 2019

Related U.S. Application Data

(63) Continuation of application No. 15/210,199, filed on Jul. 14, 2016, now abandoned, which is a continuation of application No. PCT/EP2015/050426, filed on Jan. 12, 2015.

(30) Foreign Application Priority Data

Jan. 15, 2014 (EP) .................................... 14151320
Apr. 25, 2014 (EP) .................................... 14165923

(51) Int. Cl.

*C07K 16/46* (2006.01)
*C07K 16/1271* (2026.01)
*C07K 16/22* (2006.01)
*A61K 39/00* (2006.01)

(52) U.S. Cl.

CPC ........ *C07K 16/468* (2013.01); *C07K 16/1271* (2013.01); *C07K 16/22* (2013.01); *A61K 2039/505* (2013.01); *A61K 2039/54* (2013.01); *C07K 2317/31* (2013.01); *C07K 2317/33* (2013.01); *C07K 2317/41* (2013.01); *C07K 2317/52* (2013.01); *C07K 2317/524* (2013.01); *C07K 2317/526* (2013.01); *C07K 2317/53* (2013.01); *C07K 2317/71* (2013.01); *C07K 2317/92* (2013.01); *C07K 2317/94* (2013.01)

(58) Field of Classification Search

None
See application file for complete search history.

(56) References Cited

U.S. PATENT DOCUMENTS 6,277,375 B1 8/2001 Ward
6,737,056 B1 5/2004 Presta
6,821,505 B2 11/2004 Ward
7,183,076 B2 2/2007 Arathoon et al.
7,572,897 B2 8/2009 Graus et al.
7,695,936 B2 4/2010 Carter et al.
7,923,538 B2 * 4/2011 Shitara ............... C07K 16/2887 530/387.3
7,951,917 B1 5/2011 Arathoon et al.
8,227,577 B2 7/2012 Klein et al.
8,268,314 B2 9/2012 Baehner et al.
8,703,132 B2 4/2014 Imhof-Jung et al.
9,266,967 B2 2/2016 Klein et al.
9,695,233 B2 7/2017 Duerr et al.
11,091,541 B2 8/2021 Roche
2005/0249723 A1 11/2005 Lazar
2006/0067930 A1 3/2006 Adams et al.
2006/0173170 A1 8/2006 Chamberlain et al.
2007/0219133 A1 * 9/2007 Lazar ..................... A61P 25/00 424/133.1
2008/0112961 A1 5/2008 Stavenhagen et al.
2009/0092596 A1 4/2009 Haley et al.
2009/0136936 A1 5/2009 Georgiou et al.
2009/0162360 A1 * 6/2009 Klein .................. C07K 16/468 424/136.1
2010/0093979 A1 4/2010 Lazar
2010/0111967 A1 5/2010 Baehner et al.
2010/0158909 A1 6/2010 McDonagh et al.
2010/0184959 A1 7/2010 Guler-Gane et al.
2010/0203046 A1 8/2010 van Vlijmen et al.

(Continued)

FOREIGN PATENT DOCUMENTS

CA 3159061 A1 8/2013
EP 1601697 B1 5/2007

(Continued)

OTHER PUBLICATIONS

Jansson et al (FEMS, 20:69-78, 1998).*
Taustian et al (MABS, 8(4):828-838, 2016).*
The extended European Search Report, mailed on May 14, 2021, in the related European Appl. No. 20214926.6.
Roopenian et al., "FcRn: the neonatal Fc receptor comes of age" Nat Rev/Immunol 7:715-725 (Sep. 2007).
Dall'Acqua et al., "Increasing the affinity of a human IgG1 for the neonatal Fc receptor: biological consequences" J Immunol 169(9):5171-5180 (Nov. 1, 2002).
Dall'Acqua et al., "Properties of human IgG1s engineered for enhanced binding to the neonatal Fc receptor (FcRn)" J Biol Chem 281(33):23514-23524 (Aug. 2006).

(Continued)

*Primary Examiner* — Brad Duffy

(57) ABSTRACT

Herein is reported a polypeptide comprising a first polypeptide and a second polypeptide each comprising in N-terminal to C-terminal direction at least a portion of an immunoglobulin hinge region, which comprises one or more cysteine residues, an immunoglobulin CH2-domain and an immunoglobulin CH3-domain, wherein i) the first polypeptide comprises the mutations I253A, H310A and H435A and the second polypeptide comprises the mutations H310A, H433A and Y436A, or
ii) the first polypeptide comprises the mutations I253A, H310A and H435A and the second polypeptide comprises the mutations L251D, L314D and L432D, or
iii) the first polypeptide comprises the mutations I253A, H310A and H435A and the second polypeptide comprises the mutations L251S, L314S and L432S.

11 Claims, 21 Drawing Sheets

Specification includes a Sequence Listing.

(56) References Cited

U.S. PATENT DOCUMENTS

| | | | |
|---|---|---|---|
| 2010/0256339 | A1 | 10/2010 | Bossenmaier et al. |
| 2010/0272720 | A1 | 10/2010 | Lo et al. |
| 2010/0331527 | A1 | 12/2010 | Davis et al. |
| 2011/0054151 | A1 | 3/2011 | Lazar et al. |
| 2011/0171124 | A1 | 7/2011 | Bugaj et al. |
| 2011/0236388 | A1 | 9/2011 | Baehner et al. |
| 2011/0288276 | A1 | 11/2011 | Oganesyan et al. |
| 2012/0134984 | A1 | 5/2012 | Lubman et al. |
| 2012/0251531 | A1 | 10/2012 | Baehner et al. |
| 2012/0282280 | A1 | 11/2012 | Bramlage et al. |
| 2012/0321627 | A1 | 12/2012 | Baehner et al. |
| 2013/0039913 | A1 | 2/2013 | Labrijn et al. |
| 2013/0078249 | A1 | 3/2013 | Ast et al. |
| 2013/0131319 | A1 | 5/2013 | Igawa et al. |
| 2013/0247234 | A1 | 9/2013 | Mcwhirter et al. |
| 2014/0017244 | A1 | 1/2014 | Duerr et al. |
| 2014/0105889 | A1 | 4/2014 | Igawa et al. |
| 2014/0303356 | A1 | 10/2014 | Gramer et al. |
| 2015/0175707 | A1 | 6/2015 | De Jong et al. |
| 2015/0239991 | A1 | 8/2015 | Blein et al. |
| 2015/0274797 | A1 | 10/2015 | Lo et al. |

FOREIGN PATENT DOCUMENTS

| | | | |
|---|---|---|---|
| EP | 2698431 | B1 | 9/2020 |
| NO | 2005047327 | A2 | 5/2005 |
| WO | 9734631 | A1 | 9/1997 |
| WO | 9845331 | A1 | 10/1998 |
| WO | 2004035752 | A2 | 4/2004 |
| WO | 2004092219 | A2 | 10/2004 |
| WO | 2005005635 | A2 | 1/2005 |
| WO | 2005016967 | A2 | 2/2005 |
| WO | 2005035752 | A2 | 4/2005 |
| WO | 2005058967 | A2 | 6/2005 |
| WO | 2005061541 | A1 | 7/2005 |
| WO | 2005077981 | A2 | 8/2005 |
| WO | 2006031370 | A2 | 3/2006 |
| WO | 2006039137 | A1 | 4/2006 |
| WO | 2006053301 | A2 | 5/2006 |
| WO | 2006/072620 | A1 | 7/2006 |
| WO | 2006/106905 | A1 | 12/2006 |
| WO | 2007110339 | A1 | 10/2007 |
| WO | 2008048545 | A2 | 4/2008 |
| WO | 2008077546 | A1 | 7/2008 |
| WO | 2009045389 | A2 | 4/2009 |
| WO | 2009052439 | A2 | 4/2009 |
| WO | 2009058492 | A2 | 5/2009 |
| WO | 2009089004 | A1 | 7/2009 |
| WO | 2009126304 | A1 | 10/2009 |
| WO | 2010040508 | A1 | 4/2010 |
| WO | 2010045193 | A1 | 4/2010 |
| WO | 2010048123 | A2 | 4/2010 |
| WO | 2010066868 | A2 | 6/2010 |
| WO | 2010099137 | A2 | 9/2010 |
| WO | 2010112193 | A1 | 10/2010 |
| WO | 2010121766 | A1 | 10/2010 |
| WO | 2010/151792 | A1 | 12/2010 |
| WO | 2011008517 | A2 | 1/2011 |
| WO | 2011/097603 | A1 | 8/2011 |
| WO | 2011/117329 | A1 | 9/2011 |
| WO | 2011109584 | A2 | 9/2011 |
| WO | 2011117330 | A1 | 9/2011 |
| WO | 2011131746 | A2 | 10/2011 |
| WO | 2012058768 | A1 | 5/2012 |
| WO | 2012069557 | A1 | 5/2012 |
| WO | 2012083370 | A1 | 6/2012 |
| WO | 2012093125 | A1 | 7/2012 |
| WO | 2012125850 | A1 | 9/2012 |
| WO | 2012130831 | A1 | 10/2012 |
| WO | 2012133782 | A1 | 10/2012 |
| WO | 2013/004842 | A2 | 1/2013 |
| WO | 2013/004842 | A3 | 1/2013 |
| WO | 2013041462 | A1 | 3/2013 |
| WO | 2013056233 | A1 | 4/2013 |
| WO | 2013/060867 | A2 | 5/2013 |
| WO | 2013/060867 | A3 | 5/2013 |
| WO | 2013063702 | A1 | 5/2013 |
| WO | 2013166594 | A1 | 11/2013 |
| WO | 2014/006217 | A1 | 1/2014 |
| WO | 2014/006217 | A9 | 1/2014 |
| WO | 2014009465 | A1 | 1/2014 |
| WO | 2014019727 | A1 | 2/2014 |
| WO | 2014036385 | A1 | 3/2014 |
| WO | 2014/177460 | A1 | 11/2014 |
| WO | 2014/177461 | A1 | 11/2014 |
| WO | 2014177459 | A2 | 11/2014 |
| WO | 2015071330 | A1 | 5/2015 |

OTHER PUBLICATIONS

Schaefer et al., "Immunoglobulin domain crossover as a generic approach for the production of bispecific IgG antibodies" Proceedings of the National Academy of Sciences 108(27):11187-11192 (Jul. 5, 2011).

De Lau et al., "Absence of preferential homologous H/L chain association in hybrid hybridomas" J Immunol 146:906-914 ( 1991).

Harakas, "Biospecific affinity chromatography" Bioprocess Technol 18:259-316 ( 1994).

International Search Report and Written Opinion of the International Searching Authority.

Carter, "Bispecific human IgG by design" J Immunol Methods 248(1-2):7-15 (Feb. 1, 2001).

Bjorck et al., "Purification and some properties of streptococcal protein G, A novel IgG-binding reagent" J Immunol 133(2):969-974 (Aug. 1984).

Huber et al., "Crystallization and stoichiometry of binding of a complex between a rat intestinal Fc receptor and Fc" J Mol Biol 230:1077-1083 ( 1993).

Kim et al., "Mapping the site on human IgG for binding of the MHC class I-related receptor, FcRn" Eur J Immunol 29(9):2819-2825 (Sep. 1999).

Duhamel et al., "pH gradient elution of human IgG1, IgG2 and IgG4 from protein A-sepharose" J Immunol Methods 31:211-217 ( 1979).

Lindhofer et al., "Preferential species-restricted heavy/light chain pairing in rat/mouse quadromas" J Immunol 155:219-225 ( 1995).

Ridgway et al., "'Knobs-into-holes' engineering of antibody C\\\subscript:H\\\3 domains for heavy chain heterodimerization" Protein Eng 9(7):617-621 ( 1996).

Medesan et al., "Localization of the site of the IgG molecule that regulates maternofetal transmission in mice" Eur J Immunol 26(10):2533-2536 (Oct. 1996).

MacLennan, J., "Engineering microprotein ligands for large-scale affinity purification" Bio/Technology 13:1180 (Nov. 1995).

Amersham Pharmacia Biotech "Antibody Purification" ( 2000).

Salvalaglio et al., "Molecular modeling of protein A affinity chromatography" J Chrom A 1216:8678-8686 ( 2009).

Richman et al., "The binding of staphylococcal protein A by the sera of different animal species" J Immunol 128(5):2300-2305 (May 1982).

Medesan et al., "Delineation of the amino acid residues involved in transcytosis and catabolism of mouse IgG1" J Immunol 158(5):2211-2217 (Mar. 1, 1997).

Merchant et al., "An efficient route to human bispecific IgG" Nat Biotechnol 16(7):677-681 ( 1998).

Cain, "Crossing over to bispecificity" Science Business Exchange 4:1-3 ( 2011).

Atwell et al., "Stable heterodimers from remodeling the domain interface of a homodimer using a phage display library" J Mol Biol 270(1):26-35 ( 1997).

Shields et al., "High Resolution Mapping of the Binding Site on Human IgGI for FcyRI, FcyRII, FcyRIII, and FcRn and design of IgG1 variants with improved binding to the RcyR" J Biol Chem 276(9):6591-6604 (Mar. 2, 2001).

Qiao et al., "Dependence of antibody-mediated presentation of antigen on FcRn" PNAS 105(27):9337-9342 ( 2008).

Abdiche et al., "The neonatal Fc receptor (FcRn) binds indenpendently to both sites of the IgG homodimer with identical affinity" mAbs 7( Suppl 2):331-343 (Apr. 2016).

(56) References Cited

OTHER PUBLICATIONS

Kuo et al., "Neonatal Fc receptor: from immunity to therapeutics" J Clin Immunol 30:777-789 ( 2010).
Yeung et al., "Engineering human IgG1 affinity to human neonatal Fc receptor: impact of affinity improvement on pharmacokinetics in primates" J Immunol 182:7663-7671 ( 2009).
Kim et al., "Identifying amino acid residues that influence plasma clearance of murine IgG1 fragments by site-directed mutagenesis" Eur J Immunol 24(3):542-548 (Mar. 1994).
Kim et al., "FcRn receptor-mediated pharmacokinetics of therapeutic IgG in the eye" Molec Vision 15:2803-2812 (Dec. 16, 2009).
Jendeberg et al., "Engineering of Fc\\\subscript:1\\\ and Fc\\\subscript:3\\\ from human immunoglobulin G to analyse subclass specificity for staphylococcal protein A" J Immunol Methods 201:25-34 ( 1997).
Hober et al., "Protein A chromatography for antibody purification" J Chrom B 848:40-47 ( 2007).
Martin et al., "Crystal structure at 2.8 A of an FcRn/heterodimeric Fc complex: mechanism of pH-dependent binding" Mol Cell 7(4):867-877 (Apr. 2001).
Zhu et al., "Remodeling domain interfaces to enhance heterodimer formation" Protein Sci 6(4):781-788 (Apr. 1997).
Firan et al., "The MHC class I-related receptor, FcRn, plays an essential role in the maternofetal transfer . . . " International Immunology 13(8):993-1002 ( 2001).
Igawa et al., "V\\\subscript:H\\\/V\\\subscript:L\\\ interface engineering to promote selective expression and inhibit conformational isomerization of thrombopoietin receptor agonist single-chain diabody" Prot Eng Des Sel 23:667-677 ( 2010).
Klein, C. et al., "Progress in overcoming the chain association issue in bispecific heterodimeric IgG antibodies" mAbs 4(6):653-663 ( 2012).
Adams et al., "Structure and function of the type 1 insulin-like growth factor receptor." Cell Mol Life Sci 57 (7):1050-93. (Jul. 2000).
Avdeeva Z.I., et al., "Preparations of next generation monoclonal antibodies (issues and prospects)," BIOpreparations. Prevention, Diagnosis, Treatment. 2015;(1):21-35. (In Russ.) English abstract included.
Artandi, et al., "Monoclonal IgM rheumatoid factors bind IgG at a discontinuous epitope comprised of amino acid loops from heavy-chain constant-region domains 2 and 3," Proc. Natl. Acad. Sci. USA 89 (1992) 94-98.
Bae et al., "Identification of the amino acid residues involved in human IgG transport into egg yolks of Japanese quail (*Coturnix japonica*)," Mol Immunol. Apr. 2010;47(7-8):1404-10.
Chamow et al., "A humanized, bispecific immunoadhesin-antibody that retargets CD3+ effectors to kill HIV-1-infected cells," The Journal of Immunology. 1994; 153:4268-4280 (Year: 1994).
Chiu et al., "Associations between Genetic Polymorphisms of Insulin-like Growth Factor Axis Genes and Risk for Age-Related Macular Degeneration," Invest Ophthalmol Vis Sci., 52(12): 9099-9107, Nov. 24, 2011.
Colman, PM., "Effects of amino acid sequence changes on antibody-antigen interactions," Research in Immunology, Elsevier, NY, 145(1):33-36, 1994.
Deisenhofer, "Crystallographic Refinement and Atomic Models of a Human Fc Fragment and Its Complex with fragment B of Protein A from *Staphylococcus aureus* at 2.9- and 2.8-A Resolution," Biochemistry. Apr. 28, 1981;20;9):2361-70.
Diamond B., Scharff M.D. "Somatic mutation of the T15 heavy chain gives rise to an antibody with autoantibody specificity", Proc. Natl. Acad. Sci. USA, 1984, vol. 81, abstract.
Dumont, et al., "Monomeric Fc Fusions: Impact on Pharmacokinetic and Biological Activity of Protein Therapeutics," BioDrugs 20 (2006) 151-160.
Folkman and Shing, "Angiogenesis" J Biol Chem 267(16):10931-10934 (Jun. 5, 1992).
Garner, A. Pathobiology of Ocular Disease. A Dynamic Approach "Vascular Diseases" Garner, A., Klintworth GK Eds., 2nd edition, NY:Marcel Dekker,:1625-1710 ( 1994).
Ghetie and Ward, "FcRn: the MHC class I-related receptor that is more than an IgG transporter" Immunol Today 18 (12):592-598 (Dec. 1997).
Ghetie et al., "Increasing the serum persistence of an IgG fragment by random mutagenesis," Nature Biotechnol. 15,1997, pp. 637-640.
Gillies et al., "Improving the Efficacy of Antibody-Interleukin 2 Fusion Proteins by Reducing Their Interaction with Fc Receptors," Cancer Research 59, 2159-2166, May 1, 1999.
Hezareh et al., "Effector Function Activities of a Panel of Mutants of a Broadly Neutralizing Antibody Against Human Immunodeficiency Virus Type 1," J Virol, Dec. 2001;75(24):12161-8.
Hinton et al., "An engineered human IgG1 antibody with longer serum half-life" J Immunol 176(1):346-56 ( 2006).
Jackson et al., "Human Retinal Molecular Weight Exclusion Limit and Estimate of Species Variation," Investigative Ophthalmology & Visual Science May 2003, vol. 44, 2141-2146.
Jaeger L. "Kliničeskaâ immunologiâ i allergologiâ", 2nd edition, translation from German, M.: Medicina, 1990, in 3 volumes, vol. 2, pp. 484-485.
JArilin A.A., "Osnovy immunologii" ["Basics of Immunology"], M.: Medicina, 1999, pp. 170-171, figure 41.
Kenanova et al., "Tailoring the Pharmacokinetics and Positron Emission Tomography Imaging Properties of Anti-Carcinoembryonic Antigen Single-Chain Fv-Fc Antibody Fragments," Cancer Res 65(2): 622-630 (Year: 2005).
Kim, et al., "Localization of the Site of the Murine IgG1 Molecule That Is Involved in Binding to the Murine Intestinal Fc Receptor," Eur J Immunol 24 (10), 2429-2434.
Kim, et al., "Mapping of the Neonatal Fc Receptor in the Rodent Eye," Invest. Ophthalmol. Vis. Sci. 49 (2008), pp. 2025-2029.
Kim, "Catabolismof the Murine IgG1 Molecule: Evidence that Both CH2-CH3 Domain Interfaces are Required for Jersistence of IgG1 in the Circulation of Mice," Scan J. Immunol. 40 (1994), 457-465.
Klagsbrun and D'Amore, "Regulators of angiogenesis" Ann Rev Physiol 53:217-239, ( 1991).
Kuo, T.T. et al., "Neonatal Fc receptor and IgG-based therapeutic" mAbs 3(5):422-430 ( 2011).
LeRoith et al., "Molecular and cellular aspects of the insulin-like growth factor I receptor" Endocr Rev 16(2):143-63 (Apr. 1995).
Magadelaine-Beuzelin et al., "Therapeutic antibodies in ophthalmology: old is new again," MAbs. Mar.-Apr. 2010;22):176-80.
Martin et al., "Characterization of the 2:1 Complex between the Class I MHC-Related Fc Receptor and Its Fc Ligand in Solution," Biochemistry 1999, 38, 12639-12647.
Mimoto et al., "Novel asymmetrically engineered antibody Fc variant with superior FcyR binding affinity and specificity compared with afucosylated Fc variant," mAbs 5:2, 229-236; Mar./Apr. 2013; © 2013 Landes Bioscience.
Ohno et al., "Antigen-binding specificities of antibodies are primarily determined by seven residues of VH," Proc Natl Acad Sci USA_82_1985, pp. 2945-2949.
Paul, WE. Fundamental Immunology, 3rd ed. Raven Press, NY, Chap. 9, pp. 292-295, 1993.
Petkova et al.," Enhanced half-life of genetically engineered human IgG1 antibodies in a humanized FcRn mouse model: potential application in humorally mediated autoimmune disease," International Immunology, vol. 18, No. 12, pp. 1759-1769.
Powner et al., "Expression of Neonatal Fc Receptor in the Eye," Invest Ophthalmol Vis Sci. Mar. 2014; 55(3): 1607-1615.
Presta et al., "Molecular engineering and design of therapeutic antibodies," Current Opinion in Immunology 2008, 20:460-470.
Raghavan et al., "Fc Receptors And Their Interactions With Immunoglobulins," Annu. Rev. Cell Dev. Biol. 1996. 12:181-220.
Raghavan et al., "Analysis of the pH Dependence of the Neonatal Fc Receptor/Immunoglobulin Gnteraction Using Antibody and Receptor Variants," Biochemistry 1995, 34, 14649-14657.
Roitt, A. et al., Immunology, Moscow, "Mir", 2000, p. 98_EN Translation.
Roitt, A. et al., Immunology, Moscow, "Mir" (2000) pp. 110-111 (copy and English translation attached).
Rudikoff et al. "Single amino acid substitution altering antigen-binding specificity," Proc. Natl. Acad. Sci. USA, 79:1979-1983, 1982.

(56) References Cited

OTHER PUBLICATIONS

Sauer-Eriksson et al., "Crystal structure of the C2 fragment of streptococcal protein G in complex with the Fc domain of human IgG," Structure, vol. 3, Issue 3, Mar. 1995, pp. 265-278.
Stein brook, "The Price of Sight Ranibizumab, Bevacizumab, and the Treatment of Macular Degeneration," The New England Journal of Medicine 355(14):1409-1412 ( 2006).
Tesar et al., "Ligand Valency Affects Transcytosis, Recycling and Intracellular Trafficking Mediated by the Neonatal Fc Receptor," Traffic 7 (2006) 1127.
Vidarsson et al., "FcRn: an IgG receptor on phagocytes with a novel role in phagocytosis," Blood. Nov. 15, 2006;108;10):3573-9.
Yasmina et al., "The neonatal Fc receptor (FcRn) binds independently to both sites of the IgG homodimer with identical affinity" mAbs 7:331-343 (2015).
Zhang et al., "Ophthalmic drug discovery: novel targets and mechanisms for retinal diseases and glaucoma," Nat Rev Drug Discov. Jun. 15, 2012;11(7):541-59.
Brazilian search report, mailed on Oct. 7, 2019, in the related BR112016014969-6.
Chinese Office Action, mailed on Mar. 22, 2019, in the related Chinese Patent Application No. 201580003626.0.
The Chinese Office Action, mailed on Apr. 2, 2018, in the related Chinese Patent Appl. No. 201480024044.6.
Chinese Office Action, mailed on Jun. 4, 2020, in the related Chinese Patent Application No. 201480023252.4.
Chilean Office Action, mailed on Apr. 2, 2018, in the related Chilean Patent Appl. No. 201503174.
Columbian Office Action, mailed on Jul. 25, 2019, in the related Columbian Patent Application No. 15260305.
Israeli Office Action, mailed on Sep. 17, 2020, in the related Israeli Patent Application No. 274398.
Japanese Office Action, mailed on Jul. 5, 2018, in the related Japanese Patent Application No. 2016-511014.
Japanese Office Action, mailed on Nov. 20, 2018, in the related Japanese Patent Application No. 2016-546942.
Japanese Office Action, mailed on Dec. 4, 2018, in the related Japanese Patent Application No. 2016-546941.
Japanese Decision to Grant a Patent, mailed on Nov. 8, 2019, in the related Japanese Appl. No. 2016-511014.
Japanese Office Action, mailed on Apr. 28, 2020, in the related Japanese Patent Application No. 2016-546941.
Japanese Office Action, mailed on Jun. 2, 2020, in the related Japanese Patent Application No. 2019-097631.
Korean Office Action, mailed on Aug. 31, 2020 , in the related Korean Appl. No. 2015-7031019.
Korean Office Action, mailed on Sep. 21, 2020, in the related Korean Patent Application No. 10-2015-7033963.
New Zealand Office Action, mailed on Oct. 30, 2020, in the related New Zealand Appl. No. 751585.
Russian Office Action, mailed on Jun. 22, 2018, in the related Russian Patent Application No. 2016133346.
Russian Office Action, mailed on Aug. 8, 2018, in the related Russian Patent Application No. 2016133347.
Russian Office Action, mailed on Mar. 13, 2019, in the related Russian Patent Application No. 2016133347.
Russian Office Action, mailed on Oct. 31, 2018, in the related Russian Patent Application No. 2016133345.
Russian Office Action, mailed on Sep. 6, 2018, in the related Russian Patent Application No. 2015145719.
Russian Office Action, mailed on Oct. 18, 2018, in the related Russian Patent Application No. 2015145719.
Russian Office Action, mailed on Apr. 27, 2020, in the related Russian Patent Application No. 2016133345.
Russian Office Action, mailed on May 27, 2020, in the related Russian Patent Application No. 2016 133 346.
Taiwanese Search Report, mailed on Jun. 28, 2019, in the related Taiwanese Patent Application No. 103115072.
Taiwanese Office Action, mailed on May 26, 2020, in the related Taiwanese Appl. No. 108105062. (Translation).
The International Search Report and Written Opinion, mailed on Nov. 7, 2014, in the related PCT Appl. No. PCT/EP2014/058416.
The International Search Report and Written Opinion, mailed on Apr. 21, 2015, in the related PCT Appl. No. PCT/EP2015/050389.
The International Search Report and Written Opinion, mailed on Apr. 28, 2015, in the related PCT Appl. No. PCT/EP2015/050425.
The International Search Report and Written Opinion, mailed on Jul. 23, 2014, in the related PCT Appl. No. PCT/EP2014/058418.
The International Search Report and Written Opinion, mailed on Oct. 9, 2014, in the related PCT Appl. No. PCT/EP2014/058417.
The European Search Report and Opinion, mailed on Sep. 24, 2013,in the related European Appl. No. 13165725.6.
The European Search Report and Opinion, mailed on Nov. 4, 2014,in the related European Appl. No. 15700545.5.
The European Communication, mailed on Oct. 19, 2017, in the related European Appl. No. 15700545.5.
The European Search Report and Opinion, mailed on Oct. 27, 2014,in the related European Appl. No. 15700148.8.
The European Communication, mailed on Jan. 17, 2018, in the related European Appl. No. 15700148.8.
The European Search Report and Opinion, mailed on Oct. 27, 2014,in the related European Appl. No. 15703229.3.
The European Communication, mailed on Feb. 22, 2018, in the related European Appl. No. 15703229.3.
The European Search Report and Opinion, mailed on Sep. 25, 2013,in the related European Appl. No. 14721295.5.
The European Communication, mailed on Sep. 29, 2016, in the related European Appl. No. 14721295.5.
The European Search Report and Opinion, mailed on Sep. 24, 2013,in the related European Appl. No. 14721806.9.
The European Communications, mailed on Oct. 24, 2016 and Apr. 24, 2017, in the related European Appl. No. 14721806.9.
The European Search Report and Opinion, mailed on Mar. 27, 2018, in the related European Appl. No. 17205688.9.
The European Search Report and Opinion, mailed on Feb. 24, 2020,in the related European Appl. No. 19183116.3.
US Office Actions, mailed on Dec. 13, 2017, Mar. 15, 2018 and Sep. 5, 2018, in the related U.S. Appl. No. 14/785,900.
US Office Actions, mailed on Dec. 13, 2017, Mar. 16, 2018 and Sep. 6, 2018, in the related U.S. Appl. No. 14/927,022.
US Office Actions, mailed on Jan. 10, 2017, Jun. 2, 2017 and Jan. 23, 2018, in the related U.S. Appl. No. 15/210,464.
US Office Actions, mailed on Jun. 26, 2017 and Oct. 17, 2017, in the related U.S. Appl. No. 15/210,199.
US Office Actions, mailed on Jun. 26, 2017 and Oct. 16, 2017, in the related U.S. Appl. No. 15/210, 218.
US Office Actions, mailed on Aug. 10, 2020 and Nov. 17, 2020, in the related U.S. Appl. No. 15/947,377.
US Office Actions, mailed on Jun. 29, 2016, Nov. 4, 2016, Jul. 3, 2017, Aug. 28, 2018, Mar. 14, 2019, Jan. 2, 2020, Aug. 31, 2020 and Dec. 14, 2020, in the related U.S. Appl. No. 14/926,982.
US Office Actions, mailed on Aug. 10, 2017, Dec. 12, 2017, Apr. 23, 2018, Jun. 7, 2019 and Feb. 13, 2020, in the related U.S. Appl. No. 14/926,844.
US Office Actions, mailed on Nov. 6, 2019, Dec. 20, 2019, Jul. 30, 2020 and Nov. 13, 2020, in the related U.S. Appl. No. 16/244,378.
U.S. Appl. No. 14/785,900, filed Oct. 21, 2015.
U.S. Appl. No. 14/927,022, filed Oct. 29, 2015.
U.S. Appl. No. 14/926,844, filed Oct. 29, 2015.
U.S. Appl. No. 14/926,982, filed Oct. 29, 2015.
U.S. Appl. No. 15/210,218, filed Jul. 14, 2016.
Serial No. Not yet assigned filed Apr. 6, 2018.
U.S. Appl. No. 15/210,199, filed Jul. 14, 2016.
U.S. Appl. No. 15/210,464, filed Jul. 14, 2016.
The Canadian Office Action, mailed on Feb. 2, 2021, in the related Canadian Patent Appl. No. 2,931,986.
Yang et al., "Assessment of naturally occurring covalent and total dimer levels in human IgG1 and IgG2" Molecular Immunology 58:108-115 ( 2014).
McAuley et al., "Contributions of a disulfide bond to the structure, stability, and dimerization of human IgG1 antibody CH3 domain," Protein Sci. Jan. 2008; 17(1): 95-106.

(56) References Cited

OTHER PUBLICATIONS

US Office Action, mailed on Mar. 17, 2021, in the related U.S. Appl. No. 14/926,982.
US Office Actions, mailed on Feb. 9, 2021 and Apr. 20, 2021, in the related U.S. Appl. No. 14/926,844.
The US Office Action, mailed on Nov. 30, 2021, in the related U.S. Appl. No. 16/422,147.
The English translation of the Korean Office Action, mailed on Jul. 30, 2021, in the related Korean Patent Application No. 10-2016-7018968.
The Canadian Office Action, mailed on Feb. 23, 2021, in the related Canadian Patent Appl. No. 2,932,364.
The US Office Action, mailed on May 20, 2021, in the related U.S. Appl. No. 15/947,377.
The Notice of Allowance, mailed on May 26, 2021, in the related U.S. Appl. No. 14/926,844.
The US Office Action, mailed on Dec. 30, 2022, in the related U.S. Appl. No. 16/590,938.
The US Office Action, mailed on Jan. 12, 2023, in the related U.S. Appl. No. 15/947,377.
DeLano et al., "Convergent Solutions to Binding at a Protein-Protein Interface," Science, 287:1279-1283, Feb. 18, 2000.
Jansson et al., "All individual domains of staphylococcal protein A show Fab binding," FEMS Immunology and Medical Microbiology 20 (1998) 69-78.
The Chinese Office Action, mailed on Feb. 27, 2023, in the related Chinese Patent Appl. No. 201911344011.0.
The English translation of the Chinese Office Action, mailed on Nov. 25, 2022, in the related Chinese Patent Appl. No. 201911266804.5.
The English translation of the Decision to Grant dated Jul. 26, 2022, in the related Russian Patent Application No. 2020122367/10(038452).
Spiekermann et al., "Receptor-mediated Immunoglobulin G Transport Across Mucosal Barriers in Adult Life: Functional Expression of FcRn in the Mammalian Lung," J Exp Med (2002) 196 (3): 303-310.
Ying, et al., "Soluble Monomeric IgG1 Fc*" The Journal of Biological Chemistry 287(23):19399-19408 (Jun. 1, 2012).
The English translation of the Japanese Office Action, mailed on May 16, 2022, in the related Japanese Patent Application No. 2021-092002.
Canadian Office Action, mailed on Feb. 17, 2022, in the related Canadian Patent Appl. No. 2,904,805.
The International Search Report and Written Opinion, mailed on Apr. 8, 2015, in the related PCT Appl. No. PCT/EP2015/050426.
The English translation of the Chinese Office Action, mailed on Jan. 24, 2024, in the related Chinese Patent Appl. No. 202110445639.0.
The Third Party Observations, posted on Dec. 1, 2023, in the related European Patent Appl. No. 15700545.5.
The English translation of the Chinese Office Action, mailed on Aug. 28, 2023, in the related Chinese Patent Appl. No. 202110445639.0.
The English translation of the Japanese Office Action, mailed on Aug. 29, 2023, in the related Japanese Patent Appl. No. 2022-010878.
The English translation (Google Translate) of the Argentina Office Action, mailed on Dec. 22, 2023, in related Argentina Application No. 20140101718.
The US Office Action, mailed on Jan. 16, 2025, in the related U.S. Appl. No. 17/373,062.
The English translation of the Reexamination Notification, mailed on Apr. 17, 2025, in the related Chinese Appl. No. 201480023252.4.
US Office Action, mailed on Aug. 4, 2021, in the related U.S. Appl. No. 16/422,147.
US Office Actions, mailed on Feb. 1, 2022, May 5, 2022, May 20, 2022 and Feb. 16, 2024, in the related U.S. Appl. No. 16/590,938.
US Office Action, mailed on Oct. 8, 2021, in the related U.S. Appl. No. 16/244,378.
US Office Action, mailed on Oct. 23, 2024, in the related U.S. Appl. No. 18/079,307.
US Office Action, mailed on Mar. 13, 2024, in the related U.S. Appl. No. 17/373,062.
US Office Action, mailed on Jun. 12, 2025, in the related U.S. Appl. No. 17/825,314.
US Office Action, mailed on Aug. 13, 2025, in the related U.S. Appl. No. 17/373,062.

* cited by examiner

| Knob | | | Hole | | | |
|---|---|---|---|---|---|---|
| Pos 1 | Pos 2 | Pos 3 | Pos 1 | Pos 2 | Pos 3 | |
| I253A | H310A | H435A | I253A | H310A | H435A | No Binding |
| --- | --- | --- | I253A | H310A | H435A | Binding |
| I253A | H310A | H435A | --- | H310A | --- | No Binding |
| I253A | H310A | H435A | --- | --- | H435A | No Binding |

| Sample | Mutation (Hole) | RT (Min) |
|---|---|---|
| Anti-VEGF/ANG2 Antibody (0096) | - | 51.88 |
| Anti-VEGF/ANG2 Antibody (0097) | I253A/H310A/H435A | 46.61 |
| Anti-VEGF/ANG2 Antibody (0098) | H310A/H433A/Y436A | 46.67 |
| Anti-VEGF/ANG2 Antibody (0099) | L251D/L314D/Y432D | 46.25 |
| Anti-VEGF/ANG2 Antibody (0100) | M252Y/S254T/T256E | 56.17 |

FC-REGION VARIANTS WITH MODIFIED FCRN- AND MAINTAINED PROTEIN A-BINDING PROPERTIES

CROSS-REFERENCE TO RELATED APPLICATIONS

This application is a continuation of U.S. patent application Ser. No. 15/210,199, filed on Jul. 14, 2016, which is a continuation of International Patent Application No. PCT/EP2015/050426, having an international filing date of Jan. 12, 2015, the entire contents of which are incorporated herein by reference, and which claims benefit under 35 U.S.C. § 119 to European Patent Application No. 14151320.0, filed on Jan. 15, 2014 and European Patent Application No. 14165923.5, filed on Apr. 25, 2014.

SEQUENCE LISTING

This application contains a Sequence Listing submitted via EFS-Web and hereby incorporated by reference in its entirety. Said ASCII copy, created Apr. 5, 2018, is named P31953US1_SequenceListing.txt, 308,727 bytes in size.

BACKGROUND OF THE INVENTION

Herein are reported IgG Fc-regions that have been modified with respect to Fc-receptor binding without impairing their purification properties.

The demand for cost efficient production processes has led to the necessity of optimization of the downstream purification, including one or more affinity chromatography steps. Larger volumes to be processed and harder requirements for the cleaning-in-place (CIP) protocols are some of the features that need to be solved (Hober, S., J. Chrom. B. 848 (2007) 40-47).

The purification of monoclonal antibodies by means of selective Fc-region affinity ligands is the most promising methodology for the large-scale production of therapeutic monoclonal antibodies. In fact, this procedure does not require establishing any interaction with the antigen specific part of the antibody, i.e. the Fab domain, which is, thus, left intact and can retain its properties (see Salvalaglio, M., et al., J. Chrom. A 1216 (2009) 8678-8686).

Due to its selectiveness, an affinity-purification step is employed early in the purification chain and thereby the number of successive unit operations can be reduced (see Hober supra; MacLennan, J., Biotechnol. 13 (1995) 1180; Harakas, N. K., Bioprocess Technol. 18 (1994) 259).

The ligands most adopted to bind selectively IgG are Staphylococcal protein A and protein G, which are able to establish highly selective interactions with the Fc-region of most IgGs in a region known as "consensus binding site" (CBS) (DeLano, W. L., et al., Science 287 (2000) 1279), which is located at the hinge region between the CH2 and CH3 domains of the Fc-region.

Staphylococcal protein A (SPA) is a cell wall associated protein domain exposed on the surface of the Gram-positive bacterium *Staphylococcus aureus*. SPA has high affinity to IgG from various species, for instance human, rabbit and guinea pig IgG but only weak interaction with bovine and mouse IgG (see the following Table) (see Hober supra; Duhamel, R. C., et al., J. Immunol. Methods 31 (1979) 211; Björk, L. and Kronvall, G., Immunol. J. 133 (1984) 969; Richman, D. D., et al., J. Immunol. 128 (1982) 2300; Amersham Pharmacia Biotech, Handbook, Antibody Purification (2000)).

| species | subclass | protein A binding |
|---|---|---|
| human | IgG1 | ++ |
| | IgG2 | ++ |
| | IgG3 | -- |
| | IgG4 | ++ |
| | IgA | variable |
| | IgD | − |
| | IgM | variable |
| rabbit | no distinction | ++ |
| guinea pig | IgG1 | ++ |
| | IgG2 | ++ |
| bovine | | + |
| mouse | IgG1 | + |
| | IgG2a | ++ |
| | IgG2b | + |
| | IgG3 | + |
| | IgM | variable |
| chicken | IgY | − |

++: strong binding/
+: medium binding/
−: weak or no interaction

The heavy chain hinge-region between the CH2 and CH3 domains of IgG is able to bind several proteins beyond protein A, such as the neonatal Fc receptor (FcRn) (see DeLano and Salvalaglio supra).

The SPA CBS comprehends a hydrophobic pocket on the surface of the antibody. The residues composing the IgG CBS are Ile 253, Ser 254, Met 252, Met 423, Tyr 326, His 435, Asn 434, His 433, Arg 255, and Glu 380 (numbering of the IgG heavy chain residues according to the Kabat EU index numbering system). The charged amino acids (Arg 255, Glu 380) are placed around a hydrophobic knob formed by Ile 253 and Ser 254. This (can) result in the establishment of polar and hydrophilic interactions (see Salvalaglio supra).

In general, the protein A-IgG interaction can be described using two main binding sites: the first is positioned in the heavy chain CH2 domain and is characterized by hydrophobic interactions between Phe 132, Leu 136, Ile 150 (of protein A) and the IgG hydrophobic knob constituted by Ile 253 and Ser 254, and by one electrostatic interaction between Lys 154 (protein A) and Thr 256 (IgG). The second site is located in the heavy chain CH3 domain and is dominated by electrostatic interactions between Gln 129 and Tyr 133 (protein A) and His 433, Asn 434, and His 435 (IgG) (see Salvalaglio supra).

Lindhofer, H., et al. (J. Immunol. 155 (1995) 219-225) report preferential species-restricted heavy/light chain pairing in rat/mouse quadromas.

Jedenberg, L., et al. (J. Immunol. Meth. 201 (1997) 25-34) reported that SPA-binding analyses of two Fc variants (Fc13 and Fc31, each containing an isotypic dipeptide substitution from the respective other isotype) showed that Fc1 and Fc31 interact with SPA, while Fc3 and Fc13 lack detectable SPA binding. The rendered SPA binding of the Fc-region variant Fc31 is concluded to result from the introduced dipeptide substitution R435H and F436Y.

Today the focus with respect to therapeutic monoclonal antibodies is on the generation and use of bispecific or even multispecific antibodies specifically binding to two or more targets (antigens).

The basic challenge in generating multispecific heterodimeric IgG antibodies from four antibody chains (two different heavy chains and two different light chains) in one expression cell line is the so-called chain association issue (see Klein, C., et al., mAbs 4 (2012) 653-663). The required use of different chains as the left and the right arm of the multispecific antibody leads to antibody mixtures upon expression in one cell: the two heavy chains are able to (theoretically) associate in four different combinations (two thereof are identical), and each of those can associate in a stochastic manner with the light chains, resulting in $2^4$ (=a total of 16) theoretically possible chain combinations. Of the 16 theoretically possible combinations ten can be found of which only one corresponds to the desired functional bispecific antibody (De Lau, W. B., et al., J. Immunol. 146 (1991) 906-914). The difficulties in isolating this desired bispecific antibody out of complex mixtures and the inherent poor yield of 12.5% at a theoretical maximum make the production of a bispecific antibody in one expression cell line extremely challenging.

To overcome the chain association issue and enforce the correct association of the two different heavy chains, in the late 1990s Carter et al. from Genentech invented an approach termed "knobs-into-holes" (KiH) (see Carter, P., J. Immunol. Meth. 248 (2001) 7-15; Merchant, A. M., et al., Nat. Biotechnol. 16 (1998) 677-681; Zhu, Z., et al., Prot. Sci. 6 (1997) 781-788; Ridgway, J. B., et al., Prot. Eng. 9 (1996) 617-621; Atwell, S., et al., J. Mol. Biol. 270(1997) 26-35; and U.S. Pat. No. 7,183,076). Basically, the concept relies on modifications of the interface between the two CH3 domains of the two heavy chains of an antibody where most interactions occur. A bulky residue is introduced into the CH3 domain of one antibody heavy chain and acts similarly to a key ("knob"). In the other heavy chain, a "hole" is formed that is able to accommodate this bulky residue, mimicking a lock. The resulting heterodimeric Fc-region can be further stabilized by the introduction/formation of artificial disulfide bridges. Notably, all KiH mutations are buried within the CH3 domains and not "visible" to the immune system. In addition, properties of antibodies with KiH mutations such as (thermal) stability, FcγR binding and effector functions (e.g., ADCC, FcRn binding) and pharmacokinetic (PK) behavior are not affected.

Correct heavy chain association with heterodimerization yields above 97% can be achieved by introducing six mutations: S354C, T366W in the "knob" heavy chain and Y349C, T366S, L368A, Y407V in the "hole" heavy chain (see Carter supra; numbering of the residues according to the Kabat EU index numbering system). While hole-hole homodimers may occur, knob-knob homodimers typically are not observed. Hole-hole dimers can either be depleted by selective purification procedures or by procedures as outlined below.

While the issue of random heavy chain association has been addressed, also correct light chain association has to be ensured. Similar to the KiH CH3 domain approach, efforts have been undertaken to investigate asymmetric light chain-heavy chain interactions that might ultimately lead to full bispecific IgGs.

Roche recently developed the CrossMab approach as a possibility to enforce correct light chain pairing in bispecific heterodimeric IgG antibodies when combining it with the KiH technology (see Klein supra; Schaefer. W., et al., Proc. Natl. Acad. Sci. USA 108 (2011) 11187-11192; Cain, C., SciBX 4 (2011) 1-4). This allows the generation of bispecific or even multispecific antibodies in a generic fashion. In this format, one arm of the intended bispecific antibody is left untouched. In the second arm, the whole Fab region, or the VH-VL domains or the CH1-CL domains are exchanged by domain crossover between the heavy and light chain. As a consequence, the newly formed "crossed" light chain does not associate with the (normal, i.e. not-crossed) heavy chain Fab region of the other arm of the bispecific antibody any longer. Thus, the correct "light chain" association can be enforced by this minimal change in domain arrangement (see Schaefer supra).

Zhu et al. introduced several sterically complementary mutations, as well as disulfide bridges, in the two VL/VH interfaces of diabody variants. When the mutations VL Y87A/F98M and VH V37F/L45W were introduced into the anti-p185HER2 VL/VH interface, a heterodimeric diabody was recovered with >90% yield while maintaining overall yield and affinity compared with the parental diabody (see Zhu supra).

Researchers from Chugai have similarly designed bispecific diabodies by introduction of mutations into the VH-VL interfaces (mainly conversion of Q39 in VH and Q38 in VL to charged residues) to foster correct light chain association (WO 2006/106905; Igawa, T., et al., Prot. Eng. Des. Sel. 23 (2010) 667-677).

In WO2011097603 a common light chain mouse is reported.

In WO2010151792 a bispecific antibody format providing ease of isolation is provided, comprising immunoglobulin heavy chain variable domains that are differentially modified, i.e. heterodimeric, in the CH3 domain, wherein the differential modifications are non-immunogenic or substantially non-immunogenic with respect to the CH3 modifications, and at least one of the modifications results in a differential affinity for the bispecific antibody for an affinity reagent such as protein A, and the bispecific antibody is isolable from a disrupted cell, from medium, or from a mixture of antibodies based on its affinity for protein A.

The neonatal Fc-receptor (FcRn) is important for the metabolic fate of antibodies of the IgG class in vivo. The FcRn functions to salvage IgG from the lysosomal degradation pathway, resulting in reduced clearance and increased half-life. It is a heterodimeric protein consisting of two polypeptides: a 50 kDa class I major histocompatibility complex-like protein (α-FcRn) and a 15 kDa β2-microglobulin (β2m). FcRn binds with high affinity to the CH2-CH3 portion of the Fc-region of an antibody of the class IgG. The interaction between an antibody of the class IgG and the FcRn is pH dependent and occurs in a 1:2 stoichiometry, i.e. one IgG antibody molecule can interact with two FcRn molecules via its two heavy chain Fc-region polypeptides (see e.g. Huber, A. H., et al., J. Mol. Biol. 230 (1993) 1077-1083).

Thus, an IgGs in vitro FcRn binding properties/characteristics are indicative of its in vivo pharmacokinetic properties in the blood circulation.

In the interaction between the FcRn and the Fc-region of an antibody of the IgG class different amino acid residues of the heavy chain CH2- and CH3-domain are participating.

Different mutations that influence the FcRn binding and therewith the half-live in the blood circulation are known. Fc-region residues critical to the mouse Fc-region-mouse FcRn interaction have been identified by site-directed mutagenesis (see e.g. Dall'Acqua, W. F., et al. J. Immunol 169 (2002) 5171-5180). Residues I253, H310, H433, N434, and H435 (numbering according to Kabat EU index numbering system) are involved in the interaction (Medesan, C., et al., Eur. J. Immunol. 26 (1996) 2533-2536; Firan, M., et al., Int. Immunol. 13 (2001) 993-1002; Kim, J. K., et al., Eur. J. Immunol. 24 (1994) 542-548). Residues I253, H310, and H435 were found to be critical for the interaction of human Fc-region with murine FcRn (Kim, J. K., et al., Eur. J. Immunol. 29 (1999) 2819-2885).

Methods to increase Fc-region (and likewise IgG) binding to FcRn have been performed by mutating various amino acid residues in the Fc-region: Thr 250, Met 252, Ser 254, Thr 256, Thr 307, Glu 380, Met 428, His 433, and Asn 434 (see Kuo, T. T., et al., J. Clin. Immunol. 30 (2010) 777-789; Ropeenian, D. C., et al., Nat. Rev. Immunol. 7 (2007) 715-725).

The combination of the mutations M252Y, S254T, T256E have been described by Dall'Acqua et al. to improve FcRn binding by protein-protein interaction studies (Dall'Acqua, W. F., et al. J. Biol. Chem. 281 (2006) 23514-23524). Studies of the human Fc-region-human FcRn complex have shown that residues I253, S254, H435, and Y436 are crucial for the interaction (Firan, M., et al., Int. Immunol. 13 (2001) 993-1002; Shields, R. L., et al., J. Biol. Chem. 276 (2001) 6591-6604). In Yeung, Y. A., et al. (J. Immunol. 182 (2009) 7667-7671) various mutants of residues 248 to 259 and 301 to 317 and 376 to 382 and 424 to 437 have been reported and examined.

In WO 2014/006217 dimeric proteins with triple mutations are reported. Crystal structure at 2.8 Angstrom of an FcRn/heterodimeric Fc complex regarding the mechanism of pH-dependent binding was reported by Martin, W., et al. (Mol. Cell. 7 (2001) 867-877). In U.S. Pat. No. 6,277,375 immunoglobulin like domains with increased half-lives are reported in WO 2013/004842. Shields, R. L., et al., reported high resolution mapping of the binding site on human IgG1 for Fc gamma RI, Fc gamma RII, Fc gamma RIII, and FcRn and design of IgG1 variants with improved binding to the Fc gamma R (Biochem. Mol. Biol. 276 (2001) 6591-6604). The delineation of the amino acid residues involved in transcytosis and catabolism of mouse IgG1 was reported by Medesan, C., et al. (J. Immunol. 158 (1997) 2211-2217). In US 2010/0272720 antibody fusion proteins with a modified FcRn binding site are reported. The production of heterodimeric proteins is reported in WO 2013/060867. Qiao, S.-W., et al. reported the dependence of antibody-mediated presentation of antigen on FcRn (Proc. Natl. Acad. Sci. USA 105 (2008) 9337-9342.

SUMMARY OF THE INVENTION

Herein are reported variant Fc-regions that specifically bind to *Staphylococcus* protein A and that do not bind to human FcRn. These variant Fc-regions contain specific amino acid mutations in the CH2- and CH3-domain. It has been found that these mutations when used either in the hole chain or the knob chain of a heterodimeric Fc-region allow for the purification of the heterodimeric Fc-region, i.e. the separation of a heterodimeric Fc-region from a homodimeric Fc-region.

One aspect as reported herein is a (dimeric) polypeptide comprising a first polypeptide comprising in N-terminal to C-terminal direction at least a portion of an immunoglobulin hinge region, which comprises one or more cysteine residues, an immunoglobulin CH2-domain and an immunoglobulin CH3-domain, and a second polypeptide comprising in N-terminal to C-terminal direction at least a portion of an immunoglobulin hinge region, which comprises one or more cysteine residues, an immunoglobulin CH2-domain and an immunoglobulin CH3-domain, wherein (numbering according to the Kabat EU index numbering system)

i) the first polypeptide comprises the mutations I253A, H310A and H435A and the second polypeptide comprises the mutations H310A, H433A and Y436A, or ii) the first polypeptide comprises the mutations I253A, H310A and H435A and the second polypeptide comprises the mutations L251D, L314D and L432D, or iii) the first polypeptide comprises the mutations I253A, H310A and H435A and the second polypeptide comprises the mutations L251S, L314S and L432S and, wherein the first polypeptide and the second polypeptide are connected by one or more disulfide bridges in the at least a portion of an immunoglobulin hinge region.

In one embodiment the (dimeric) polypeptide does not specifically bind to the human FcRn and does specifically bind to Staphylococcal protein A.

In one embodiment the (dimeric) polypeptide is a homodimeric polypeptide.

In one embodiment the (dimeric) polypeptide is a heterodimeric polypeptide.

In one embodiment the first polypeptide further comprises the mutations Y349C, T366S, L368A and Y407V ("hole") and the second polypeptide comprises the mutations S354C and T366W ("knob").

In one embodiment the first polypeptide further comprises the mutations S354C, T366S, L368A and Y407V ("hole") and the second polypeptide comprises the mutations Y349C and T366W ("knob").

In one embodiment the immunoglobulin hinge region, the immunoglobulin CH2-domain and the immunoglobulin CH3-domain of the first and the second polypeptide are of the human IgG1 subclass. In one embodiment the first polypeptide and the second polypeptide each further comprise the mutations L234A and L235A. In one embodiment the first polypeptide and the second polypeptide each further comprise the mutation P329G. In one embodiment the first polypeptide and the second polypeptide each further comprise the mutations L234A, L235A and P329G.

In one embodiment the immunoglobulin hinge region, the immunoglobulin CH2-domain and the immunoglobulin CH3-domain of the first and the second polypeptide are of the human IgG2 subclass. In one embodiment the first polypeptide and the second polypeptide each further comprise the mutations H268Q, V309L, A330S and P331S.

In one embodiment the immunoglobulin hinge region, the immunoglobulin CH2-domain and the immunoglobulin CH3-domain of the first and the second polypeptide are of the human IgG2 subclass. In one embodiment the first polypeptide and the second polypeptide each further comprise the mutations V234A, G237A, P238S, H268A, V309L, A330S and P331S.

In one embodiment the immunoglobulin hinge region, the immunoglobulin CH2-domain and the immunoglobulin CH3-domain of the first and the second polypeptide are of the human IgG4 subclass. In one embodiment the first polypeptide and the second polypeptide each further comprise the mutations S228P and L235E. In one embodiment the first polypeptide and the second polypeptide each further comprise the mutation P329G. In one embodiment the first polypeptide and the second polypeptide each further comprise the mutations S228P, L235E and P329G.

In one embodiment the immunoglobulin hinge region, the immunoglobulin CH2-domain and the immunoglobulin CH3-domain of the first and the second polypeptide are of the human IgG4 subclass. In one embodiment the first polypeptide and the second polypeptide each further comprise the mutations S228P, L234A and L235A. In one embodiment the first polypeptide and the second polypeptide each further comprise the mutation P329G. In one embodiment the first polypeptide and the second polypeptide each further comprise the mutations S228P, L234A, L235A and P329G.

In one embodiment the first and the second polypeptide further comprise the mutation Y436A.

In one embodiment the (dimeric) polypeptide is an Fc-region fusion polypeptide.

In one embodiment the (dimeric) polypeptide is an (full length) antibody.

In one embodiment the (full length) antibody is a monospecific antibody. In one embodiment the monospecific antibody is a monovalent monospecific antibody. In one embodiment the monospecific antibody is a bivalent monospecific antibody.

In one embodiment the (full length) antibody is a bispecific antibody. In one embodiment the bispecific antibody is a bivalent bispecific antibody. In one embodiment the bispecific antibody is a tetravalent bispecific antibody.

In one embodiment the (full length) antibody is a trispecific antibody. In one embodiment the trispecific antibody is a trivalent trispecific antibody. In one embodiment the trispecific antibody is a tetravalent trispecific antibody.

One aspect as reported herein is an antibody comprising a first polypeptide comprising in N-terminal to C-terminal direction a first heavy chain variable domain, an immunoglobulin CH1-domain of the subclass IgG1, an immunoglobulin hinge region of the subclass IgG1, an immunoglobulin CH2-domain of the subclass IgG1 and an immunoglobulin CH3-domain of the subclass IgG1, a second polypeptide comprising in N-terminal to C-terminal direction a second heavy chain variable domain, an immunoglobulin CH1-domain of the subclass IgG1, an immunoglobulin hinge region of the subclass IgG1, an immunoglobulin CH2-domain of the subclass IgG1 and an immunoglobulin CH3-domain of the subclass IgG1, a third polypeptide comprising in N-terminal to C-terminal direction a first light chain variable domain and a light chain constant domain, a fourth polypeptide comprising in N-terminal to C-terminal direction a second light chain variable domain and a light chain constant domain, wherein the first heavy chain variable domain and the first light chain variable domain form a first binding site that specifically binds to a first antigen, wherein the second heavy chain variable domain and the second light chain variable domain form a second binding site that specifically binds to a second antigen, wherein i) the first polypeptide comprises the mutations Y349C, T366S, L368A, and Y407V, L234A, L235A and P329G and the second polypeptide comprises the mutations S354C, and T366W, L234A, L235A and P329G, or ii) the first polypeptide comprises the mutations S354C, T366S, L368A, Y407V, L234A, L235A and P329G and the second polypeptide comprises the mutations Y349C, T366W, L234A, L235A and P329G, and wherein (numbering according to the Kabat EU index numbering system)

i) the first polypeptide comprises the mutations I253A, H310A and H435A and the second polypeptide comprises the mutations H310A, H433A and Y436A, or ii) the first polypeptide comprises the mutations I253A, H310A and H435A and the second polypeptide comprises the mutations L251D, L314D and L432D, or iii) the first polypeptide comprises the mutations I253A, H310A and H435A and the second polypeptide comprises the mutations L251S, L314S and L432S, and wherein the first polypeptide and the second polypeptide are connected by one or more disulfide bridges in the hinge region.

One aspect as reported herein is an antibody comprising a first polypeptide comprising in N-terminal to C-terminal direction a first heavy chain variable domain, an immunoglobulin light chain constant domain, an immunoglobulin hinge region of the subclass IgG1, an immunoglobulin CH2-domain of the subclass IgG1 and an immunoglobulin CH3-domain of the subclass IgG1, a second polypeptide comprising in N-terminal to C-terminal direction a second heavy chain variable domain, an immunoglobulin CH1-domain of the subclass IgG1, an immunoglobulin hinge region of the subclass IgG1, an immunoglobulin CH2-domain of the subclass IgG1 and an immunoglobulin CH3-domain of the subclass IgG1, a third polypeptide comprising in N-terminal to C-terminal direction a first light chain variable domain and an immunoglobulin CH1-domain of the subclass IgG1, a fourth polypeptide comprising in N-terminal to C-terminal direction a second light chain variable domain and a light chain constant domain, wherein the first heavy chain variable domain and the first light chain variable domain form a first binding site that specifically binds to a first antigen, wherein the second heavy chain variable domain and the second light chain variable domain form a second binding site that specifically binds to a second antigen, wherein i) the first polypeptide comprises the mutations Y349C, T366S, L368A, and Y407V, L234A, L235A and P329G and the second polypeptide comprises the mutations S354C, and T366W, L234A, L235A and P329G, or ii) the first polypeptide comprises the mutations S354C, T366S, L368A, Y407V, L234A, L235A and P329G and the second polypeptide comprises the mutations Y349C, T366W, L234A, L235A and P329G, and wherein (numbering according to the Kabat EU index numbering system)

i) the first polypeptide comprises the mutations I253A, H310A and H435A and the second polypeptide comprises the mutations H310A, H433A and Y436A, or ii) the first polypeptide comprises the mutations I253A, H310A and H435A and the second polypeptide comprises the mutations L251D, L314D and L432D, or iii) the first polypeptide comprises the mutations I253A, H310A and H435A and the second polypeptide comprises the mutations L251S, L314S and L432S, and wherein the first polypeptide and the second polypeptide are connected by one or more disulfide bridges in the hinge region.

One aspect as reported herein is an antibody comprising a first polypeptide comprising in N-terminal to C-terminal direction a first heavy chain variable domain, an immunoglobulin CH1-domain of the subclass IgG4, an immunoglobulin hinge region of the subclass IgG4, an immunoglobulin CH2-domain of the subclass IgG4 and an immunoglobulin CH3-domain of the subclass IgG4, a second polypeptide comprising in N-terminal to C-terminal direction a second heavy chain variable domain, an immunoglobulin CH1-domain of the subclass IgG4, an immunoglobulin hinge region of the subclass IgG4, an immunoglobulin CH2-domain of the subclass IgG4 and an immunoglobulin CH3-domain of the subclass IgG4, a third polypeptide comprising in N-terminal to C-terminal direction a first light chain variable domain and a light chain constant domain, a fourth polypeptide comprising in N-terminal to C-terminal direction a second light chain variable domain and a light chain constant domain, wherein the first heavy chain variable domain and the first light chain variable domain form a first binding site that specifically binds to a first antigen, wherein the second heavy chain variable domain and the second light chain variable domain form a second binding site that specifically binds to a second antigen, wherein i) the first polypeptide comprises the mutations Y349C, T366S, L368A, and Y407V, S228P, L235E and P329G and the second polypeptide comprises the mutations S354C, and T366W, S228P, L235E and P329G, or ii) the first polypeptide comprises the mutations S354C, T366S, L368A, Y407V, S228P, L235E and P329G and the second polypeptide comprises the mutations Y349C, T366W, S228P, L235E and P329G, and wherein (numbering according to the Kabat EU index numbering system)

i) the first polypeptide comprises the mutations I253A, H310A and H435A and the second polypeptide comprises the mutations H310A, H433A and Y436A, or ii) the first polypeptide comprises the mutations I253A, H310A and H435A and the second polypeptide comprises the mutations L251D, L314D and L432D, or iii) the first polypeptide comprises the mutations I253A, H310A and H435A and the second polypeptide comprises the mutations L251S, L314S and L432S, and wherein the first polypeptide and the second polypeptide are connected by one or more disulfide bridges in the hinge region.

One aspect as reported herein is an antibody comprising a first polypeptide comprising in N-terminal to C-terminal direction a first heavy chain variable domain, an immunoglobulin light chain constant domain, an immunoglobulin hinge region of the subclass IgG4, an immunoglobulin CH2-domain of the subclass IgG4 and an immunoglobulin CH3-domain of the subclass IgG4, a second polypeptide comprising in N-terminal to C-terminal direction a second heavy chain variable domain, an immunoglobulin CH1-domain of the subclass IgG4, an immunoglobulin hinge region of the subclass IgG4, an immunoglobulin CH2-domain of the subclass IgG4 and an immunoglobulin CH3-domain of the subclass IgG4, a third polypeptide comprising in N-terminal to C-terminal direction a first light chain variable domain and an immunoglobulin CH1-domain of the subclass IgG4, a fourth polypeptide comprising in N-terminal to C-terminal direction a second light chain variable domain and a light chain constant domain, wherein the first heavy chain variable domain and the first light chain variable domain form a first binding site that specifically binds to a first antigen, wherein the second heavy chain variable domain and the second light chain variable domain form a second binding site that specifically binds to a second antigen, wherein i) the first polypeptide comprises the mutations Y349C, T366S, L368A, and Y407V, S228P, L235E and P329G and the second polypeptide comprises the mutations S354C, and T366W, S228P, L235E and P329G, or ii) the first polypeptide comprises the mutations S354C, T366S, L368A, Y407V, S228P, L235E and P329G and the second polypeptide comprises the mutations Y349C, T366W, S228P, L235E and P329G, and wherein (numbering according to the Kabat EU index numbering system)

i) the first polypeptide comprises the mutations I253A, H310A and H435A and the second polypeptide comprises the mutations H310A, H433A and Y436A, or ii) the first polypeptide comprises the mutations I253A, H310A and H435A and the second polypeptide comprises the mutations L251D, L314D and L432D, or iii) the first polypeptide comprises the mutations I253A, H310A and H435A and the second polypeptide comprises the mutations L251S, L314S and L432S, and wherein the first polypeptide and the second polypeptide are connected by one or more disulfide bridges in the hinge region.

One aspect as reported herein is an antibody comprising a first polypeptide comprising in N-terminal to C-terminal direction a first heavy chain variable domain, an immunoglobulin CH1-domain of the subclass IgG1, an immunoglobulin hinge region of the subclass IgG1, an immunoglobulin CH2-domain of the subclass IgG1, an immunoglobulin CH3-domain of the subclass IgG1, a peptidic linker and a first scFv, a second polypeptide comprising in N-terminal to C-terminal direction a second heavy chain variable domain, an immunoglobulin CH1-domain of the subclass IgG1, an immunoglobulin hinge region of the subclass IgG1, an immunoglobulin CH2-domain of the subclass IgG1, an immunoglobulin CH3-domain of the subclass IgG1, a peptidic linker and a second scFv, a third polypeptide comprising in N-terminal to C-terminal direction a first light chain variable domain and a light chain constant domain, a fourth polypeptide comprising in N-terminal to C-terminal direction a second light chain variable domain and a light chain constant domain, wherein the first heavy chain variable domain and the first light chain variable domain form a first binding site that specifically binds to a first antigen, and the second heavy chain variable domain and the second light chain variable domain form a second binding site that specifically binds to a first antigen, and the first and the second scFv specifically bind to a second antigen, wherein i) the first polypeptide comprises the mutations Y349C, T366S, L368A, and Y407V, L234A, L235A and P329G and the second polypeptide comprises the mutations S354C, and T366W, L234A, L235A and P329G, or ii) the first polypeptide comprises the mutations S354C, T366S, L368A, Y407V, L234A, L235A and P329G and the second polypeptide comprises the mutations Y349C, T366W, L234A, L235A and P329G, and wherein (numbering according to the Kabat EU index numbering system)

i) the first polypeptide comprises the mutations I253A, H310A and H435A and the second polypeptide comprises the mutations H310A, H433A and Y436A, or ii) the first polypeptide comprises the mutations I253A, H310A and H435A and the second polypeptide comprises the mutations L251D, L314D and L432D, or iii) the first polypeptide comprises the mutations I253A, H310A and H435A and the second polypeptide comprises the mutations L251S, L314S and L432S, and wherein the first polypeptide and the second polypeptide are connected by one or more disulfide bridges in the hinge region.

One aspect as reported herein is an antibody comprising a first polypeptide comprising in N-terminal to C-terminal direction a first heavy chain variable domain, an immunoglobulin light chain constant domain, an immunoglobulin hinge region of the subclass IgG1, an immunoglobulin CH2-domain of the subclass IgG1, an immunoglobulin CH3-domain of the subclass IgG1, a peptidic linker and a first scFv, a second polypeptide comprising in N-terminal to C-terminal direction a second heavy chain variable domain, an immunoglobulin CH1-domain of the subclass IgG1, an immunoglobulin hinge region of the subclass IgG1, an immunoglobulin CH2-domain of the subclass IgG1, an immunoglobulin CH3-domain of the subclass IgG1, a peptidic linker and a second scFv, a third polypeptide comprising in N-terminal to C-terminal direction a first light chain variable domain and an immunoglobulin CH1-domain of the subclass IgG1, a fourth polypeptide comprising in N-terminal to C-terminal direction a second light chain variable domain and a light chain constant domain, wherein the first heavy chain variable domain and the first light chain variable domain form a first binding site that specifically binds to a first antigen, and the second heavy chain variable domain and the second light chain variable domain form a second binding site that specifically binds to a first antigen, and the first and the second scFv specifically bind to a second antigen, wherein i) the first polypeptide comprises the mutations Y349C, T366S, L368A, and Y407V, L234A, L235A and P329G and the second polypeptide comprises the mutations S354C, and T366W, L234A, L235A and P329G, or ii) the first polypeptide comprises the mutations S354C, T366S, L368A, Y407V, L234A, L235A and P329G and the second polypeptide comprises the mutations Y349C, T366W, L234A, L235A and P329G, and wherein (numbering according to the Kabat EU index numbering system)

i) the first polypeptide comprises the mutations I253A, H310A and H435A and the second polypeptide comprises the mutations H310A, H433A and Y436A, or ii) the first polypeptide comprises the mutations I253A, H310A and H435A and the second polypeptide comprises the mutations L251D, L314D and L432D, or iii) the first polypeptide comprises the mutations I253A, H310A and H435A and the second polypeptide comprises the mutations L251S, L314S and L432S, and wherein the first polypeptide and the second polypeptide are connected by one or more disulfide bridges in the hinge region.

One aspect as reported herein is a method for producing a (dimeric) polypeptide as reported herein comprising the following steps:

a) cultivating a mammalian cell comprising one or more nucleic acids encoding the (dimeric) polypeptide, b) recovering the (dimeric) polypeptide from the cultivation medium, and c) purifying the (dimeric) polypeptide with a protein A affinity chromatography and thereby producing the (dimeric) polypeptide.

One aspect as reported herein is the use of the combination of the mutations H310A, H433A and Y436A for separating heterodimeric polypeptides from homodimeric polypeptides.

One aspect as reported herein is the use of the combination of the mutations L251D, L314D and L432D for separating heterodimeric polypeptides from homodimeric polypeptides.

One aspect as reported herein is the use of the combination of the mutations L251S, L314S and L432S for separating heterodimeric polypeptides from homodimeric polypeptides.

One aspect as reported herein is the use of the combination of the mutations I253A, H310A and H435A in a first Fc-region polypeptide in combination with the combination of the mutations H310A, H433A and Y436A in a second Fc-region polypeptide for separating heterodimeric Fc-regions comprising the first and the second Fc-region polypeptide from homodimeric Fc-regions.

One aspect as reported herein is the use of the combination of the mutations I253A, H310A and H435A in a first Fc-region polypeptide in combination with the combination of the mutations L251D, L314D and L432D in a second Fc-region polypeptide for separating heterodimeric Fc-regions comprising the first and the second Fc-region polypeptide from homodimeric Fc-regions.

One aspect as reported herein is the use of the combination of the mutations I253A, H310A and H435A in a first Fc-region polypeptide in combination with the combination of the mutations L251S, L314S and L432S in a second Fc-region polypeptide for separating heterodimeric Fc-regions comprising the first and the second Fc-region polypeptide from homodimeric Fc-regions.

In one embodiment of the previous three aspects i) the first Fc-region polypeptide further comprises the mutations Y349C, T366S, L368A and Y407V and the second Fc-region polypeptide further comprises the mutations S354C and T366W, or ii) the first polypeptide comprises the mutations S354C, T366S, L368A, and Y407V, and the second polypeptide comprises the mutations Y349C and T366W.

In one embodiment both Fc-region polypeptides comprise in N-terminal to C-terminal direction a heavy chain variable domain, an immunoglobulin CH1-domain, an immunoglobulin hinge region, an immunoglobulin CH2-domain and an immunoglobulin CH3-domain. In one embodiment the hinge region and the immunoglobulin domains are all of the IgG1 subclass or all of the IgG4 subclass.

One aspect as reported herein is method of treatment of a patient suffering from ocular vascular diseases by administering a (dimeric) polypeptide or antibody as reported herein to a patient in the need of such treatment.

One aspect as reported herein is a (dimeric) polypeptide or an antibody as reported herein for intravitreal application.

One aspect as reported herein is a (dimeric) polypeptide or an antibody as reported herein for use as a medicament.

One aspect as reported herein is a (dimeric) polypeptide or an antibody as reported herein for the treatment of vascular eye diseases.

One aspect as reported herein is a pharmaceutical formulation comprising a (dimeric) polypeptide or an antibody as reported herein and optionally a pharmaceutically acceptable carrier.

For using an antibody that targets/binds to antigens not only present in the eye but also in the remaining body a short systemic half-live after passage of the blood-ocular-barrier from the eye into the blood is beneficial in order to avoid systemic side effects.

Additionally an antibody that specifically binds to ligands of a receptor is only effective in the treatment of eye-diseases if the antibody-antigen complex is removed from the eye, i.e. the antibody functions as a transport vehicle for receptor ligands out of the eye and thereby inhibits receptor signaling.

It has been found by the current inventors that an antibody comprising an Fc-region that does not bind to the human neonatal Fc-receptor, i.e. a (dimeric) polypeptide as reported herein, is transported across the blood-ocular barrier. This is surprising as the antibody does not bind to human FcRn although binding to FcRn is considered to be required for transport across the blood-ocular-barrier.

One aspect as reported herein is the use of a (dimeric) polypeptide or an antibody as reported herein for the transport of a soluble receptor ligand from the eye over the blood-ocular-barrier into the blood circulation.

One aspect as reported herein is the use of a (dimeric) polypeptide or an antibody as reported herein for the removal of one or more soluble receptor ligands from the eye.

One aspect as reported herein is the use of a (dimeric) polypeptide or an antibody as reported herein for the treatment of eye diseases, especially of ocular vascular diseases.

One aspect as reported herein is the use of a (dimeric) polypeptide or an antibody as reported herein for the transport of one or more soluble receptor ligands from the intravitreal space to the blood circulation.

One aspect as reported herein is a (dimeric) polypeptide or an antibody as reported herein for use in treating an eye disease.

One aspect as reported herein is a (dimeric) polypeptide or an antibody as reported herein for use in the transport of a soluble receptor ligand from the eye over the blood-ocular-barrier into the blood circulation.

One aspect as reported herein is a (dimeric) polypeptide or an antibody as reported herein for use in the removal of one or more soluble receptor ligands from the eye.

One aspect as reported herein is a (dimeric) polypeptide or an antibody as reported herein for use in treating eye diseases, especially ocular vascular diseases.

One aspect as reported herein is a (dimeric) polypeptide or an antibody as reported herein for use in the transport of one or more soluble receptor ligands from the intravitreal space to the blood circulation.

One aspect as reported herein is a method of treating an individual having an ocular vascular disease comprising administering to the individual an effective amount of a (dimeric) polypeptide or an antibody as reported herein.

One aspect as reported herein is a method for transporting a soluble receptor ligand from the eye over the blood-ocular-barrier into the blood circulation in an individual comprising administering to the individual an effective amount of a (dimeric) polypeptide or an antibody as reported herein to transport a soluble receptor ligand from the eye over the blood-ocular-barrier into the blood circulation.

One aspect as reported herein is a method the removal of one or more soluble receptor ligands from the eye in an individual comprising administering to the individual an effective amount of a (dimeric) polypeptide or an antibody as reported herein to remove one or more soluble receptor ligands from the eye.

One aspect as reported herein is a method for the transport of one or more soluble receptor ligands from the intravitreal space to the blood circulation in an individual comprising administering to the individual an effective amount of a (dimeric) polypeptide or an antibody as reported herein to transport of one or more soluble receptor ligands from the intravitreal space to the blood circulation.

One aspect as reported herein is a method for transporting a soluble receptor ligand from the intravitreal space or the eye over the blood-ocular-barrier into the blood circulation in an individual comprising administering to the individual an effective amount of a (dimeric) polypeptide or an antibody as reported herein to transport a soluble receptor ligand from the eye over the blood-ocular-barrier into the blood circulation.

In one embodiment the (dimeric) polypeptide is a bispecific antibody. In one embodiment the bispecific antibody is a bivalent bispecific antibody. In one embodiment the bispecific antibody is a tetravalent bispecific antibody.

In one embodiment the (dimeric) polypeptide is a trispecific antibody. In one embodiment the trispecific antibody is a trivalent trispecific antibody. In one embodiment the trispecific antibody is a tetravalent trispecific antibody.

In one embodiment the (dimeric) polypeptide is a CrossMab.

In one embodiment the (dimeric) polypeptide is an Fc-region fusion polypeptide.

In one embodiment the first polypeptide further comprises the mutations Y349C, T366S, L368A and Y407V and the second polypeptide further comprises the mutations S354C and T366W.

In one embodiment the first polypeptide further comprises the mutations S354C, T366S, L368A and Y407V and the second polypeptide further comprises the mutations Y349C and T366W.

In one embodiment the antibody or the Fc-region fusion polypeptide is of the subclass IgG1. In one embodiment the antibody or the Fc-region fusion polypeptide further comprise the mutations L234A and L235A. In one embodiment the antibody or the Fc-region fusion polypeptide further comprise the mutation P329G.

In one embodiment the antibody or the Fc-region fusion polypeptide is of the subclass IgG2. In one embodiment the antibody or the Fc-region fusion polypeptide further comprise the mutations V234A, G237A, P238S, H268A, V309L, A330S and P331S.

In one embodiment the antibody or the Fc-region fusion polypeptide is of the subclass IgG4. In one embodiment the antibody or the Fc-region fusion polypeptide further comprise the mutations S228P and L235E. In one embodiment the antibody or the Fc-region fusion polypeptide further comprise the mutation P329G.

DETAILED DESCRIPTION OF EMBODIMENTS OF THE INVENTION

I. Definitions

Figure 1:
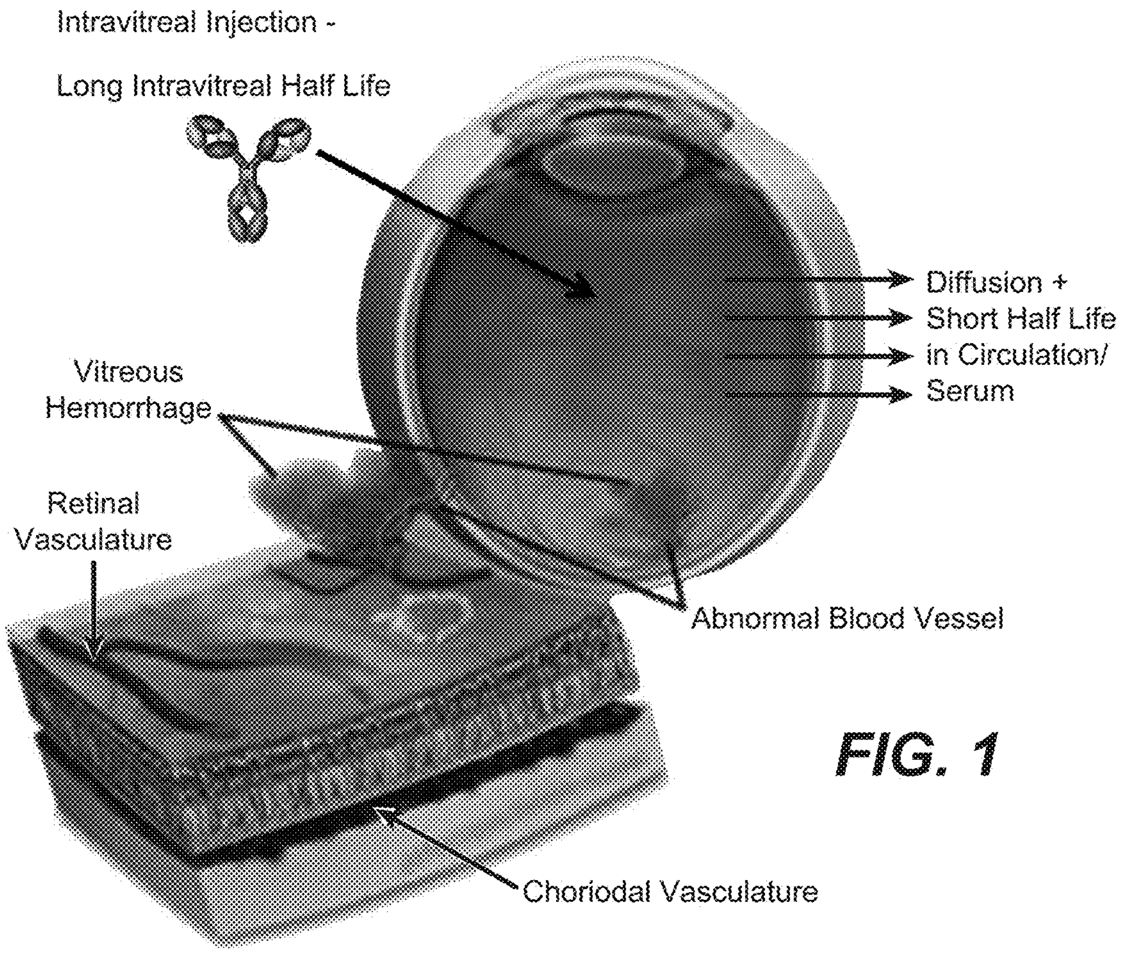
FIG. 1: Scheme of concept and advantages of anti-VEGF/ANG2 antibodies of the IgG1 or IgG4 subclass with IHH- AAA mutation (combination of mutations I253A, H310A and H435A (numbering according to the Kabat EU index numbering system)).

The term "about" denotes a range of +/−20% of the thereafter following numerical value. In one embodiment the term about denotes a range of +/−10% of the thereafter following numerical value. In one embodiment the term about denotes a range of +/−5% of the thereafter following numerical value.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence alterations. In some embodiments, the number of amino acid alterations are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

An "affinity matured" antibody refers to an antibody with one or more alterations in one or more hypervariable regions (HVRs), compared to a parent antibody which does not possess such alterations, such alterations resulting in an improvement in the inity of the antibody for antigen.

The term "alteration" denotes the mutation (substitution), insertion (addition), or deletion of one or more amino acid residues in a parent antibody or fusion polypeptide, e.g. a fusion polypeptide comprising at least an FcRn binding portion of an Fc-region, to obtain a modified antibody or fusion polypeptide. The term "mutation" denotes that the specified amino acid residue is substituted for a different amino acid residue. For example the mutation L234A denotes that the amino acid residue lysine at position 234 in an antibody Fc-region (polypeptide) is substituted by the amino acid residue alanine (substitution of lysine with alanine) (numbering according to the Kabat EU index numbering system).

A "naturally occurring amino acid residues" denotes an amino acid residue from the group consisting of alanine (three letter code: Ala, one letter code: A), arginine (Arg, R), asparagine (Asn, N), aspartic acid (Asp, D), cysteine (Cys, C), glutamine (Gln, Q), glutamic acid (Glu, E), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophane (Trp, W), tyrosine (Tyr, Y), and valine (Val, V).

The term "amino acid mutation" denotes the substitution of at least one existing amino acid residue with another different amino acid residue (=replacing amino acid residue). The replacing amino acid residue may be a "naturally occurring amino acid residues" and selected from the group consisting of alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V). The replacing amino acid residue may be a "non-naturally occurring amino acid residue". See e.g. U.S. Pat. No. 6,586,207, WO 98/48032, WO 03/073238, US 2004/0214988, WO 2005/35727, WO 2005/74524, Chin, J. W., et al., J. Am. Chem. Soc. 124 (2002) 9026-9027; Chin, J. W. and Schultz, P. G., ChemBioChem 11 (2002) 1135-1137; Chin, J. W., et al., PICAS United States of America 99 (2002) 11020-11024; and, Wang, L. and Schultz, P. G., Chem. (2002) 1-10 (all entirely incorporated by reference herein).

The term "amino acid deletion" denotes the removal of at least one amino acid residue at a predetermined position in an amino acid sequence.

The term "ANG-2" as used herein refers to human angiopoietin-2 (ANG-2) (alternatively abbreviated with ANGPT2 or ANG2) (SEQ ID NO: 31) which is described e.g. in Maisonpierre, P. C., et al, Science 277 (1997) 55-60 and Cheung, A. H., et al., Genomics 48 (1998) 389-91. The angiopoietins-1 (SEQ ID NO: 32) and -2 were discovered as ligands for the Ties, a family of tyrosine kinases that is selectively expressed within the vascular endothelium (Yancopoulos, G. D., et al., Nature 407 (2000) 242-248). There are now four definitive members of the angiopoietin family. Angiopoietin-3 and -4 (ANG-3 and ANG-4) may represent widely diverged counterparts of the same gene locus in mouse and man (Kim, I., et al., FEBS Let, 443 (1999) 353-356; Kim, I., et al., J. Biol. Chem. 274 (1999) 26523-26528). ANG-1 and ANG-2 were originally identified in tissue culture experiments as agonist and antagonist, respectively (see for ANG-1: Davis, S., et al., Cell 87 (1996) 1161-1169; and for ANG-2: Maisonpierre, P. C., et al., Science 277 (1997) 55-60). All of the known angiopoietins bind primarily to Tie2 (SEQ ID NO: 33), and both ANG-1 and -2 bind to Tie2 with an affinity of 3 nM (Kd) (Maisonpierre, P. C., et al., Science 277 (1997) 55-60).

The term "antibody" herein is used in the broadest sense and encompasses various antibody structures, including but not limited to monoclonal antibodies, multispecific antibodies (e.g. bispecific antibodies, trispecific antibodies), and antibody fragments so long as they exhibit the desired antigen-, and/or protein A and/or FcRn-binding activity.

The term "asymmetric Fc-region" denotes a pair of Fc-region polypeptides that have different amino acid residues at corresponding positions according to the Kabat EU index numbering system.

The term "asymmetric Fc-region with respect to FcRn binding" denotes an Fc-region that consists of two polypeptide chains that have different amino acid residues at corresponding positions, whereby the positions are determined according to the Kabat EU index numbering system, whereby the different positions affect the binding of the Fc-region to the human neonatal Fc-receptor (FcRn). For the purpose herein the differences between the two polypeptide chains of the Fc-region in an "asymmetric Fc-region with respect to FcRn binding" do not include differences that have been introduced to facilitate the formation of heterodimeric Fc-regions, e.g. for the production of bispecific antibodies. These differences can also be asymmetric, i.e. the two chains have differences at non corresponding amino acid residues according to the Kabat EU index numbering system. These differences facilitate heterodimerization and reduce homodimerization. Examples of such differences are the so-called "knobs into holes" substitutions (see, e.g., U.S. Pat. No. 7,695,936 and US 2003/0078385). The following knobs and holes substitutions in the individual polypeptide chains of an Fc-region of an IgG antibody of subclass IgG1 have been found to increase heterodimer formation: 1) Y407T in one chain and T366Y in the other chain; 2) Y407A in one chain and T366W in the other chain; 3) F405A in one chain and T394W in the other chain; 4) F405W in one chain and T394S in the other chain; 5) Y407T in one chain and T366Y in the other chain; 6) T366Y and F405A in one chain and T394W and Y407T in the other chain; 7) T366W and F405W in one chain and T394S and Y407A in the other chain; 8) F405W and Y407A in one chain and T366W and T394S in the other chain; and 9) T366W in one chain and T366S, L368A, and Y407V in the other chain, whereby the last listed is especially suited. In addition, changes creating new disulfide bridges between the two Fc-region polypeptide chains facilitate heterodimer formation (see, e.g., US 2003/0078385). The following substitutions resulting in appropriately spaced apart cysteine residues for the formation of new intra-chain disulfide bonds in the individual polypeptide chains of an Fc-region of an IgG antibody of subclass IgG1 have been found to increase heterodimer formation: Y349C in one chain and S354C in the other; Y349C in one chain and E356C in the other; Y349C in one chain and E357C in the other; L351C in one chain and S354C in the other; T394C in one chain and E397C in the other; or D399C in one chain and K392C in the other. Further examples of heterodimerization facilitating amino acid changes are the so-called "charge pair substitutions" (see, e.g., WO 2009/089004). The following charge pair substitutions in the individual polypeptide chains of an Fc-region of an IgG antibody of subclass IgG1 have been found to increase heterodimer formation: 1) K409D or K409E in one chain and D399K or D399R in the other chain; 2) K392D or K392E in one chain and D399K or D399R in the other chain; 3) K439D or K439E in one chain and E356K or E356R in the other chain; 4) K370D or K370E in one chain and E357K or E357R in the other chain; 5) K409D and K360D in one chain plus D399K and E356K in the other chain; 6) K409D and K370D in one chain plus D399K and E357K in the other chain; 7) K409D and K392D in one chain plus D399K, E356K, and E357K in the other chain; 8) K409D and K392D in one chain and D399K in the other chain; 9) K409D and K392D in one chain and D399K and E356K in the other chain; 10) K409D and K392D in one chain and D399K and D357K in the other chain; 11) K409D and K370D in one chain and D399K and D357K in the other chain; 12) D399K in one chain and K409D and K360D in the other chain; and 13) K409D and K439D in one chain and D399K and E356K on the other.

The term "binding (to an antigen)" denotes the binding of an antibody to its antigen in an in vitro assay, in one embodiment in a binding assay in which the antibody is bound to a surface and binding of the antigen to the antibody is measured by Surface Plasmon Resonance (SPR). Binding means a binding affinity ($K_D$) of $10^{-8}$ M or less, in some embodiments of $10^{-13}$ to $10^{-8}$ M, in some embodiments of $10^{-13}$ to $10^{-9}$ M.

Binding can be investigated by a BIAcore assay (GE Healthcare Biosensor AB, Uppsala, Sweden). The affinity of the binding is defined by the terms $k_a$ (rate constant for the association of the antibody from the antibody/antigen complex), $k_d$ (dissociation constant), and $K_D(k_d/k_a)$.

The term "chimeric" antibody refers to an antibody in which a portion of the heavy and/or light chain is derived from a particular source or species, while the remainder of the heavy and/or light chain is derived from a different source or species.

The term "CH2-domain" denotes the part of an antibody heavy chain polypeptide that extends approximately from EU position 231 to EU position 340 (EU numbering system according to Kabat). In one embodiment a CH2 domain has the amino acid sequence of SEQ ID NO: 09: APELLGG PSVFLFPPKP KDTLMISRTP EVTCVWDVS HEDPE-VKFNW YVDGVEVHNA KTKPREEQ E STYRWSVLT VLHQDWLNGK EYKCKVSNKA LPAPIEKTIS KAK.

The term "CH3-domain" denotes the part of an antibody heavy chain polypeptide that extends approximately from EU position 341 to EU position 446. In one embodiment the CH3 domain has the amino acid sequence of SEQ ID NO: 10: GQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPG.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, β, ε, γ, and μ, respectively.

The term "comparable length" denotes that two polypeptides comprise the identical number of amino acid residues or can be different in length by one or more and up to 10 amino acid residues at most. In one embodiment the (Fc-region) polypeptides comprise the identical number of amino acid residues or differ by a number of from 1 to 10 amino acid residues. In one embodiment the (Fc-region) polypeptides comprise the identical number of amino acid residues or differ by a number of from 1 to 5 amino acid residues. In one embodiment the (Fc-region) polypeptides comprise the identical number of amino acid residues or differ by a number of from 1 to 3 amino acid residues.

"Effector functions" refer to those biological activities attributable to the Fc-region of an antibody, which vary with the antibody class. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B-cell activation.

An "effective amount" of an agent, e.g., a pharmaceutical formulation, refers to an amount effective, at dosages and for periods of time necessary, to achieve the desired therapeutic or prophylactic result.

The term "Fc-fusion polypeptide" denotes a fusion of a binding domain (e.g. an antigen binding domain such as a single chain antibody, or a polypeptide such as a ligand of a receptor) with an antibody Fc-region that exhibits the desired target-, protein A- and FcRn-binding activity.

The term "Fc-region of human origin" denotes the C-terminal region of an immunoglobulin heavy chain of human origin that contains at least a part of the hinge region, the CH2 domain and the CH3 domain. In one embodiment, a human IgG heavy chain Fc-region extends from Cys226, or from Pro230, to the carboxyl-terminus of the heavy chain. In one embodiment the Fc-region has the amino acid sequence of SEQ ID NO: 60. However, the C-terminal lysine (Lys447) of the Fc-region may or may not be present.

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, MD (1991) and is referred to as "numbering according to Kabat" herein. Specifically the Kabat numbering system (see pages 647-660) of Kabat, et al., Sequences of Proteins of Immunological Interest, 5th ed., Public Health Service, National Institutes of Health, Bethesda, MD (1991) is used for the light chain constant domain CL of kappa and lambda isotype and the Kabat EU index numbering system (see pages 661-723) is used for the constant heavy chain domains (CH1, Hinge, CH2 and CH3).

The term "FcRn" denotes the human neonatal Fc-receptor. FcRn functions to salvage IgG from the lysosomal degradation pathway, resulting in reduced clearance and increased half-life. The FcRn is a heterodimeric protein consisting of two polypeptides: a 50 kDa class I major histocompatibility complex-like protein (α-FcRn) and a 15 kDa β2-microglobulin (β2m). FcRn binds with high affinity to the CH2-CH3 portion of the Fc-region of IgG. The interaction between IgG and FcRn is strictly pH dependent and occurs in a 1:2 stoichiometry, with one IgG binding to two FcRn molecules via its two heavy chains (Huber, A. H., et al., J. Mol. Biol. 230 (1993) 1077-1083). FcRn binding occurs in the endosome at acidic pH (pH<6.5) and IgG is released at the neutral cell surface (pH of about 7.4). The pH-sensitive nature of the interaction facilitates the FcRn-mediated protection of IgGs pinocytosed into cells from intracellular degradation by binding to the receptor within the acidic environment of endosomes. FcRn then facilitates the recycling of IgG to the cell surface and subsequent release into the blood stream upon exposure of the FcRn-IgG complex to the neutral pH environment outside the cell.

The term "FcRn binding portion of an Fc-region" denotes the part of an antibody heavy chain polypeptide that extends approximately from EU position 243 to EU position 261 and approximately from EU position 275 to EU position 293 and approximately from EU position 302 to EU position 319 and approximately from EU position 336 to EU position 348 and approximately from EU position 367 to EU position 393 and EU position 408 and approximately from EU position 424 to EU position 440. In one embodiment one or more of the following amino acid residues according to the EU numbering of Kabat are altered F243, P244, P245 P, K246, P247, K248, D249, T250, L251, M252, I253, S254, R255, T256, P257, E258, V259, T260, C261, F275, N276, W277, Y278, V279, D280, V282, E283, V284, H285, N286, A287, K288, T289, K290, P291, R292, E293, V302, V303, S304, V305, L306, T307, V308, L309, H310, Q311, D312, W313, L314, N315, G316, K317, E318, Y319, I336, S337, K338, A339, K340, G341, Q342, P343, R344, E345, P346, Q347, V348, C367, V369, F372, Y373, P374, S375, D376, I377, A378, V379, E380, W381, E382, S383, N384, G385, Q386, P387, E388, N389, Y391, T393, S408, S424, C425, S426, V427, M428, H429, E430, A431, L432, H433, N434, H435, Y436, T437, Q438, K439, and S440 (EU numbering).

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "full length antibody" denotes an antibody having a structure substantially similar to a native antibody structure comprising four polypeptides or having heavy chains that contain an Fc-region as defined herein. A full length antibody may comprise further domains, such as e.g. a scFv or a scFab conjugated to one or more of the chains of the full length antibody. These conjugates are also encompassed by the term full length antibody.

The term "dimeric polypeptide" denotes a complex comprising at least two polypeptides that are associated covalently. The complex may comprise further polypeptides that are also associated covalently or non-covalently with the other polypeptides. In one embodiment the dimeric polypeptide comprises two or four polypeptides.

The terms "heterodimer" or "heterodimeric" denote a molecule that comprises two polypeptides (e.g. of comparable length), wherein the two polypeptides have an amino acid sequence that have at least one different amino acid residue in a corresponding position, whereby corresponding position is determined according to the Kabat EU index numbering system.

The terms "homodimer" and "homodimeric" denote a molecule that comprises two polypeptides of comparable length, wherein the two polypeptides have an amino acid sequence that is identical in corresponding positions, whereby corresponding positions are determined according to the Kabat EU index numbering system.

A dimeric polypeptide as reported herein can be homodimeric or heterodimeric which is determined with respect to mutations or properties in focus. For example, with respect to FcRn and/or protein A binding (i.e. the focused on properties) a dimeric polypeptide is homodimeric (i.e. both polypeptides of the dimeric polypeptide comprise these mutations) with respect to the mutations H310A, H433A and Y436A (these mutations are in focus with respect to FcRn and/or protein A binding property of the dimeric polypeptide) but at the same time heterodimeric with respect to the mutations Y349C, T366S, L368A and Y407V (these mutations are not in focus as these mutations are directed to the heterodimerization of the dimeric polypeptide and not to the FcRn/protein A binding properties) as well as the mutations S354C and T366W, respectively (the first set is comprised only in the first polypeptide whereas the second set is comprised only in the second polypeptide). Further for example, a dimeric polypeptide as reported herein can be heterodimeric with respect to the mutations I253A, H310A, H433A, H435A and Y436A (i.e. these mutations are directed all to the FcRn and/or protein A binding properties of the dimeric polypeptide), i.e. one polypeptide comprises the mutations I253A, H310A and H435A, whereas the other polypeptide comprises the mutations H310A, H433A and Y436A.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al., Sequences of Proteins of Immunological Interest, 5th ed., Bethesda MD (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

The term "derived from" denotes that an amino acid sequence is derived from a parent amino acid sequence by introducing alterations at at least one position. Thus a derived amino acid sequence differs from the corresponding parent amino acid sequence at at least one corresponding position (numbering according to Kabat EU index for antibody Fc-regions). In one embodiment an amino acid sequence derived from a parent amino acid sequence differs by one to fifteen amino acid residues at corresponding positions. In one embodiment an amino acid sequence derived from a parent amino acid sequence differs by one to ten amino acid residues at corresponding positions. In one embodiment an amino acid sequence derived from a parent amino acid sequence differs by one to six amino acid residues at corresponding positions. Likewise a derived amino acid sequence has a high amino acid sequence identity to its parent amino acid sequence. In one embodiment an amino acid sequence derived from a parent amino acid sequence has 80% or more amino acid sequence identity. In one embodiment an amino acid sequence derived from a parent amino acid sequence has 90% or more amino acid sequence identity. In one embodiment an amino acid sequence derived from a parent amino acid sequence has 95% or more amino acid sequence identity.

The term "human Fc-region polypeptide" denotes an amino acid sequence which is identical to a "native" or "wild-type" human Fc-region polypeptide. The term "variant (human) Fc-region polypeptide" denotes an amino acid sequence which derived from a "native" or "wild-type" human Fc-region polypeptide by virtue of at least one "amino acid alteration". A "human Fc-region" is consisting of two human Fc-region polypeptides. A "variant (human) Fc-region" is consisting of two Fc-region polypeptides, whereby both can be variant (human) Fc-region polypeptides or one is a human Fc-region polypeptide and the other is a variant (human) Fc-region polypeptide.

In one embodiment the human Fc-region polypeptide has the amino acid sequence of a human IgG1 Fc-region polypeptide of SEQ ID NO: 60, or of a human IgG2 Fc-region polypeptide of SEQ ID NO: 61, or of a human IgG4 Fc-region polypeptide of SEQ ID NO: 63 with the mutations as reported herein. In one embodiment the variant (human) Fc-region polypeptide is derived from an Fc-region polypeptide of SEQ ID NO: 60, or 61, or 63 and has at least one amino acid mutation compared to the Fc-region polypeptide of SEQ ID NO: 60, or 61, or 63. In one embodiment the variant (human) Fc-region polypeptide comprises/has from about one to about ten amino acid mutations, and in one embodiment from about one to about five amino acid mutations. In one embodiment the variant (human) Fc-region polypeptide has at least about 80% homology with a human Fc-region polypeptide of SEQ ID NO: 60, or 61, or 63. In one embodiment the variant (human) Fc-region polypeptide has least about 90% homology with a human Fc-region polypeptide of SEQ ID NO: 60, or 61, or 63. In one embodiment the variant (human) Fc-region polypeptide has at least about 95% homology with a human Fc-region polypeptide of SEQ ID NO: 60, or 61, or 63.

The variant (human) Fc-region polypeptide derived from a human Fc-region polypeptide of SEQ ID NO: 60, or 61, or 63 is defined by the amino acid alterations that are contained. Thus, for example, the term P329G denotes a variant (human) Fc-region polypeptide derived human Fc-region polypeptide with the mutation of proline to glycine at amino acid position 329 relative to the human Fc-region polypeptide of SEQ ID NO: 60, or 61, or 63.

A human IgG1 Fc-region polypeptide has the following amino acid sequence:

```
                                          (SEQ ID NO: 60)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.
```

A human IgG1 Fc-region derived Fc-region polypeptide with the mutations L234A, L235A has the following amino acid sequence:

```
                                          (SEQ ID NO: 64)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.
```

A human IgG1 Fc-region derived Fc-region polypeptide with Y349C, T366S, L368A and Y407V mutations has the following amino acid sequence:

```
                                          (SEQ ID NO: 65)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPGK.
```

A human IgG1 Fc-region derived Fc-region polypeptide with S354C, T366W mutations has the following amino acid sequence:

```
                                          (SEQ ID NO: 66)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGK.
```

A human IgG1 Fc-region derived Fc-region polypeptide with L234A, L235A mutations and Y349C, T366S, L368A, Y407V mutations has the following amino acid sequence:

```
                                          (SEQ ID NO: 67)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPGK.
```

A human IgG1 Fc-region derived Fc-region polypeptide with a L234A, L235A and S354C, T366W mutations has the following amino acid sequence:

```
                                          (SEQ ID NO: 68)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGK.
```

A human IgG1 Fc-region derived Fc-region polypeptide with a P329G mutation has the following amino acid sequence:

(SEQ ID NO: 69)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.

A human IgG1 Fc-region derived Fc-region polypeptide with L234A, L235A mutations and P329G mutation has the following amino acid sequence:

(SEQ ID NO: 70)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.

A human IgG1 Fc-region derived Fc-region polypeptide with a P239G mutation and Y349C, T366S, L368A, Y407V mutations has the following amino acid sequence:

(SEQ ID NO: 71)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPGK.

A human IgG1 Fc-region derived Fc-region polypeptide with a P329G mutation and S354C, T366W mutation has the following amino acid sequence:

(SEQ ID NO: 72)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGK.

A human IgG1 Fc-region derived Fc-region polypeptide with L234A, L235A, P329G and Y349C, T366S, L368A, Y407V mutations has the following amino acid sequence:

(SEQ ID NO: 73)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVCTLPPSRDELTKNQVSLSCAVK

-continued

GFYPSDIAVEWESNGQPENNYKTTPPVLDSDGSFFLVSKLTVDKSRWQQG

NVFSCSVMHEALHNHYTQKSLSLSPGK.

A human IgG1 Fc-region derived Fc-region polypeptide with L234A, L235A, P329G mutations and S354C, T366W mutations has the following amino acid sequence:

(SEQ ID NO: 74)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGK.

A human IgG4 Fc-region polypeptide has the following amino acid sequence:

(SEQ ID NO: 63)
ESKYGPPCPSCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK.

A human IgG4 Fc-region derived Fc-region polypeptide with S228P and L235E mutations has the following amino acid sequence:

(SEQ ID NO: 75)
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK.

A human IgG4 Fc-region derived Fc-region polypeptide with S228P, L235E mutations and P329G mutation has the following amino acid sequence:

(SEQ ID NO: 76)
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLGSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK.

A human IgG4 Fc-region derived Fc-region polypeptide with S354C, T366W mutations has the following amino acid sequence:

(SEQ ID NO: 77)
ESKYGPPCPSCPAPEFLGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLPSSIEKTISKAKGQPREPQVYTLPPCQEEMTKNQVSLWCL
VKGFYPSDIAVEWESNGQPENNYKTTPPVLDSDGSFFLYSRLTVDKSRWQ
EGNVFSCSVMHEALHNHYTQKSLSLSLGK.

A human IgG4 Fc-region derived Fc-region polypeptide with Y349C, T366S, L368A, Y407V mutations has the following amino acid sequence:

(SEQ ID NO: 78)
ESKYGPPCPSCPAPEFLGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLPSSIEKTISKAKGQPREPQVCTLPPSQEEMTKNQVSLSCA
VKGFYPSDIAVEWESNGQPENNYKTTPPVLDSDGSFFLVSRLTVDKSRWQ
EGNVFSCSVMHEALHNHYTQKSLSLSLGK.

A human IgG4 Fc-region derived Fc-region polypeptide with a S228P, L235E and S354C, T366W mutations has the following amino acid sequence:

(SEQ ID NO: 79)
ESKYGPPCPPCPAPEFEGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLPSSIEKTISKAKGQPREPQVYTLPPCQEEMTKNQVSLWCL
VKGFYPSDIAVEWESNGQPENNYKTTPPVLDSDGSFFLYSRLTVDKSRWQ
EGNVFSCSVMHEALHNHYTQKSLSLSLGK.

A human IgG4 Fc-region derived Fc-region polypeptide with a S228P, L235E and Y349C, T366S, L368A, Y407V mutations has the following amino acid sequence:

(SEQ ID NO: 80)
ESKYGPPCPPCPAPEFEGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLPSSIEKTISKAKGQPREPQVCTLPPSQEEMTKNQVSLSCA
VKGFYPSDIAVEWESNGQPENNYKTTPPVLDSDGSFFLVSRLTVDKSRWQ
EGNVFSCSVMHEALHNHYTQKSLSLSLGK.

A human IgG4 Fc-region derived Fc-region polypeptide with a P329G mutation has the following amino acid sequence:

(SEQ ID NO: 81)
ESKYGPPCPSCPAPEFLGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLGSSIEKTISKAKGQPREPQVYTLPPSQEEMTKNQVSLTCL

-continued

VKGFYPSDIAVEWESNGQPENNYKTTPPVLDSDGSFFLYSRLTVDKSRWQ
EGNVFSCSVMHEALHNHYTQKSLSLSLGK.

A human IgG4 Fc-region derived Fc-region polypeptide with a P239G and Y349C, T366S, L368A, Y407V mutations has the following amino acid sequence:

(SEQ ID NO: 82)
ESKYGPPCPSCPAPEFLGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLGSSIEKTISKAKGQPREPQVCTLPPSQEEMTKNQVSLSCA
VKGFYPSDIAVEWESNGQPENNYKTTPPVLDSDGSFFLVSRLTVDKSRWQ
EGNVFSCSVMHEALHNHYTQKSLSLSLGK.

A human IgG4 Fc-region derived Fc-region polypeptide with a P329G and S354C, T366W mutations has the following amino acid sequence:

(SEQ ID NO: 83)
ESKYGPPCPSCPAPEFLGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLGSSIEKTISKAKGQPREPQVYTLPPCQEEMTKNQVSLWCL
VKGFYPSDIAVEWESNGQPENNYKTTPPVLDSDGSFFLYSRLTVDKSRWQ
EGNVFSCSVMHEALHNHYTQKSLSLSLGK.

A human IgG4 Fc-region derived Fc-region polypeptide with a S228P, L235E, P329G and Y349C, T366S, L368A, Y407V mutations has the following amino acid sequence:

(SEQ ID NO: 84)
ESKYGPPCPPCPAPEFEGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLGSSIEKTISKAKGQPREPQVCTLPPSQEEMTKNQVSLSCA
VKGFYPSDIAVEWESNGQPENNYKTTPPVLDSDGSFFLVSRLTVDKSRWQ
EGNVFSCSVMHEALHNHYTQKSLSLSLGK.

A human IgG4 Fc-region derived Fc-region polypeptide with a S228P, L235E, P329G and S354C, T366W mutations has the following amino acid sequence:

(SEQ ID NO: 85)
ESKYGPPCPPCPAPEFEGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLGSSIEKTISKAKGQPREPQVYTLPPCQEEMTKNQVSLWCL
VKGFYPSDIAVEWESNGQPENNYKTTPPVLDSDGSFFLYSRLTVDKSRWQ
EGNVFSCSVMHEALHNHYTQKSLSLSLGK.

An alignment of the different human Fc-regions is shown below (Kabat EU index numbering system):

```
                                                       2
                                                       1
                                                       6(IgG1, 2, 4)
IGG1 .......... .......... .......... .......... .....EPKSC
IGG2 .......... .......... .......... .......... .....ERKCC
IGG3 KTPLGDTTHT CPRCPEPKSC DTPPPCPRCP EPKSCDTPPP CPRCPEPKSC
IGG4 .......... .......... .......... .......... .....ESKYG
     -- HINGE ------------------------------------------

               2                     2
               3                     5
               0                     0
IGG1 DKTHTCPPCP APELLGGPSV FLFPPKPKDT LMISRTPEVT CVVVDVSHED
IGG2 ...VECPPCP APP.VAGPSV FLFPPKPKDT LMISRTPEVT CVVVDVSHED
IGG3 DTPPPCPRCP APELLGGPSV FLFPPKPKDT LMISRTPEVT CVVVDVSHED
IGG4 ...PPCPSCP APEFLGGPSV FLFPPKPKDT LMISRTPEVT CVVVDVSQED
     -- HINGE -|-- CH2 ---------------------------------

                                    3
                                    0
                                    0
IGG1 PEVKFNWYVD GVEVHNAKTK PREEQYNSTY RVVSVLTVLH QDWLNGKEYK
IGG2 PEVQFNWYVD GVEVHNAKTK PREEQFNSTF RVVSVLTVVH QDWLNGKEYK
IGG3 PEVQFKWYVD GVEVHNAKTK PREEQYNSTF RVVSVLTVLH QDWLNGKEYK
IGG4 PEVQFNWYVD GVEVHNAKTK PREEQFNSTY RVVSVLTVLH QDWLNGKEYK
     -- CH2 --------------------------------------------

                                    3
                                    5
                                    0
IGG1 CKVSNKALPA PIEKTISKAK GQPREPQVYT LPPSRDELTK NQVSLTCLVK
IGG2 CKVSNKGLPA PIEKTISKTK GQPREPQVYT LPPSREEMTK NQVSLTCLVK
IGG3 CKVSNKALPA PIEKTISKTK GQPREPQVYT LPPSREEMTK NQVSLTCLVK
IGG4 CKVSNKGLPS SIEKTISKAK GQPREPQVYT LPPSQEEMTK NQVSLTCLVK
     -- CH2 ------- CH2 --|-- CH3 ----------------------

                                    4
                                    0
                                    0
IGG1 GFYPSDIAVE WESNGQPENN YKTTPPVLDS DGSFFLYSKL TVDKSRWQQG
IGG2 GFYPSDISVE WESNGQPENN YKTTPPMLDS DGSFFLYSKL TVDKSRWQQG
IGG3 GFYPSDIAVE WESSGQPENN YNTTPPMLDS DGSFFLYSKL TVDKSRWQQG
IGG4 GFYPSDIAVE WESNGQPENN YKTTPPVLDS DGSFFLYSRL TVDKSRWQEG
     -- CH3 --------------------------------------------

                                  4
                                  4
                                  7
IGG1 NVFSCSVMHE ALHNHYTQKS LSLSPGK
IGG2 NVFSCSVMHE ALHNHYTQKS LSLSPGK
IGG3 NIFSCSVMHE ALHNRFTQKS LSLSPGK
IGG4 NVFSCSVMHE ALHNHYTQKS LSLSLGK
     -- CH3 ----------------------|
```

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., the CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain which are hypervariable in sequence ("complementarity determining regions" or "CDRs") and form structurally defined loops ("hypervariable loops"), and/or contain the antigen-contacting residues ("antigen contacts"). Generally, antibodies comprise six HVRs; three in the VH (H1, H2, H3), and three in the VL (L1, L2, L3). HVRs as denoted herein include (a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);

(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, MD (1991), NIH Publication 91-3242.);

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56

(L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to the Kabat EU index numbering system (Kabat et al., supra).

The term "IGF-1R" as used herein, refers to any native IGF-1R from any vertebrate source, including mammals such as primates (e.g. humans) and rodents (e.g., mice and rats), unless otherwise indicated. The term encompasses "full-length", unprocessed IGF-1R as well as any form of IGF-1R that results from processing in the cell. The term also encompasses naturally occurring variants of IGF-1R, e.g., splice variants or allelic variants. The amino acid sequence of human IGF-1R is shown in SEQ ID NO: 11.

An "individual" or "subject" is a mammal. Mammals include, but are not limited to, domesticated animals (e.g. cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., size exclusion chromatography, ion exchange or reverse phase HPLC). For review of methods for assessment of antibody purity, see, e.g., Flatman, S. et al., J. Chrom. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-IGF-1R antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (c) and lambda (2), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$ where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject., A pharmaceutically acceptable carrier includes, but is not limited to, a buffer, excipient, stabilizer, or preservative.

The term "peptidic linker" as used herein denotes a peptide with amino acid sequences, which is in one embodiment of synthetic origin. The peptidic linker is in one embodiment a peptide with an amino acid sequence with a length of at least 30 amino acids, in one embodiment with a length of 32 to 50 amino acids. In one embodiment the peptidic linker is a peptide with an amino acid sequence with a length of 32 to 40 amino acids. In one embodiment the peptidic linker is (G×S)n with G=glycine, S=serine, (x=3, n=8, 9 or 10) or (x=4 and n=6, 7 or 8), in one embodiment with x=4, n=6 or 7, in one embodiment with x=4, n=7. In one embodiment the peptidic linker is $(G_4S)_6G_2$.

The term "recombinant antibody", as used herein, denotes all antibodies (chimeric, humanized and human) that are prepared, expressed, created or isolated by recombinant means. This includes antibodies isolated from a host cell such as a NS0 or CHO cell, or from an animal (e.g. a mouse) that is transgenic for human immunoglobulin genes, or antibodies expressed using a recombinant expression vector transfected into a host cell. Such recombinant antibodies have variable and constant regions in a rearranged form. The recombinant antibodies can be subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies or Fc-region fusion polypeptides as reported herein are used to delay development of a disease or to slow the progression of a disease.

The term "valent" as used within the current application denotes the presence of a specified number of binding sites in a (antibody) molecule. As such, the terms "bivalent", "tetravalent", and "hexavalent" denote the presence of two binding site, four binding sites, and six binding sites, respectively, in a (antibody) molecule. The bispecific antibodies as reported herein are in one preferred embodiment "bivalent".

The term "variable region" or "variable domain" refer to the domain of an antibody heavy or light chain that is involved in binding of the antibody to its antigen. The variable domains of the heavy chain and light chain (VH and VL, respectively) of an antibody generally have similar structures, with each domain comprising four framework regions (FRs) and three hypervariable regions (HVRs) (see, e.g., Kindt, T. J. et al. Kuby Immunology, 6th ed., W.H. Freeman and Co., N.Y. (2007), page 91). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (see, e.g., Portolano, S. et al., J. Immunol. 150 (1993) 880-887; Clackson, T. et al., Nature 352 (1991) 624-628).

The term "ocular vascular disease" includes, but is not limited to intraocular neovascular syndromes such as diabetic retinopathy, diabetic macular edema, retinopathy of prematurity, neovascular glaucoma, retinal vein occlusions, central retinal vein occlusions, macular degeneration, age-related macular degeneration, retinitis pigmentosa, retinal angiomatous proliferation, macular telangectasia, ischemic retinopathy, iris neovascularization, intraocular neovascularization, corneal neovascularization, retinal neovascularization, choroidal neovascularization, and retinal degeneration (see e.g. Garner, A., Vascular diseases, In: Pathobiology of ocular disease, A dynamic approach, Garner, A., and Klintworth, G. K., (eds.), 2nd edition, Marcel Dekker, New York (1994), pp. 1625-1710).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The term "VEGF" as used herein refers to human vascular endothelial growth factor (VEGF/VEGF-A,) the 165-amino acid human vascular endothelial cell growth factor (amino acid 27-191 of precursor sequence of human VEGF165: SEQ ID NO: 30; amino acids 1-26 represent the signal peptide), and related 121, 189, and 206 vascular endothelial cell growth factor isoforms, as described by Leung, D. W., et al., Science 246 (1989) 1306-1309; Houck et al., Mol. Endocrin. 5 (1991) 1806-1814; Keck, P. J., et al., Science 246 (1989) 1309-1312 and Connolly, D. T., et al., J. Biol. Chem. 264 (1989) 20017-20024; together with the naturally occurring allelic and processed forms of those growth factors. VEGF is involved in the regulation of normal and abnormal angiogenesis and neovascularization associated with tumors and intraocular disorders (Ferrara, N., et al., Endocrin. Rev. 18 (1997) 4-25; Berkman, R. A., et al., J. Clin. Invest. 91 (1993) 153-159; Brown, L. F., et al., Human Pathol. 26 (1995)86-91; Brown, L. F., et al., Cancer Res. 53 (1993) 4727-4735; Mattern, J., et al., Brit. J. Cancer. 73 (1996) 931-934; and Dvorak, H. F., et al., Am. J. Pathol. 146 (1995) 1029-1039). VEGF is a homodimeric glycoprotein that has been isolated from several sources and includes several isoforms. VEGF shows highly specific mitogenic activity for endothelial cells.

The term "with (the) mutation IHH-AAA" as used herein refers to the combination of the mutations I253A (Ile253Ala), H310A (His310Ala), and H435A (His435Ala) and the term "with (the) mutation HHY-AAA" as used herein refers to the combination of the mutations H310A (His310Ala), H433A (His433Ala), and Y436A (Tyr436Ala)

and the term "with (the) mutation YTE" as used herein refers to the combination of mutations M252Y (Met252Tyr), S254T (Ser254Thr), and T256E (Thr256Glu) in the constant heavy chain region of IgG1 or IgG4 subclass, wherein the numbering is according to the Kabat EU index numbering system.

The term "with (the) mutations P329G LALA" as used herein refers to the combination of the mutations L234A (Leu235Ala), L235A (Leu234Ala) and P329G (Pro329Gly) in the constant heavy chain region of IgG1 subclass, wherein the numbering is according to the Kabat EU index numbering system. The term "with (the) mutation SPLE" as used herein refers to the combination of the mutations S228P (Ser228Pro) and L235E (Leu235Glu) in the constant heavy chain region of IgG4 subclass, wherein the numbering is according to the Kabat EU index numbering system. The term "with (the) mutation SPLE and P329G" as used herein refers to the combination of the mutations S228P (Ser228Pro), L235E (Leu235Glu) and P329G (Pro329Gly) in the constant heavy chain region of IgG4 subclass, wherein the numbering is according to the Kabat EU index numbering system.

II. Compositions and Methods

In one aspect, the invention is based, in part, on the finding that specific mutations or combination of mutations which influence the binding of an immunoglobulin Fc-region to the neonatal Fc-receptor (FcRn), i.e. which reduce or even eliminate the binding of the Fc-region to FcRn, do not simultaneously eliminate the binding of the Fc-region to Staphylococcal protein A. This has a profound effect on the purification process that can be employed as e.g. no specific and species limited affinity chromatography materials, such as e.g. KappaSelect which only binds to antibodies comprising a kappa light chain, are required. Thus, with the combination of mutations as reported herein it is possible at the same time to reduce or even eliminate the binding to FcRn while maintaining the binding to Staphylococcal protein A.

In one aspect, the invention is based, in part, on the finding that by using different mutations in the Fc-regions of each heavy chain of a heterodimeric molecule, such as e.g. a bispecific antibody, can be provided that on the one hand has a reduced or even eliminated binding to FcRn but on the other hand maintains the ability to bind to Staphylococcal protein A. This binding to Staphylococcal protein A can be used to separate the heterodimeric molecule from homodimeric by-products. For example by combining the mutations I253A, H310A and H435A in one heavy chain Fc-region with the mutations H310A, H433A and Y436A in the other heavy chain Fc-region using the knobs-into-hole approach a heterodimeric Fc-region can be obtained that on the one hand does not bind to FcRn (both sets of mutations are silent with respect to the human FcRn) but maintains binding to Staphylococcal protein A (the heavy chain Fc-region with the mutations I253A, H310A and H435A does not bind to FcRn and does not bind to Staphylococcal protein A, whereas the heavy chain Fc-region with the mutations H310A, H433A and Y436A does not bind to FcRn but does still bind to Staphylococcal protein A). Thus, standard protein A affinity chromatography can be used to remove the homodimeric hole-hole by-product as this no longer binds to Staphylococcal protein A). Thus, by combining the knobs-into-holes approach with the mutations I253A, H310A and H435A in the hole chain and the mutations H310A, H433A and Y436A in the knobs chain the purification/separation of the heterodimeric knobs-into-holes product from the homodimeric hole-hole by-product can be facilitated.

In one aspect, the invention is based, in part, on the finding that antibodies for intravitreal application are beneficial that do not have FcRn-binding as these antibodies can cross the blood-retinal-barrier, do not have substantially prolonged or shortened half-lives in the eye and are cleared fast from the blood circulation resulting in no or very limited systemic side effects outside the eye. Antibodies of the invention are useful, e.g., for the diagnosis or treatment of ocular vascular diseases.

The invention is based, at least in part, on the finding that by using different mutations in each of the Fc-region polypeptides of an Fc-region a heterodimeric molecule, such as e.g. a bispecific antibody, can be provided that has tailor-made FcRn-binding and therewith antibodies can be provided that have a tailor-made systemic half-life.

The combination of mutations I253A, H310A, H435A, or L251D, L314D, L432D, or L251S, L314S, L432S result in a loss of the binding to protein A, whereas the combination of mutations I253A, H310A, H435A, or H310A, H433A, Y436A, or L251D, L314D, L432D result in a loss of the binding to the human neonatal Fc receptor.

The following table presents an exemplary overview of the amino acid residues in an Fc-region that are involved in interactions or have been changed to modify interactions.

| | interaction with | | KiH | | protein A | effect of mutations on |
|---|---|---|---|---|---|---|
| residue | protein A | FcRn | knob | hole | binding | FcRn binding |
| Pro238 | | | | | | P238A increase |
| Thr250 | | | | | | T250Q/M428L increase |
| Leu251 | main-chain contact | | | | | |
| Met252 | hydrophobic packing | | | | | M252W increase; M252Y increase; M252Y/T256Q increase; M252F/T256D increase; M252Y/S254T/T256E increase |
| Ile253 | main-chain contact; hydrogen bonding; significant binding reduction if mutated to Ala | interaction | | | | I253A reduction |

-continued

| | interaction with | | KiH | | protein A | effect of mutations on |
|---|---|---|---|---|---|---|
| residue | protein A | FcRn | knob | hole | binding | FcRn binding |
| Ser254 | polar interaction; hydrogen bonding | | | | | S254A reduction; M252Y/S254T/T256E increase |
| Arg255 | salt-bridge | | | | | R255A reduction |
| Thr256 | | | | | | T256A increase; T256Q increase; T256P increase; M252Y/T256Q reduction; M252F/T256D reduction; M252Y/S254T/T256E increase |
| Pro257 | | | | | | P257I/Q311I increase; P257I/N434H increase |
| Glu272 | | | | | | E272A increase |
| Asp280 | | | | | | D280K increase |
| His285 | | | | | | reduction |
| Lys288 | | | | | | K288A reduction; K288A/N434A increase |
| Val305 | | | | | | V305A increase |
| Thr307 | | | | | | T307A increase; T307A/E380A/N434A increase; T307Q/N434A increase; T307Q/N434S increase; T307Q/E380A/N434A increase |
| Val308 | | | | | | V308P/N434A increase |
| Leu309 | | | | | | L309A reduction |
| His310 | | interaction | | | | H310A reduction; H310Q/H433N reduction |
| Gln311 | polar or charged interaction | | | | | Q311A increase; P257I/Q311I increase |
| Asp312 | | | | | | D312A increase |
| Leu314 | hydrophobic interaction | | | | | |
| Lys317 | | | | | | K317A increase |
| Ala339 | | | | | | A339T increase |
| Tyr349 | | | | Y349C | | |
| Ser354 | | | S354C | | | |
| Thr366 | | | T366W | T366S | | |
| Leu368 | | | | L368A | | |
| Asp376 | | | | | | D376A increase; D376V/N434H increase |
| Ala378 | | | | | | A378Q increase |
| Glu380 | salt-bridge | | | | | E380A increase E380A/N434A increase; T307A/E380A/N434A increase; T307Q/E380A/N434A increase |
| Glu382 | | | | | | E3 82A increase |
| Gly385 | | | | | | G385H increase; G385A/Q386P/N389S increase |
| Gln386 | | | | | | G385A/Q386P/N389S increase |
| Asn389 | | | | | | G385A/Q386P/N389S increase |
| Tyr407 | | | | Y407V | | |
| Ser415 | | | | | | S415A reduction |
| Ser424 | | | | | | S424A increase |
| Met428 | | | | | | M428L increase; T250Q/M428L increase |
| Leu432 | polar or charged interaction | | | | | |

-continued

| | interaction with | | KiH | | protein A | effect of mutations on |
|---|---|---|---|---|---|---|
| residue | protein A | FcRn | knob | hole | binding | FcRn binding |
| His433 | polar or charged interaction; salt-bridge | interaction | | | | H433A reduction; H310Q/H433N reduction; H433K/N434F/Y436Hin crease; H433R/N434Y/Y436Hin crease; H433K/N434F increase |
| Asn434 | hydrogen bonding; significant binding reduction if replaced by Ala | interaction | | | | N434W/Y/F/A/H increase; K288A/N434A increase; E380A/N434A increase; T307A/E380A/N434A increase; N434F/Y436H increase; H433K/N434F/Y436Hin crease; H433R/N434Y/Y436Hin crease; H433K/N434F increase; P257I/N434H increase; D376V/N434H increase; T307Q/N434A increase; T307Q/N434S increase; V308P/N434A increase; T307Q/E380A/N434A increase |
| His435 | hydrophobic packing; significant binding reduction if mutated to Ala | interaction | | | H435R/Y4 36F eliminates binding to protein A | H435A reduction; H435R reduction |
| Tyr436 | hydrophobic packing; significant binding reduction if replaced by Ala | interaction | | | H435R/Y4 36F eliminates binding to protein A | Y436A reduction; N434F/Y436H increase; H433K/N434F/Y436Hin crease; H433R/N434Y/Y436H increase |

The modifications as reported herein alter the binding specificity for one or more Fc receptors such as the human FcRn. At the same time some of the mutations which alter the binding to human FcRn do not alter the binding to Staphylococcal protein A.

In one embodiment the combination of mutations as reported herein does alter or does substantially alter the serum half-life of the dimeric polypeptide as compared with a corresponding dimeric polypeptide that lacks this combination of mutations. In one embodiment the combination of mutations further does not alter or does not substantially alter the binding of the dimeric polypeptide to protein A as compared with a corresponding dimeric polypeptide that lacks this combination of mutations.

A. The Neonatal Fe-Receptor (FcRn)

The neonatal Fc-receptor (FcRn) is important for the metabolic fate of antibodies of the IgG class in vivo. The FcRn functions to salvage wild-type IgG from the lysosomal degradation pathway, resulting in reduced clearance and increased half-life. It is a heterodimeric protein consisting of two polypeptides: a 50 kDa class I major histocompatibility complex-like protein (α-FcRn) and a 15 kDa β2-microglobulin (β2m). FcRn binds with high affinity to the CH2-CH3 portion of the Fc-region of an antibody of the class IgG. The interaction between an antibody of the IgG class and the FcRn is pH dependent and occurs in a 1:2 stoichiometry, i.e. one IgG antibody molecule can interact with two FcRn molecules via its two heavy chain Fc-region polypeptides (see e.g. Huber, A. H., et al., J. Mol. Biol. 230 (1993) 1077-1083).

Thus, an IgGs in vitro FcRn binding properties/characteristics are indicative of its in vivo pharmacokinetic properties in the blood circulation.

In the interaction between the FcRn and the Fc-region of an antibody of the IgG class different amino acid residues of the heavy chain CH2- and CH3-domain are participating. The amino acid residues interacting with the FcRn are located approximately between EU position 243 and EU position 261, approximately between EU position 275 and EU position 293, approximately between EU position 302 and EU position 319, approximately between EU position 336 and EU position 348, approximately between EU position 367 and EU position 393, at EU position 408, and approximately between EU position 424 and EU position 440. More specifically the following amino acid residues according to the EU numbering of Kabat are involved in the interaction between the Fc-region and the FcRn: F243, P244, P245 P, K246, P247, K248, D249, T250, L251, M252, I253, S254, R255, T256, P257, E258, V259, T260, C261, F275, N276, W277, Y278, V279, D280, V282, E283, V284, H285, N286, A287, K288, T289, K290, P291, R292, E293, V302, V303, S304, V305, L306, T307, V308, L309, H310, Q311, D312, W313, L314, N315, G316, K317, E318, Y319, I336, S337, K338, A339, K340, G341, Q342, P343, R344, E345, P346, Q347, V348, C367, V369, F372, Y373, P374, S375, D376, I377, A378, V379, E380, W381, E382, S383, N384, G385, Q386, P387, E388, N389, Y391, T393, S408, S424, C425, S426, V427, M428, H429, E430, A431, L432, H433, N434, H435, Y436, T437, Q438, K439, and S440.

Site-directed mutagenesis studies have proven that the critical binding sites in the Fc-region of IgGs for FcRn are Histidine 310, Histidine 435, and Isoleucine 253 and to a lesser extent Histidine 433 and Tyrosine 436 (see e.g. Kim, J. K., et al., Eur. J. Immunol. 29 (1999) 2819-2825; Raghavan, M., et al., Biochem. 34 (1995) 14649-14657; Medesan, C., et al., J Immunol. 158 (1997) 2211-2217).

Methods to increase IgG binding to FcRn have been performed by mutating IgG at various amino acid residues: Threonine 250, Methionine 252, Serine 254, Threonine 256, Threonine 307, Glutamic acid 380, Methionine 428, Histidine 433, and Asparagine 434 (see Kuo, T. T., et al., J. Clin. Immunol. 30 (2010) 777-789).

In some cases antibodies with reduced half-life in the blood circulation are desired. For example, drugs for intravitreal application should have a long half-live in the eye and a short half-life in the blood circulation of the patient. Such antibodies also have the advantage of increased exposure to a disease site, e.g. in the eye.

Different mutations that influence the FcRn binding and therewith the half-live in the blood circulation are known. Fc-region residues critical to the mouse Fc-region-mouse FcRn interaction have been identified by site-directed mutagenesis (see e.g. Dall'Acqua, W. F., et al. J. Immunol 169 (2002) 5171-5180). Residues I253, H310, H433, N434, and H435 (EU numbering according to Kabat) are involved in the interaction (Medesan, C., et al., Eur. J. Immunol. 26 (1996) 2533-2536; Firan, M., et al., Int. Immunol. 13 (2001) 993-1002; Kim, J. K., et al., Eur. J. Immunol. 24 (1994) 542). Residues I253, H310, and H435 were found to be critical for the interaction of human Fc with murine FcRn (Kim, J. K., et al., Eur. J. Immunol. 29 (1999) 2819-2855). Residues M252Y, S254T, T256E have been described by Dall'Acqua et al. to improve FcRn binding by protein-protein interaction studies (Dall'Acqua, W. F., et al. J. Biol. Chem. 281 (2006) 23514-23524). Studies of the human Fc-human FcRn complex have shown that residues I253, S254, H435, and Y436 are crucial for the interaction (Firan, M., et al., Int. Immunol. 13 (2001) 993-1002; Shields, R. L., et al., J. Biol. Chem. 276 (2001) 6591-6604). In Yeung, Y. A., et al. (J. Immunol. 182 (2009) 7667-7671) various mutants of residues 248 to 259 and 301 to 317 and 376 to 382 and 424 to 437 have been reported and examined. Exemplary mutations and their effect on FcRn binding are listed in the following Table.

TABLE

| mutation | effect on FcRn binding | half-live in the circulation | reference |
|---|---|---|---|
| H285<br>H310Q/H433N<br>(murine IgG1) | reduced<br>(murine) | reduced<br>(in mouse) | Kim, J. K., Scand. J. Immunol. 40 (1994) 457-465 |
| I253A<br>H310A<br>H435A<br>H436A<br>(murine IgG1) | reduced<br>(murine) | reduced<br>(in mouse) | Ghetie, V. and Ward, E. S., Immunol. Today 18 (1997) 592-598 |
| T252L/T254S/T256F<br>T252A/T254S/T256A<br>(murine IgG1) | increased<br>(murine) | increased<br>(in mouse) | Ghetie, V. and Ward, E. S., Immunol. Today 18 (1997) 592-598 |
| I253A<br>H310A<br>H435A<br>H436A<br>H433A/N434Q<br>(murine IgG1) | reduced<br>(murine) | reduced<br>(in mouse) | Medesan, C., et al., J. Immunol. 158 (1997) 2211-2217 |
| I253A<br>H310A<br>H435A<br>H435R<br>(human IgG1) | reduced<br>H310A: <0.1 rel. binding to muFcRn<br>(murine) | reduced<br>(in mouse) | Kim, J. K., Eur. J. Immunol. 29 (1999) 2819-2825 |
| H433A<br>(human IgG1) | 1.1 rel. binding to muFcRn, 0.4 rel. binding hu FcRn<br>(murine) | | Kim, J. K., Eur. J. Immunol. 29 (1999) 2819-2825 |
| I253A<br>S254A<br>H435A<br>Y436A<br>(human IgG1) | reduced<br><0.1 relative binding to huFcRn | reduced | Shields, R. L., et al., J. Biol. Chem. 276 (2001) 6591-6604 |
| R255A<br>K288A<br>L309A<br>S415A<br>H433A<br>(human IgG1) | reduced<br>(human) | reduced | Shields, R. L., et al., J. Biol. Chem. 276 (2001) 6591-6604 |
| P238A<br>T256A<br>E272A<br>V305A | increased<br>(human) | increased | Shields, R. L., et al., J. Biol. Chem. 276 (2001) 6591-6604 |

TABLE-continued

| mutation | effect on FcRn binding | half-live in the circulation | reference |
|---|---|---|---|
| T307A<br>Q311A<br>D312A<br>K317A<br>D376A<br>A378Q<br>E380A<br>E382A<br>S424A<br>N434A<br>K288A/N434A<br>E380A/N434A<br>T307A/E380A/N434A<br>(human IgG1) | | | |
| H435A<br>(humanized IgG1) | reduced<br><0.1 rel. binding to huFcRn | reduced | Firan, M., et al., Int. Immunol. 13 (2001) 993-1002 |
| I253A (no binding)<br>M252W<br>M252Y<br>M252Y/T256Q<br>M252F/T256D<br>N434F/Y436H<br>M252Y/S254T/T256E<br>G385A/Q386P/N389S<br>H433K/N434F/Y436H<br>H433R/N434Y/Y436H<br>G385R/Q386T/P387R/N389P<br>M252Y/S254T/T256E/H433K/N434F/Y436H<br>M252Y/S254T/T256E/G385R/Q386T/P387R/N389P<br>(human IgG1) | increased (murine and human) | reduced (in mouse) | Dall'Acqua, J. Immunol. 169 (2002) 5171-5180 |
| M428L<br>T250Q/M428L<br>(human IgG2) | increased (human) | increased (in monkey) | Hinton, P. R., et al., J. Biol. Chem. 279 (2004) 6213-6216 |
| M252Y/S254T/T256E +<br>H433K/N434F<br>(human IgG) | increased (human) | increased (in mouse) | Vaccaro, C., et al., Nat. Biotechnol. 23 (2005) 1283-1288 |
| T307A/E380A/N434A<br>(chimeric IgG1) | increased | increased in transgenic mouse | Pop, L. M., et al., Int. Immunopharmacol. 5 (2005) 1279-1290 |
| T250Q<br>E380A<br>M428L<br>N434A<br>K288A/N434A<br>E380A/N434A<br>T307A/E380A/N434A<br>(human IgG1) | increased (human) | increased in transgenic mouse | Petkova, S. B., et al., Int. Immunol 18 (2006) 1759-1769 |
| I253A<br>(human IgG1) | reduced (human) | reduced in transgenic mouse | Petkova, S. B., et al., Int. Immunol 18 (2006) 1759-1769 |
| S239D/A330L/I332E<br>M252Y/S254T/T256E<br>(humanized) | increased (human and Cynomolgus) | increased in Cynomolgus | Dall'Acqua, W. F., et al., J. Biol. Chem. 281 (2006) 23514-23524 |
| T250Q<br>M428L<br>T250Q/M428L<br>(human IgG1) | increased (human) | increased in Rhesus apes | Hinton, P. R., et al., J. Immunol. 176 (2006) 346-356 |
| T250Q/M428L<br>P257I/Q311I<br>(humanized IgG1) | increased (mouse and Cynomolgus) | no change in Cynomolgus increased in mouse | Datta-Mannan, A., et al., J. Biol. Chem. 282 (2007) 1709-1717 |
| P257I/Q311I<br>P257I/N434H<br>D376V/N434H | increased at pH 6 (human, | reduced in mice P257I/N434H reduced in | Datta-Mannan, A., et al., Drug |

TABLE-continued

| mutation | effect on FcRn binding | half-live in the circulation | reference |
|---|---|---|---|
| (humanized IgG1) | Cynomolgus, mouse) | Cynomolgus | Metab. Dispos. 35 (2007) 86-94 |
| abrogate FcRn binding:<br>I253<br>H310<br>H433<br>H435<br>reduce FcRn binding:<br>Y436<br>increased FcRn binding:<br>T250<br>N252<br>S254<br>T256<br>T307<br>M428<br>N434 | increased and reduced | reducing the binding ability of IgG for FcRn reduces its serum persistence; a higher-affinity FcRn-IgG interaction prolongs the half-lives of IgG and Fc-coupled drugs in the serum | Ropeenian, D. C. and Akilesh, S., *Nat. Rev. Immunol.* 7 (2007) 715-725 |
| N434A<br>T307Q/N434A<br>T307Q/N434S<br>V308P/N434A<br>T307Q/E380A/N434A<br>(human IgG1) | increased (Cynomolgus monkey) | increased in Cynomolgus monkey | Yeung, Y. A., et al., Cancer Res. 70 (2010) 3269-3277 |
| 256P<br>280K<br>339T<br>385H<br>428L<br>434W/Y/F/A/H<br>(human IgG) | increased at neutral pH | | WO 2011/122011 |

It has been found that one mutation one-sided in one Fc-region polypeptide is sufficient to weaken the binding significantly. The more mutations are introduced into the Fc-region the weaker the binding to the FcRn becomes. But one-sided asymmetric mutations are not sufficient to completely inhibit FcRn binding. Mutations on both sides are necessary to completely inhibit FcRn binding.

The results of a symmetric engineering of an IgG1 Fc-region to influence FcRn binding is shown in the following table (alignment of mutations and retention time on an FcRn-affinity chromatography column).

TABLE

| effector function influencing mutations | FcRn-binding influencing mutation 1 | FcRn-binding influencing mutation 2 | FcRn-binding influencing mutation 3 | FcRn-affinity column retention time [min] |
|---|---|---|---|---|
| L234A/L235A/P329G | — | — | — | 45.3 |
| L234A/L235A/P329G | I253A | H310A | H435A | 2.3 |
| L234A/L235A/P329G | I253A | — | — | 2.7 |
| L234A/L235A/P329G | — | H310A | — | 2.4 |
| L234A/L235A/P329G | — | — | H435A | 2.7 |
| L234A/L235A/P329G | I253A | H310A | — | 2.3 |
| L234A/L235A/P329G | I253A | — | H435A | 2.3 |
| L234A/L235A/P329G | — | H310A | H435A | 2.4 |
| L234A/L235A/P329G | — | H310A | Y436A | 2.3 |
| L234A/L235A/P329G | H310A | H433A | Y436A | 2.4 |
| L234A/L235A/P329G | — | — | Y436A | 41.3 |

Retention times below 3 minutes correspond to no binding as the substance is in the flow-through (void peak).

The single mutation H310A is the most silent symmetrical mutation to delete any FcRn-binding.

The symmetric single mutation I253A and H435A result in a relative shift of retention time of 0.3 to 0.4 min. This can be generally regarded as a non-detectable binding.

The single mutation Y436A results in detectable interaction strength to the FcRn affinity column. Without being bound by this theory this mutation could have an effect on FcRn mediated in vivo half-life which can be differentiated from a zero interaction such as the combination of the I253A, H310A and H435A mutations (IHH-AAA mutation).

The results obtained with a symmetrically modified anti-HER2 antibody are presented in the following table (see WO 2006/031370 for reference).

TABLE

| mutation | retention time [min] |
|---|---|
| I253H | no binding |
| M252D | no binding |
| S254D | no binding |
| R255D | 41.4 |
| M252H | 43.6 |
| K288E | 45.2 |
| L309H | 45.5 |
| E258H | 45.6 |
| T256H | 46.0 |
| K290H | 46.2 |
| D98E | 46.2 |
| wild-type | 46.3 |
| K317H | 46.3 |
| Q311H | 46.3 |
| E430H | 46.4 |
| T307H | 47.0 |
| N434H | 52.0 |

Figure 9:
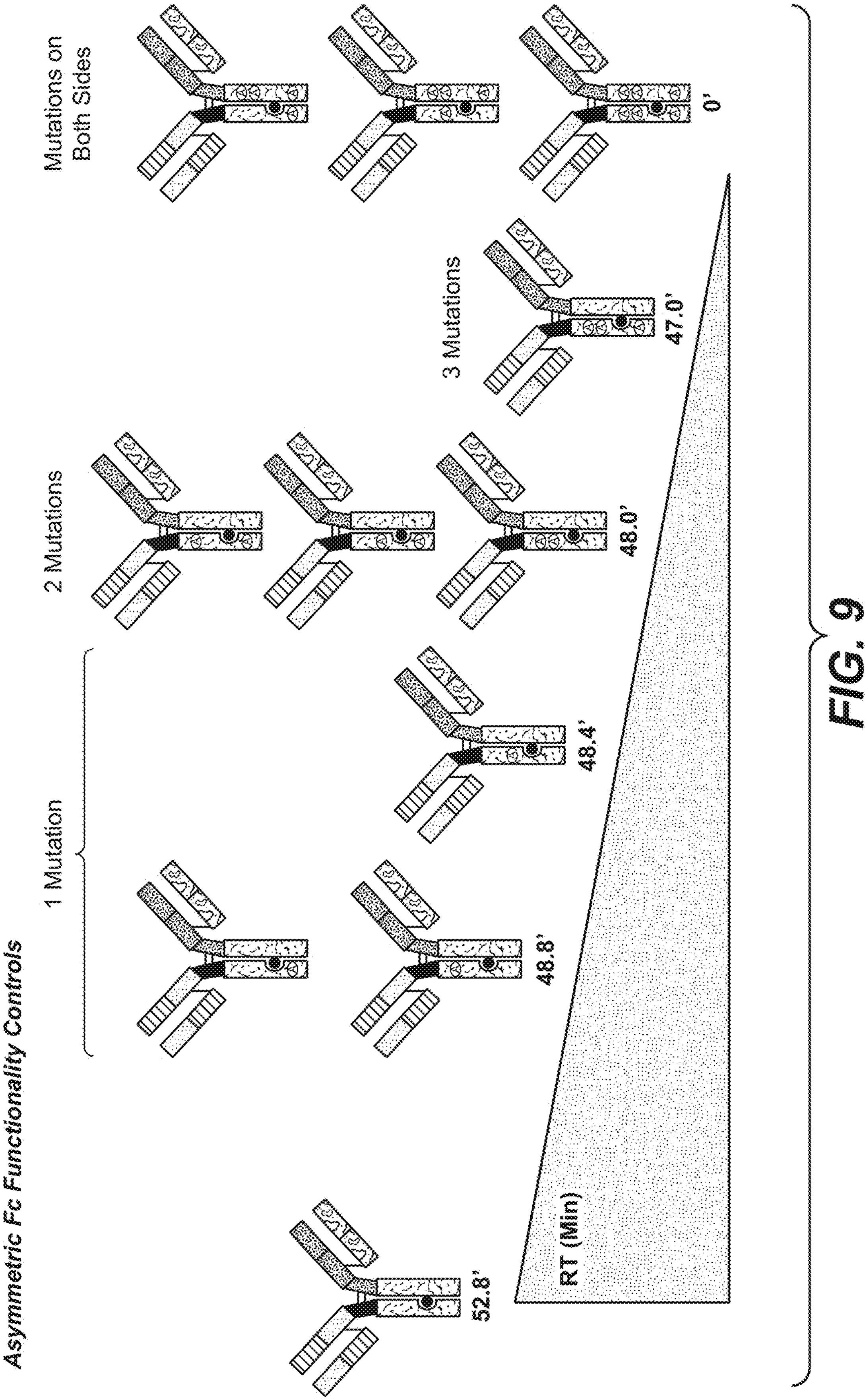
FIG. 9: Change of retention time in an FcRn affinity chromatography depending on the number of mutations introduced into the Fc-region.
Figure 10:
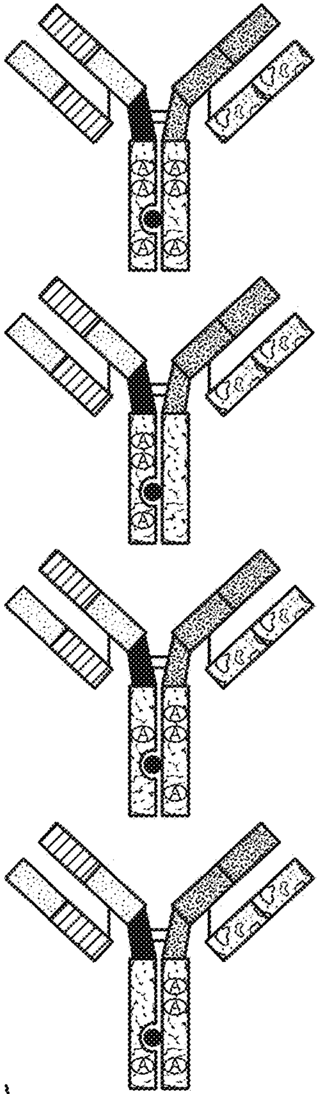
FIG. 10: Change of FcRn-binding depending on asymmetric distribution of mutations introduced into the Fc-region.
Figure 11:
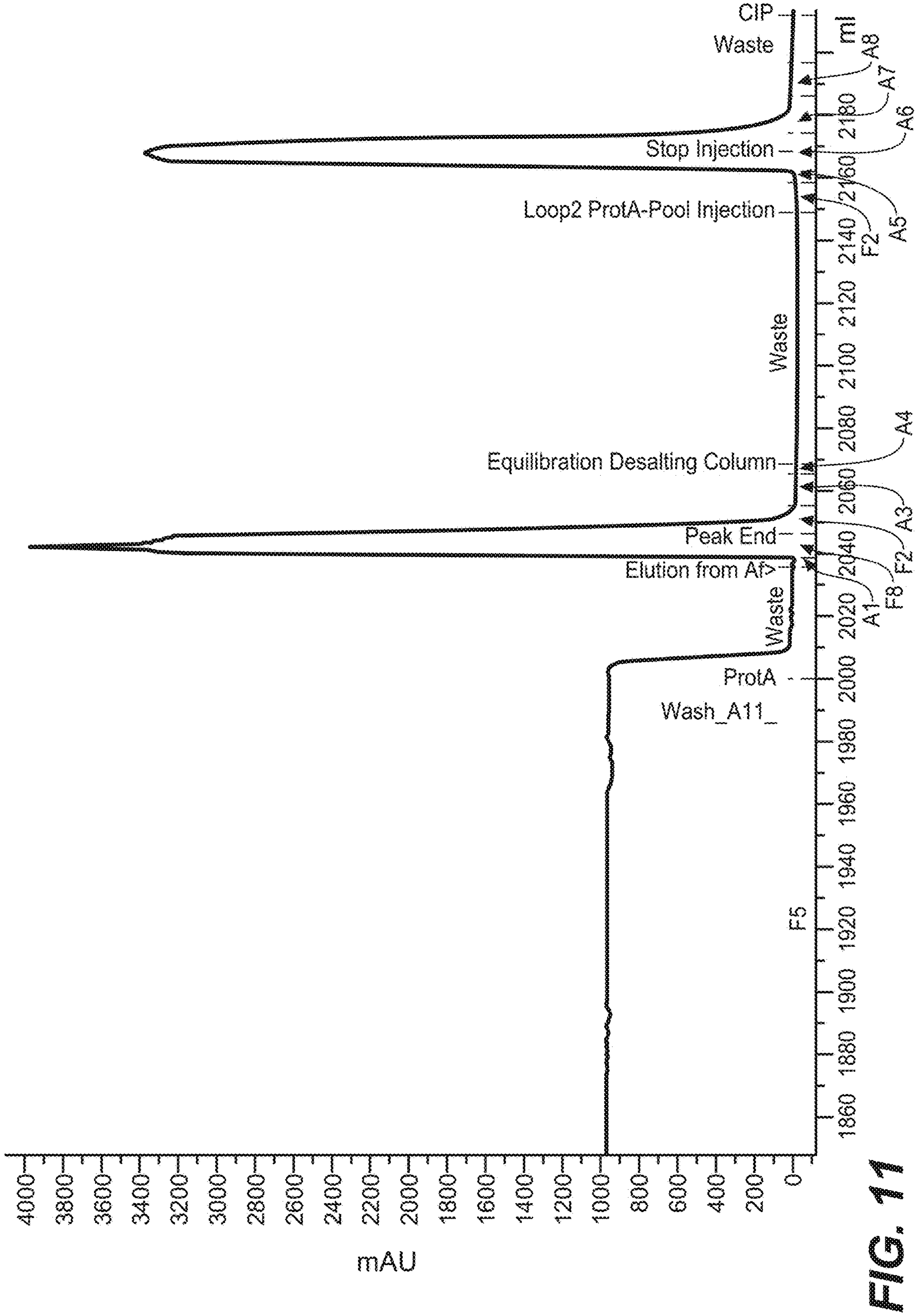
FIG. 11: Elution chromatogram of a bispecific anti-VEGF/ANG2 antibody (VEGF/ANG2-0121) with the combination of the mutations H310A, H433A and Y436A in both heavy chains from two consecutive protein A affinity chromatography columns.
Figure 12:
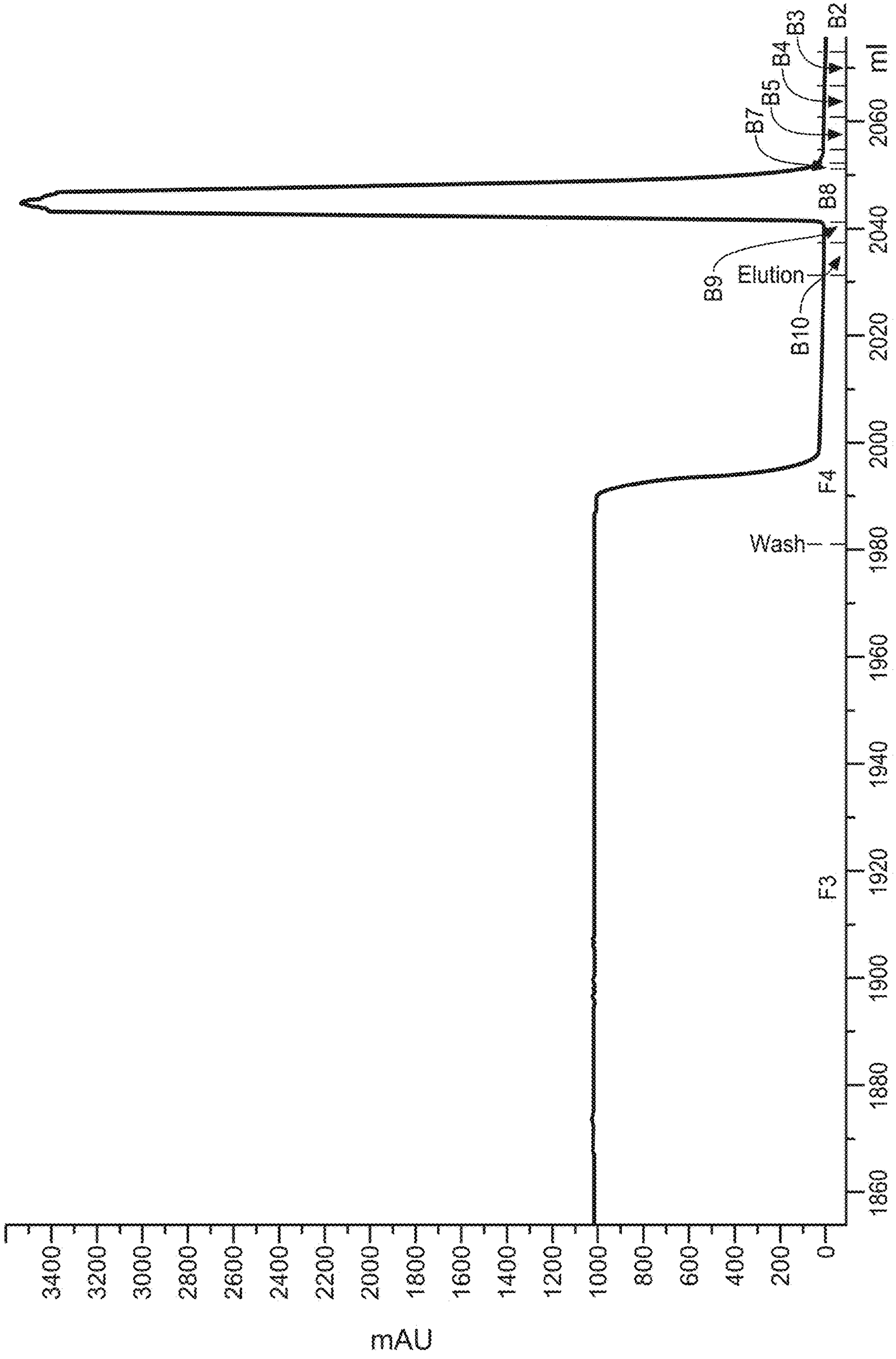
FIG. 12: Elution chromatogram of an anti-IGF-1R antibody (IGF-1R-0045) with the mutations H310A, H433A and Y436A in both heavy chains from a protein A affinity chromatography column.
Figure 13:
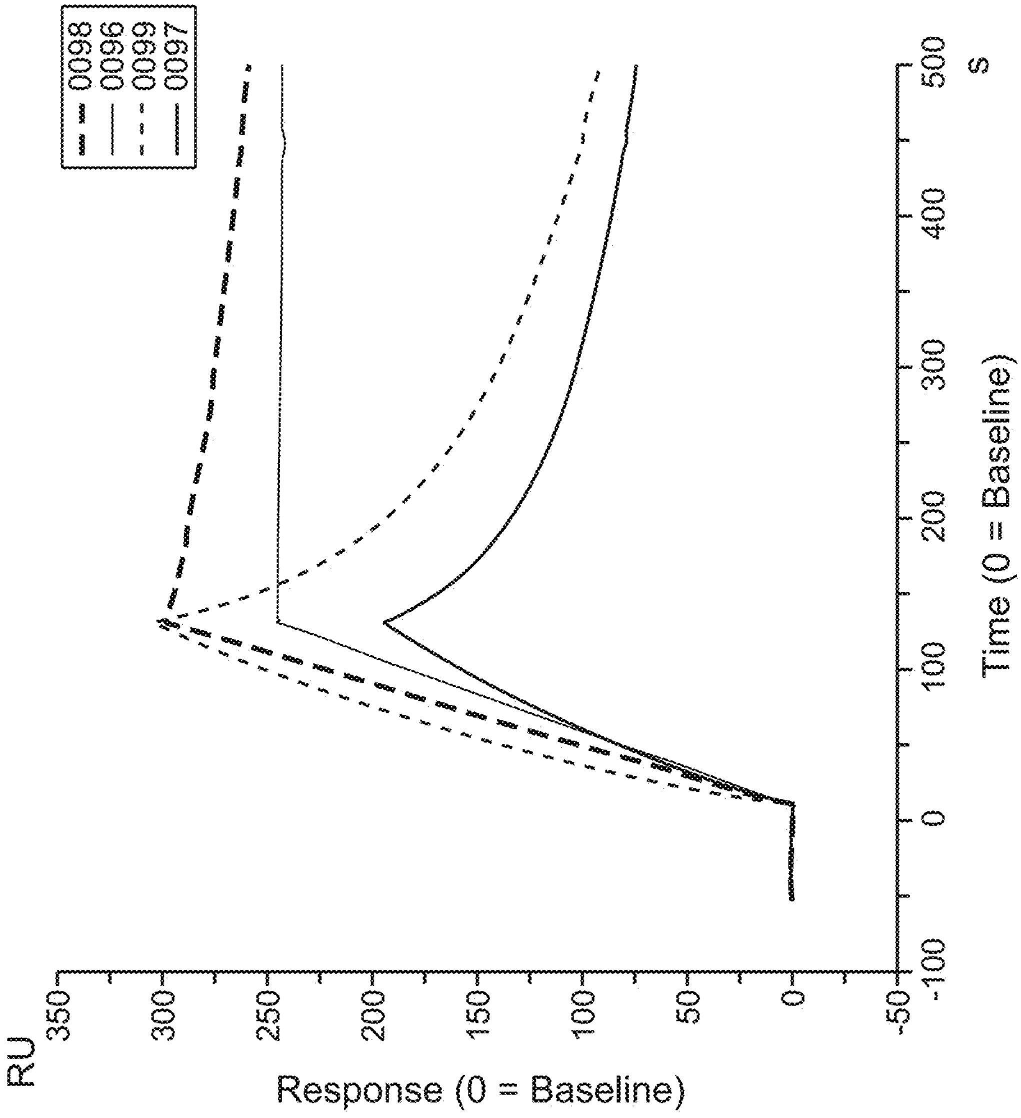
FIG. 13: Binding of IgG Fc-region modified anti-VEGF/ANG2 antibodies to immobilized protein A on a CM5 chip.
Figure 14:
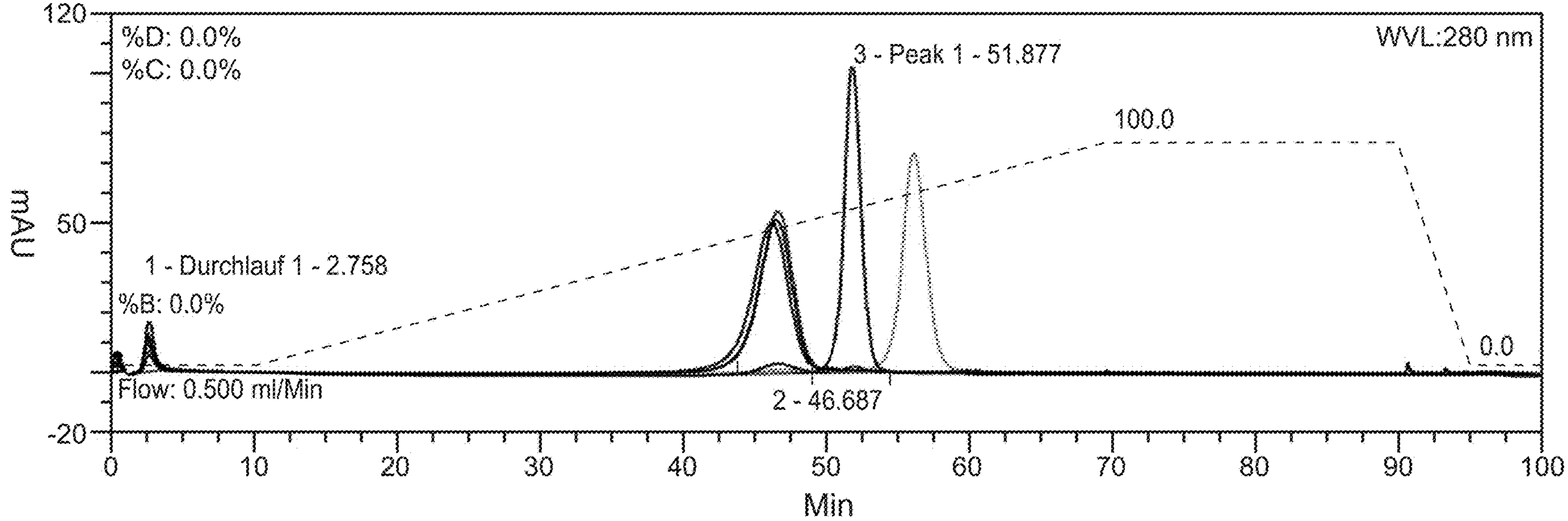
FIG. 14: Elution chromatogram of different anti-VEGF/ANG2 antibodies on an FcRn affinity column.

The effect of the introduction of asymmetric FcRn-binding affecting mutations in the Fc-region has been exemplified with a bispecific antibody assembled using the knobs-into-holes technology (see e.g. U.S. Pat. No. 7,695,936, US 2003/0078385; "hole chain" mutations: S354C/T366W, "knob chain" mutations: Y349C/T366S/L368A/Y407V). The effect of the asymmetrically introduced mutations on FcRn-binding can easily be determined using an FcRn affinity chromatography method (see FIG. 9 and the following Table). Antibodies that have a later elution from the FcRn affinity column, i.e. that have a longer retention time on the FcRn affinity column, have a longer half-life in vivo, and vice versa.

TABLE

| FcRn affecting mutation | retention time on FcRn affinity column |
|---|---|
| one chain with M252Y/S254T/T256E | 56.2 min. |
| none | 51.8 min. |
| one chain with I253A or H435A | 48.8 min. |
| one chain with H310A | 48.4 min. |
| one chain with I253A/H435A or I253A/H310A or H310A/H435A | 48.0 min. |
| one chain with H310A/H433A/Y436A | 46.7 min. |
| one chain with I253A/H310A/H435A | 46.6 min. |
| one chain with L251D/L314D/L432D | 46.3 min. |
| first chain with I253A/H310A/H435A and second chain with H310A or H435A or I253A/H310A/H435A | no binding |

The effect of the introduction of asymmetric FcRn-binding affecting mutations in the Fc-region has further been exemplified with a monospecific anti-IGF-1R antibody assembled using the knobs-into-holes technology in order to allow the introduction of asymmetric mutations (see e.g. U.S. Pat. No. 7,695,936, US 2003/0078385; "hole chain" mutations: S354C/T366W, "knob chain" mutations: Y349C/T366S/L368A/Y407V). The effect of the asymmetrically introduced mutations on FcRn-binding can easily be determined using an FcRn affinity chromatography method (see the following Table). Antibodies that have a later elution from the FcRn affinity column, i.e. that have a longer retention time on the FcRn affinity column, have a longer half-life in vivo, and vice versa.

TABLE

| FcRn affecting mutation | retention time on FcRn affinity column |
|---|---|
| one chain with M252Y/S254T/T256E | 57.6 min. |
| none | 53.0 min. |
| one chain with H310A/H433A/Y436A | 42.4 min. |
| one chain with I253A/H310A/H435A | 42.0 min. |
| one chain with L251D/L314D/L432D | 40.9 min. |
| first chain with I253A/H310A/H435A and second chain with H310A or H435A or I253A/H310A/H435A | no binding |

The asymmetric IHH-AAA and LLL-DDD mutation (LLL-DDD-mutation=combination of the mutations L251D, L314D and L432D) show weaker binding than the corresponding parent or wild-type antibody.

The symmetric HHY-AAA mutation (=combination of the mutations H310A, H433A and Y436A) results in an Fc-region that does no longer bind to the human FcRn whereas the binding to protein A is maintained (see FIGS. 11, 12, 13 and 14).

The effect of the introduction of asymmetric FcRn-binding affecting mutations in the Fc-region has further been exemplified with a monospecific anti-IGF-1R antibody (IGF-1R), a bispecific anti-VEGF/ANG2 antibody (VEGF/ANG2), and a full length antibody with fusions to the C-terminus of both heavy chains (fusion) assembled using the knobs-into-holes technology in order to allow the introduction of asymmetric mutations (see e.g. U.S. Pat. No. 7,695,936, US 2003/0078385; "hole chain" mutations: S354C/T366W, "knob chain" mutations: Y349C/T366S/L368A/Y407V). The effect of the introduced mutations on FcRn-binding and protein A binding can easily be determined using an FcRn affinity chromatography method, a protein A affinity chromatography method and SPR-based methods (see the following Table).

| antibody | further mutation in knob chain | further mutation in hole chain | FcR binding affecting mutations | FcRn binding (SPR) | FcRn binding (column) | protein A binding (SPR) | protein A binding (column) |
|---|---|---|---|---|---|---|---|
| VEGF/ ANG2 0096 | none | none | L234A L235A P329G | yes | yes | stable binding | yes |
| VEGF/ ANG2 0097 | none | I253A H310A H435A | L234A L235A P329G | yes | yes | fast off-rate | yes |
| VEGF/ ANG2 0098 | none | H310A H433A Y436A | L234A L235A P329G | yes | yes | stable binding | yes |
| VEGF/ ANG2 0099 | none | L251D L314D L432D | L234A L235A P329G | reduced | reduced | fast off-rate | yes |

-continued

| antibody | further mutation in knob chain | further mutation in hole chain | FcR binding affecting mutations | FcRn binding (SPR) | FcRn binding (column) | protein A binding (SPR) | protein A binding (column) |
|---|---|---|---|---|---|---|---|
| VEGF/ ANG2 0100 | none | M252Y S254T T256E | L234A L235A P329G | in- creased | in- creased | n.d. | yes |
| VEGF/ ANG2 0016 | I253A H310A H435A | I253A H310A H435A | L234A L235A P329G | n.d. | no | n.d. | no |
| VEGF/ ANG2 0121 | H310A H433A Y436A | H310A H433A Y436A | L234A L235A P329G | n.d. | n.d. | n.d. | yes |
| IGF-1R 0033 | none | none | none | yes | yes | n.d. | yes |
| IGF-1R 0034 | none | I253A H310A H435A | L234A L235A P329G | n.d. | yes | n.d. | yes |
| IGF-1R 0035 | none | H310A H433A Y436A | none | reduced | reduced | n.d. | yes |
| IGF-1R 0037 | none | L251D L314D L432D | L234A L235A P329G | n.d. | yes | n.d. | yes |
| IGF-1R 0036 | none | M252Y S254T T256E | L234A L235A P329G | n.d. | yes | n.d. | yes |
| IGF-1R 0045 | H310A H433A Y436A | H310A H433A Y436A | none | n.d. | n.d. | n.d. | yes |
| fusion 0008 | none | none | L234A L235A P329G | n.d. | yes | n.d. | n.d. |
| fusion 0019 | I253A | I253A | L234A L235A P329G | n.d. | no | n.d. | n.d. |
| fusion 0020 | H310A | H310A | L234A L235A P329G | n.d. | no | n.d. | n.d. |
| fusion 0021 | H435A | H435A | L234A L235A P329G | n.d. | no | n.d. | n.d. |
| fusion 0038 | Y436A | Y436A | L234A L235A P329G | n.d. | reduced | n.d. | n.d. |
| fusion 0022 | I253A H310A | I253A H310A | L234A L235A P329G | n.d. | no | n.d. | n.d. |
| fusion 0023 | I253A H435A | I253A H435A | L234A L235A P329G | n.d. | no | n.d. | n.d. |
| fusion 0036 | H310A H435A | H310A H435A | L234A L235A P329G | n.d. | no | n.d. | n.d. |
| fusion 0037 | H310A Y436A | H310A Y436A | L234A L235A P329G | n.d. | no | n.d. | n.d. |
| fusion 0018 | I253A H310A H435A | I253A H310A H435A | L234A L235A P329G | n.d. | no | n.d. | n.d. |
| fusion 0019 | H310A H433A Y436A | H310A H433A Y436A | L234A L235A P329G | n.d. | no | n.d. | n.d. |

One aspect as reported herein is an antibody or Fc-region fusion polypeptide comprising the variant human IgG class Fc-region as reported herein.

The Fc-region (dimeric polypeptide) as reported herein when contained in an Fc-region fusion polypeptide or a full length antibody confers the above described characteristics to the molecule. The fusion partner can be any molecules having a biological activity who's in vivo half-live shall be reduced or increased, i.e. who's in vivo half-live shall be clearly defined and tailor-made for its intended application.

Fc-region fusion polypeptides may comprise e.g. a variant (human) IgG class Fc-region as reported herein and a receptor protein that binds to a target including a ligand, such as, for example, TNFR-Fc-region fusion polypeptide (TNFR=human tumor necrosis factor receptor), or IL-1R-Fc-region fusion polypeptide (IL-1R=human interleukin-1 receptor), or VEGFR-Fc-region fusion polypeptides (VEGFR=human vascular endothelial growth factor receptor), or ANG2R-Fc-region fusion polypeptides (ANG2R=human angiopoietin 2 receptor).

Fc-region fusion polypeptides may comprise e.g. a variant (human) IgG class Fc-region as reported herein and an antibody fragment that binds to a target including, such as, for example, an antibody Fab fragment, scFvs (see e.g. Nat. Biotechnol. 23 (2005) 1126-1136), or domain antibodies (dAbs) (see e.g. WO 2004/058821, WO 2003/002609).

Fc-region fusion polypeptides may comprise e.g. a variant (human) IgG class Fc-region as reported herein and a receptor ligand (either naturally occurring or artificial).

Antibodies, e.g. full length antibodies or CrossMabs, can comprise a variant (human) human IgG class Fc-region as reported herein.

B. Ocular Vascular Diseases

Ocular vascular diseases are any pathological condition characterized by altered or unregulated proliferation and invasion of new blood vessels into the structures of ocular tissues such as the retina or cornea.

In one embodiment the ocular vascular disease is selected from the group consisting of wet age-related macular degeneration (wet AMD), dry age-related macular degeneration (dry AMD), diabetic macular edema (DME), cystoid macular edema (CME), non-proliferative diabetic retinopathy (NPDR), proliferative diabetic retinopathy (PDR), cystoid macular edema, vasculitis (e.g. central retinal vein occlusion), papilloedema, retinitis, conjunctivitis, uveitis, choroiditis, multifocal choroiditis, ocular histoplasmosis, blepharitis, dry eye (Sjogren's disease) and other ophthalmic diseases wherein the eye disease or disorder is associated with ocular neovascularization, vascular leakage, and/or retinal edema.

The antibody comprising the dimeric polypeptide as reported herein is useful in the prevention and treatment of wet AMD, dry AMD, CME, DME, NPDR, PDR, blepharitis, dry eye and uveitis, in one preferred embodiment wet AMD, dry AMD, blepharitis, and dry eye, also in one preferred embodiment CME, DME, NPDR and PDR, also in one preferred embodiment blepharitis, and dry eye, in particular wet AMD and dry AMD, and also particularly wet AMD.

In some embodiments, the ocular vascular disease is selected from the group consisting of wet age-related macular degeneration (wet AMD), macular edema, retinal vein occlusions, retinopathy of prematurity, and diabetic retinopathy.

Other diseases associated with corneal neovascularization include, but are not limited to, epidemic keratoconjunctivitis, Vitamin A deficiency, contact lens overwear, atopic keratitis, superior limbic keratitis, pterygium keratitis sicca, Sjogren's disease, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, rheumatoid arthritis, systemic lupus, polyarteritis, trauma, Wegener's sarcoidosis, Scleritis, Steven's Johnson disease, periphigoid radial keratotomy, and corneal graph rejection.

Diseases associated with retinal/choroidal neovascularization include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, retinitis pigmentosa, retina edema (including macular edema), Eale's disease, Bechet's disease, infections causing a retinitis or choroiditis, presumed ocular histoplasmosis, Best's disease, myopia, optic pits, Stargart's disease, pars planitis, chronic retinal detachment, hyperviscosity syndromes, toxoplasmosis, trauma and post-laser complications.

Other diseases include, but are not limited to, diseases associated with rubeosis (neovascularization of the angle) and diseases caused by the abnormal proliferation of fibrovascular or fibrous tissue including all forms of proliferative vitreoretinopathy.

Retinopathy of prematurity (ROP) is a disease of the eye that affects prematurely born babies. It is thought to be caused by disorganized growth of retinal blood vessels which may result in scarring and retinal detachment. ROP can be mild and may resolve spontaneously, but may lead to blindness in serious cases. As such, all preterm babies are at risk for ROP, and very low birth weight is an additional risk factor. Both oxygen toxicity and relative hypoxia can contribute to the development of ROP.

Macular degeneration is a medical condition predominantly found in elderly adults in which the center of the inner lining of the eye, known as the macula area of the retina, suffers thinning, atrophy, and in some cases, bleeding. This can result in loss of central vision, which entails inability to see fine details, to read, or to recognize faces. According to the American Academy of Ophthalmology, it is the leading cause of central vision loss (blindness) in the United States today for those over the age of fifty years. Although some macular dystrophies that affect younger individuals are sometimes referred to as macular degeneration, the term generally refers to age-related macular degeneration (AMD or ARMD).

Age-related macular degeneration begins with characteristic yellow deposits in the macula (central area of the retina which provides detailed central vision, called fovea) called drusen between the retinal pigment epithelium and the underlying choroid. Most people with these early changes (referred to as age-related maculopathy) have good vision. People with drusen can go on to develop advanced AMD. The risk is considerably higher when the drusen are large and numerous and associated with disturbance in the pigmented cell layer under the macula. Large and soft drusen are related to elevated cholesterol deposits and may respond to cholesterol lowering agents or the Rheo Procedure.

Advanced AMD, which is responsible for profound vision loss, has two forms: dry and wet. Central geographic atrophy, the dry form of advanced AMD, results from atrophy to the retinal pigment epithelial layer below the retina, which causes vision loss through loss of photoreceptors (rods and cones) in the central part of the eye. While no treatment is available for this condition, vitamin supplements with high doses of antioxidants, lutein and zeaxanthin, have been demonstrated by the National Eye Institute and others to slow the progression of dry macular degeneration and in some patients, improve visual acuity.

Retinitis pigmentosa (RP) is a group of genetic eye conditions. In the progression of symptoms for RP, night blindness generally precedes tunnel vision by years or even decades. Many people with RP do not become legally blind until their 40s or 50s and retain some sight all their life. Others go completely blind from RP, in some cases as early as childhood. Progression of RP is different in each case. RP is a type of hereditary retinal dystrophy, a group of inherited disorders in which abnormalities of the photoreceptors (rods and cones) or the retinal pigment epithelium (RPE) of the retina lead to progressive visual loss. Affected individuals first experience defective dark adaptation or nyctalopia (night blindness), followed by reduction of the peripheral visual field (known as tunnel vision) and, sometimes, loss of central vision late in the course of the disease.

Macular edema occurs when fluid and protein deposits collect on or under the macula of the eye, a yellow central area of the retina, causing it to thicken and swell. The swelling may distort a person's central vision, as the macula is near the center of the retina at the back of the eyeball. This area holds tightly packed cones that provide sharp, clear central vision to enable a person to see form, color, and detail that is directly in the line of sight. Cystoid macular edema is a type of macular edema that includes cyst formation.

C. Antibody Purification with a *Staphylococcus* Protein A Affinity Chromatography Column In one aspect, a dimeric polypeptide comprising a first polypeptide and a second polypeptide each comprising in N-terminal to C-terminal direction at least a portion of an immunoglobulin hinge region, which comprises one or more cysteine residues, an immunoglobulin CH2-domain and an immunoglobulin CH3-domain, wherein i) the first and the second polypeptide comprise the mutations H310A, H433A and Y436A, or ii) the first and the second polypeptide comprise the mutations L251D, L314D and L432D, or iii) the first polypeptide comprises the mutations I253A, H310A and H435A and the second polypeptide comprises the mutations H310A, H433A and Y436A, or iv) the first polypeptide comprises the mutations I253A, H310A and H435A and the second polypeptide comprises the mutations L251D, L314D and L432D is provided.

These dimeric polypeptides have due to the mutations the properties of not binding to human FcRn whereas the binding to Staphylococcal protein A is maintained.

Thus, these antibodies can be purified, i.e. separated from unwanted by-products by using conventional protein A affinity materials, such as MabSelectSure. It is not required to use highly sophisticated but species limited affinity materials, such as e.g. KappaSelect, which is only useable with antibodies comprising a light chain of the kappa subclass. Additionally it is not required to adopt the purification method if a modification/exchange of the light chain subclass is made (see FIGS. 11 and 12, respectively).

One aspect as reported herein is a method for producing a dimeric polypeptide as reported herein comprising the following steps:

a) cultivating a mammalian cell comprising one or more nucleic acids encoding a dimeric polypeptide as reported herein, b) recovering the dimeric polypeptide from the cultivation medium, and c) purifying the dimeric polypeptide with a protein A affinity chromatography and thereby producing the dimeric polypeptide.

One aspect as reported herein is the use of the mutations H310A, H433A and Y436A for separating heterodimeric polypeptides from homodimeric polypeptides.

One aspect as reported herein is the use of the mutations L251D, L314D and L432D for separating heterodimeric polypeptides from homodimeric polypeptides.

One aspect as reported herein is the use of the mutations I253A, H310A and H435A in a first polypeptide in combination with the mutations H310A, H433A and Y436A in a second polypeptide for separating heterodimeric polypeptides comprising the first and the second polypeptide from homodimeric polypeptides.

One aspect as reported herein is the use of the mutations I253A, H310A and H435A in a first polypeptide in combination with the mutations L251D, L314D and L432D in a second polypeptide for separating heterodimeric polypeptides comprising the first and the second polypeptide from homodimeric polypeptides.

In one embodiment of the previous three aspects the first polypeptide further comprises the mutations Y349C, T366S, L368A and Y407V and the second polypeptide further comprises the mutations S354C and T366W.

In one embodiment of the previous three aspects the first polypeptide further comprises the mutations S354C, T366S, L368A and Y407V and the second polypeptide further comprises the mutations Y349C and T366W.

One aspect as reported herein is the use of the mutation Y436A for increasing the binding of a dimeric Fc-region polypeptide to Staphylococcal protein A.

Figure 15:
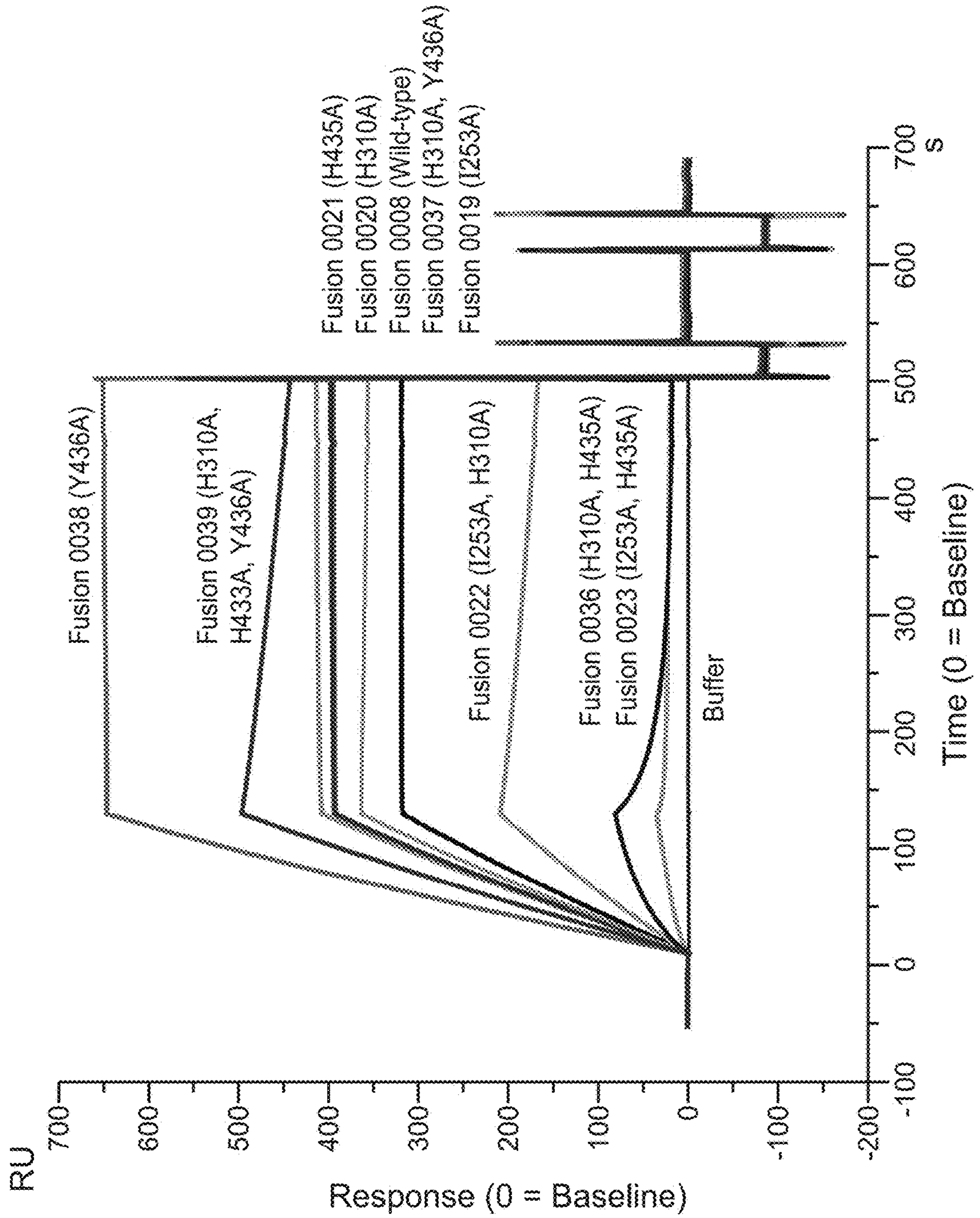
FIG. 15: Binding of different fusion polypeptides to Staphylococcal protein A (SPR).
Figure 16:
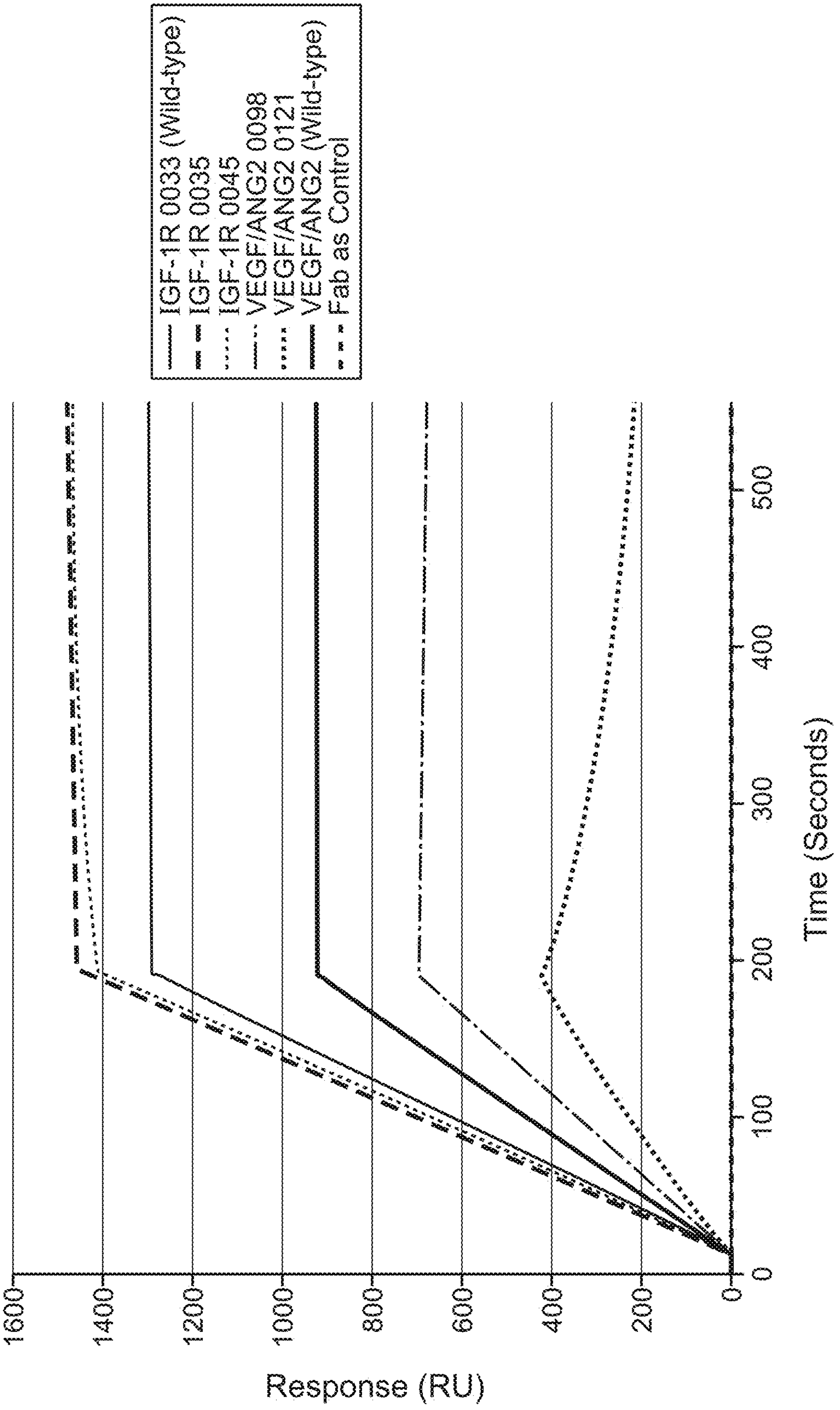
FIG. 16: Binding of different anti-VEGF/ANG2 antibody and anti-IGF-1R antibody mutants to immobilized protein A (SPR).

It has been found that by introducing the mutation Y436A the binding of an Fc-region to Staphylococcal protein A (SPA) can be increased. This is advantageous e.g. if additional mutations are introduced that reduce the binding to SPA, such as e.g. I253A and H310A or H310A and H435A (see FIG. 15).

One aspect as reported herein is a dimeric polypeptide comprising a first polypeptide and a second polypeptide each comprising in N-terminal to C-terminal direction at least a portion of an immunoglobulin hinge region, which comprises one or more cysteine residues, an immunoglobulin CH2-domain and an immunoglobulin CH3-domain, wherein the first, the second or the first and the second polypeptide comprise the mutation Y436A (numbering according to the Kabat EU index numbering system).

In one embodiment the first and the second polypeptide comprise the mutation Y436A.

One aspect as reported herein is a bispecific antibody providing ease of isolation/purification comprising immunoglobulin heavy chain Fc-regions that are differentially modified, wherein at least one of the modifications results in i) a differential affinity of the bispecific antibody for protein A and ii) a differential affinity of the bispecific antibody for the human FcRn, and the bispecific antibody is isolable from a disrupted cell, from medium, or from a mixture of antibodies based on its affinity for protein A.

In one embodiment the bispecific antibody elutes at a pH value above pH 4.0.

In one embodiment the bispecific antibody is isolated using a protein A affinity chromatography and a pH gradient or pH step, wherein the pH gradient or pH step includes the addition of a salt. In a specific embodiment, the salt is present at a concentration of about 0.5 molar to about 1 molar. In one embodiment, the salt is selected from the group consisting of lithium, sodium, and potassium salts of acetate; sodium and potassium bicarbonates; lithium, sodium, and potassium carbonates; lithium, sodium, potassium, and magnesium chlorides; sodium and potassium fluorides; sodium, potassium, and calcium nitrates; sodium and potassium phosphates; and calcium and magnesium sulfates. In one embodiment the salt is a halide salt of an alkaline metal or alkaline earth metal. In one preferred embodiment the salt is sodium chloride.

In one aspect the dimeric polypeptide comprises a first polypeptide that is modified as reported herein and a second polypeptide that is not modified regarding protein A and FcRn binding, so as to form a heterodimeric polypeptide, wherein the differential modification results in the dimeric polypeptide eluting from a protein A affinity material at 0.5, 0.6, 0.7, 0.8, 0.9, 1.0, 1.2, 1.3, or 1.4 pH unit(s) higher than a corresponding dimeric polypeptide that lacks the differential modification. In one embodiment, the differentially modified dimeric polypeptide elutes at a pH of 4 or higher, whereas the unmodified dimeric polypeptide elutes at a pH of 3.5 or lower. In one embodiment, the differentially modified dimeric polypeptide elutes at a pH of about 4, whereas the unmodified dimeric polypeptide elutes at a pH of about 2.8-3.5, 2.8-3.2, or 2.8-3. In these embodiments, "unmodified" refers to lack of the modification H310A, H433A and Y436A (Kabat EU index numbering system) in both of the polypeptides.

For chromatographic runs the addition of 0.5 molar to 1 molar salt (e.g. NaCl) may improve the separation of homodimeric polypeptide and heterodimeric polypeptide, especially if derived from the human IgG1 subclass. The addition of salt to the elution solution increasing the pH value can broaden the pH range for elution such that e.g. a pH step gradient could successfully separate the two species.

Accordingly, in one embodiment a method for separating a bispecific antibody comprising a heterodimeric IgG Fc-region with one chain comprising mutations as reported herein, comprises a step of employing a pH gradient in the presence of a salt. In one embodiment, the salt is present at a concentration sufficient to maximize the pH difference between elution from a protein A chromatography material of an IgG Fc-region homodimer and an IgG Fc-region heterodimer. In one embodiment the salt is present at a concentration of about 0.5 molar to about 1 molar. In one embodiment the salt is a salt of an alkaline metal or an alkaline earth metal and a halogen. In one embodiment the salt is a chloride salt of an alkaline metal or an alkaline earth metal, such as e.g. NaCl, KCl, LiCl, CaCl2, or MgCl2. In one embodiment the pH gradient is from about pH 4 to about pH 5. In one embodiment the gradient is a linear gradient. In one embodiment, the pH gradient is a step gradient. In one embodiment the method comprises applying to an equilibrated protein A affinity column a solution of about pH 4. In one embodiment the bispecific antibody comprising the heterodimeric IgG Fc-region with respect to the modifications as reported herein elutes from the protein A affinity chromatography material in one or more fractions substantially free of non-heterodimeric bispecific antibody.

The dimeric polypeptide as reported herein is produced by recombinant means. Thus, one aspect of the current invention is a nucleic acid encoding the dimeric polypeptide as reported herein and a further aspect is a cell comprising the nucleic acid encoding the dimeric polypeptide as reported herein. Methods for recombinant production are widely known in the state of the art and comprise protein expression in prokaryotic and eukaryotic cells with subsequent isolation of the dimeric polypeptide and usually purification to a pharmaceutically acceptable purity. For the expression of the dimeric polypeptides as aforementioned in a host cell, nucleic acids encoding the respective first and second polypeptides are inserted into expression vectors by standard methods. Expression is performed in appropriate prokaryotic or eukaryotic host cells like CHO cells, NS0 cells, SP2/0 cells, HEK293 cells, COS cells, PER.C6 cells, yeast, or *E. coli* cells, and the dimeric polypeptide is recovered from the cells (cultivation supernatant or cells after lysis).

General methods for recombinant production of antibodies are well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-160; Werner, R. G., Drug Res. 48 (1998) 870-880.

Accordingly one aspect as reported herein is a method for the production of a dimeric polypeptide as reported herein, comprising the steps of a) transforming a host cell with one or more vectors comprising nucleic acid molecules encoding a dimeric polypeptide as reported herein,
b) culturing the host cell under conditions that allow synthesis of the dimeric polypeptide, and
c) recovering the dimeric polypeptide from the culture and thereby producing the dimeric polypeptide.

In one embodiment the recovering step under c) includes the use of an immunoglobulin Fc-region specific capture reagent. In one embodiment this Fc-region specific capture reagent is used in a bind-and-elute-mode). Examples of such Fc-region specific capture reagents are e.g. *Staphylococcus* protein A-based affinity chromatography columns, which are based on a highly rigid agarose base matrix that allows high flow rates and low back pressure at large scale. They feature a ligand that binds to the dimeric polypeptide, i.e. its Fc-region. The ligands are attached to the matrix via a long hydrophilic spacer arm to make it easily available for binding to the target molecule.

The dimeric polypeptides as reported herein are suitably separated from the culture medium by conventional immunoglobulin purification procedures such as, for example, protein A-Sepharose, hydroxylapatite chromatography, gel electrophoresis, dialysis, or affinity chromatography. B-cells or hybridoma cells can serve as a source of DNA and RNA encoding the dimeric polypeptide. DNA and RNA encoding the monoclonal antibodies are readily isolated and sequenced using conventional procedures. Once isolated, the DNA may be inserted into expression vectors, which are then transfected into host cells such as HEK 293 cells, CHO cells, or myeloma cells that do not otherwise produce dimeric polypeptides, to obtain the synthesis of recombinant monoclonal dimeric polypeptides in the host cells.

Purification of antibodies is performed in order to eliminate cellular components or other contaminants, e.g. other cellular nucleic acids or proteins, by standard techniques, including alkaline/SDS treatment, CsCl banding, column chromatography, agarose gel electrophoresis, and others well known in the art (see Ausubel, F., et al., ed. Current Protocols in Molecular Biology, Greene Publishing and Wiley Interscience, New York (1987)). Different methods are well established and widespread used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102).

One aspect of the invention is a pharmaceutical formulation comprising a dimeric polypeptide or an antibody as reported herein. Another aspect of the invention is the use of a dimeric polypeptide or an antibody as reported herein for the manufacture of a pharmaceutical formulation. A further aspect of the invention is a method for the manufacture of a pharmaceutical formulation comprising a dimeric polypeptide or an antibody as reported herein. In another aspect, the present invention provides a formulation, e.g. a pharmaceutical formulation, containing a dimeric polypeptide or an antibody as reported herein, formulated together with a pharmaceutical carrier.

A formulation as reported herein can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

Many possible modes of delivery can be used, including, but not limited to intraocular application or topical application. In one embodiment the application is intraocular and includes, but it's not limited to subconjunctival injection, intracanieral injection, injection into the anterior chamber via the termporai limbus, intrastromal injection, intracorneal injection, subretinal injection, aqueous humor injection, subtenon injection or sustained delivery device, intravitreal injection (e.g., front, mid or back vitreal injection). In one embodiment the application is topical and includes, but it's not limited to eye drops to the cornea.

In one embodiment the dimeric polypeptide as reported herein or the pharmaceutical formulation as reported herein is administered via intravitreal application, e.g. via intravitreal injection. This can be performed in accordance with standard procedures known in the art. See, e.g., Ritter et al., J. Clin. Invest. 116 (2006) 3266-3276; Russelakis-Carneiro et al., Neuropathol. Appl. Neurobiol. 25 (1999) 196-206; and Wray et al., Arch. Neurol. 33 (1976) 183-185.

In some embodiments, therapeutic kits of the invention can contain one or more doses of a dimeric polypeptide as reported herein present in a pharmaceutical formulation as described herein, a suitable device for intravitreal injection of the pharmaceutical formulation, and an instruction detailing suitable subjects and protocols for carrying out the injection. In these embodiments, the formulations are typically administered to the subject in need of treatment via intravitreal injection. This can be performed in accordance with standard procedures known in the art (see, e.g., Ritter et al., J. Clin. Invest. 116 (2006) 3266-3276; Russelakis-Carneiro et al., Neuropathol. Appl. Neurobiol. 25 (1999) 196-206; and Wray et al., Arch. Neurol. 33 (1976) 183-185).

The formulation may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the formulations. In addition, prolonged absorption of the injectable pharmaceutical form may be brought about by the inclusion of agents which delay absorption such as aluminum monostearate and gelatin.

Regardless of the route of administration selected, the compounds as reported herein, which may be used in a suitable hydrated form, and/or the pharmaceutical formulations as reported herein, are formulated into pharmaceutically acceptable dosage forms by conventional methods known to those of skill in the art.

Actual dosage levels of the active ingredients in the pharmaceutical formulation as reported herein may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The formulation must be sterile and fluid to the extent that the formulation is deliverable by syringe. In addition to water, the carrier in one preferred embodiment is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

The formulation can comprise an ophthalmic depot formulation comprising an active agent for subconjunctival administration. The ophthalmic depot formulation comprises microparticles of essentially pure active agent, e.g., a dimeric polypeptide as reported herein. The microparticles comprising a dimeric polypeptide as reported herein can be embedded in a biocompatible pharmaceutically acceptable polymer or a lipid encapsulating agent. The depot formulations may be adapted to release all of substantially all the active material over an extended period of time. The polymer or lipid matrix, if present, may be adapted to degrade sufficiently to be transported from the site of administration after release of all or substantially all the active agent. The depot formulation can be liquid formulation, comprising a pharmaceutical acceptable polymer and a dissolved or dispersed active agent. Upon injection, the polymer forms a depot at the injections site, e.g. by gelifying or precipitating.

Another aspect of the invention is a dimeric polypeptide or an antibody as reported herein for use in the treatment of ocular vascular diseases.

One embodiment of the invention is a dimeric polypeptide or an antibody as reported herein for use in the treatment of ocular vascular diseases.

Another aspect of the invention is the pharmaceutical formulation for use in the treatment of ocular vascular diseases.

Another aspect of the invention is the use of a dimeric polypeptide or an antibody as reported herein for the manufacture of a medicament for the treatment of ocular vascular disease.

Another aspect of the invention is method of treatment of patient suffering from ocular vascular diseases by administering a dimeric polypeptide or an antibody as reported herein to a patient in the need of such treatment.

It is herewith expressly stated that the term "comprising" as used herein comprises the term "consisting of". Thus, all aspects and embodiments that contain the term "comprising" are likewise disclosed with the term "consisting of".

D. Modifications

In a further aspect, a dimeric polypeptide according to any of the above embodiments may incorporate any of the features, singly or in combination, as described in Sections 1-6 below:

1. Antibody Affinity

In one embodiment, Kd is measured using a BIACORE R surface plasmon resonance assay. For example, an assay using a BIACORE®-2000 or a BIACORE®-3000 (GE Healthcare Inc., Piscataway, NJ) is performed at 25° C. with immobilized binding partner CMS chips at ~10 response units (RU). In one embodiment, carboxymethylated dextran biosensor chips (CMS, GE Healthcare Inc.) are activated with N-ethyl-N'-(3-dimethylaminopropyl)-carbodiimide hydrochloride (EDC) and N-hydroxysuccinimide (NHS) according to the supplier's instructions. Binding partner is diluted with 10 mM sodium acetate, pH 4.8, to 5 μg/mL (~0.2 nM) before injection at a flow rate of 5 μl/minute to achieve approximately 10 response units (RU) of coupled binding partner. Following the injection of the binding partner, 1 M ethanolamine is injected to block non-reacted groups. For kinetics measurements, two-fold serial dilutions of the dimeric polypeptide containing fusion polypeptide or antibody (0.78 nM to 500 nM) are injected in PBS with 0.05% polysorbate 20 (TWEEN-20™) surfactant (PBST) at 25° C. at a flow rate of approximately 25 μL/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$ (see, e.g., Chen, Y. et al., J. Mol. Biol. 293 (1999) 865-881). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Chimeric and Humanized Antibodies

In certain embodiments, a dimeric polypeptide as reported herein is a chimeric antibody. Certain chimeric antibodies are described, e.g., in U.S. Pat. No. 4,816,567; and Morrison, S. L., et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I., et al., Nature 332 (1988) 323-329; Queen, C., et al., Proc. Natl. Acad. Sci. USA 86 (1989) 10029-10033; U.S. Pat. Nos. 5,821,337, 7,527,791, 6,982,321, and 7,087,409; Kashmiri, S. V., et al., Methods 36 (2005) 25-34 (describing specificity determining region (SDR) grafting); Padlan, E. A., Mol. Immunol. 28 (1991) 489-498 (describing "resurfacing"); Dall'Acqua, W. F. et al., Methods 36 (2005) 43-60 (describing "FR shuffling"); Osbourn, J. et al., Methods 36 (2005) 61-68; and Klimka, A. et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J., et al., J. Immunol. 151 (1993) 2296-2308; framework regions derived from the consensus sequence of human antibodies of a particular subgroup of light or heavy chain variable regions (see, e.g., Carter, P., et al., Proc. Natl. Acad. Sci. USA 89 (1992) 4285-4289; and Presta, L. G., et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

3. Human Antibodies

In certain embodiments, a dimeric polypeptide as reported herein is a human antibody. Human antibodies can be produced using various techniques known in the art. Human antibodies are described generally in van Dijk, M. A. and van de Winkel, J. G., Curr. Opin. Pharmacol. 5 (2001) 368-374 and Lonberg, N., Curr. Opin. Immunol. 20 (2008) 450-459.

Human antibodies maybe prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, N., Nat. Biotech. 23 (2005) 1117-1125. See also, e.g., U.S. Pat. Nos. 6,075,181 and 6,150,584 describing XENOMOUSE™ technology; U.S. Pat. No. 5,770,429 describing HuMAB® technology; U.S. Pat. No. 7,041,870 describing K-M MOUSE® technology, and US 2007/0061900, describing VelociMouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor, D., J. Immunol. 133 (1984) 3001-3005; Brodeur, B. R., et al., Monoclonal Antibody Production Techniques and Applications, Marcel Dekker, Inc., New York (1987), pp. 51-63; and Boerner, P., et al., J. Immunol. 147 (1991) 86-95). Human antibodies generated via human B-cell hybridoma technology are also described in Li, J., et al., Proc. Natl. Acad. Sci. USA 103 (2006) 3557-3562. Additional methods include those described, for example, in U.S. Pat. No. 7,189,826 (describing production of monoclonal human IgM antibodies from hybridoma cell lines) and Ni, J., Xiandai Mianyixue 26 (2006) 265-268 (describing human-human hybridomas). Human hybridoma technology (Trioma technology) is also described in Vollmers, H. P. and Brandlein, S., Histology and Histopathology 20 (2005) 927-937 and Vollmers, H. P. and Brandlein, S., Methods and Findings in Experimental and Clinical Pharmacology 27 (2005) 185-191.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

4. Library-Derived Antibodies

In certain embodiments a dimeric polypeptide as reported herein is a library-derived antibody. Library-derived antibodies may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom, H. R. et al., Methods in Molecular Biology 178 (2001) 1-37 and further described, e.g., in the McCafferty, J. et al., Nature 348 (1990) 552-554; Clackson, T. et al., Nature 352 (1991) 624-628; Marks, J. D. et al., J. Mol. Biol. 222 (1992) 581-597; Marks, J. D. and Bradbury, A., Methods in Molecular Biology 248 (2003) 161-175; Sidhu, S. S. et al., J. Mol. Biol. 338 (2004) 299-310; Lee, C. V. et al., J. Mol. Biol. 340 (2004) 1073-1093; Fellouse, F. A., Proc. Natl. Acad. Sci. USA 101 (2004) 12467-12472; and Lee, C. V. et al., J. Immunol. Methods 284 (2004) 119-132.

In certain phage display methods, repertoires of VH and VL genes are separately cloned by polymerase chain reaction (PCR) and recombined randomly in phage libraries, which can then be screened for antigen-binding phage as described in Winter, G., et al., Ann. Rev. Immunol. 12 (1994) 433-455. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths, A. D., et al., EMBO J. 12 (1993) 725-734. Finally, naive libraries can also be made synthetically by cloning non-rearranged V-gene segments from stem cells, and using PCR primers containing random sequence to encode the highly variable CDR3 regions and to accomplish rearrangement in vitro, as described by Hoogenboom, H. R. and Winter, G., J. Mol. Biol. 227 (1992) 381-388. Patent publications describing human antibody phage libraries include, for example: U.S. Pat. No. 5,750,373, and US 2005/0079574, US 2005/0119455, US 2005/0266000, US 2007/0117126, US 2007/0160598, US 2007/0237764, US 2007/0292936, and US 2009/0002360.

Antibodies or antibody fragments isolated from human antibody libraries are considered human antibodies or human antibody fragments herein.

5. Multispecific Antibodies

In certain embodiments, a dimeric polypeptide as reported herein is a multispecific antibody, e.g. a bispecific antibody. Multispecific antibodies are monoclonal antibodies that have binding specificities for at least two different sites. In certain embodiments, one of the binding specificities is for a first antigen and the other is for a different second antigen. In certain embodiments, bispecific antibodies may bind to two different epitopes of the same antigen. Bispecific antibodies may also be used to localize cytotoxic agents to cells which express at least one of the antigens. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A., et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M. et al., Science 229 (1985) 81-83); using leucine zippers to produce bi-specific antibodies (see, e.g., Kostelny, S. A., et al., J. Immunol. 148 (1992) 1547-1553; using "diabody" technology for making bispecific antibody fragments (see, e.g., Holliger, P. et al., Proc. Natl. Acad. Sci. USA 90 (1993) 6444-6448); and using single-chain Fv (scFv) dimers (see, e.g. Gruber, M et al., J. Immunol. 152 (1994) 5368-5374); and preparing trispecific antibodies as described, e.g., in Tutt, A. et al., J. Immunol. 147 (1991) 60-69).

Engineered antibodies with three or more functional antigen binding sites, including "Octopus antibodies," are also included herein (see, e.g. US 2006/0025576).

The antibody or fragment herein also includes a "Dual Acting Fab" or "DAF" (see, US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793.

6. Antibody Variants

In certain embodiments, a dimeric polypeptide as reported herein is an antibody. In further embodiment amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in the Table below under the heading of "preferred substitutions". More substantial changes are provided in the following Table under the heading of "exemplary substitutions", and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or residues that contact antigen, with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen can be used. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc-region, the carbohydrate attached thereto may be altered. Native antibodies produced by mammalian cells typically comprise a branched, biantennary oligosaccharide that is generally attached by an N-linkage to Asn297 of the CH2 domain of the Fc-region. See, e.g., Wright, A. and Morrison, S. L., TIBTECH 15 (1997) 26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc-region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc-region (EU numbering of Fc-region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A. et al., J. Mol. Biol. 336 (2004) 1239-1249; Yamane-Ohnuki, N. et al., Biotech. Bioeng. 87 (2004) 614-622. Examples of cell lines capable of producing defucosylated antibodies include Lec13 CHO cells deficient in protein fucosylation (Ripka, J., et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N., et al., Biotech. Bioeng. 87 (2004) 614-622; Kanda, Y., et al., Biotechnol. Bioeng. 94 (2006) 680-688; and WO 2003/085107).

Antibodies variants are further provided with bisected oligosaccharides, e.g., in which a biantennary oligosaccharide attached to the Fc-region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc-region are also provided. Such antibody variants may have improved CDC function. Such antibody variants are described, e.g., in WO 1997/30087; WO 1998/58964; and WO 1999/22764.

c) Fc-Region Variants

In certain embodiments, one or more further amino acid modifications may be introduced into a dimeric polypeptide as reported herein, thereby generating an Fc-region variant. The Fc-region variant may comprise a human Fc-region sequence (e.g., a human IgG1, IgG2, IgG3 or IgG4 Fc-region) comprising an amino acid modification (e.g. a substitution/mutation) at one or more amino acid positions.

In certain embodiments, the invention contemplates a dimeric polypeptide that possesses some but not all effector functions, which make it a desirable candidate for applications in which the half-life of the dimeric polypeptide in vivo is important yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the dimeric polypeptide antibody lacks FcγR binding (hence likely lacking ADCC activity), but retains FcRn binding ability. The primary cells for mediating ADCC, NK cells, express FcγRIII only, whereas monocytes express FcγR1, FcγRII and FcγRIII. FcR expression on hematopoietic cells is summarized in Table 3 on page 464 of Ravetch, J. V. and Kinet, J. P., Annu. Rev. Immunol. 9 (1991) 457-492. Non-limiting examples of in vitro assays to assess ADCC activity of a molecule of interest are described in U.S. Pat. No. 5,500,362 (see, e.g. Hellstrom, I. et al., Proc. Natl. Acad. Sci. USA 83 (1986) 7059-7063; and Hellstrom, I. et al., Proc. Natl. Acad. Sci. USA 82 (1985) 1499-1502); U.S. Pat. No. 5,821,337 (see Bruggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. C1q binding assays may also be carried out to confirm that the dimeric polypeptide is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H. et al., J. Immunol. Methods 202 (1996) 163-171; Cragg, M. S. et al., Blood 101 (2003) 1045-1052; and Cragg, M. S. and M. J. Glennie, Blood 103 (2004) 2738-2743). FcRn binding and in vivo clearance/half-life determinations can also be performed using methods known in the art (see, e.g., Petkova, S. B. et al., Int. Immunol. 18 (2006) 1759-1769).

Dimeric polypeptides with reduced effector function include those with substitution of one or more of Fc-region residues 238, 265, 269, 270, 297, 327 and 329 (U.S. Pat. No. 6,737,056). Such Fc-region variants include Fc-regions with substitutions at two or more of amino acid positions 265, 269, 270, 297 and 327, including the so-called "DANA" Fc-region mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields, R. L. et al., J. Biol. Chem. 276 (2001) 6591-6604)

In certain embodiments, a dimeric polypeptide variant comprises an Fc-region with one or more amino acid substitutions which improve ADCC, e.g., substitutions at positions 298, 333, and/or 334 of the Fc-region (EU numbering of residues).

In some embodiments, alterations are made in the Fc-region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc-region with one or more substitutions therein which improve binding of the Fc-region to FcRn. Such Fc-region variants include those with substitutions at one or more of Fc-region residues: 238, 256, 265, 272, 286, 303, 305, 307, 311, 312, 317, 340, 356, 360, 362, 376, 378, 380, 382, 413, 424 or 434, e.g., substitution of Fc-region residue 434 (U.S. Pat. No. 7,371,826).

See also Duncan, A. R. and Winter, G., Nature 322 (1988) 738-740; U.S. Pat. Nos. 5,648,260; 5,624,821; and WO 94/29351 concerning other examples of Fc-region variants.

d) Cysteine Engineered Antibody Variants

In certain embodiments, it may be desirable to create cysteine engineered dimeric polypeptides, e.g., in analogy to "thioMAbs," in which one or more residues of an antibody are substituted with cysteine residues. In particular embodiments, the substituted residues occur at accessible sites of the dimeric polypeptide. By substituting those residues with cysteine, reactive thiol groups are thereby positioned at accessible sites of the dimeric polypeptide and may be used to conjugate the dimeric polypeptide to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and 5400 (EU numbering) of the heavy chain Fc-region. Cysteine engineered dimeric polypeptides may be generated as described, e.g., in U.S. Pat. No. 7,521,541.

e) Derivatives

In certain embodiments, a dimeric polypeptide as reported herein may be further modified to contain additional non-proteinaceous moieties that are known in the art and readily available. The moieties suitable for derivatization of the dimeric polypeptide include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or non-branched. The number of polymers attached to the dimeric polypeptide may vary, and if more than one polymer is attached, they can be the same or different molecules. In general, the number and/or type of polymers used for derivatization can be determined based on considerations including, but not limited to, the particular properties or functions of the dimeric polypeptide to be improved, whether the dimeric polypeptide derivative will be used in a therapy under defined conditions, etc.

In another embodiment, conjugates of a dimeric polypeptide as reported herein and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the dimeric polypeptide-non-proteinaceous moiety are killed.

f) Heterodimerization

There exist several approaches for CH3-modifications to enforce the heterodimerization, which are well described e.g. in WO 96/27011, WO 98/050431, EP 1870459, WO 2007/110205, WO 2007/147901, WO 2009/089004, WO 2010/129304, WO 2011/90754, WO 2011/143545, WO 2012058768, WO 2013157954, WO 2013096291. Typically in all such approaches the first CH3 domain and the second CH3 domains are both engineered in a complementary manner so that each CH3 domain (or the heavy chain comprising it) cannot longer homodimerize with itself but is forced to heterodimerize with the complementary engineered other CH3 domain (so that the first and second CH3 domain heterodimerize and no homodimers between the two first or the two second CH3 domains are formed). These different approaches for improved heavy chain heterodimerization are contemplated as different alternatives in combination with the heavy-light chain modifications (VH and VL exchange/replacement in one binding arm and the introduction of substitutions of charged amino acids with opposite charges in the CH1/CL interface) in the multispecific antibodies according to the invention which reduce light chain mispairing an Bence-Jones type side products.

In one preferred embodiment of the invention (in case the multispecific antibody comprises CH3 domains in the heavy chains) the CH3 domains of said multispecific antibody according to the invention can be altered by the "knob-into-holes" technology which is described in detail with several examples in e.g. WO 96/027011, Ridgway, J. B., et al., Protein Eng. 9 (1996) 617-621; and Merchant, A. M., et al., Nat. Biotechnol. 16 (1998) 677-681; WO 98/050431. In this method the interaction surfaces of the two CH3 domains are altered to increase the heterodimerization of both heavy chains containing these two CH3 domains. Each of the two CH3 domains (of the two heavy chains) can be the "knob", while the other is the "hole". The introduction of a disulfide bridge further stabilizes the heterodimers (Merchant, A. M., et al., Nature Biotech. 16 (1998) 677-681; Atwell, S., et al., J. Mol. Biol. 270 (1997) 26-35) and increases the yield.

Thus in one embodiment of the invention said multispecific antibody (comprises a CH3 domain in each heavy chain and) is further characterized in that the first CH3 domain of the first heavy chain of the antibody under a) and the second CH3 domain of the second heavy chain of the antibody under b) each meet at an interface which comprises an original interface between the antibody CH3 domains.

wherein said interface is altered to promote the formation of the multispecific antibody, wherein the alteration is characterized in that:

i) the CH3 domain of one heavy chain is altered, so that within the original interface of the CH3 domain of one heavy chain that meets the original interface of the CH3 domain of the other heavy chain within the multispecific antibody, an amino acid residue is replaced with an amino acid residue having a larger side chain volume, thereby generating a protuberance within the interface of the CH3 domain of one heavy chain which is positionable in a cavity within the interface of the CH3 domain of the other heavy chain and ii) the CH3 domain of the other heavy chain is altered, so that within the original interface of the second CH3 domain that meets the original interface of the first CH3 domain within the multispecific antibody an amino acid residue is replaced with an amino acid residue having a smaller side chain volume, thereby generating a cavity within the interface of the second CH3 domain within which a protuberance within the interface of the first CH3 domain is positionable.

Preferably said amino acid residue having a larger side chain volume is selected from the group consisting of arginine (R), phenylalanine (F), tyrosine (Y), tryptophan (W).

Preferably said amino acid residue having a smaller side chain volume is selected from the group consisting of alanine (A), serine (S), threonine (T), valine (V).

In one aspect of the invention both CH3 domains are further altered by the introduction of cysteine (C) as amino acid in the corresponding positions of each CH3 domain such that a disulfide bridge between both CH3 domains can be formed.

In one preferred embodiment, said multispecific antibody comprises a amino acid T366W mutation in the first CH3 domain of the "knobs chain" and amino acid T366S, L368A, Y407V mutations in the second CH3 domain of the "hole chain". An additional interchain disulfide bridge between the CH3 domains can also be used (Merchant, A. M., et al., Nature Biotech. 16 (1998) 677-681) e.g. by introducing an amino acid Y349C mutation into the CH3 domain of the "hole chain" and an amino acid E356C mutation or an amino acid S354C mutation into the CH3 domain of the "knobs chain".

In one preferred embodiment, said multispecific antibody (which comprises a CH3 domain in each heavy chain) comprises amino acid S354C, T366W mutations in one of the two CH3 domains and amino acid Y349C, T366S, L368A, Y407V mutations in the other of the two CH3 domains (the additional amino acid S354C mutation in one CH3 domain and the additional amino acid Y349C mutation in the other CH3 domain forming an interchain disulfide bridge) (numbering according to Kabat).

Other techniques for CH3-modifications to enforcing the heterodimerization are contemplated as alternatives of the invention and described e.g. in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291.

In one embodiment the heterodimerization approach described in EP 1 870 459A1, can be used alternatively. This approach is based on the by the introduction of substitutions/mutations of charged amino acids with the opposite charge at specific amino acid positions of the in the CH3/CH3 domain interface between both heavy chains. One preferred embodiment for said multispecific antibody are amino acid R409D; K370E mutations in the first CH3 domain of the (of the multispecific antibody) and amino acid D399K; E357K mutations in the seconds CH3 domain of the multispecific antibody (numbering according to Kabat).

In another embodiment said multispecific antibody comprises a amino acid T366W mutation in the CH3 domain of the "knobs chain" and amino acid T366S, L368A, Y407V mutations in the CH3 domain of the "hole chain" and additionally amino acid R409D; K370E mutations in the CH3 domain of the "knobs chain" and amino acid D399K; E357K mutations in the CH3 domain of the "hole chain".

In another embodiment said multispecific antibody comprises amino acid S354C, T366W mutations in one of the two CH3 domains and amino acid Y349C, T366S, L368A, Y407V mutations in the other of the two CH3 domains or said multispecific antibody comprises amino acid Y349C, T366W mutations in one of the two CH3 domains and amino acid S354C, T366S, L368A, Y407V mutations in the other of the two CH3 domains and additionally amino acid R409D; K370E mutations in the CH3 domain of the "knobs chain" and amino acid D399K; E357K mutations in the CH3 domain of the "hole chain".

In one embodiment the heterodimerization approach described in WO2013/157953 can be used alternatively. In one embodiment a first CH3 domain comprises amino acid T366K mutation and a second CH3 domain polypeptide comprises amino acid L351D mutation. In a further embodiment the first CH3 domain comprises further amino acid L351K mutation. In a further embodiment the second CH3 domain comprises further amino acid mutation selected from Y349E, Y349D and L368E (preferably L368E).

In one embodiment the heterodimerization approach described in WO2012/058768 can be used alternatively. In one embodiment a first CH3 domain comprises amino acid L351Y, Y407A mutations and a second CH3 domain comprises amino acid T366A, K409F mutations. In a further embodiment the second CH3 domain comprises a further amino acid mutation at position T411, D399, 5400, F405, N390, or K392 e.g. selected from a) T411 N, T411 R, T411Q, T411 K, T411D, T411E or T411W, b) D399R, D399W, D399Y or D399K, c S400E, S400D, S400R, or S400K F4051, F405M, F405T, F405S, F405V or F405W N390R, N390K or N390D K392V, K392M, K392R, K392L, K392F or K392E. In a further embodiment a first CH3 domain comprises amino acid L351Y, Y407A mutations and a second CH3 domain comprises amino acid T366V, K409F mutations. In a further embodiment a first CH3 domain comprises amino acid Y407A mutations and a second CH3 domain comprises amino acid T366A, K409F mutations. In a further embodiment the second CH3 domain comprises a further amino acid K392E, T411E, D399R and S400R mutations.

In one embodiment the heterodimerization approach described in WO2011/143545 can be used alternatively e.g. with the amino acid modification at a position selected from the group consisting of 368 and 409.

In one embodiment the heterodimerization approach described in WO2011/090762 which also uses the knobs-into-holes technology described above can be used alternatively. In one embodiment a first CH3 domain comprises amino acid T366W mutations and a second CH3 domain comprises amino acid Y407A mutations. In one embodiment a first CH3 domain comprises amino acid T366Y mutations and a second CH3 domain comprises amino acid Y407T mutations.

In one embodiment the multispecific antibody is of IgG2 isotype and the heterodimerization approach described in WO2010/129304 can be used alternatively.

In one embodiment the heterodimerization approach described in WO2009/089004 can be used alternatively. In one embodiment a first CH3 domain comprises amino acid substitution of K392 or N392 with a negative-charged amino acid (e.g. glutamic acid (E), or aspartic acid (D), preferably K392D or N392D) and a second CH3 domain comprises amino acid substitution of D399, E356, D356, or E357 with a positive-charged amino acid (e.g. Lysine (K) or arginine (R), preferably D399K, E356K, D356K, or E357K and more preferably D399K and E356K. In a further embodiment the first CH3 domain further comprises amino acid substitution of K409 or R409 with a negative-charged amino acid (e.g. glutamic acid (E), or aspartic acid (D), preferably K409D or R409D). In a further embodiment the first CH3 domain further or alternatively comprises amino acid substitution of K439 and/or K370 with a negative-charged amino acid (e.g. glutamic acid (E), or aspartic acid (D)).

In one embodiment the heterodimerization approach described in WO2007/147901 can be used alternatively. In one embodiment a first CH3 domain comprises amino acid K253E, D282K, and K322D mutations and a second CH3 domain comprises amino acid D239K, E240K, and K292D mutations.

In one embodiment the heterodimerization approach described in WO2007/110205 can be used alternatively.

E. Recombinant Methods and Compositions

Antibodies may be produced using recombinant methods and compositions, e.g., as described in U.S. Pat. No. 4,816,567. In one embodiment, isolated nucleic acid(s) encoding a dimeric polypeptide as reported herein is(are) provided. Such nucleic acid may encode an amino acid sequence comprising the first polypeptide and/or an amino acid sequence comprising the second polypeptide of the dimeric polypeptide. In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the first polypeptide of the dimeric polypeptide and an amino acid sequence comprising the second polypeptide of the dimeric polypeptide, or (2) a first vector comprising a nucleic acid that encodes an amino acid sequence comprising the first polypeptide of the dimeric polypeptide and a second vector comprising a nucleic acid that encodes an amino acid sequence comprising the second polypeptide of the dimeric polypeptide. In one embodiment, the host cell is eukaryotic, e.g. a Chinese Hamster Ovary (CHO) cell or lymphoid cell (e.g., Y0, NS0, Sp20 cell). In one embodiment, a method of making a dimeric polypeptide as reported herein is provided, wherein the method comprises culturing a host cell comprising a nucleic acid encoding the dimeric polypeptide, as provided above, under conditions suitable for expression of the dimeric polypeptide, and optionally recovering the antibody from the host cell (or host cell culture medium).

For recombinant production of a dimeric polypeptide as reported herein, nucleic acid encoding a dimeric polypeptide, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the variant Fc-region polypeptide(s) and the heavy and light chains of the antibody).

Suitable host cells for cloning or expression of dimeric polypeptide-encoding vectors include prokaryotic or eukaryotic cells described herein. For example, dimeric polypeptides may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, NJ (2003), pp. 245-254, describing expression of antibody fragments in *E. coli*.). After expression, the dimeric polypeptide may be isolated from the bacterial cell paste in a soluble fraction and can be further purified.

In addition to prokaryotes, eukaryotic microbes such as filamentous fungi or yeast are suitable cloning or expression hosts for dimeric polypeptide-encoding vectors, including fungi and yeast strains whose glycosylation pathways have been "humanized" resulting in the production of a dimeric polypeptide with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated a dimeric polypeptide are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (HEK293 or 293 cells as described, e.g., in Graham, F. L., et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor (MMT 060562); TRI cells, as described, e.g., in Mather, J. P., et al., Annals N.Y. Acad. Sci. 383 (1982) 44-68; MRC 5 cells; and FS4 cells. Other useful mammalian host cell lines include Chinese hamster ovary (CHO) cells, including DHFR$^-$ CHO cells (Urlaub, G., et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, NJ (2004), pp. 255-268.

F. Combination Treatment

In certain embodiments the dimeric polypeptide as reported herein or pharmaceutical formulation as reported herein is administered alone (without an additional therapeutic agent) for the treatment of one or more ocular vascular diseases described herein.

In other embodiments the dimeric polypeptide antibody or pharmaceutical formulation as reported herein is administered in combination with one or more additional therapeutic agents or methods for the treatment of one or more vascular eye diseases described herein.

In other embodiments, the dimeric polypeptide or pharmaceutical formulation as reported herein is formulated in combination with one or more additional therapeutic agents and administered for the treatment of one or more vascular eye diseases described herein.

In certain embodiments, the combination treatments provided herein include that the dimeric polypeptide or pharmaceutical formulation as reported herein is administered sequentially with one or more additional therapeutic agents for the treatment of one or more ocular vascular diseases described herein.

The additional therapeutic agents include, but are not limited to, Tryptophanyl-tRNA synthetase (TrpRS), EyeOOl (anti-VEGF PEGylated aptamer), squalamine, RETAANE™ (anecortave acetate for depot suspension; Alcon, Inc.), Combretastatin A4 Prodrug (CA4P), MACUGEN™, MIFEPREX™ (mifepristone-ru486), subtenon triamcinolone acetonide, intravitreal crystalline triamcinolone acetonide, Prinomastat (AG3340—synthetic matrix metalloproteinase inhibitor, Pfizer), fluocinolone acetonide (including fluocinolone intraocular implant, Bausch & Lomb/Control Delivery Systems), VEGFR inhibitors (Sugen), VEGF-Trap (Regeneron/Aventis), VEGF receptor tyrosine kinase inhibitors such as 4-(4-bromo-2-fluoroanilino)-6-methoxy-7-(1-methylpiperidin-4-ylmethoxy)quinazoline (ZD6474), 4-(4-fluoro-2-methylindol-5-yloxy)-6-methoxy-7-(3-pyrrolidin-1-ylpropoxy)quinazoline (AZD2171), vatalanib (PTK787) and SU1 1248 (sunitinib), linomide, and inhibitors of integrin v.beta.3 function and angiostatin.

Other pharmaceutical therapies that can be used in combination with the dimeric polypeptide or pharmaceutical formulation as reported herein, including, but are not limited to, VISUDYNE™ with use of a non-thermal laser, PKC 412, Endovion (NeuroSearch A/S), neurotrophic factors, including by way of example Glial Derived Neurotrophic Factor and Ciliary Neurotrophic Factor, diatazem, dorzolamide, Phototrop, 9-cis-retinal, eye medication (including Echo Therapy) including phospholine iodide or echothiophate or carbonic anhydrase inhibitors, AE-941 (AEterna Laboratories, Inc.), Sirna-027 (Sima Therapeutics, Inc.), pegaptanib (NeXstar Pharmaceuticals/Gilead Sciences), neurotrophins (including, by way of example only, NT-4/5, Genentech), Candy (Acuity Pharmaceuticals), INS-37217 (Inspire Pharmaceuticals), integrin antagonists (including those from Jerini AG and Abbott Laboratories), EG-3306 (Ark Therapeutics Ltd.), BDM-E (BioDiem Ltd.), thalidomide (as used, for example, by EntreMed, Inc.), cardiotrophin-1 (Genentech), 2-methoxyestradiol (Allergan/Oculex), DL-8234 (Toray Industries), NTC-200 (Neurotech), tetrathiomolybdate (University of Michigan), LYN-002 (Lynkeus Biotech), microalgal compound (Aquasearch/Albany, Mera Pharmaceuticals), D-9120 (Celltech Group plc.), ATX-S10 (Hamamatsu Photonics), TGF-beta 2 (Genzyme/Celtrix), tyrosine kinase inhibitors (Allergan, SUGEN, Pfizer), NX-278-L (NeXstar Pharmaceuticals/Gilead Sciences), Opt-24 (OPTIS France SA), retinal cell ganglion neuroprotectants (Cogent Neurosciences), N-nitropyrazole derivatives (Texas A&M University System), KP-102 (Krenitsky Pharmaceuticals), cyclosporin A, Timited retinal translocation, photodynamic therapy, (including, by way of example only, receptor-targeted PDT, Bristol-Myers Squibb, Co.; porfimer sodium for injection with PDT; verteporfin, QLT Inc.; rostaporfin with PDT, Miravent Medical Technologies; talaporfin sodium with PDT, Nippon Petroleum; motexafin lutetium, Pharmacyclics, Inc.), antisense oligonucleotides (including, by way of example, products tested by Novagali Pharma SA and ISIS-13650, Isis Pharmaceuticals), laser photocoagulation, drusen lasering, macular hole surgery, macular translocation surgery, implantable miniature telescopes, Phi-Motion Angiography (also known as Micro-Laser Therapy and Feeder Vessel Treatment), Proton Beam Therapy, microstimulation therapy, Retinal Detachment and Vitreous Surgery, Scleral Buckle, Submacular Surgery, Transpupillary Thermotherapy, Photosystem I therapy, use of RNA interference (RNAi), extracorporeal rheopheresis (also known as membrane differential filtration and Rheotherapy), microchip implantation, stem cell therapy, gene replacement therapy, ribozyme gene therapy (including gene therapy for hypoxia response element, Oxford Biomedica; Lentipak, Genetix; PDEF gene therapy, GenVec), photoreceptor/retinal cells transplantation (including transplantable retinal epithelial cells, Diacrin, Inc.; retinal cell transplant, Cell Genesys, Inc.), and acupuncture.

Any anti-angiogenic agent can be used in combination with the dimeric polypeptide or pharmaceutical formulation as reported herein, including, but not limited to, those listed by Carmeliet and Jain (Nature 407 (2000) 249-257). In certain embodiments, the anti-angiogenic agent is another VEGF antagonist or a VEGF receptor antagonist such as VEGF variants, soluble VEGF receptor fragments, aptamers capable of blocking VEGF or VEGFR, neutralizing anti-VEGFR antibodies, low molecule weight inhibitors of VEGFR tyrosine kinases and any combinations thereof and these include anti-VEGF aptamers (e.g. Pegaptanib), soluble recombinant decoy receptors (e.g. VEGF Trap). In certain embodiments, the anti-angiogenic agent is include corticosteroids, angiostatic steroids, anecortave acetate, angiostatin, endostatin, small interfering RNA's decreasing expression of VEGFR or VEGF ligand, post-VEGFR blockade with tyrosine kinase inhibitors, MMP inhibitors, IGFBP3, SDF-1 blockers, PEDF, gamma-secretase, Delta-like ligand 4, integrin antagonists, HIF-1 alpha blockade, protein kinase CK2 blockade, and inhibition of stem cell (i.e. endothelial progenitor cell) homing to the site of neovascularization using vascular endothelial cadherin (CD-144) and stromal derived factor (SDF)-I antibodies. Small molecule RTK inhibitors targeting VEGF receptors including PTK787 can also be used. Agents that have activity against neovascularization that are not necessarily anti-VEGF compounds can also be used and include anti-inflammatory drugs, m-Tor inhibitors, rapamycin, everolismus, temsirolismus, cyclospohne, anti-TNF agents, anti-complement agents, and non-steroidal anti-inflammatory agents. Agents that are neuroprotective and can potentially reduce the progression of dry macular degeneration can also be used, such as the class of drugs called the "neurosteroids". These include drugs such as dehydroepiandrosterone (DHEA) (Brand names: Prastera® and Fidelin®), dehydroepiandrosterone sulfate, and pregnenolone sulfate. Any AMD (age-related macular degeneration) therapeutic agent can be used in combination with the dimeric polypeptide or pharmaceutical formulation as reported herein, including but not limited to verteporfin in combination with PDT, pegaptanib sodium, zinc, or an antioxidant(s), alone or in any combination.

G. Pharmaceutical Formulations

Pharmaceutical formulations of a dimeric polypeptide as reported herein are prepared by mixing such dimeric polypeptide having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US 2005/0260186 and US 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

H. Therapeutic Methods and Compositions

Any of the dimeric polypeptides as reported herein may be used in therapeutic methods.

In one aspect, a dimeric polypeptide as reported herein for use as a medicament is provided. In further aspects, a dimeric polypeptide for use in treating ocular vascular diseases is provided. In certain embodiments, a dimeric polypeptide for use in a method of treatment is provided. In certain embodiments, the invention provides a dimeric polypeptide for use in a method of treating an individual having an ocular vascular disease comprising administering to the individual an effective amount of the dimeric polypeptide as reported herein. In one such embodiment, the method further comprises administering to the individual an effective amount of at least one additional therapeutic agent, e.g., as described above in section D. In further embodiments, the invention provides a dimeric polypeptide for use in inhibiting angiogenesis in the eye. In certain embodiments, the invention provides a dimeric polypeptide for use in a method of inhibiting angiogenesis in an individual comprising administering to the individual an effective of the dimeric polypeptide to inhibit angiogenesis. An "individual" according to any of the above embodiments is in one preferred embodiment a human.

In a further aspect, the invention provides for the use of a dimeric polypeptide in the manufacture or preparation of a medicament. In one embodiment, the medicament is for treatment of an ocular vascular disease. In a further embodiment, the medicament is for use in a method of treating an ocular vascular disease comprising administering to an individual having an ocular vascular disease an effective amount of the medicament. In one such embodiment, the method further comprises administering to the individual an effective amount of at least one additional therapeutic agent, e.g., as described above. In a further embodiment, the medicament is for inhibiting angiogenesis. In a further embodiment, the medicament is for use in a method of inhibiting angiogenesis in an individual comprising administering to the individual an amount effective of the medicament to inhibit angiogenesis. An "individual" according to any of the above embodiments may be a human.

In a further aspect, the invention provides a method for treating a vascular eye disease. In one embodiment, the method comprises administering to an individual having such a vascular eye disease an effective amount of a dimeric polypeptide as reported herein. In one such embodiment, the method further comprises administering to the individual an effective amount of at least one additional therapeutic agent, as described below. An "individual" according to any of the above embodiments may be a human.

In a further aspect, the invention provides a method for inhibiting angiogenesis in the eye in an individual. In one embodiment, the method comprises administering to the individual an effective amount of a dimeric polypeptide as reported herein to inhibit angiogenesis. In one embodiment, an "individual" is a human.

In a further aspect, the invention provides pharmaceutical formulations comprising any of the dimeric polypeptides as reported herein, e.g., for use in any of the above therapeutic methods. In one embodiment, a pharmaceutical formulation comprises any of the dimeric polypeptides as reported herein and a pharmaceutically acceptable carrier. In another embodiment, a pharmaceutical formulation comprises any of the dimeric polypeptides as reported herein and at least one additional therapeutic agent, e.g., as described below.

Dimeric polypeptide as reported herein can be used either alone or in combination with other agents in a therapy. For instance, a dimeric polypeptide as reported herein may be co-administered with at least one additional therapeutic agent A dimeric polypeptide as reported herein (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Dimeric polypeptides as reported herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The dimeric polypeptide need not be, but is optionally formulated with one or more agents currently used to prevent or treat the disorder in question. The effective amount of such other agents depends on the amount of dimeric polypeptide present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a dimeric polypeptide as reported herein (when used alone or in combination with one or more other additional therapeutic agents) will depend on the type of disease to be treated, the type of dimeric polypeptide, the severity and course of the disease, whether the dimeric polypeptide is administered for preventive or therapeutic purposes, previous therapy, the patient's clinical history and response to the dimeric polypeptide, and the discretion of the attending physician. The dimeric polypeptide is suitably administered to the patient at one time or over a series of treatments. Depending on the type and severity of the disease, about 1 μg/kg to 15 mg/kg (e.g. 0.5 mg/kg-10 mg/kg) of dimeric polypeptide can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the dimeric polypeptide would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the dimeric polypeptide). An initial higher loading dose, followed by one or more lower doses may be administered. The progress of this therapy is easily monitored by conventional techniques and assays.

III. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a dimeric polypeptide as reported herein. The label or package insert indicates that the composition is used for treating the condition of choice. Moreover, the article of manufacture may comprise (a) a first container with a composition contained therein, wherein the composition comprises a dimeric polypeptide as reported herein; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate as reported herein in place of or in addition to a dimeric polypeptide as reported herein.

IV. Specific Embodiments

1. A dimeric polypeptide comprising
   a first polypeptide and a second polypeptide each comprising in N-terminal to C-terminal direction at least a portion of an immunoglobulin hinge region, which comprises one or more cysteine residues, an immunoglobulin CH2-domain and an immunoglobulin CH3-domain,
   wherein
   i) the first and the second polypeptide comprise the mutations H310A, H433A and Y436A, or
   ii) the first and the second polypeptide comprise the mutations L251D, L314D and L432D, or
   iii) the first and the second polypeptide comprise the mutations L251S, L314S and L432S, or
   iv) the first polypeptide comprises the mutations I253A, H310A and H435A and the second polypeptide comprises the mutations H310A, H433A and Y436A, or
   v) the first polypeptide comprises the mutations I253A, H310A and H435A and the second polypeptide comprises the mutations L251D, L314D and L432D, or
   vi) the first polypeptide comprises the mutations I253A, H310A and H435A and the second polypeptide comprises the mutations L251S, L314S and L432S.
2. The dimeric polypeptide according to item 1, characterized in that the dimeric polypeptide does not specifically bind to the human FcRn and does specifically bind to Staphylococcal protein A.
3. The dimeric polypeptide according to any one of items 1 to 2, characterized in that the dimeric polypeptide is a homodimeric polypeptide.

4. The dimeric polypeptide according to any one of items 1 to 2, characterized in that the dimeric polypeptide is a heterodimeric polypeptide.
5. The dimeric polypeptide according to any one of items 1 to 4, characterized in that i) the first polypeptide further comprises the mutations Y349C, T366S, L368A and Y407V and the second polypeptide comprises the mutations S354C and T366W, or ii) the first polypeptide further comprises the mutations S354C, T366S, L368A and Y407V and the second polypeptide comprises the mutations Y349C and T366W.
6. The dimeric polypeptide according to any one of items 1 to 5, characterized in that the immunoglobulin hinge region, the immunoglobulin CH2-domain and the immunoglobulin CH3-domain are of the human IgG1 subclass.
7. The dimeric polypeptide according to any one of items 1 to 6, characterized in that the first polypeptide and the second polypeptide further comprise the mutations L234A and L235A.
8. The dimeric polypeptide according to any one of items 1 to 5, characterized in that the immunoglobulin hinge region, the immunoglobulin CH2-domain and the immunoglobulin CH3-domain are of the human IgG2 subclass optionally with the mutations V234A, G237A, P238S, H268A, V309L, A330S and P331S.
9. The dimeric polypeptide according to any one of items 1 to 5, characterized in that the immunoglobulin hinge region, the immunoglobulin CH2-domain and the immunoglobulin CH3-domain are of the human IgG4 subclass.
10. The dimeric polypeptide according to any one of items 1 to 5 and 9, characterized in that the first polypeptide and the second polypeptide further comprise the mutations S228P and L235E.
11. The dimeric polypeptide according to any one of items 1 to 10, characterized in that the first polypeptide and the second polypeptide further comprise the mutation P329G.
12. The dimeric polypeptide according to any one of items 1 to 11, characterized in that the dimeric polypeptide is an Fc-region fusion polypeptide.
13. The dimeric polypeptide according to any one of items 1 to 11, characterized in that the dimeric polypeptide is an (full length) antibody.
14. The dimeric polypeptide according to any one of items 1 to 11 and 13, characterized in that the (full length) antibody is a monospecific antibody.
15. The dimeric polypeptide according to any one of items 1 to 11 and 13 to 14, characterized in that the monospecific antibody is a monovalent monospecific antibody.
16. The dimeric polypeptide according to any one of items 1 to 11 and 13 to 15, characterized in that the monospecific antibody is a bivalent monospecific antibody.
17. The dimeric polypeptide according to any one of items 1 to 11 and 13, characterized in that the (full length) antibody is a bispecific antibody.
18. The dimeric polypeptide according to any one of items 1 to 11 and 13 and 17, characterized in that the bispecific antibody is a bivalent bispecific antibody.
19. The dimeric polypeptide according to any one of items 1 to 11 and 13 and 17 to 18, characterized in that the bispecific antibody is a tetravalent bispecific antibody.
20. The dimeric polypeptide according to any one of items 1 to 11 and 13, characterized in that the (full length) antibody is a trispecific antibody.
21. The dimeric polypeptide according to any one of items 1 to 11 and 13 and 20, characterized in that the trispecific antibody is a trivalent trispecific antibody.
22. The dimeric polypeptide according to any one of items 1 to 11 and 13 and 20 to 21, characterized in that the trispecific antibody is a tetravalent trispecific antibody.
23. A dimeric polypeptide comprising
   a first polypeptide and a second polypeptide each comprising in N-terminal to C-terminal direction at least a portion of an immunoglobulin hinge region, which comprises one or more cysteine residues, an immunoglobulin CH2-domain and an immunoglobulin CH3-domain,
   wherein the first, the second or the first and the second polypeptide comprise the mutation Y436A (numbering according to the Kabat EU index numbering system).
24. The dimeric polypeptide according to item 23, characterized in that the first and the second polypeptide comprise the mutation Y436A.
25. The dimeric polypeptide according to any one of items 23 to 24, characterized in that the dimeric polypeptide does not specifically bind to the human FcRn and does specifically bind to Staphylococcal protein A.
26. The dimeric polypeptide according to any one of items 23 to 25, characterized in that the dimeric polypeptide is a homodimeric polypeptide.
27. The dimeric polypeptide according to any one of items 23 to 25, characterized in that the dimeric polypeptide is a heterodimeric polypeptide.
28. The dimeric polypeptide according to any one of items 23 to 27, characterized in that
   a) the first polypeptide further comprises the mutations Y349C, T366S, L368A and Y407V and the second polypeptide comprises the mutations S354C and T366W,
   or
   the first polypeptide further comprises the mutations S354C, T366S, L368A and Y407V and the second polypeptide comprises the mutations Y349C and T366W, and/or
   b) i) the first and the second polypeptide comprise the mutations H310A, H433A and Y436A, or
   ii) the first and the second polypeptide comprise the mutations L251D, L314D and L432D, or
   iii) the first and the second polypeptide comprise the mutations L251S, L314S and L432S, or
   iv) the first polypeptide comprises the mutations I253A, H310A and H435A and the second polypeptide comprises the mutations H310A, H433A and Y436A, or
   v) the first polypeptide comprises the mutations I253A, H310A and H435A and the second polypeptide comprises the mutations L251D, L314D and L432D, or
   vi) the first polypeptide comprises the mutations I253A, H310A and H435A and the second polypeptide comprises the mutations L251S, L314S and L432S.
29. The dimeric polypeptide according to any one of items 23 to 28, characterized in that the immunoglobulin hinge region, the immunoglobulin CH2-domain and the immunoglobulin CH3-domain are of the human IgG1 subclass.

30. The dimeric polypeptide according to any one of items 23 to 29, characterized in that the first polypeptide and the second polypeptide further comprise the mutations L234A and L235A.
31. The dimeric polypeptide according to any one of items 23 to 28, characterized in that the immunoglobulin hinge region, the immunoglobulin CH2-domain and the immunoglobulin CH3-domain are of the human IgG2 subclass optionally with the mutations V234A, G237A, P238S, H268A, V309L, A330S and P331S.
32. The dimeric polypeptide according to any one of items 23 to 28, characterized in that the immunoglobulin hinge region, the immunoglobulin CH2-domain and the immunoglobulin CH3-domain are of the human IgG4 subclass.
33. The dimeric polypeptide according to any one of items 23 to 28 and 32, characterized in that the first polypeptide and the second polypeptide further comprise the mutations S228P and L235E.
34. The dimeric polypeptide according to any one of items 23 to 33, characterized in that the first polypeptide and the second polypeptide further comprise the mutation P329G.
35. The dimeric polypeptide according to any one of items 23 to 34, characterized in that the dimeric polypeptide is an Fc-region fusion polypeptide.
36. The dimeric polypeptide according to any one of items 23 to 34, characterized in that the dimeric polypeptide is an (full length) antibody.
37. The dimeric polypeptide according to any one of items 23 to 34 and 36, characterized in that the (full length) antibody is a monospecific antibody.
38. The dimeric polypeptide according to any one of items 23 to 34 and 36 to 37, characterized in that the monospecific antibody is a monovalent monospecific antibody.
39. The dimeric polypeptide according to any one of items 23 to 34 and 36 to 38, characterized in that the monospecific antibody is a bivalent monospecific antibody.
40. The dimeric polypeptide according to any one of items 23 to 34 and 36, characterized in that the (full length) antibody is a bispecific antibody.
41. The dimeric polypeptide according to any one of items 23 to 34 and 36 and 40, characterized in that the bispecific antibody is a bivalent bispecific antibody.
42. The dimeric polypeptide according to any one of items 23 to 34 and 36 and 40 to 41, characterized in that the bispecific antibody is a tetravalent bispecific antibody.
43. The dimeric polypeptide according to any one of items 23 to 34 and 36, characterized in that the (full length) antibody is a trispecific antibody.
44. The dimeric polypeptide according to any one of items 23 to 34 and 36 and 43, characterized in that the trispecific antibody is a trivalent trispecific antibody.
45. The dimeric polypeptide according to any one of items 23 to 34 and 36 and 43 to 44, characterized in that the trispecific antibody is a tetravalent trispecific antibody.
46. A dimeric polypeptide comprising
   a first polypeptide comprising in N-terminal to C-terminal direction a first heavy chain variable domain, an immunoglobulin CH1-domain of the subclass IgG1, an immunoglobulin hinge region of the subclass IgG1, an immunoglobulin CH2-domain of the subclass IgG1 and an immunoglobulin CH3-domain of the subclass IgG1,
   a second polypeptide comprising in N-terminal to C-terminal direction a second heavy chain variable domain, an immunoglobulin CH1-domain of the subclass IgG1, an immunoglobulin hinge region of the subclass IgG1, an immunoglobulin CH2-domain of the subclass IgG1 and an immunoglobulin CH3-domain of the subclass IgG1,
   a third polypeptide comprising in N-terminal to C-terminal direction a first light chain variable domain and a light chain constant domain,
   a fourth polypeptide comprising in N-terminal to C-terminal direction a second light chain variable domain and a light chain constant domain,
   wherein the first heavy chain variable domain and the first light chain variable domain form a first binding site that specifically binds to a first antigen,
   wherein the second heavy chain variable domain and the second light chain variable domain form a second binding site that specifically binds to a second antigen,
   wherein i) the first polypeptide comprises the mutations Y349C, T366S, L368A and Y407V and the second polypeptide comprises the mutations S354C and T366W, or ii) the first polypeptide comprises the mutations S354C, T366S, L368A and Y407V and the second polypeptide comprises the mutations Y349C and T366W,
   wherein the first and the second polypeptide further comprise the mutations L234A, L235A and P329G, and
   wherein
      i) the first and the second polypeptide comprise the mutations H310A, H433A and Y436A, or
      ii) the first and the second polypeptide comprise the mutations L251D, L314D and L432D, or
      iii) the first and the second polypeptide comprise the mutations L251S, L314S and L432S, or
      iv) the first polypeptide comprises the mutations I253A, H310A and H435A and the second polypeptide comprises the mutations H310A, H433A and Y436A, or
      v) the first polypeptide comprises the mutations I253A, H310A and H435A and the second polypeptide comprises the mutations L251D, L314D and L432D, or
      vi) the first polypeptide comprises the mutations I253A, H310A and H435A and the second polypeptide comprises the mutations L251S, L314S and L432S.
47. A dimeric polypeptide comprising
   a first polypeptide comprising in N-terminal to C-terminal direction a first heavy chain variable domain, an immunoglobulin light chain constant domain, an immunoglobulin hinge region of the subclass IgG1, an immunoglobulin CH2-domain of the subclass IgG1 and an immunoglobulin CH3-domain of the subclass IgG1,
   a second polypeptide comprising in N-terminal to C-terminal direction a second heavy chain variable domain, an immunoglobulin CH1-domain of the subclass IgG1, an immunoglobulin hinge region of the subclass IgG1, an immunoglobulin CH2-domain of the subclass IgG1 and an immunoglobulin CH3-domain of the subclass IgG1, a third polypeptide comprising in N-terminal to C-terminal direction a first light chain variable domain and an immunoglobulin CH1-domain of the subclass IgG1, a fourth polypeptide comprising in N-terminal to C-terminal direction a second light chain variable domain and a light chain constant domain, wherein the first heavy chain variable domain and the first light chain variable domain form a first binding site that specifically binds to a first antigen, wherein the second heavy chain variable domain and the second light chain variable domain form a second binding site that specifically binds to a second antigen, wherein i) the first polypeptide comprises the mutations Y349C, T366S, L368A and Y407V and the second polypeptide comprises the mutations S354C and T366W, or ii) the first polypeptide comprises the mutations S354C, T366S, L368A and Y407V and the second polypeptide comprises the mutations Y349C and T366W, wherein the first and the second polypeptide further comprise the mutations L234A, L235A and P329G, and wherein i) the first and the second polypeptide comprise the mutations H310A, H433A and Y436A, or ii) the first and the second polypeptide comprise the mutations L251D, L314D and L432D, or iii) the first and the second polypeptide comprise the mutations L251S, L314S and L432S, or iv) the first polypeptide comprises the mutations I253A, H310A and H435A and the second polypeptide comprises the mutations H310A, H433A and Y436A, or v) the first polypeptide comprises the mutations I253A, H310A and H435A and the second polypeptide comprises the mutations L251D, L314D and L432D, or vi) the first polypeptide comprises the mutations I253A, H310A and H435A and the second polypeptide comprises the mutations L251S, L314S and L432S.

48. A dimeric polypeptide comprising a first polypeptide comprising in N-terminal to C-terminal direction a first heavy chain variable domain, an immunoglobulin CH1-domain of the subclass IgG4, an immunoglobulin hinge region of the subclass IgG4, an immunoglobulin CH2-domain of the subclass IgG4 and an immunoglobulin CH3-domain of the subclass IgG4, a second polypeptide comprising in N-terminal to C-terminal direction a second heavy chain variable domain, an immunoglobulin CH1-domain of the subclass IgG4, an immunoglobulin hinge region of the subclass IgG4, an immunoglobulin CH2-domain of the subclass IgG4 and an immunoglobulin CH3-domain of the subclass IgG4, a third polypeptide comprising in N-terminal to C-terminal direction a first light chain variable domain and a light chain constant domain, a fourth polypeptide comprising in N-terminal to C-terminal direction a second light chain variable domain and a light chain constant domain, wherein the first heavy chain variable domain and the first light chain variable domain form a first binding site that specifically binds to a first antigen, wherein the second heavy chain variable domain and the second light chain variable domain form a second binding site that specifically binds to a second antigen, wherein i) the first polypeptide comprises the mutations Y349C, T366S, L368A and Y407V and the second polypeptide comprises the mutations S354C and T366W, or ii) the first polypeptide comprises the mutations S354C, T366S, L368A and Y407V and the second polypeptide comprises the mutations Y349C and T366W, wherein the first and the second polypeptide further comprise the mutations S228P, L235E and P329G, and wherein i) the first and the second polypeptide comprise the mutations H310A, H433A and Y436A, or ii) the first and the second polypeptide comprise the mutations L251D, L314D and L432D, or iii) the first and the second polypeptide comprise the mutations L251S, L314S and L432S, or iv) the first polypeptide comprises the mutations I253A, H310A and H435A and the second polypeptide comprises the mutations H310A, H433A and Y436A, or v) the first polypeptide comprises the mutations I253A, H310A and H435A and the second polypeptide comprises the mutations L251D, L314D and L432D, or vi) the first polypeptide comprises the mutations I253A, H310A and H435A and the second polypeptide comprises the mutations L251S, L314S and L432S.

49. A dimeric polypeptide comprising a first polypeptide comprising in N-terminal to C-terminal direction a first heavy chain variable domain, an immunoglobulin light chain constant domain, an immunoglobulin hinge region of the subclass IgG4, an immunoglobulin CH2-domain of the subclass IgG4 and an immunoglobulin CH3-domain of the subclass IgG4, a second polypeptide comprising in N-terminal to C-terminal direction a second heavy chain variable domain, an immunoglobulin CH1-domain of the subclass IgG4, an immunoglobulin hinge region of the subclass IgG4, an immunoglobulin CH2-domain of the subclass IgG4 and an immunoglobulin CH3-domain of the subclass IgG4, a third polypeptide comprising in N-terminal to C-terminal direction a first light chain variable domain and an immunoglobulin CH1-domain of the subclass IgG4, a fourth polypeptide comprising in N-terminal to C-terminal direction a second light chain variable domain and a light chain constant domain, wherein the first heavy chain variable domain and the first light chain variable domain form a first binding site that specifically binds to a first antigen, wherein the second heavy chain variable domain and the second light chain variable domain form a second binding site that specifically binds to a second antigen, wherein i) the first polypeptide comprises the mutations Y349C, T366S, L368A and Y407V and the second polypeptide comprises the mutations S354C and T366W, or ii) the first polypeptide comprises the mutations S354C, T366S, L368A and Y407V and the second polypeptide comprises the mutations Y349C and T366W, wherein the first and the second polypeptide further comprise the mutations S228P, L235E and P329G, and wherein i) the first and the second polypeptide comprise the mutations H310A, H433A and Y436A, or ii) the first and the second polypeptide comprise the mutations L251D, L314D and L432D, or iii) the first and the second polypeptide comprise the mutations L251S, L314S and L432S, or iv) the first polypeptide comprises the mutations I253A, H310A and H435A and the second polypeptide comprises the mutations H310A, H433A and Y436A, or v) the first polypeptide comprises the mutations I253A, H310A and H435A and the second polypeptide comprises the mutations L251D, L314D and L432D, or vi) the first polypeptide comprises the mutations I253A, H310A and H435A and the second polypeptide comprises the mutations L251S, L314S and L432S.

50. A dimeric polypeptide comprising a first polypeptide comprising in N-terminal to C-terminal direction a first heavy chain variable domain, an immunoglobulin CH1-domain of the subclass IgG1, an immunoglobulin hinge region of the subclass IgG1, an immunoglobulin CH2-domain of the subclass IgG1, an immunoglobulin CH3-domain of the subclass IgG1, a peptidic linker and a first scFv, a second polypeptide comprising in N-terminal to C-terminal direction a second heavy chain variable domain, an immunoglobulin CH1-domain of the subclass IgG1, an immunoglobulin hinge region of the subclass IgG1, an immunoglobulin CH2-domain of the subclass IgG1, an immunoglobulin CH3-domain of the subclass IgG1, a peptidic linker and a second scFv, a third polypeptide comprising in N-terminal to C-terminal direction a first light chain variable domain and a light chain constant domain, a fourth polypeptide comprising in N-terminal to C-terminal direction a second light chain variable domain and a light chain constant domain, wherein the first heavy chain variable domain and the first light chain variable domain form a first binding site that specifically binds to a first antigen, the second heavy chain variable domain and the second light chain variable domain form a second binding site that specifically binds to a first antigen, the first and the second scFv specifically bind to a second antigen, wherein i) the first polypeptide comprises the mutations Y349C, T366S, L368A and Y407V and the second polypeptide comprises the mutations S354C and T366W, or ii) the first polypeptide comprises the mutations S354C, T366S, L368A and Y407V and the second polypeptide comprises the mutations Y349C and T366W, wherein the first and the second polypeptide further comprise the mutations L234A, L235A and P329G, and wherein i) the first and the second polypeptide comprise the mutations H310A, H433A and Y436A, or ii) the first and the second polypeptide comprise the mutations L251D, L314D and L432D, or iii) the first and the second polypeptide comprise the mutations L251S, L314S and L432S, or iv) the first polypeptide comprises the mutations I253A, H310A and H435A and the second polypeptide comprises the mutations H310A, H433A and Y436A, or v) the first polypeptide comprises the mutations I253A, H310A and H435A and the second polypeptide comprises the mutations L251D, L314D and L432D, or vi) the first polypeptide comprises the mutations I253A, H310A and H435A and the second polypeptide comprises the mutations L251S, L314S and L432S.

51. A dimeric polypeptide comprising a first polypeptide comprising in N-terminal to C-terminal direction a first heavy chain variable domain, an immunoglobulin light chain constant domain, an immunoglobulin hinge region of the subclass IgG1, an immunoglobulin CH2-domain of the subclass IgG1, an immunoglobulin CH3-domain of the subclass IgG1, a peptidic linker and a first scFv, a second polypeptide comprising in N-terminal to C-terminal direction a second heavy chain variable domain, an immunoglobulin CH1-domain of the subclass IgG1, an immunoglobulin hinge region of the subclass IgG1, an immunoglobulin CH2-domain of the subclass IgG1, an immunoglobulin CH3-domain of the subclass IgG1, a peptidic linker and a second scFv, a third polypeptide comprising in N-terminal to C-terminal direction a first light chain variable domain and an immunoglobulin CH1-domain of the subclass IgG1, a fourth polypeptide comprising in N-terminal to C-terminal direction a second light chain variable domain and a light chain constant domain, wherein the first heavy chain variable domain and the first light chain variable domain form a first binding site that specifically binds to a first antigen, the second heavy chain variable domain and the second light chain variable domain form a second binding site that specifically binds to a first antigen, and the first and the second scFv specifically bind to a second antigen, wherein i) the first polypeptide comprises the mutations Y349C, T366S, L368A and Y407V and the second polypeptide comprises the mutations S354C and T366W, or ii) the first polypeptide comprises the mutations S354C, T366S, L368A and Y407V and the second polypeptide comprises the mutations Y349C and T366W, wherein the first and the second polypeptide further comprise the mutations L234A, L235A and P329G, and wherein i) the first and the second polypeptide comprise the mutations H310A, H433A and Y436A, or ii) the first and the second polypeptide comprise the mutations L251D, L314D and L432D, or iii) the first and the second polypeptide comprise the mutations L251S, L314S and L432S, or iv) the first polypeptide comprises the mutations I253A, H310A and H435A and the second polypeptide comprises the mutations H310A, H433A and Y436A, or v) the first polypeptide comprises the mutations I253A, H310A and H435A and the second polypeptide comprises the mutations L251D, L314D and L432D, or vi) the first polypeptide comprises the mutations I253A, H310A and H435A and the second polypeptide comprises the mutations L251S, L314S and L432S.

52. A method for producing a dimeric polypeptide according to any one of items 1 to 51 comprising the following steps:

a) cultivating a mammalian cell comprising one or more nucleic acids encoding the dimeric polypeptide according to any one of items 1 to 51, b) recovering the dimeric polypeptide from the cultivation medium, and c) purifying the dimeric polypeptide with a protein A affinity chromatography.

53. Use of the mutation Y436A for increasing the binding of a dimeric polypeptide to protein A.

54. Use of the mutations H310A, H433A and Y436A for separating heterodimeric polypeptides from homodimeric polypeptides.

55. Use of the mutations L251D, L314D, L432D, or the mutations L251S, L314S, L432S for separating heterodimeric polypeptides from homodimeric polypeptides.

56. Use of the mutations I253A, H310A and H435A in a first polypeptide in combination with the mutations H310A, H433A and Y436A in a second polypeptide for separating heterodimeric polypeptides comprising the first and the second polypeptide from homodimeric polypeptides.

57. Use of the mutations I253A, H310A and H435A in a first polypeptide in combination with the mutations L251D, L314D, L432D or the mutations L251S, L314S, L432S in a second polypeptide for separating heterodimeric polypeptides comprising the first and the second polypeptide from homodimeric polypeptides.

58. The use according to any one of items 53 to 57, characterized in that i) the first polypeptide further comprises the mutations Y349C, T366S, L368A and Y407V and the second polypeptide further comprises the mutations S354C and T366W, or ii) the first polypeptide comprises the mutations S354C, T366S, L368A and Y407V and the second polypeptide comprises the mutations Y349C and T366W.

59. A method of treatment of a patient suffering from ocular vascular diseases by administering a dimeric polypeptide according to any one of items 1 to 51 to a patient in the need of such treatment.

60. A dimeric polypeptide according to any one of items 1 to 51 for intravitreal application.

61. A dimeric polypeptide according to any one of items 1 to 51 for the treatment of vascular eye diseases.

62. A pharmaceutical formulation comprising a dimeric polypeptide according to any one of items 1 to 51 and optionally a pharmaceutically acceptable carrier.

63. Use of a dimeric polypeptide according to any one of items 1 to 51 for the transport of a soluble receptor ligand from the eye over the blood-ocular-barrier into the blood circulation.

64. Use of a dimeric polypeptide according to any one of items 1 to 51 for the removal of one or more soluble receptor ligands from the eye.

65. Use of a dimeric polypeptide according to any one of items 1 to 51 for the treatment of eye diseases, especially of ocular vascular diseases.

66. Use of a dimeric polypeptide according to any one of items 1 to 51 for the transport of one or more soluble receptor ligands from the intravitreal space to the blood circulation.

67. A dimeric polypeptide according to any one of items 1 to 51 for use in treating an eye disease.

68. A dimeric polypeptide according to any one of items 1 to 51 for use in the transport of a soluble receptor ligand from the eye over the blood-ocular-barrier into the blood circulation.

69. A dimeric polypeptide according to any one of items 1 to 51 for use in the removal of one or more soluble receptor ligands from the eye.

70. A dimeric polypeptide according to any one of items 1 to 51 for use in treating eye diseases, especially ocular vascular diseases.

71. A dimeric polypeptide according to any one of items 1 to 51 for use in the transport of one or more soluble receptor ligands from the intravitreal space to the blood circulation.

72. A method of treating an individual having an ocular vascular disease comprising administering to the individual an effective amount of a dimeric polypeptide according to any one of items 1 to 51.

73. A method for transporting a soluble receptor ligand from the eye over the blood-ocular-barrier into the blood circulation in an individual comprising administering to the individual an effective amount of a dimeric polypeptide according to any one of items 1 to 51 to transport a soluble receptor ligand from the eye over the blood-ocular-barrier into the blood circulation.

74. A method the removal of one or more soluble receptor ligands from the eye in an individual comprising administering to the individual an effective amount of a dimeric polypeptide according to any one of items 1 to 51 to remove one or more soluble receptor ligands from the eye.

75. A method for the transport of one or more soluble receptor ligands from the intravitreal space to the blood circulation in an individual comprising administering to the individual an effective amount of a dimeric polypeptide according to any one of items 1 to 51 to transport of one or more soluble receptor ligands from the intravitreal space to the blood circulation.

76. A method for transporting a soluble receptor ligand from the intravitreal space or the eye over the blood-ocular-barrier into the blood circulation in an individual comprising administering to the individual an effective amount of a dimeric polypeptide according to any one of items 1 to 51 to transport a soluble receptor ligand from the eye over the blood-ocular-barrier into the blood circulation.

V. Examples

The following are examples of methods and compositions of the invention. It is understood that various other embodiments may be practiced, given the general description provided above.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Methods

Electrospray Ionization Mass Spectrometry (ESI-MS)

Protein aliquots (50 μg) were deglycosylated by adding 0.5 μL N-Glycanase plus (Roche) and sodium phosphate buffer (0.1 M, pH 7.1) to obtain a final sample volume of 115 μL. The mixture was incubated at 37° C. for 18 h. Afterwards for reduction and denaturing 60 μL 0.5 M TCEP (Pierce) in 4 M guanidine*HCl (Pierce) and 50 μL 8 M guanidine*HCl were added. The mixture was incubated at 37° C. for 30 min. Samples were desalted by size exclusion chromatography (Sepharose G-25, isocratic, 40% acetonitrile with 2% formic acid). ESI mass spectra (+ve) were recorded on a Q-TOF instrument (maXis, Bruker) equipped with a nano ESI source (TriVersa NanoMate, Advion). MS parameter settings were as follows: Transfer: Funnel RF, 400 Vpp; ISCID Energy, 0 eV; Multipole RF, 400 Vpp; Quadrupole: Ion Energy, 4.0 eV; Low Mass, 600 m/z; Source: Dry Gas, 8 L/min; Dry Gas Temperature, 160° C.; Collision Cell: Collision Energy, 10 eV; Collision RF: 2000 Vpp; Ion Cooler: Ion Cooler RF, 300 Vpp; Transfer Time: 120 μs; Pre Puls Storage, 10 μs; scan range m/z 600 to 2000. For data evaluation in-house developed software (MassAnalyzer) was used.

FcRn Surface Plasmon Resonance (SPR) Analysis

The binding properties of wild-type antibody and the mutants to FcRn were analyzed by surface plasmon resonance (SPR) technology using a BIAcore T100 instrument (BIAcore AB, Uppsala, Sweden). This system is well established for the study of molecular interactions. It allows a continuous real-time monitoring of ligand/analyte bindings and thus the determination of kinetic parameters in various assay settings. SPR-technology is based on the measurement of the refractive index close to the surface of a gold coated biosensor chip. Changes in the refractive index indicate mass changes on the surface caused by the interaction of immobilized ligand with analyte injected in solution. If molecules bind to an immobilized ligand on the surface the mass increases, in case of dissociation the mass decreases. In the current assay, the FcRn receptor was immobilized onto a BIAcore CM5-biosensor chip (GE Healthcare Bioscience, Uppsala, Sweden) via amine coupling to a level of 400 Response units (RU). The assay was carried out at room temperature with PBS, 0.05% Tween20 pH 6.0 (GE Healthcare Bioscience) as running and dilution buffer. 200 nM of samples were injected at a flow rate of 50 μL/min at room temperature. Association time was 180 sec., dissociation phase took 360 sec. Regeneration of the chip surface was reached by a short injection of HBS-P, pH 8.0. Evaluation of SPR-data was performed by comparison of the biological response signal height at 180 sec. after injection and at 300 sec. after injection. The corresponding parameters are the RU max level (180 sec. after injection) and late stability (300 sec. after end of injection).

Protein A Surface Plasmon Resonance (SPR) Analysis

The assay is based on surface plasmon resonance spectroscopy. Protein A is immobilized onto the surface of a SPR biosensor. By injecting the sample into the flow cells of the SPR spectrometer it forms a complex with the immobilized protein A resulting in an increasing mass on the sensor chip surface, and therefore to a higher response (as 1 RU is defined as 1 pg/mm$^2$). Afterwards the sensor chip is regenerated by dissolving the sample-protein A-complex. The gained responses are then evaluated for the signal high in response units (RU) and the dissociation behavior Around 3500 response units (RU) of protein A (20 μg/mL) were coupled onto a CMS chip (GE Healthcare) at pH 4.0 by using the amine coupling kit of GE Healthcare.

The sample and system buffer was HBS-P+(0.01 M HEPES, 0.15 M NaCl, 0.005% Surfactant P20 Sterile-filtered, pH 7.4). Flow cell temperature was set to 25° C. and sample compartment temperature to 12° C. The system was primed with running buffer. Then, a 5 nM solutions of the sample constructs were injected for 120 seconds with a flow rate of 30 μL/min, followed by a 300 seconds dissociation phase. Then the sensor chip surface was regenerated by two 30 seconds long injections of Glycine-HCl pH 1.5 at a flow rate of 30 μL/min. Each sample was measured as a triplicate.

Bispecific Antibodies and their Respective Sequences

| Description | Sequences |
|---|---|
| anti-VEGF/ANG2 CrossMab IgG1 with IHH-AAA mutations | SEQ ID NO: 34, SEQ ID NO: 35, SEQ ID NO: 36, SEQ ID NO: 37 |
| anti-VEGF/ANG2 CrossMab IgG1 wild type (without IHH-AAA mutations) | SEQ ID NO: 52, SEQ ID NO: 53, SEQ ID NO: 54, SEQ ID NO: 55 |
| anti-VEGF/ANG2 CrossMab IgG1 with IHH-AAA mutations and P329G LALA mutations | SEQ ID NO: 38, SEQ ID NO: 39, SEQ ID NO: 40, SEQ ID NO: 41 |
| anti-VEGF/ANG2 CrossMab IgG1 with P329G LALA mutations only (without IHH-AAA mutations) | SEQ ID NO: 56, SEQ ID NO: 57, SEQ ID NO: 58, SEQ ID NO: 59 |
| anti-VEGF/ANG2 CrossMab IgG4 with IHH-AAA mutations and with SPLE mutations | SEQ ID NO: 42, SEQ ID NO: 43, SEQ ID NO: 44, SEQ ID NO: 45 |
| anti-VEGF/ANG2 OAscFab IgG1 with IHH-AAA mutations | SEQ ID NO: 46, SEQ ID NO: 47, SEQ ID NO: 48 |
| <VEGF-ANG-2> OAscFab IgG4 with IHH-AAA mutations and with SPLE mutations | SEQ ID NO: 49, SEQ ID NO: 50, SEQ ID NO: 51 |
| anti-VEGF/ANG2 CrossMab IgG1 with HHY-AAA mutations | SEQ ID NO: 102, SEQ ID NO: 103, SEQ ID NO: 36, SEQ ID NO: 37 |
| anti-VEGF/ANG2 CrossMab IgG1 with HHY-AAA mutations and P329G LALA mutations | SEQ ID NO: 104, SEQ ID NO: 105, SEQ ID NO: 36, SEQ ID NO: 37 |
| anti-VEGF/ANG2 CrossMab IgG4 with HHY-AAA mutations and with SPLE mutations | SEQ ID NO: 106, SEQ ID NO: 107, SEQ ID NO: 58, SEQ ID NO: 59 |
| <VEGF-ANG-2> OAscFab IgG1 with HHY-AAA mutations | SEQ ID NO: 108, SEQ ID NO: 109, SEQ ID NO: 48 |
| <VEGF-ANG-2> OAscFab IgG4 with HHY-AAA mutations and with SPLE mutations | SEQ ID NO: 110, SEQ ID NO: 111, SEQ ID NO: 51 |

The term "with (the) mutation IHH-AAA" as used herein refers the combination of the mutations I253A (Ile253Ala), H310A (His310Ala), and H435A (His435Ala) in a constant heavy chain region of IgG1 or IgG4 subclass (numbering according to the Kabat EU index numbering system), the term "with (the) mutation HHY-AAA" as used herein refers the combination of the mutations H310A (His310Ala), H433A (His433Ala) and Y436A (Tyr436Ala) in a constant heavy chain region of IgG1 or IgG4 subclass (numbering according to the Kabat EU index numbering system), the term "with (the) mutation P329G LALA" as used herein refers to the combination of the mutations L234A (Leu234Ala), L235A (Leu235Ala) and P329G (Pro329Gly) in a constant heavy chain region of IgG1 subclass (numbering according to the Kabat EU index numbering system), and the term "with (the) mutation SPLE" as used herein refers to the combination of the mutations S228P (Ser228Pro) and L235E (Leu235Glu) in a constant heavy chain region of IgG4 subclass (numbering according to the Kabat EU index numbering system).

| Description | Sequences |
|---|---|
| <IGF-1R> IgG1 wt | SEQ ID NO: 88 |
| | SEQ ID NO: 89 |
| <IGF-1R> IgG1 with | SEQ ID NO: 88 |
| I253A, H310A, H435A | SEQ ID NO: 90 |
| <IGF-1R> IgG1 with | SEQ ID NO: 88 |
| M252Y, S254T, T256E | SEQ ID NO: 91 |
| <IgF-1R> IgG1 wt, KiH | SEQ ID NO: 88 |
| | SEQ ID NO: 92 |
| | SEQ ID NO: 93 |
| <IgF-1R> IgG1 knob wt, | SEQ ID NO: 88 |
| hole I253A, H310A, | SEQ ID NO: 94 |
| H435A | SEQ ID NO: 95 |
| <IGF-1R> IgG1 knob wt, | SEQ ID NO: 88 |
| hole H310A, H433A, | SEQ ID NO: 96 |
| Y436A | SEQ ID NO: 97 |
| <IGF-1R> IgG1 knob wt, | SEQ ID NO: 88 |
| hole M252Y, S254T, | SEQ ID NO: 98 |
| T256E | SEQ ID NO: 99 |
| <IGF-1R> IgG1 knob wt, | SEQ ID NO: 88 |
| hole L251D, L314D, | SEQ ID NO: 100 |
| L432D | SEQ ID NO: 101 |
| <IGF-1R> IgG1 with | SEQ ID NO: 88 |
| H310A, H433A, Y436A | SEQ ID NO: 112 |

General

General information regarding the nucleotide sequences of human immunoglobulin light and heavy chains is given in: Kabat, E. A., et al., Sequences of Proteins of Immunological Interest, 5th ed., Public Health Service, National Institutes of Health, Bethesda, MD (1991). Amino acid residues of antibody chains are numbered and referred to according to EU numbering (Edelman, G. M., et al., Proc. Natl. Acad. Sci. USA 63 (1969) 78-85; Kabat, E. A., et al., Sequences of Proteins of Immunological Interest, 5th ed., Public Health Service, National Institutes of Health, Bethesda, MD (1991)).

Recombinant DNA Techniques

Standard methods were used to manipulate DNA as described in Sambrook, J. et al., Molecular Cloning: A laboratory manual; Cold Spring Harbor Laboratory Press, Cold Spring Harbor, New York (1989). The molecular biological reagents were used according to the manufacturer's instructions.

Gene Synthesis

Desired gene segments were ordered according to given specifications at Geneart (Regensburg, Germany).

DNA Sequence Determination

DNA sequences were determined by double strand sequencing performed at MediGenomix GmbH (Martinsried, Germany) or SequiServe GmbH (Vaterstetten, Germany).

DNA and Protein Sequence Analysis and Sequence Data Management

The GCG's (Genetics Computer Group, Madison, Wisconsin) software package version 10.2 and Infomax's Vector NT1 Advance suite version 8.0 was used for sequence creation, mapping, analysis, annotation and illustration.

Expression Vectors

For the expression of the described antibodies expression vectors for transient expression (e.g. in HEK293-F cells) based either on a cDNA organization with or without a CMV-Intron A promoter or on a genomic organization with a CMV promoter were used.

Beside the antibody expression cassette the vectors contained:

- an origin of replication which allows replication of this vector in *E. coli,*
- a ß-lactamase gene which confers ampicillin resistance in *E. coli*., and
- the dihydrofolate reductase gene from *Mus musculus* as a selectable marker in eukaryotic cells.

The transcription unit of the antibody gene was composed of the following elements:

- unique restriction site(s) at the 5' end,
- the immediate early enhancer and promoter from the human cytomegalovirus,
- in the case of the cDNA organization followed by the Intron A sequence,
- a 5'-untranslated region of a human immunoglobulin gene,
- a nucleic acid encoding an immunoglobulin heavy chain signal sequence,
- a nucleic acid encoding the human antibody chain (wild-type or with domain exchange) either as cDNA or in genomic organization with the immunoglobulin exon-intron organization,
- a 3' non-translated region with a polyadenylation signal sequence, and
- unique restriction site(s) at the 3' end.

The nucleic acids encoding the antibody chains were generated by PCR and/or gene synthesis and assembled by known recombinant methods and techniques by connection of the according nucleic acid segments e.g. using unique restriction sites in the respective vectors. The subcloned nucleic acid sequences were verified by DNA sequencing. For transient transfections larger quantities of the vectors were prepared by vector preparation from transformed *E. coli* cultures (Nucleobond AX, Macherey-Nagel).

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

The bispecific antibodies were expressed by transient co-transfection of the respective expression vectors in HEK29-F cells growing in suspension as described below.

Example 1

Expression and Purification

Transient Transfections in HEK293-F System

The monospecific and bispecific antibodies were generated by transient transfection with the respective vectors (e.g. encoding the heavy and modified heavy chain, as well as the corresponding light and modified light chain) using the HEK293-F system (Invitrogen) according to the manufacturer's instruction. Briefly, HEK293-F cells (Invitrogen) growing in suspension either in a shake flask or in a stirred fermenter in serum-free FreeStyle™ 293 expression medium (Invitrogen) were transfected with a mix of the respective expression vectors and 293Fectin™ or fectin (Invitrogen). For 2 L shake flask (Corning) HEK293-F cells were seeded at a density of 1*$10^6$ cells/mL in 600 mL and incubated at 120 rpm, 8% $CO_2$. The day after the cells were transfected at a cell density of approx. 1.5*$10^6$ cells/mL with approx. 42 mL mix of A) 20 mL Opti-MEM (Invitrogen) with 600 μg total vector DNA (1 μg/mL) encoding the heavy or modified heavy chain, respectively and the corresponding light chain in an equimolar ratio and B) 20 ml Opti-MEM with 1.2 mL 293 fectin or fectin (2 μL/mL). According to the glucose consumption glucose solution was added during the course of the fermentation. The supernatant containing the secreted antibody was harvested after 5-10 days and antibodies were either directly purified from the supernatant or the supernatant was frozen and stored.

Purification

Bispecific antibodies were purified from cell culture supernatants by affinity chromatography using MabSelect-Sure-Sepharose™ (for non-IHH-AAA mutants) (GE Healthcare, Sweden) or KappaSelect-Agarose (for IHH-AAA mutants) (GE Healthcare, Sweden), hydrophobic interaction chromatography using butyl-Sepharose (GE Healthcare, Sweden) and Superdex 200 size exclusion (GE Healthcare, Sweden) chromatography.

Briefly, sterile filtered cell culture supernatants were captured on a MabSelectSuRe resin equilibrated (non-IHH-AAA mutations and wild-type antibodies) with PBS buffer (10 mM $Na_2HPO_4$, 1 mM $KH_2PO_4$, 137 mM NaCl and 2.7 mM KCl, pH 7.4), washed with equilibration buffer and eluted with 25 mM sodium citrate at pH 3.0. The IHH-AAA mutants were captured on a KappaSelect resin equilibrated with 25 mM Tris, 50 mM NaCl, pH 7.2, washed with equilibration buffer and eluted with 25 mM sodium citrate pH 2.9. The eluted antibody fractions were pooled and neutralized with 2 M Tris, pH 9.0. The antibody pools were prepared for hydrophobic interaction chromatography by adding 1.6 M ammonium sulfate solution to a final concentration of 0.8 M ammonium sulfate and the pH adjusted to pH 5.0 using acetic acid. After equilibration of the butyl-Sepharose resin with 35 mM sodium acetate, 0.8 M ammonium sulfate, pH 5.0, the antibodies were applied to the resin, washed with equilibration buffer and eluted with a linear gradient to 35 mM sodium acetate pH 5.0. The (monospecific or bispecific) antibody containing fractions were pooled and further purified by size exclusion chromatography using a Superdex 200 26/60 GL (GE Healthcare, Sweden) column equilibrated with 20 mM histidine, 140 mM NaCl, pH 6.0. The (monospecific or bispecific) antibody containing fractions were pooled, concentrated to the required concentration using Vivaspin ultrafiltration devices (Sartorius Stedim Biotech S. A., France) and stored at −80° C.

TABLE

Yields of bispecific <VEGF-ANG-2> antibodies

| | VEGF/ANG2-0015 (without IHH-AAA mutation) | VEGF/ANG2-0016 (with IHH-AAA mutation) | VEGF/ANG2-0121 (with HHY-AAA mutation) |
|---|---|---|---|
| titer supernatant | 64 μg/mL, (2 L = 128 mg) | n.a. (2 L scale) | 60.8 μg/mL (2 L = 121.60 mg) |
| protein A (MabSelectSure) | 118 mg (~70% monomer) | n.a. | 100.5 mg (pool1 + pool2) |
| Kappa Select | n.a. | 117 mg (~83% monomer) | n.a. |
| Butyl Sepharose | 60 mg | 57 mg | 49 mg |
| SEC | 35 mg (>95% monomer) | 38 mg (>95% monomer) | 32.4 mg (>95% monomer) |

Purity and antibody integrity were analyzed after each purification step by CE-SDS using microfluidic Labchip technology (Caliper Life Science, USA). Five μL of protein solution was prepared for CE-SDS analysis using the HT Protein Express Reagent Kit according manufacturer's instructions and analyzed on Labchip GXII system using a HT Protein Express Chip. Data were analyzed using Labchip GX Software.

TABLE

Removal of typical side products by different sequential purification steps determined by CE-SDS.

| | VEGF/ANG2-0015 | | | | | | VEGF/ANG2-0016 | | | | | |
|---|---|---|---|---|---|---|---|---|---|---|---|---|
| | % peak area* * analysis: CE-SDS (Caliper Labchip GXII) | | | | | | | | | | | |
| purification step | mAb | ¾ Ab | (HC)2 | ½ Ab | (LC)2 | LC | mAb | ¾ Ab | (HC)2 | ½ Ab | (LC)2 | LC |
| MAb Select Sure | 55.7 | 19 | 10.6 | 9.8 | 3.5 | 0.9 | | | — | | | |
| Kappa Select | | | — | | | | 63 | 13.4 | 3.5 | 6.1 | 5.8 | 7.4 |
| Butyl-Sepharose | 81.4 | 1.9 | 2.3 | 8.2 | 3.6 | 1.8 | 76.2 | 1.3 | 0.7 | 8.3 | 7.7 | 5.8 |
| Superdex 200 SEC | 92.4 | 1.8 | 2.6 | 1.4 | 0.5 | 0.5 | 99 | 1.1 | n.d. | n.d. | n.d. | n.d. |

The aggregate content of antibody samples was analyzed by high-performance SEC using a Superdex 200 analytical size-exclusion column (GE Healthcare, Sweden) in 2×PBS (20 mM $Na_2HPO_4$, 2 mM $KH_2PO_4$, 274 mM NaCl and 5.4 mM KCl, pH 7.4) running buffer at 25° C. 25 μg protein were injected on the column at a flow rate of 0.75 mL/min and eluted isocratic over 50 minutes.

Analogously the anti-VEGF/ANG2 antibodies VEGF/ANG2-0012 and VEGF/ANG2-0201 were prepared and purified with the following yields:

| | VEGF/ANG2-0012 (with IHH-AAA mutation) | VEGF/ ANG2-0201 (without IHH-AAA mutation) |
|---|---|---|
| titer //amount | — | 36 μg/mL/72 mg |
| scale | 2.1 L | 2 L |
| protein A (MabSelectSure) | — | 66 mg (~95% monomer) |
| KappaSelect | 43 mg (~65% monomer) | — |
| Butyl Sepharose | — | 45 mg |
| SEC | 14 mg | 21 mg (>98% monomer) |
| yield hydroxylapatite | 8.5 mg (>98% monomer) | |
| total yield (recovery) | 8.5 mg (20%) | 21 mg (30%) |

Also the anti-VEGF/ANG2 bispecific antibodies anti-VEGF/ANG2 CrossMAb_IgG4 with IHH-AAA mutation and with SPLE mutation (SEQ ID NO: 42, SEQ ID NO: 43, SEQ ID NO: 44, SEQ ID NO: 45), anti-VEGF/ANG2 OAscFab IgG1 with IHH-AAA mutation (SEQ ID NO: 46, SEQ ID NO: 47, SEQ ID NO: 48), anti-VEGF/ANG2 OAscFab IgG4 with IHH-AAA mutation and with SPLE mutation (SEQ ID NO: 49, SEQ ID NO: 50, SEQ ID NO: 51), anti-VEGF/ANG2 CrossMab IgG1 with HHY-AAA mutation and P329G LALA mutation (SEQ ID NO: 90, SEQ ID NO: 91, SEQ ID NO: 40, SEQ ID NO: 41), anti-VEGF/ANG2 CrossMab IgG4 with HHY-AAA mutation and SPLE mutation (SEQ ID NO: 92, SEQ ID NO: 93, SEQ ID NO: 44, SEQ ID NO: 45), anti-VEGF/ANG2 OAscFab IgG1 with HHY-AAA mutation (SEQ ID NO: 94, SEQ ID NO: 95, SEQ ID NO: 48), and anti-VEGF/ANG2 OAscFab IgG4 with HHY-AAA mutation and SPLE mutation (SEQ ID NO: 96, SEQ ID NO: 97, SEQ ID NO: 51) and also the anti-IGF-1R monospecific antibodies anti-IGF-1R wild-type (SEQ ID NO: 88, SEQ ID NO: 89), anti-IGF-1R IgG1 with IHH-AAA mutation (SEQ ID NO: 88, SEQ ID NO: 90), anti-IGF-1R IgG1 with YTE mutation (SEQ ID NO: 88, SEQ ID NO: 91), anti-IGF-1R IgG1 wild-type with KiH mutation (SEQ ID NO: 88, SEQ ID NO: 92, SEQ ID NO: 93), anti-IGF-1R IgG1 with KiH mutation and the IHH-AAA mutation in the hole chain (SEQ ID NO: 88, SEQ ID NO: 94, SEQ ID NO: 95), anti-IGF-1R IgG1 with KiH mutation and the HHY-AAA mutation in the hole chain (SEQ ID NO: 88, SEQ ID NO: 96, SEQ ID NO: 97), anti-IGF-1R IgG1 with KiH mutation and the YTE mutation (SEQ ID NO: 88, SEQ ID NO: 98, SEQ ID NO: 99), anti-IGF-1R IgG1 with KiH mutation and the DDD mutation (SEQ ID NO: 88, SEQ ID NO: 100, SEQ ID NO: 101), and anti-IGF-1R IgG1 with HHY-AAA mutation (SEQ ID NO: 88, SEQ ID NO: 112) can be prepared and purified analogously.

Example 2

Analytics & Developability

Small-Scale DLS-Based Viscosity Measurement.

Viscosity measurement was essentially performed as described in (He, F. et al., Analytical Biochemistry 399 (2009) 141-143). Briefly, samples are concentrated to various protein concentrations in 200 mM arginine succinate, pH 5.5, before polystyrene latex beads (300 nm diameter) and Polysorbate 20 (0.02% v/v) are added. Samples are transferred into an optical 384-well plate by centrifugation through a 0.4 μm filter plate and covered with paraffin oil. The apparent diameter of the latex beads is determined by dynamic light scattering at 25° C. The viscosity of the solution can be calculated as η=η0(rh/rh,0) (η: viscosity; η0: viscosity of water; rh: apparent hydrodynamic radius of the latex beads; rh,0: hydrodynamic radius of the latex beads in water).

To allow comparison of various samples at the same concentration, viscosity-concentration data were fitted with the Mooney equation (Equation 1) (Mooney, M., Colloid. Sci., 6 (1951) 162-170; Monkos, K., Biochem. Biophys. Acta 304 (1997) 1339) and data interpolated accordingly.

$$\eta = \eta_0 \exp\left(\frac{S\Phi}{1 - K\Phi}\right) \quad \text{Equation 1}$$

(S: hydrodynamic interaction parameter of the protein; K: self-crowding factor; Φ: volume fraction of the dissolved protein)

Figure 2:
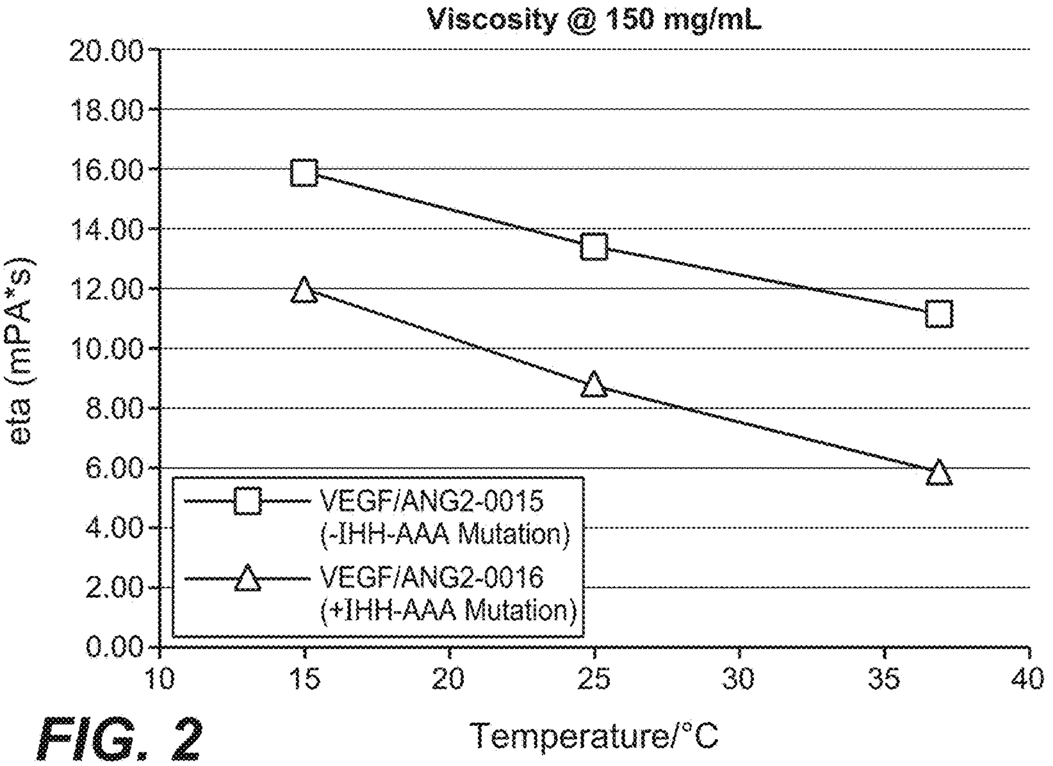
FIG. 2: Small-scale DLS-based viscosity measurement: Extrapolated viscosity at 150 mg/mL in 200 mM arginine/succinate buffer, pH 5.5 (comparison of anti-VEGF/ANG2 antibody VEGF/ANG2-0016 (with IHH-AAA mutation) with reference antibody VEGF/ANG2-0015 (without such IHH-AAA mutation)).

Results are shown in FIG. 2: VEGF/ANG2-0016 with IHH-AAA mutation in the Fc-region shows a lower viscosity at all measured temperatures compared to VEGF/ANG2-0015 without the IHH-AAA mutation in the Fc-region.

DLS Aggregation Onset Temperature

Figure 3:
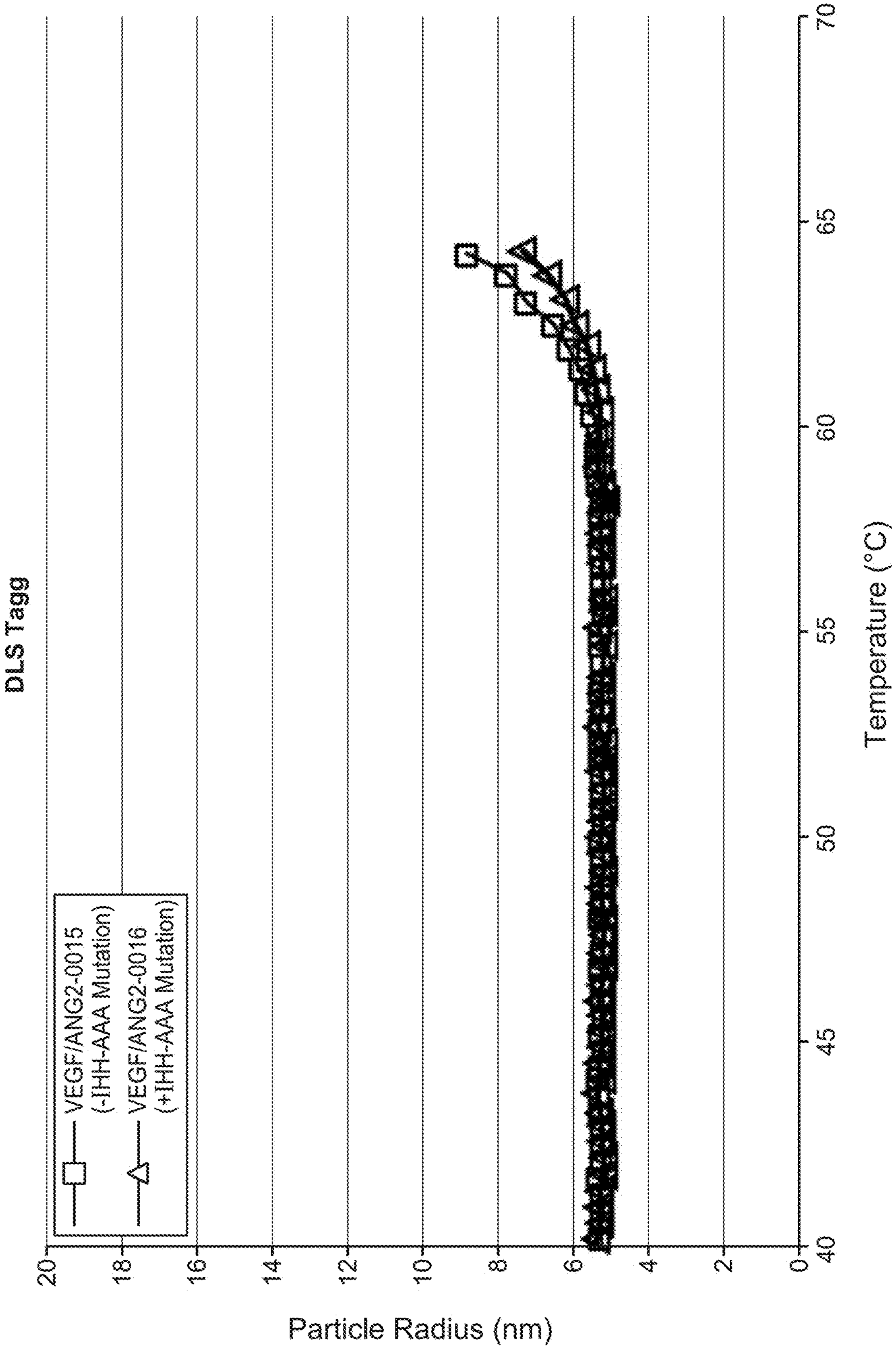
FIG. 3: DLS Aggregation depending on temperature (including DLS aggregation onset temperature) in 20 mM histidine buffer, 140 mM NaCl, pH 6.0 (comparison of anti-VEGF/ANG2 antibody as reported herein VEGF/ANG2-0016 (with IHH-AAA mutation) with reference antibody VEGF/ANG2-0015 (without such IHH-AAA mutation)).

Samples are prepared at a concentration of 1 mg/mL in 20 mM histidine/histidine hydrochloride, 140 mM NaCl, pH 6.0, transferred into an optical 384-well plate by centrifugation through a 0.4 μm filter plate and covered with paraffin oil. The hydrodynamic radius is measured repeatedly by dynamic light scattering while the samples are heated with a rate of 0.05° C./min from 25° C. to 80° C. The aggregation onset temperature is defined as the temperature at which the hydrodynamic radius starts to increase. Results are shown in FIG. 3. In FIG. 3 the aggregation of VEGF/ANG2-0015 without the IHH-AAA mutation versus VEGF/ANG2-0016 with IHH-AAA mutation in the Fc-region is shown. VEGF/ANG2-0016 showed an aggregation onset temperature of 61° C. whereas VEGF/ANG2-0015 without the IHH-AAA mutation showed an onset temperature of 60° C.

DLS Time-Course

Samples are prepared at a concentration of 1 mg/mL in 20 mM histidine/histidine hydrochloride, 140 mM NaCl, pH 6.0, transferred into an optical 384-well plate by centrifugation through a 0.4 μm filter plate and covered with paraffin oil. The hydrodynamic radius is measured repeatedly by dynamic light scattering while the samples are kept at a constant temperature of 50° C. for up to 145 hours. In this experiment, aggregation tendencies of the native, unfolded protein at elevated temperature would lead to an increase of the average particle diameter over time. This DLS-based method is very sensitive for aggregates because these contribute over-proportionally to the scattered light intensity. Even after 145 hours at 50° C. (a temperature close to the aggregation-onset temperature, see above), an average particle diameter increase of only less than 0.5 nm was found for both VEGF/ANG2-0015 and VEGF/ANG2-0016.

Seven Day Storage at 40° C. at 100 mg/mL

Figure 4:
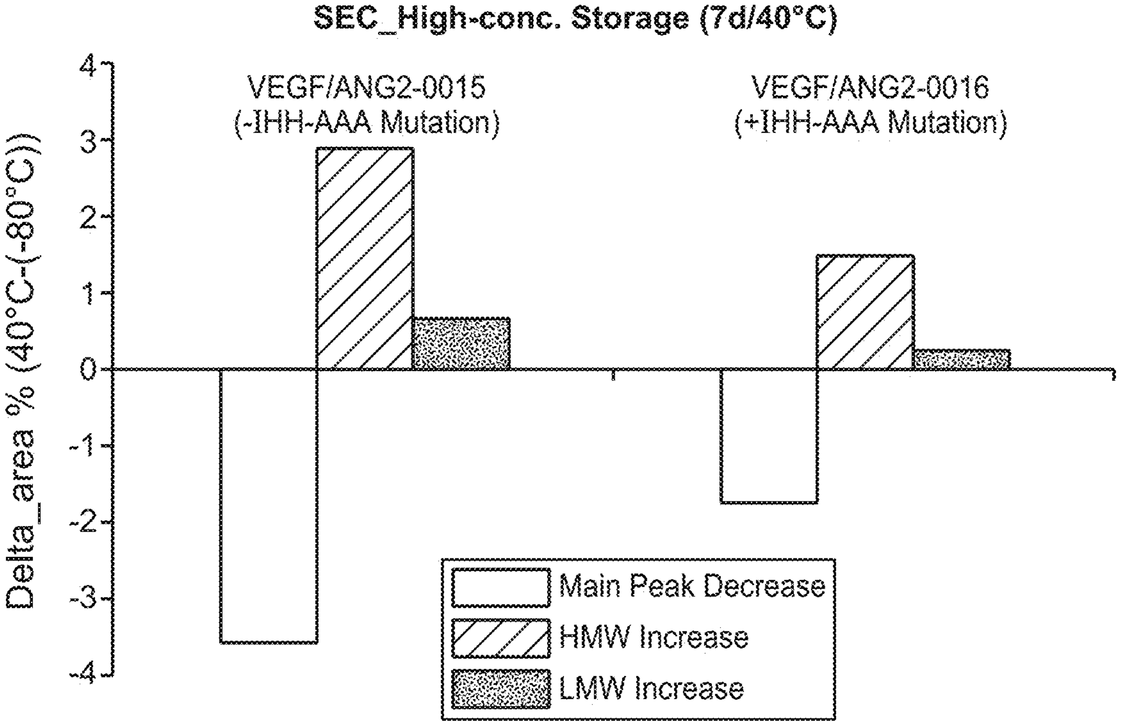
FIG. 4: Seven day storage at 40° C. at 100 mg/mL (decrease of Main Peak and High Molecular Weight (HMW) increase) (comparison of anti-VEGF/ANG2 antibody as reported herein VEGF/ANG2-0016 (with IHH-AAA mutation) which showed a lower aggregation with reference antibody VEGF/ANG2-0015 (without such IHH-AAA mutation)).

Samples are concentrated to a final concentration of 100 mg/mL in 200 mM arginine succinate, pH 5.5, sterile filtered and quiescently stored at 40° C. for 7 days. Before and after storage, the content of high and low molecular weight species (HMWs and LMWs, respectively) is determined by size-exclusion chromatography. The difference in HMW and LMW content between the stored sample and a sample measured immediately after preparation is reported as "HMW increase" and "LMW increase", respectively. Results are shown in the Table below and FIG. 4, which show that VEGF/ANG2-0015 (without IHH-AAA mutation) shows a higher reduction of the main peak and a higher HMW increase compared to VEGF/ANG2-0016 (with IHH-AAA mutation). Surprisingly VEGF/ANG2-0016 (with IHH-AAA mutation) showed a lower aggregation tendency compared to VEGF/ANG2-0015 (without IHH-AAA mutation).

TABLE

Delta Main-, HMW and LMW peaks after 7 d at 40° C.

| | delta_area %(40° C.-(−80° C.)) | | |
|---|---|---|---|
| | main Peak | HMW | LMW |
| VEGF/ANG2-0015 (without IHH-AAA mutation) | −3.56 | 2.89 | 0.67 |
| VEGF/ANG2-0016 (with IHH-AAA mutation) | −1.74 | 1.49 | 0.25 |

The functional analysis of anti-VEGF/ANG2 bispecific antibodies was assessed by Surface Plasmon Resonance (SPR) using a BIAcore® T100 or T200 instrument (GE Healthcare) at 25° C. The BIAcore® system is well established for the study of molecule interactions. SPR-technology is based on the measurement of the refractive index close to the surface of a gold coated biosensor chip. Changes in the refractive index indicate mass changes on the surface caused by the interaction of immobilized ligand with analyte injected in solution. The mass increases if molecules bind immobilized ligands on the surface, and vice versa, the mass decreases in case of dissociation of the analyte from the immobilized ligand (reflecting complex dissociation). SPR allows a continuous real-time monitoring of ligand/analyte binding and thus the determination of the association rate constant (ka), the dissociation rate constant (kd), and of the equilibrium constant ($K_D$).

Example 3

Binding to VEGF, ANG2, FcgammaR and FcRn

VEGF isoforms kinetic affinity including assessment of species-cross-reactivity

Around 12,000 resonance units (RU) of the capturing system (10 µg/mL goat anti human F(ab)'$_2$; Order Code: 28958325; GE Healthcare Bio-Sciences AB, Sweden) were coupled on a CMS chip (GE Healthcare BR-1005-30) at pH 5.0 by using an amine coupling kit supplied by GE Healthcare. The sample and system buffer was PBS-T (10 mM phosphate buffered saline including 0.05% Tween20) pH 7.4. The flow cell was set to 25° C. —and the sample block set to 12° C. —and primed with running buffer twice. The bispecific antibody was captured by injecting a 50 nM solution for 30 seconds at a flow of 5 µL/min. Association was measured by injection of human hVEGF121, mouse mVEGF120 or rat rVEGF164 in various concentrations in solution for 300 seconds at a flow of 30 µL/min starting with 300 nM in 1:3 dilutions. The dissociation phase was monitored for up to 1200 seconds and triggered by switching from the sample solution to running buffer. The surface was regenerated by 60 seconds washing with a Glycine pH 2.1 solution at a flow rate of 30 µL/min. Bulk refractive index differences were corrected by subtracting the response obtained from a goat anti human F(ab')$_2$ surface. Blank injections are also subtracted (=double referencing). For calculation of apparent $K_D$ and other kinetic parameters the Langmuir 1:1 model was used. Results are shown below.

ANG2 Solution Affinity Including Assessment of Species-Cross-Reactivity

Solution affinity measures the affinity of an interaction by determining the concentration of free interaction partners in an equilibrium mixture. The solution affinity assay involves the mixing of an anti-VEGF/ANG2 antibody, kept at a constant concentration, with a ligand (=ANG2) at varying concentrations. Maximum possible resonance units (e.g. 17,000 resonance units (RU)) of an antibody was immobilized on the CMS chip (GE Healthcare BR-1005-30) surface at pH 5.0 using an amine coupling kit supplied by GE Healthcare. The sample and system buffer was HBS-P pH 7.4. Flow cell was set to 25° C. and sample block to 12° C. and primed with running buffer twice. To generate a calibration curve increasing concentrations of ANG2 were injected into a BIAcore flow-cell containing the immobilized anti-VEGF/ANG2 antibody. The amount of bound ANG2 was determined as resonance units (RU) and plotted against the concentration. Solutions of each ligand (11 concentrations from 0 to 200 nM for the anti-VEGF/ANG2 antibody) were incubated with 10 nM ANG2 and allowed to reach equilibrium at room temperature. Free ANG2 concentrations were determined from calibration curve generated before and after measuring the response of solutions with known amounts of ANG2. A 4-parameter fit was set with XLfit4 (IDBS Software) using Model 201 using free ANG2 concentration as y-axis and used concentration of antibody for inhibition as x-axis. The affinity was calculated by determining the inflection point of this curve. The surface was regenerated by one time 30 seconds washing with a 0.85% $H_3PO_4$ solution at a flow rate of 30 µL/min. Bulk refractive index differences were corrected by subtracting the response obtained from a blank-coupled surface. Results are shown in below.

FcRn Steady State Affinity

Figure 5A:
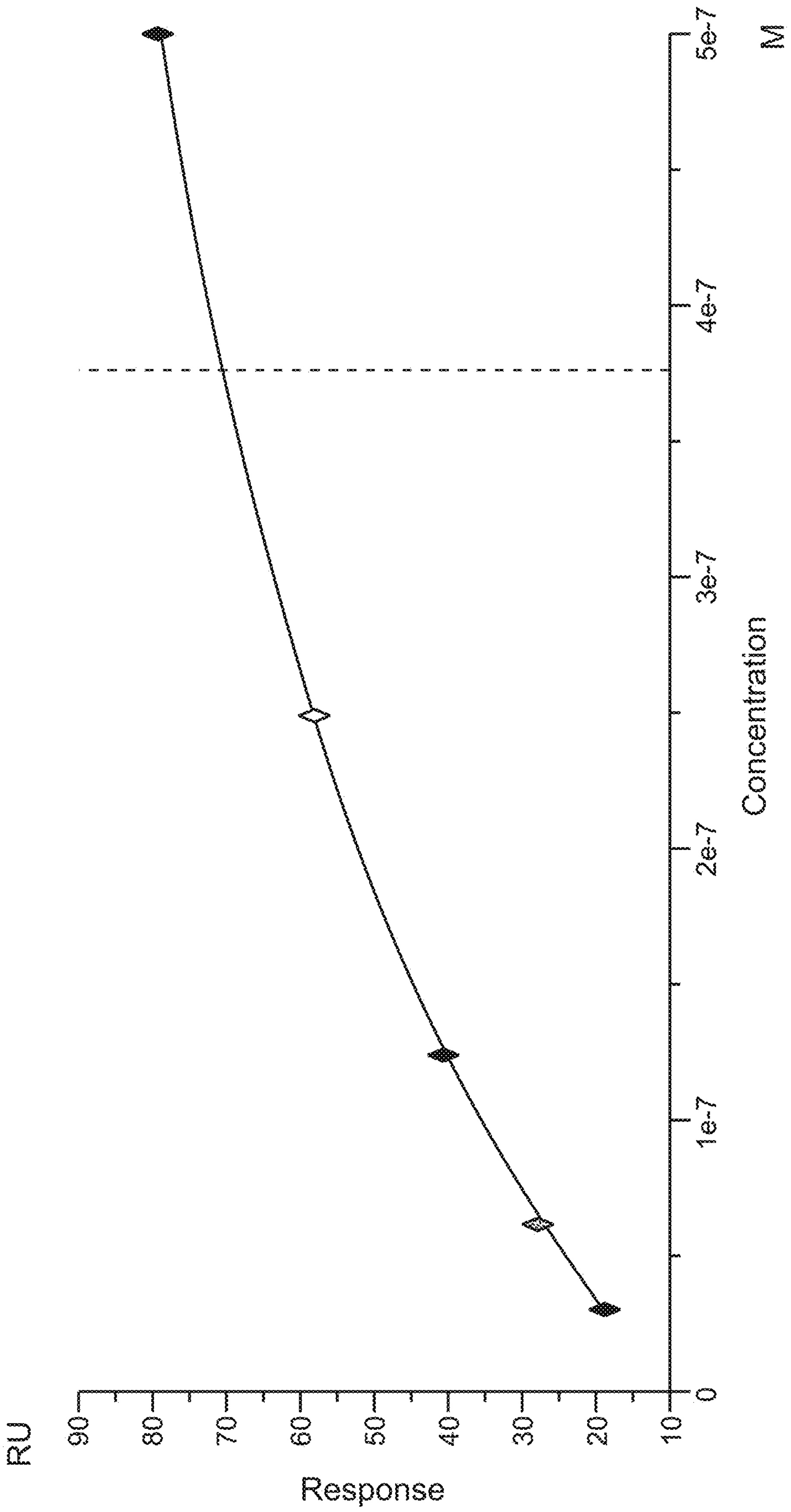
FIGS. 5A and 5B: FcRn steady state affinity of A: VEGF/ANG2-0015 (without IHH-AAA mutation) and B: VEGF/ANG2-0016 (with IHH-AAA mutation).
Figure 5B:
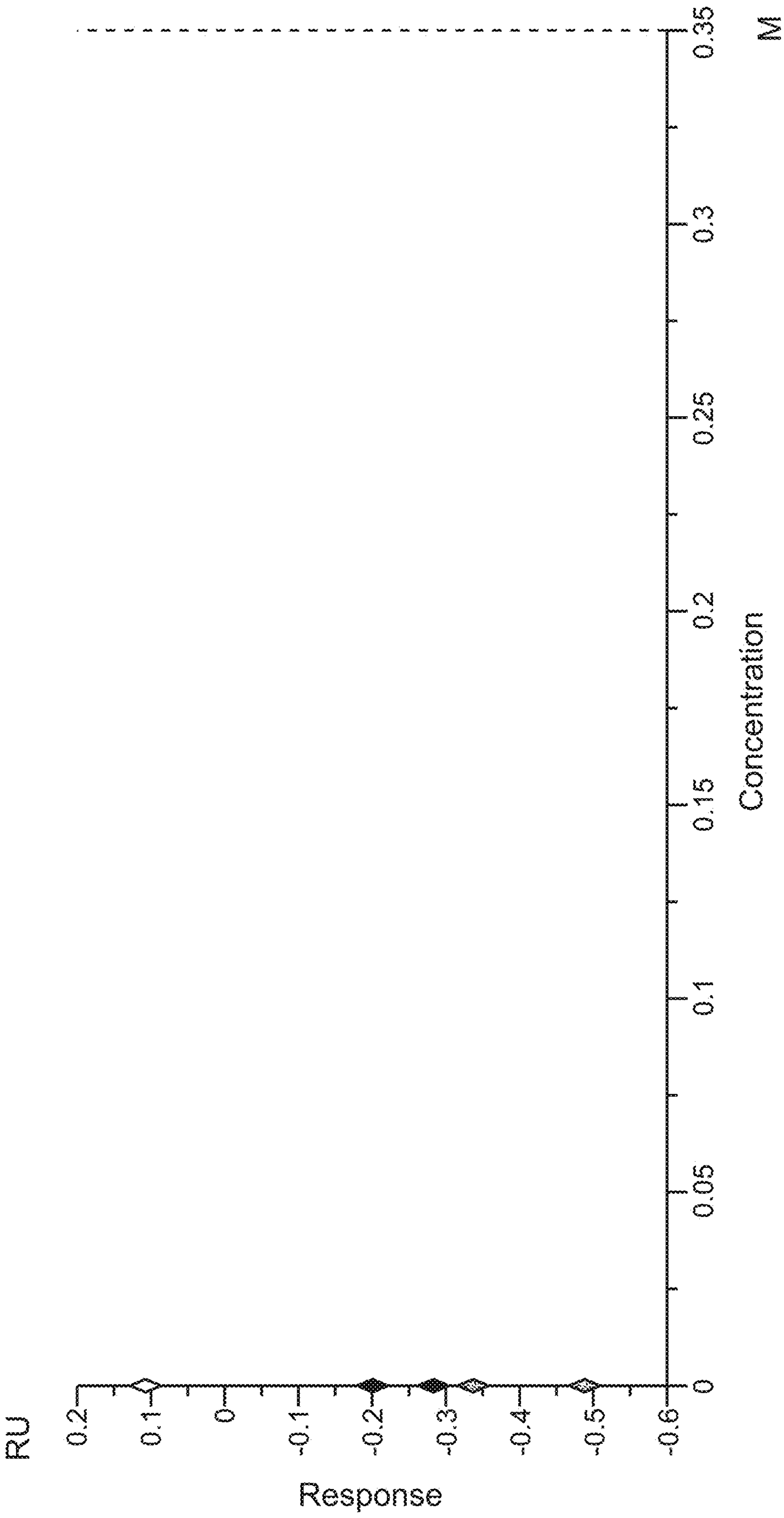

For FcRn measurement a steady state affinity was used to compare bispecific antibodies against each other. Human FcRn was diluted into coupling buffer (10 µg/mL, Na-Acetate, pH 5.0) and immobilized on a C1-Chip (GE Healthcare BR-1005-35) by targeted immobilization procedure using a BIAcore wizard to a final response of 200 RU. Flow cell was set to 25° C. and sample block to 12° C. and primed with running buffer twice. The sample and system buffer was PBS-T (10 mM phosphate buffered saline including 0.05% Tween20) pH 6.0. To assess different IgG concentrations for each antibody, a concentration of 62.5 nM, 125 nM, 250 nM, and 500 nM was prepared. Flow rate was set to 30 µL/min and the different samples were injected consecutively onto the chip surface choosing 180 seconds association time. The surface was regenerated by injected PBS-T pH 8 for 60 seconds at a flow rate of 30 µL/min. Bulk refractive index differences were corrected by subtracting the response obtained from a blank surface. Buffer injections are also subtracted (=double referencing). For calculation of steady state affinity the method from the BIA-Evaluation software was used. Briefly, the RU values were plotted against the analyzed concentrations, yielding a dose-response curve. Based on a 2-parametric fit, the upper asymptote is calculated, allowing the determination of the half-maximal RU value and hence the affinity. Results are shown in FIG. 5 and the Table below. Analogously the affinity to Cynomolgus, mouse and rabbit FcRn can be determined.

FcgammaRIIIa Measurement

Figure 6:
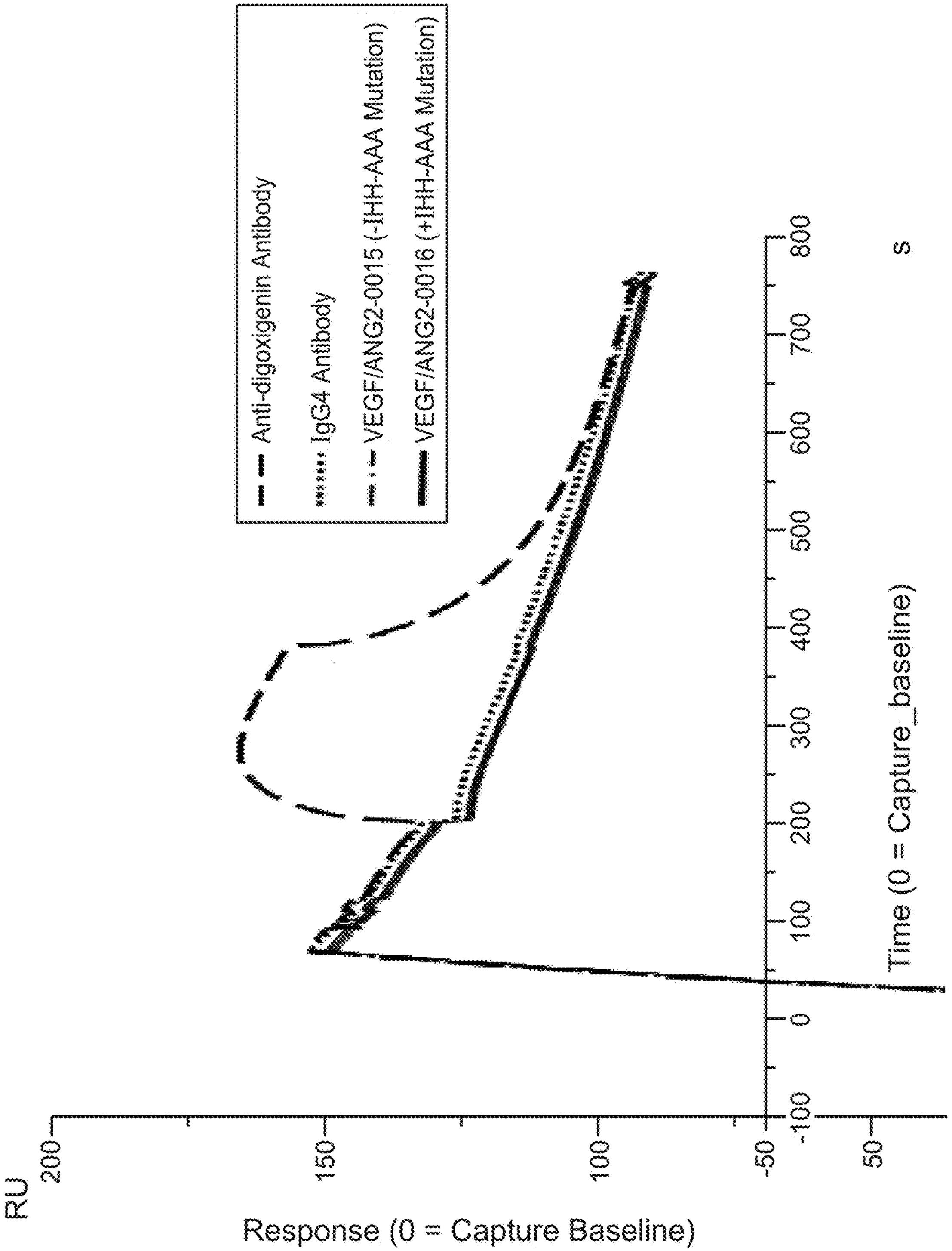
FIG. 6: FcgammaRIIIa interaction measurement of VEGF/ANG2-0015 without IHH-AAA mutation and VEGF/ANG2-0016 with IHH-AAA mutation (both are IgG1 subclass with P329G LALA mutations; as controls an anti-digoxygenin antibody (anti-Dig antibody) of IgG1 subclass and an IgG4 based antibody were used).

For FcgammaRIIIa measurement a direct binding assay was used. Around 3,000 resonance units (RU) of the capturing system (1 μg/mL Penta-His; Qiagen) were coupled on a CMS chip (GE Healthcare BR-1005-30) at pH 5.0 by using an amine coupling kit supplied by GE Healthcare. The sample and system buffer was HBS-P+pH 7.4. The flow cell was set to 25° C. —and sample block to 12° C. —and primed with running buffer twice. The FcgammaRIIIa-His-receptor was captured by injecting a 100 nM solution for 60 seconds at a flow of 5 μL/min. Binding was measured by injection of 100 nM of bispecific antibody or monospecific control antibodies (anti-digoxygenin antibody for IgG1 subclass and an IgG4 subclass antibody) for 180 seconds at a flow of 30 μL/min. The surface was regenerated by 120 seconds washing with Glycine pH 2.5 solution at a flow rate of 30 μL/min. Because FcgammaRIIIa binding differs from the Langmuir 1:1 model, only binding/no binding was determined with this assay. In a similar manner FcgammaRIa and FcgammaRIIa binding can be determined. Results are shown in FIG. 6, where it follows that by introduction of the mutations P329G LALA no more binding to FcgammaRIIIa could be detected.

Assessment of Independent VEGF- and ANG2-Binding to the Anti-VEGF/ANG2 Antibodies Around 3,500 resonance units (RU) of the capturing system (10 μg/mL goat anti-human IgG; GE Healthcare Bio-Sciences AB, Sweden) were coupled on a CM4 chip (GE Healthcare BR-1005-34) at pH 5.0 by using an amine coupling kit supplied by GE Healthcare. The sample and system buffer was PBS-T (10 mM phosphate buffered saline including 0.05% Tween20) pH 7.4. The temperature of the flow cell was set to 25° C. and of the sample block to 12° C. Before capturing, the flow cell was primed with running buffer twice.

The bispecific antibody was captured by injecting a 10 nM solution for 60 seconds at a flow of 5 μL/min. Independent binding of each ligand to the bispecific antibody was analyzed by determining the active binding capacity for each ligand, either added sequentially or simultaneously (flow of 30 μL/min):

1. Injection of human VEGF with a concentration of 200 nM for 180 seconds (identifies the single binding of the antigen).
2. Injection of human ANG2 with a concentration of 100 nM for 180 seconds (identifies single binding of the antigen).
3. Injection of human VEGF with a concentration of 200 nM for 180 seconds followed by an additional injection of human ANG2 with a concentration of 100 nM for 180 seconds (identifies binding of ANG2 in the presence of VEGF).
4. Injection of human ANG2 with a concentration of 100 nM for 180 seconds followed by an additional injection of human VEGF with a concentration of 200 nM (identifies binding of VEGF in the presence of ANG2).
5. Co-injection of human VEGF with a concentration of 200 nM and of human ANG2 with a concentration of 100 nM for 180 seconds (identifies the binding of VEGF and of ANG2 at the same time).

The surface was regenerated by 60 seconds washing with a 3 M MgCl2 solution at a flow rate of 30 μL/min. Bulk refractive index differences were corrected by subtracting the response obtained from a goat anti-human IgG surface.

The bispecific antibody is able to bind both antigens mutual independently if the resulting final signal of the approaches 3, 4 & 5 equals or is similar to the sum of the individual final signals of the approaches 1 and 2. Results are shown in the Table below, where both antibodies VEGF/ANG2-0016, VEGF/ANG2-0012 are shown to be able to bind mutual independently to VEGF and ANG2.

Assessment of Simultaneous VEGF- and ANG2-Binding to the Anti-VEGF/ANG2 Antibodies First, around 1,600 resonance units (RU) of VEGF (20 μg/mL) were coupled on a CM4 chip (GE Healthcare BR-1005-34) at pH 5.0 by using an amine coupling kit supplied by GE Healthcare. The sample and system buffer was PBS-T (10 mM phosphate buffered saline including 0.05% Tween20) pH 7.4. Flow cell was set to 25° C. and sample block to 12° C. and primed with running buffer twice. Second, 50 nM solution of the bispecific antibody was injected for 180 seconds at a flow of 30 μL/min. Third, hANG2 was injected for 180 seconds at a flow of 30 μL/min. The binding response of hANG2 depends from the amount of the bispecific antibody bound to VEGF and shows simultaneous binding. The surface was regenerated by 60 seconds washing with a 0.85% $H_3PO_4$ solution at a flow rate of 30 μL/min. Simultaneous binding is shown by an additional specific binding signal of hANG2 to the previous VEGF bound anti-VEGF/ANG2 antibodies. For both bispecific antibodies VEGF/ANG2-0015 and VEGF/ANG2-0016 simultaneous VEGF- and ANG2-binding to the anti-VEGF/ANG2 antibodies could be detected (data not shown).

TABLE

Results: Kinetic affinities to VEGF isoforms from different species

| | VEGF/ ANG2-0015 - apparent affinity | VEGF/ANG2-0016 - apparent affinity | VEGF/ANG2-0012 - apparent affinity | VEGF/ANG2-0201 - apparent affinity |
|---|---|---|---|---|
| human VEGF 121 | ≤1 pM (out of BIAcore specification) | ≤1 pM (out of BIAcore specification) | ≤1 pM (out of BIAcore specification) | ≤1 pM (out of BIAcore specification) |
| mouse VEGF 120 | no binding | no binding | no binding | no binding |
| rat VEGF 164 | 13 nM | 14 nM | 24 nM | 35 nM |

TABLE

Results: Solution affinities to ANG2

| | VEGF/ ANG2-0015 KD [nM] | VEGF/ ANG2-0016 KD [nM] | VEGF/ ANG2-0012 KD [nM] | VEGF/ ANG2-0201 KD [nM] |
|---|---|---|---|---|
| human ANG2 | 8 | 20 | 20 | n.d. |
| cyno ANG2 | 5 | 13 | 10 | n.d. |
| mouse ANG2 | 8 | 13 | 8 | n.d. |
| rabbit ANG2 | 4 | 11 | 8 | n.d. |

TABLE

Results: Affinity to FcRn of anti-VEGF/ANG2 antibodies

| | VEGF/ ANG2-0015 [affinity] | VEGF/ ANG2-0016 [affinity] | VEGF/ ANG2-0012 [affinity] | VEGF/ ANG2-0201 [affinity] |
|---|---|---|---|---|
| human FcRn | 0.8 μM | no binding | no binding | 0.8 μM |
| cynomolgus FcRn | 0.9 μM | no binding | no binding | 1.0 μM |
| mouse FcRn | 0.2 μM | no binding | no binding | 0.2 μM |

TABLE

Results Binding to FcgammaRI-IIIa

| | VEGF/ ANG2-0015 | VEGF/ ANG2-0016 | VEGF/ ANG2-0012 | VEGF/ ANG2-0201 |
|---|---|---|---|---|
| FcγRIa | no binding | no binding | binding | binding |
| FcγRIIa | no binding | no binding | no binding | binding |
| FcγRIIIa | no binding | no binding | no binding | binding |

TABLE

Results: Independent binding of VEGF- and ANG2 to anti-VEGF/ANG2 antibodies

| | ANG2 [RUmax] | VEGF [RUmax] | first VEGF then ANG2 [RUmax] | first ANG2 then VEGF [RUmax] | Co-injection ANG2 + VEGF [RUmax] |
|---|---|---|---|---|---|
| VEGF/ANG2-0016 | 174 | 50 | 211 | 211 | 211 |
| VEGF/ANG2-0012 | 143 | 43 | 178 | 177 | 178 |

Example 4

Mass Spectrometry

This section describes the characterization of anti-VEGF/ANG2 antibodies with emphasis on the correct assembly. The expected primary structures were confirmed by electrospray ionization mass spectrometry (ESI-MS) of the deglycosylated, and intact or IdeS-digested (IgG-degrading enzyme of *S. pyogenes*) anti-VEGF/ANG2 antibodies. The IdeS-digestion was performed with 100 μg purified antibody incubated with 2 μg IdeS protease (Fabricator) in 100 mmol/L $NaH_2PO_4/Na_2HPO_4$, pH 7.1 at 37° C. for 5 h. Subsequently, the antibodies were deglycosylated with N-Glycosidase F, Neuraminidase and 0-glycosidase (Roche) in 100 mmol/L $NaH_2PO_4/Na_2HPO_4$, pH 7.1 at 37° C. for up to 16 hours at a protein concentration of 1 mg/mL and subsequently desalted via HPLC on a Sephadex G25 column (GE Healthcare). The total mass was determined via ESI-MS on a maXis 4G UHR-QTOF MS system (Bruker Daltonik) equipped with a TriVersa NanoMate source (Advion).

The masses obtained for the IdeS-digested, deglycosylated (Table below), or intact, deglycosylated (Table below) molecules correspond to the predicted masses deduced from the amino acid sequences for the anti-VEGF/ANG2 antibodies consisting of two different light chains $LC_{ANG2}$ and $LC_{Lucentis}$, and two different heavy chains $HC_{ANG2}$ and $HC_{Lucentis}$.

TABLE

Masses of the deglycosylated and IdeS-digested bispecific anti-VEGF/ANG2 antibodies VEGF/ANG2-0201 (without IHH-AAA mutation) and VEGF/ANG2-0012 (with IHH-AAA mutation)

| | F(ab')$_2$ of the anti-VEGF/ANG2 antibody | | deglycosylated Fc-region of the anti-VEGF/ANG2 antibody | |
|---|---|---|---|---|
| sample | predicted average mass [Da] | observed average mass [Da] | predicted average mass [Da] | observed average mass [Da] |
| VEGF/ANG2-0201 | 99360.8 | 99360.7 | 47439.2 | 47430.1 |
| VEGF/ANG2-0012 | 99360.8 | 99361.1 | 47087.7 | 47082.0 |

TABLE

Masses of the deglycosylated anti-VEGF/ANG2 antibodies VEGF/ANG2-0016 (with IHH-AAA mutation) and VEGF/ANG2-0015 (without IHH-AAA mutation)

| | deglycosylated anti-VEGF/ANG2 antibody | |
|---|---|---|
| | predicted average mass [Da] | observed average mass [Da] |
| VEGF/ANG2-0016 | 146156.9 | 146161.2 |
| VEGF/ANG2-0015 | 146505.3 | 146509.4 |

Example 5

FcRn Chromatography

Coupling to Streptavidin Sepharose:

One gram streptavidin sepharose (GE Healthcare) was added to the biotinylated and dialyzed receptor and incubated for two hours with shaking. The receptor derivatized sepharose was filled in a 1 mL XK column (GE Healthcare).

Chromatography Using the FcRn Affinity Column:

Conditions:

column dimensions: 50 mm×5 mm bed height: 5 cm loading: 50 μg sample equilibration buffer: 20 mM MES, with 150 mM NaCl, adjusted to pH 5.5 elution buffer: 20 mM Tris/HCl, with 150 mM NaCl, adjusted to pH 8.8 elution: 7.5 CV equilibration buffer, in 30 CV to 100% elution buffer, 10 CV elution buffer Human FcRn Affinity Column Chromatography In the following Table retention times of anti-VEGF/ANG2 antibodies on affinity columns comprising human FcRn are given. Data were obtained using the conditions above.

TABLE

Results: retention times of anti-VEGF/ANG2 antibodies

| antibody | retention time [min] |
|---|---|
| VEGF/ANG2-0015 (without IHH-AAA mutation) | 78.5 |
| VEGF/ANG2-0201 (without IHH-AAA mutation) | 78.9 |
| VEGF/ANG2-0012 (with IHH-AAA mutation) | 2.7 (void-peak) |
| VEGF/ANG2-0016 (with IHH-AAA mutation) | 2.7 (void-peak) |

Example 6

Pharmacokinetic (PK) Properties of Antibodies with IHH-AAA Mutation

PK Data with FcRn Mice Transgenic for Human FcRn

In Life Phase:

The study included female C57BL/6J mice (background); mouse FcRn deficient, but hemizygous transgenic for human FcRn (huFcRn, line 276 -/tg)

Part 1:

All mice were injected once intravitreally into the right eye with 2 μL/animal of the appropriate solution (i.e. 21 μg compound/animal (VEGF/ANG2-0015 (without IHH-AAA mutation)) or 23.6 μg compound/animal (VEGF/ANG2-0016 (with IHH-AAA mutation)).

Mice were allocated to 2 groups with 6 animals each. Blood samples are taken from group 1 at 2, 24 and 96 hours and from group 2 at 7, 48 and 168 hours after dosing.

Injection into the vitreous of the right mouse eye was performed by using the NanoFil Microsyringe system for nanoliter injection from World Precision Instruments, Inc., Berlin, Germany. Mice were anesthetized with 2.5% Isoflurane and for visualization of the mouse eye a Leica MZFL 3 microscope with a 40 fold magnification and a ring-light with a Leica KL 2500 LCD lightning was used. Subsequently, 2 μL of the compound were injected using a 35-gauge needle.

Blood was collected via the retrobulbar venous plexus of the contralateral eye from each animal for the determination of the compound levels in serum.

Serum samples of at least 50 μL were obtained from blood after 1 hour at RT by centrifugation (9,300×g) at 4° C. for 3 min. Serum samples were frozen directly after centrifugation and stored frozen at −80° C. until analysis. Treated eyes of the animals of group 1 were isolated 96 hours after treatment and of the animals of group 2 168 hours after treatment. Samples were stored frozen at −80° C. until analysis.

Part 2:

All mice were injected once intravenously via the tail vein with 200 μL/animal of the appropriate solution (i.e. 21 μg compound/animal (VEGF/ANG2-0015 (without IHH-AAA mutation)) or 23.6 μg compound/animal (VEGF/ANG2-0016 (with IHH-AAA mutation)).

Mice were allocated to 2 groups with 5 animals each. Blood samples are taken from group 1 at 1, 24 and 96 hours and from group 2 at 7, 48 and 168 hours after dosing. Blood was collected via the retrobulbar venous plexus from each animal for the determination of the compound levels in serum.

Serum samples of at least 50 μL were obtained from blood after 1 hour at RT by centrifugation (9,300×g) at 4° C. for 3 min. Serum samples were frozen directly after centrifugation and stored frozen at −80° C. until analysis.

Preparation of Whole Eye Lysates (Mice)

The eye lysates were gained by physico-chemical disintegration of the whole eye from laboratory animals. For mechanical disruption, each eye was transferred into a 1.5 mL micro vial with conical bottom. After freeze and thawing, the eyes were washed with 1 mL cell washing buffer once (Bio-Rad, Bio-Plex Cell Lysis Kit, Cat. No. 171-304011). In the following step, 500 μL of freshly prepared cell lysis buffer were added and the eyes were grinded using a 1.5 mL tissue grinding pestle (Kimble Chase, 1.5 mL pestle, Art. No. 749521-1500). The mixture was then frozen and thawed five times and grinded again. To separate lysate from remaining tissue the samples were centrifuged for 4 min. at 4,500 g. After centrifuging the supernatant was collected and stored at −20° C. until further analysis in the quantification ELISA.

Analysis

The concentrations of the anti-VEGF/ANG2 antibodies in mice serum and eye lysates were determined with an enzyme linked immunosorbent assay (ELISA)

For quantification of anti-VEGF/ANG2 antibodies in mouse serum samples and eye lysates, a standard solid-phase serial sandwich immunoassay with biotinylated and digoxigenylated monoclonal antibodies used as capture and detection antibodies was performed. To verify the integrity of the bispecificity of the analyte the biotinylated capture antibody recognizes the VEGF-binding site whereas the digoxigenylated detection antibody will bind to the ANG2 binding site of the analyte. The bound immune complex of capture antibody, analyte and detection antibody on the solid phase of the streptavidin coated micro titer plate (SA-MTP) is then detected with a horseradish-peroxidase coupled to an anti-digoxigenin antibody. After washing unbound material from the SA-MTP and addition of ABTS-substrate, the gained signal is proportional to the amount of analyte bound on the solid phase of the SA-MTP. Quantification is then done by converting the measured signals of the samples into concentrations referring to calibrators analyzed in parallel.

In a first step the SA-MTP was coated with 100 μL/well of biotinylated capture antibody solution (mAb<Id<VEGF>>M-2.45.51-IgG-Bi(DDS), anti-idiotypic antibody) with a concentration of 1 μg/mL for one hour at 500 rpm on a MTP-shaker. Meanwhile calibrators, QC-samples and samples were prepared. Calibrators and QC-samples are diluted to 2% serum matrix; samples were diluted until the signals were within the linear range of the calibrators.

After coating the SA-MTP with capture antibody, the plate was washed three times with washing buffer and 300 μL/well. Subsequently 100 μL/well of the calibrators, QC-samples and samples were pipetted on the SA-MTP and incubated again for one hour at 500 rpm. The analyte was now bound with its VEGF binding site via the capture antibody to the solid phase of the SA-MTP. After incubation and removal of unbound analyte by washing the plate 100 µL/well of the first detection antibody (mAb<Id-<ANG2>>M-2.6.81-IgG-Dig(XOSu), anti-idiotypic antibody) with a concentration of 250 ng/mL was added to the SA-MTP. Again, the plate was incubated for one hour at 500 rpm on a shaker. After washing, 100 µL/well of the second detection antibody (pAb<Digoxigenin>S-Fab-POD (poly)) at a concentration of 50 mU/mL was added to the wells of the SA-MTP and the plate was incubated again for one hour at 500 rpm. After a final washing step to remove excess of detection antibody, 100 µL/well substrate (ABTS) is added. The antibody-enzyme conjugate catalyzes the color reaction of the ABTS® substrate. The signal was then measured by an ELISA reader at 405 nm wavelength (reference wavelength: 490 nm ([405/490] nm)).

Pharmacokinetic Evaluation

The pharmacokinetic parameters were calculated by non-compartmental analysis, using the pharmacokinetic evaluation program WinNonlin™ (Pharsight), version 5.2.1.

Results

A) Serum Concentrations

Figure 7A:
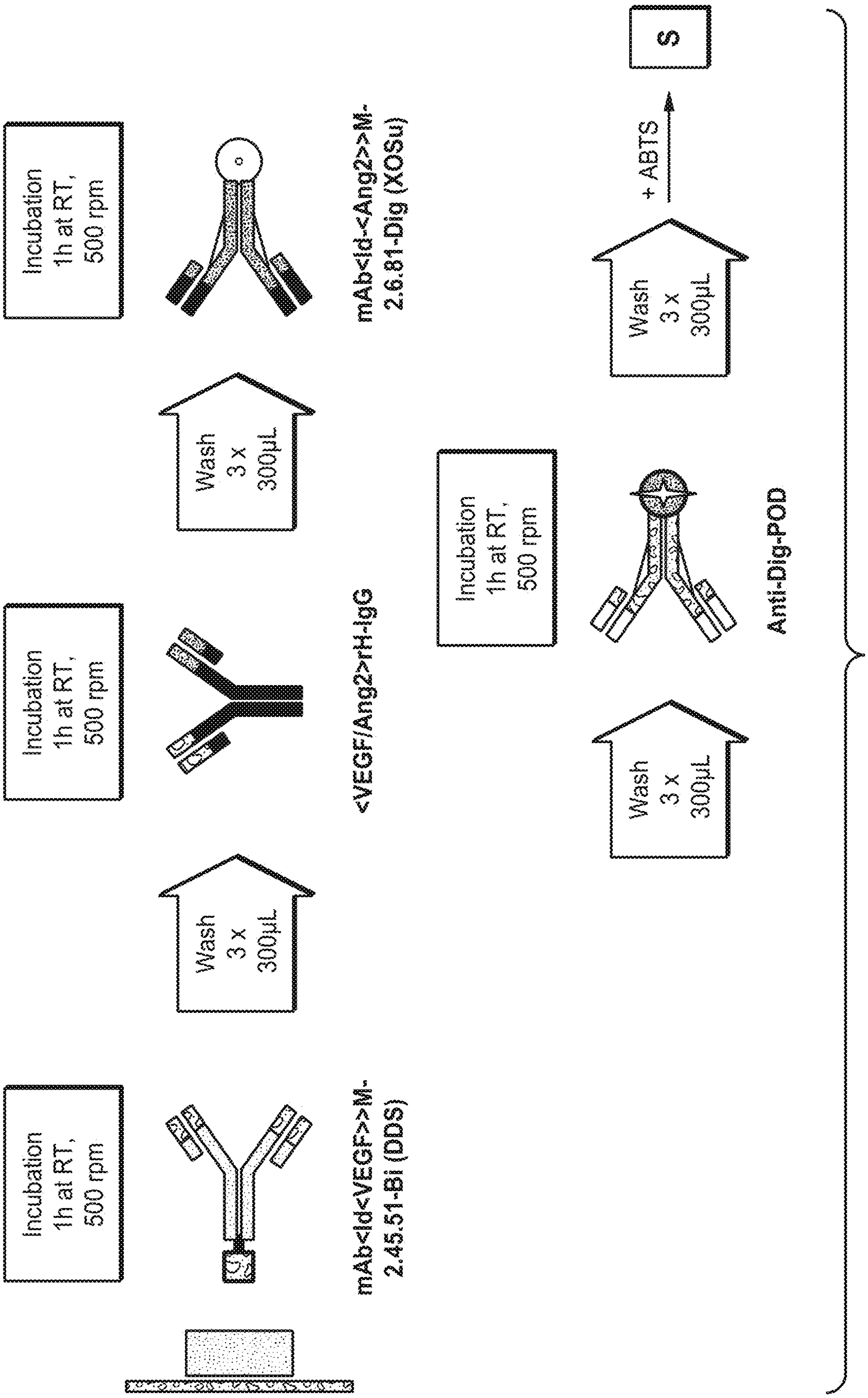
FIG. 7A: Schematic pharmacokinetic (PK) ELISA assay principle for determination of concentrations of anti-VEGF/ANG2 antibodies in serum and whole eye lysates.
Figure 7B:
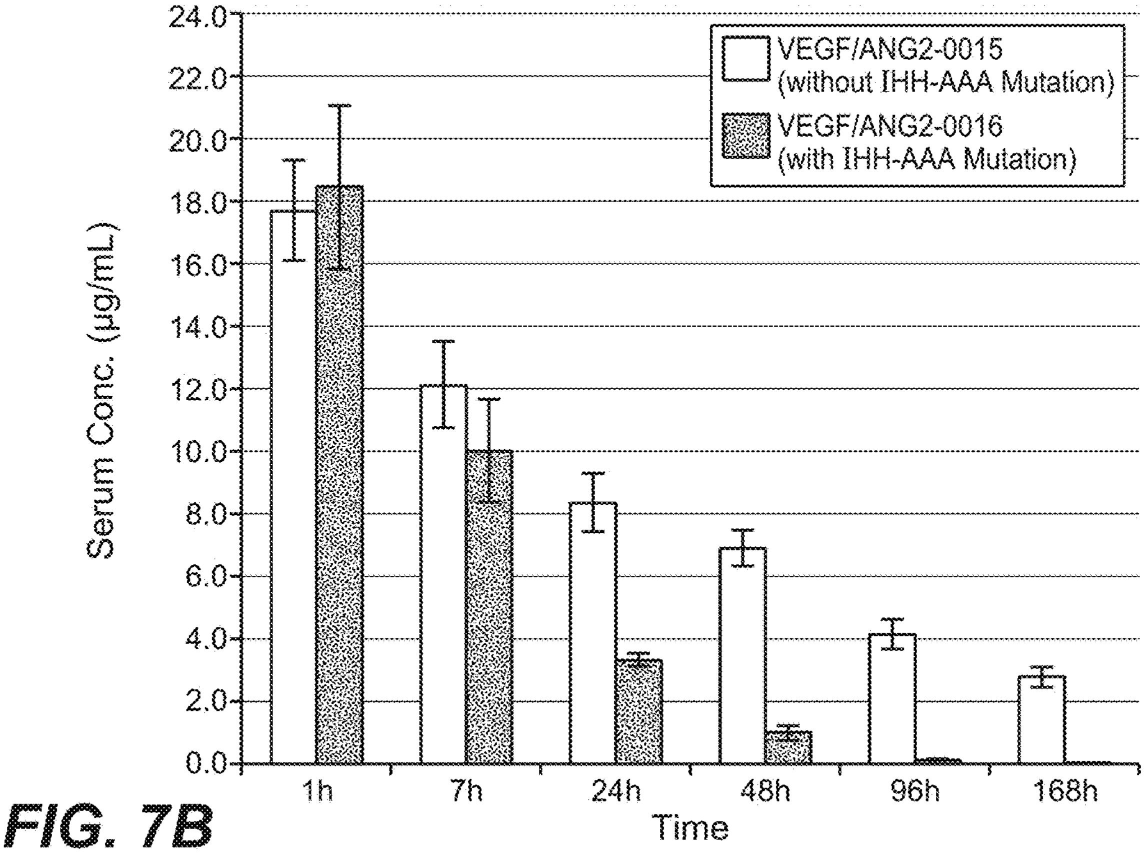
FIG. 7B: Serum concentration after intravenous (i.v.) application: comparison of VEGF/ANG2-0015 without IHH-AAA mutation and VEGF/ANG2-0016 with IHH-AAA mutation.
Figure 7C:
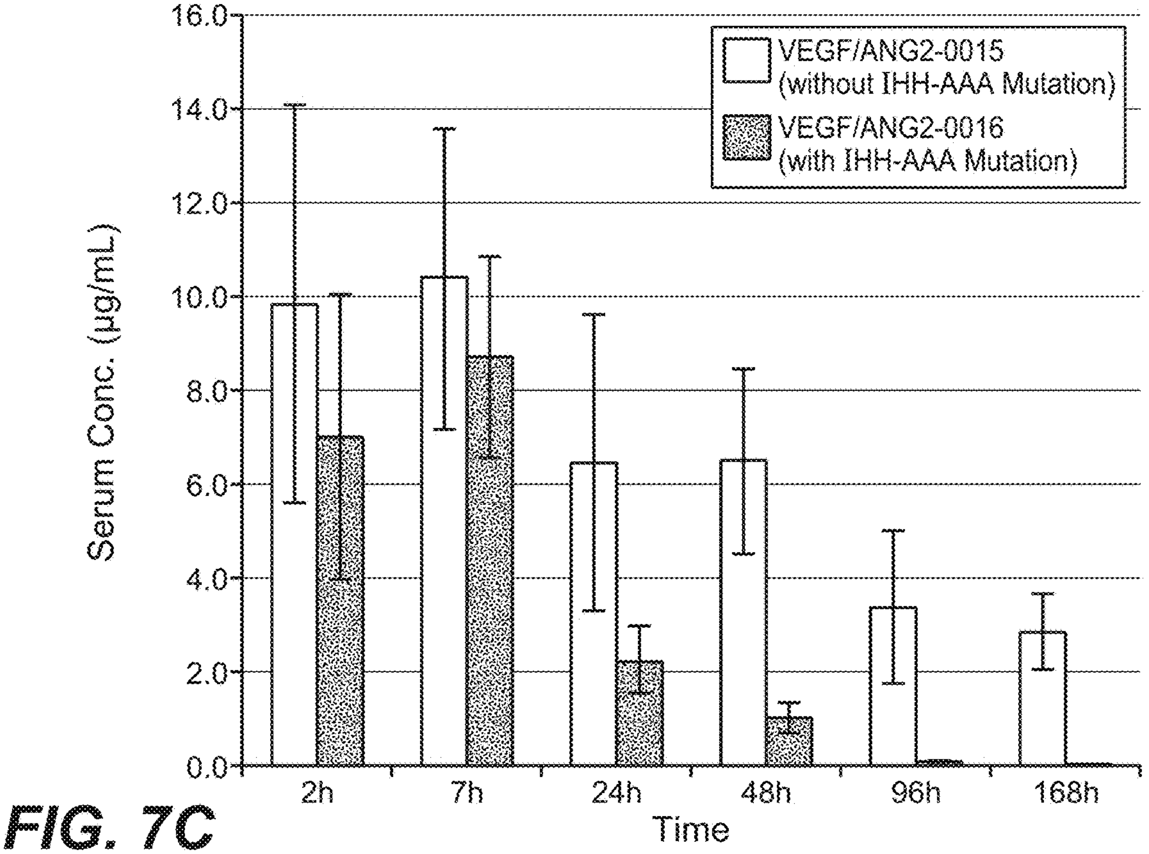
FIG. 7C: Serum concentration after intravitreal application: comparison of VEGF/ANG2-0015 without IHH-AAA mutation and VEGF/ANG2-0016 with IHH-AAA mutation.

Results for serum concentrations are shown in the following Tables and FIGS. 7B to 7C.

TABLE

VEGF/ANG2-0015 (without IHH-AAA mutation): Comparison of serum concentrations after intravitreal and intravenous application

| ID | serum concentration after intravitreal application average conc. [µg/mL] | serum concentration after intravenous application average conc. [µg/mL] |
|---|---|---|
| 1 h | | 17.7 |
| 2 h | 9.8 | |
| 7 h | 10.4 | 12.1 |
| 24 h | 6.4 | 8.3 |
| 48 h | 6.5 | 6.9 |
| 96 h | 3.4 | 4.1 |
| 168 h | 2.9 | 2.7 |

TABLE

VEGF/ANG2-0016 (with IHH-AAA mutation): Comparison of serum concentrations after intravitreal and intravenous application

| ID | serum concentration after intravitreal application average conc. [µg/mL] | serum concentration after intravenous application average conc. [µg/mL] |
|---|---|---|
| 1 h | | 18.4 |
| 2 h | 7.0 | |
| 7 h | 8.7 | 10.0 |
| 24 h | 2.2 | 3.3 |
| 48 h | 1.0 | 1.0 |
| 96 h | 0.1 | 0.1 |
| 168 h | 0.0 | 0.0 |

TABLE

VEGF/ANG2-0015 (without IHH-AAA mutation) and VEGF/ANG2-0016 (with IHH-AAA mutation): Comparison of serum concentrations after intravitreal application)

| ID | VEGF/ANG2-0015 (without IHH-AAA mutation) average conc. [µg/mL] | VEGF/ANG2-0016 (with IHH-AAA mutation) average conc. [µg/mL] |
|---|---|---|
| 2 h | 9.8 | 7.0 |
| 7 h | 10.4 | 8.7 |
| 24 h | 6.4 | 2.2 |
| 48 h | 6.5 | 1.0 |
| 96 h | 3.4 | 0.1 |
| 168 h | 2.9 | 0.0 |

TABLE

VEGF/ANG2-0015 (without IHH-AAA mutation) and VEGF/ANG2-0016 (with IHH-AAA mutation): Comparison of serum concentrations after intravenous application

| ID | VEGF/ANG2-0015 (without IHH-AAA mutation) average conc. [µg/mL] | VEGF/ANG2-0016 (with IHH-AAA mutation) average conc. [µg/mL] |
|---|---|---|
| 1 h | 17.7 | 18.4 |
| 7 h | 12.1 | 10.0 |
| 24 h | 8.3 | 3.3 |
| 48 h | 6.9 | 1.0 |
| 96 h | 4.1 | 0.1 |
| 168 h | 2.7 | 0.0 |

Results

B) Concentrations in Eye-Lysates of Left and Right Eyes

Figure 7D:
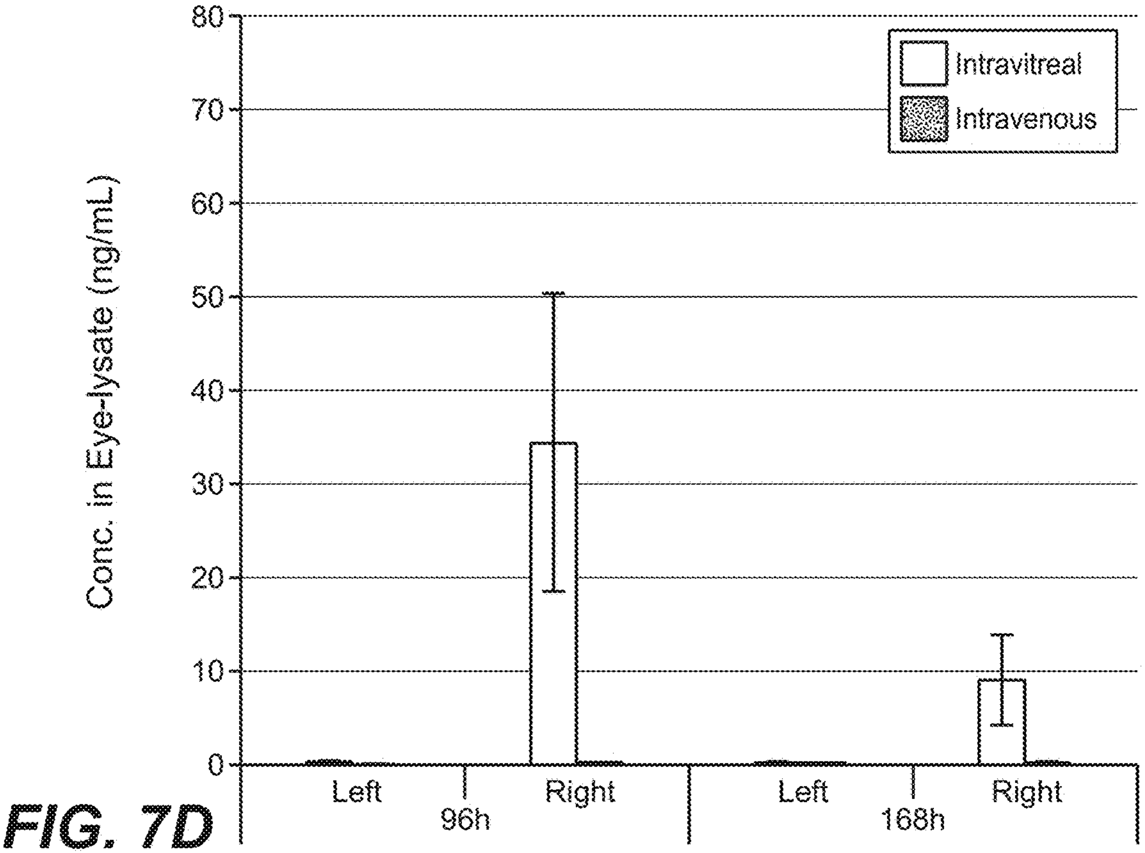
FIG. 7D: Eye lysates concentration of VEGF/ANG2-0016 (with IHH-AAA mutation) in right and left eye (after intravitreal application only into the right eye in comparison to intravenous application): significant concentrations could be detected only in the right eye after intravitreal application; after intravenous application no concentration in eye lysates could be detected due to the low serum half-life of VEGF/ANG2-0016 (with IHH-AAA mutation).
Figure 7E:
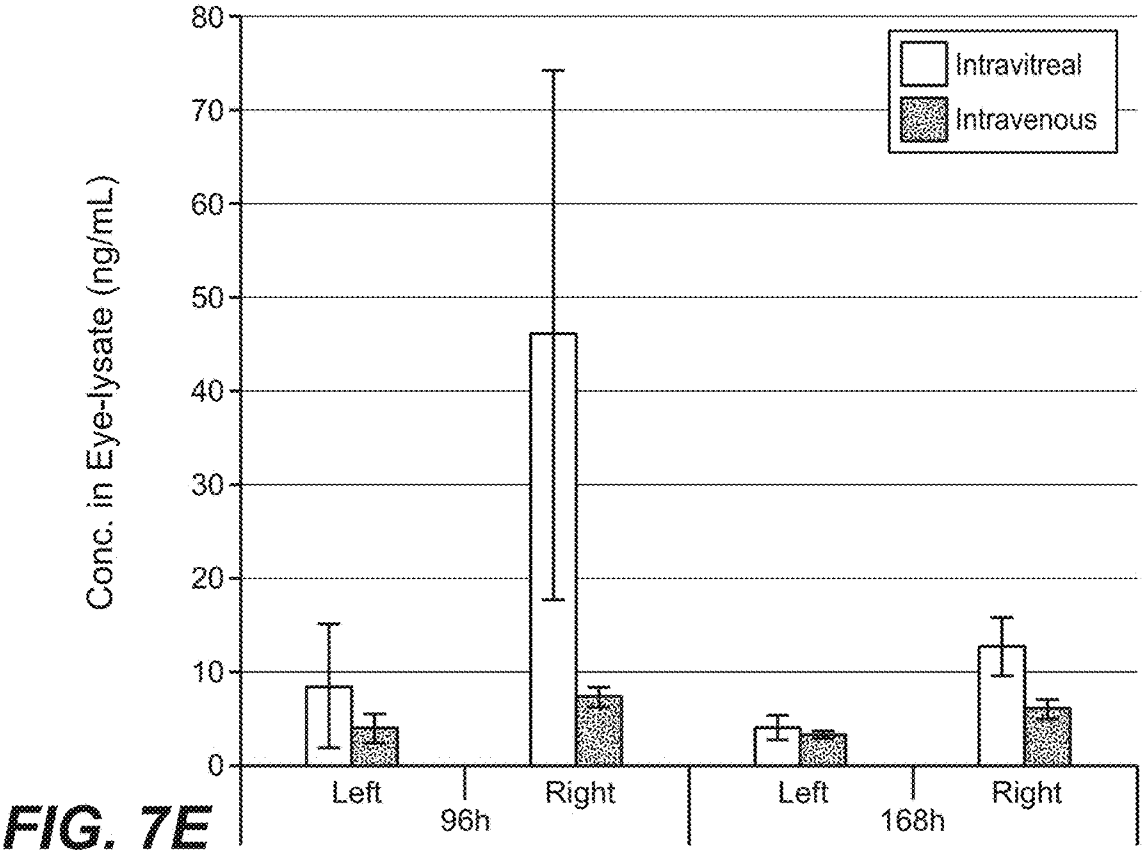
FIG. 7E: Eye lysates concentration of VEGF/ANG2-0015 (without IHH-AAA mutation) in right and left eye (after intravitreal application only into the right eye in comparison to intravenous application): in the right eye (and to some extent in the left eye) after intravitreal application concentrations of VEGF/ANG2-0015 could be detected; this indicates the diffusion from the right eye into serum and from there into the left eye, which can be explained by the long half-life of VEGF/ANG2-0015 (without IHH-AAA mutation); after intravenous application also significant concentrations in eye lysates of both eyes could be detected due to diffusion into the eyes of the serum-stable VEGF/ANG2-0015 (without IHH-AAA mutation).
Figure 8A:
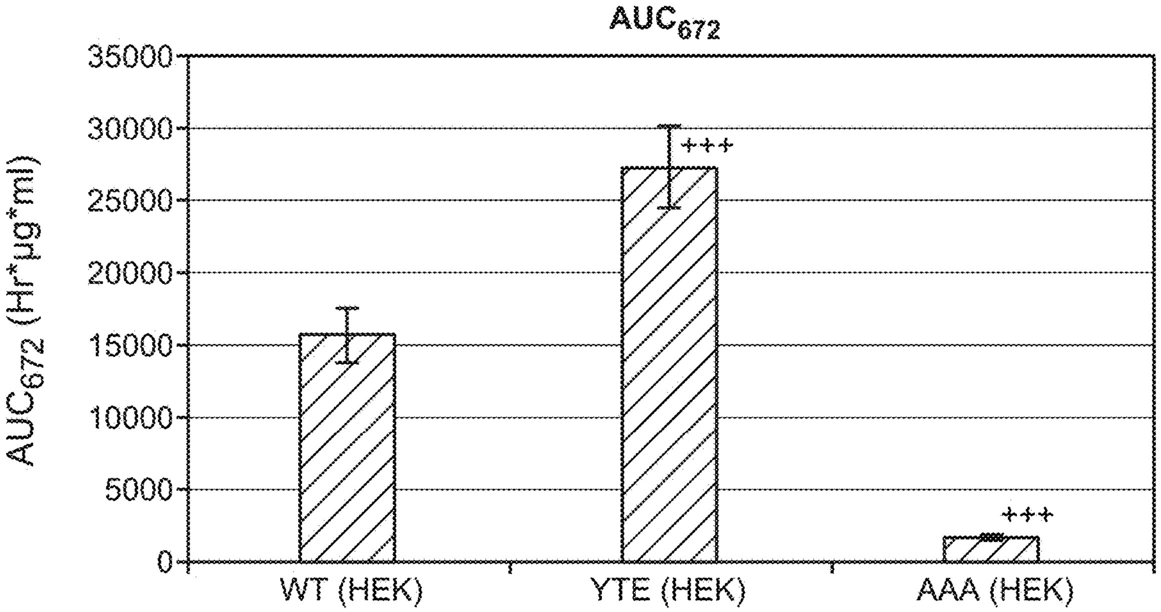
FIGS. 8A, 8B and 8C: Antibodies engineered with respect to their ability to bind FcRn display prolonged (YTE mutation) or shortened (IHH-AAA mutation) in vivo half-lives, enhanced (YTE mutation) or reduced binding (IHH-AAA mutation) compared to the reference wild-type (wt) antibody in SPR analysis as well as enhanced or reduced retention time in FcRn column chromatography; 8A PK data after single i.v. bolus application of 10 mg/kg into huFcRn transgenic male C57BL/6J mice+/−276: AUC data for wt IgG as well as YTE and IHH-AAA Fc-region-modified IgGs; 8B BIAcore sensorgram; 8C FcRn affinity column elution; wild-type anti-IGF-1R antibody (reference), YTE-mutant of anti-IGF-1R antibody, IHH-AAA-mutant of anti-IGF-1R antibody.
Figure 8B:
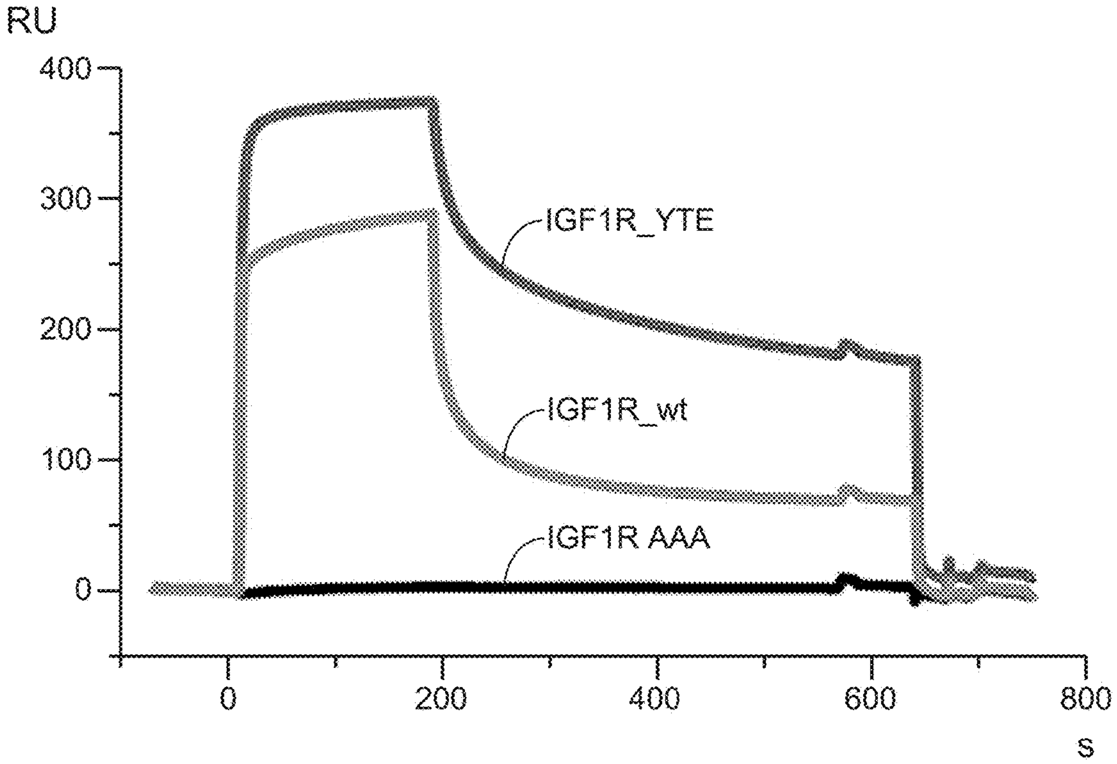
Figure 8C:
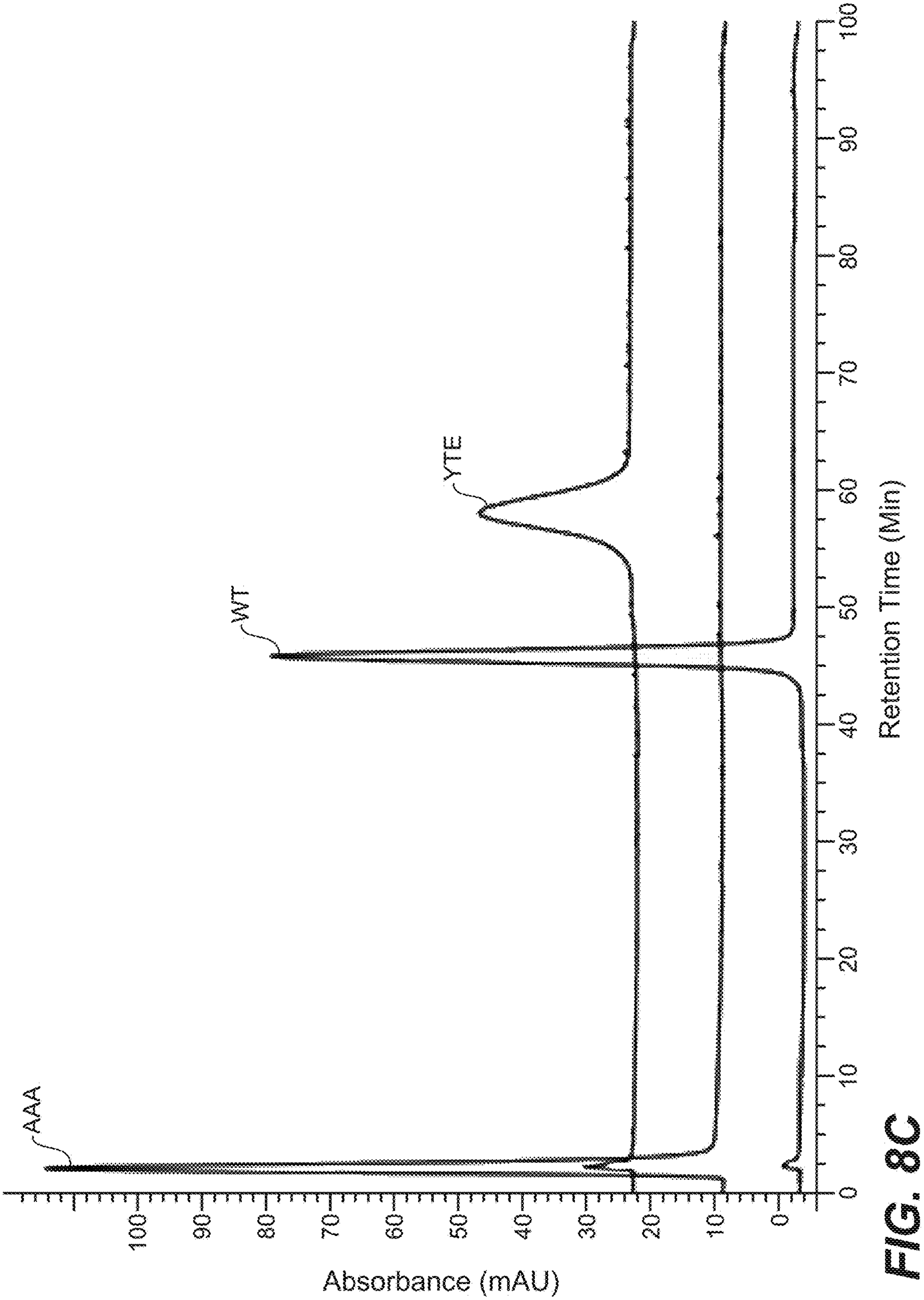

Results for concentrations in eye lysates are shown in the following Tables and FIGS. 7D to 7E.

TABLE

Concentrations of VEGF/ANG2-0015 (without IHH-AAA mutation) in eye lysates after intra vitreal application into right eye mean conc. values from n = 6 mice

| ID | | mean conc. [ng/mL] |
|---|---|---|
| 96 h | left eye | 8.7 |
| | right eye | 46.1 |
| 168 h | left eye | 4.3 |
| | right eye t | 12.9 |

TABLE

Concentrations of VEGF/ANG2-0015 (without IHH-AAA mutation) in eye lysates after intravenous application mean conc. values from n = 5 mice

| ID | | mean conc. [ng/mL] |
|---|---|---|
| 96 h | left eye | 4.2 |
| | right eye | 7.5 |
| 168 h | left eye | 3.4 |
| | right eye | 6.1 |

TABLE

| Concentrations of VEGF/ANG2-0016 (with IHH-AAA mutation) in eye lysates after intra vitreal application into right eye mean conc. values from n = 5 mice | | |
|---|---|---|
| | ID | mean conc. [ng/mL] |
| 96 h | left eye | 0.3 |
| | right eye | 34.5 |
| 168 h | left eye | 0.1 |
| | right eye | 9.0 |

TABLE

| Concentrations of VEGF/ANG2-0016 (with IHH-AAA mutation) in eye lysates after intravenous application mean conc. values from n = 5 mice | | |
|---|---|---|
| | ID | mean conc. [ng/mL] |
| 96 h | left eye | 0.0 |
| | right eye | 0.1 |
| 168 h | left eye | 0.0 |
| | right eye | 0.1 |

Summary of Results:

After intravitreal application the bispecific anti-VEGF/ANG2antibody as reported herein VEGF/ANG2-0016 (with IHH-AAA mutation) shows similar concentrations (after 96 and 168 hours) in the eye lysates as compared to the bispecific anti-VEGF/ANG2 antibody without IHH-AAA mutation VEGF/ANG2-0015.

Also after intravitreal application the bispecific anti-VEGF/ANG2 antibody as reported herein VEGF/ANG2-0016 (with IHH-AAA mutation) shows in addition a faster clearance and shorter half-life in the serum as compared to the bispecific anti-VEGF/ANG2 antibody without IHH-AAA mutation VEGF/ANG2-0015.

Example 7

Mouse Cornea Micropocket Angiogenesis Assay

To test the anti-angiogenic effect bispecific anti-VEGF/ANG2antibody with the respective VEGF binding VH and VL of SEQ ID NO: 20 and 21 and the ANG2 binding VH and VL of SEQ ID NO: 28 and 29 on VEGF-induced angiogenesis in vivo, a mouse corneal angiogenesis assay was performed. In this assay a VEGF soaked Nylaflo disc is implanted into a pocket of the avascular cornea at a fixed distance to the limbal vessels. Vessels immediately grow into the cornea towards the developing VEGF gradient. 8 to 10 weeks old female Balb/c mice were purchased from Charles River, Sulzfeld, Germany. The protocol is modified according to the method described by Rogers, M. S., et al., Nat. Protoc. 2 (2007) 2545-2550. Briefly, micropockets with a width of about 500 μm are prepared under a microscope at approximately 1 mm from the limbus to the top of the cornea using a surgical blade and sharp tweezers in the anesthetized mouse. The disc (Nylaflo®, Pall Corporation, Michigan) with a diameter of 0.6 mm is implanted and the surface of the implantation area was smoothened. Discs are incubated in corresponding growth factor or in vehicle for at least 30 min. After 3, 5 and 7 days (or alternatively only after 3, 5 or 7 days) eyes are photographed and vascular response is measured. The assay is quantified by calculating the percentage of the area of new vessels per total area of the cornea.

The discs are loaded with 300 ng VEGF or with PBS as a control and implanted for 7 days. The outgrowth of vessels from the limbus to the disc is monitored over time on day 3, 5 and/or 7. One day prior to disc implantation the antibodies are administered intravenously at a dose of 10 mg/kg (due to the intravenous application the serum-stable VEGF/ANG2-0015 (without IHH-AAA mutation) which only differs from VEGF/ANG2-0016 by the IHH-AAA mutation and has the same VEGF and ANG2 binding VHs and VLs to mediate efficacy, is used as surrogate) for testing the anti-angiogenic effect on VEGF-induced angiogenesis in vivo. Animals in the control group receive vehicle. The application volume is 10 mL/kg.

Example 8

Pharmacokinetic (PK) Properties of Antibodies with HHY-AAA Mutation

PK Data with FcRn Mice Transgenic for Human FcRn

In Life Phase:

The study included female C57BL/6J mice (background); mouse FcRn deficient, but hemizygous transgenic for human FcRn (huFcRn, line 276 −/tg)

Part 1:

All mice were injected once intravitreally into the right eye with the appropriate solution of IGF-1R 0033, IGF-1R 0035, IGF-1R 0045 (i.e. 22.2 μg compound/animal of IGF-1R 0033, 24.4 μg compound/animal IGF-1R 0035, 32.0 μg compound/animal IGF-1R and 32.0 μg compound/animal of IGF-1R 0045).

Thirteen mice were allocated to 2 groups with 6 and 7, respectively, animals each. Blood samples are taken from group 1 at 2, 24 and 96 hours and from group 2 at 7, 48 and 168 hours after dosing.

Injection into the vitreous of the right mouse eye was performed by using the NanoFil Microsyringe system for nanoliter injection from World Precision Instruments, Inc., Berlin, Germany. Mice were anesthetized with 2.5% Isoflurane and for visualization of the mouse eye a Leica MZFL 3 microscope with a 40 fold magnification and a ring-light with a Leica KL 2500 LCD lightning was used. Subsequently, 2 μL of the compound were injected using a 35-gauge needle.

Blood was collected via the retrobulbar venous plexus of the contralateral eye from each animal for the determination of the compound levels in serum.

Serum samples of at least 50 μL were obtained from blood after 1 hour at RT by centrifugation (9,300×g) at 4° C. for 3 min. Serum samples were frozen directly after centrifugation and stored frozen at −80° C. until analysis. Treated eyes of the animals of group 1 were isolated 96 hours after treatment and of the animals of group 2 168 hours after treatment. Samples were stored frozen at −80° C. until analysis.

Part 2:

All mice were injected once intravenously via the tail vein with the appropriate solution of IGF-1R 0033, IGF-1R 0035, IGF-1R 0045 (i.e. 22.2 μg compound/animal of IGF-1R 0033, 24.4 μg compound/animal IGF-1R 0035, 32.0 μg compound/animal IGF-1R and 32.0 μg compound/animal of IGF-1R 0045).

Twelve mice were allocated to 2 groups with 6 animals each. Blood samples are taken from group 1 at 1, 24 and 96 hours and from group 2 at 7, 48 and 168 hours after dosing. Blood was collected via the retrobulbar venous plexus from each animal for the determination of the compound levels in serum.

Serum samples of at least 50 μL were obtained from blood after 1 hour at RT by centrifugation (9,300×g) at 4° C. for 3 min. Serum samples were frozen directly after centrifugation and stored frozen at −80° C. until analysis.

Preparation of Cell Lysis Buffer

Carefully mix 100 μL factor 1, 50 μL factor 2 and 24.73 mL Cell Lysis buffer (all from Bio-Rad, Bio-Plex Cell Lysis Kit, Cat. No. 171-304011) and add 125 μL PMSF-solution (174.4 mg phenylmethylsulfonylfluoride diluted in 2.0 mL DMSO).

Preparation of Whole Eye Lysates (Mice)

The eye lysates were gained by physico-chemical disintegration of the whole eye from laboratory animals. For mechanical disruption each eye was transferred into a 1.5 mL micro vial with conical bottom. After thawing, the eyes were washed with 1 mL cell washing buffer once (Bio-Rad, Bio-Plex Cell Lysis Kit, Cat. No. 171-304011). In the following step 500 μL of freshly prepared cell lysis buffer were added and the eyes were grinded using a 1.5 mL tissue grinding pestle (VWR Int., Art. No. 431-0098). The mixture was then frozen and thawed five times and grinded again. To separate lysate from remaining tissue the samples were centrifuged for 4 min. at 4500×g. After centrifuging the supernatant was collected and stored at −20° C. until further analysis in the quantification ELISA Analysis (Serum)

For quantification of antibodies in mouse serum sample, a standard solid-phase serial sandwich immunoassay with biotinylated and digoxigenated monoclonal antibodies used as capture and detection antibodies is performed. Serum accounts for about 50% of the full blood sample volume.

More detailed, concentrations of the antibodies in mouse serum samples were determined by a human-IgG (Fab) specific enzyme linked immunosorbent assay. Streptavidin coated microtiter plates were incubated with the biotinylated anti-human Fab(kappa) monoclonal antibody M-1.7.10-IgG as capture antibody diluted in assay buffer for one hour at room temperature with agitation. After washing three times with phosphate-buffered saline-polysorbate 20 (Tween20), serum samples at various dilutions were added followed by second incubation for one hour at room temperature. After three repeated washings bound antibody was detected by subsequent incubation with the anti-human Fab(CH1) monoclonal antibody M-1.19.31-IgG conjugated to digoxigenin, followed by an anti-digoxigenin antibody conjugated to horseradish peroxidase (HRP). ABTS (2,2'-azino-bis(3-ethylbenzothiazoline-6-sulphonic acid); Roche Diagnostics GmbH, Mannheim, Germany) was used as HRP substrate to form a colored reaction product. Absorbance of the resulting reaction product was read at 405 nm (ABTS; reference wavelength: 490 nm).

All samples, positive and negative control samples were analyzed in replicates and calibrated against an antibody standard provided.

Analysis (Eye Lysate)

The concentrations of the analytes in mouse eye lysate samples were determined using a qualified electro-chemiluminescence immunoassay (ECLIA) method based on the ELECSYS® instrument platform (Roche Diagnostics GmbH, Mannheim, Germany) under non-GLP conditions.

The undiluted supernatant (eye lysates) was incubated with capture and detection molecules for 9 min. at 37° C. Biotinylated anti-human-Fab(kappa) monoclonal antibody M-1.7.10-IgG was used as capture molecule and a ruthenium(II)tris(bispyridyl)$_3^{2+}$ labeled anti-human-Fab(CH1) monoclonal antibody M-1.19.31-IgG was used for detection. Streptavidin-coated magnetic microparticles were added and incubated for additional 9 min. at 37° C. to allow binding of preformed immune complexes due to biotin-streptavidin interactions. The microparticles were magnetically captured on an electrode and a chemiluminescent signal generated using the co-reactant tripropyl amine (TPA). The gained signal was measured by a photomultiplier detector.

TABLE

Standard chart IGF-1R 0033

| | concentration [ng/mL] | signal mean counts | standard deviation signal counts | serum-conc. [ng/mL] | recovery [%] |
|---|---|---|---|---|---|
| standard sample 9 | 0 | 1038 | 46 | — | — |
| standard sample 8 | 0.686 | 2682 | 105 | 0.675 | 98 |
| standard sample 7 | 2.06 | 6275 | 791 | 2.06 | 100 |
| standard sample 6 | 6.17 | 15907 | 316 | 6.23 | 101 |
| standard sample 5 | 18.5 | 45455 | 1238 | 18.8 | 102 |
| standard sample 4 | 55.6 | 133940 | 949 | 55.7 | 100 |
| standard sample 3 | 167 | 388069 | 2929 | 165 | 99 |
| standard sample 2 | 500 | 1129804 | 16777 | 503 | 101 |
| standard sample 1 | 1500 | 2956965 | 60287 | 1499 | 100 |

TABLE

Standard chart IGF-1R 0035

| | concentration [ng/mL] | signal mean counts | standard deviation signal counts | serum-conc. [ng/mL] | recovery [%] |
|---|---|---|---|---|---|
| standard sample 9 | 0 | 1024 | 63 | — | — |
| standard sample 8 | 0.686 | 2817 | 38 | 0.681 | 99 |
| standard sample 7 | 2.06 | 6451 | 39 | 2.08 | 101 |

TABLE-continued

Standard chart IGF-1R 0035

| | concentration [ng/mL] | signal mean counts | standard deviation signal counts | serum-conc. [ng/mL] | recovery [%] |
|---|---|---|---|---|---|
| standard sample 6 | 6.17 | 17100 | 319 | 6.13 | 99 |
| standard sample 5 | 18.5 | 49693 | 713 | 18.6 | 100 |
| standard sample 4 | 55.6 | 146746 | 2575 | 56.1 | 101 |
| standard sample 3 | 167 | 423597 | 5068 | 165 | 99 |
| standard sample 2 | 500 | 1224244 | 11655 | 502 | 100 |
| standard sample 1 | 1500 | 3144901 | 44536 | 1499 | 100 |

TABLE

Standard chart IGF-1R 0045

| | concentration [ng/mL] | signal mean counts | standard deviation signal counts | serum-conc. [ng/mL] | recovery [%] |
|---|---|---|---|---|---|
| standard sample 9 | 0 | 1339 | 545 | — | — |
| standard sample 8 | 0.686 | 3108 | 61 | 0.622 | 91 |
| standard sample 7 | 2.06 | 7032 | 189 | 1.93 | 94 |
| standard sample 6 | 6.17 | 19175 | 750 | 6.10 | 99 |
| standard sample 5 | 18.5 | 55526 | 823 | 18.7 | 101 |
| standard sample 4 | 55.6 | 158591 | 5412 | 55.7 | 100 |
| standard sample 3 | 167 | 456316 | 28759 | 167 | 100 |
| standard sample 2 | 500 | 1274801 | 47532 | 499 | 100 |
| standard sample 1 | 1500 | 3280452 | 239523 | 1501 | 100 |

Results

A) Serum Concentrations

Figure 17:
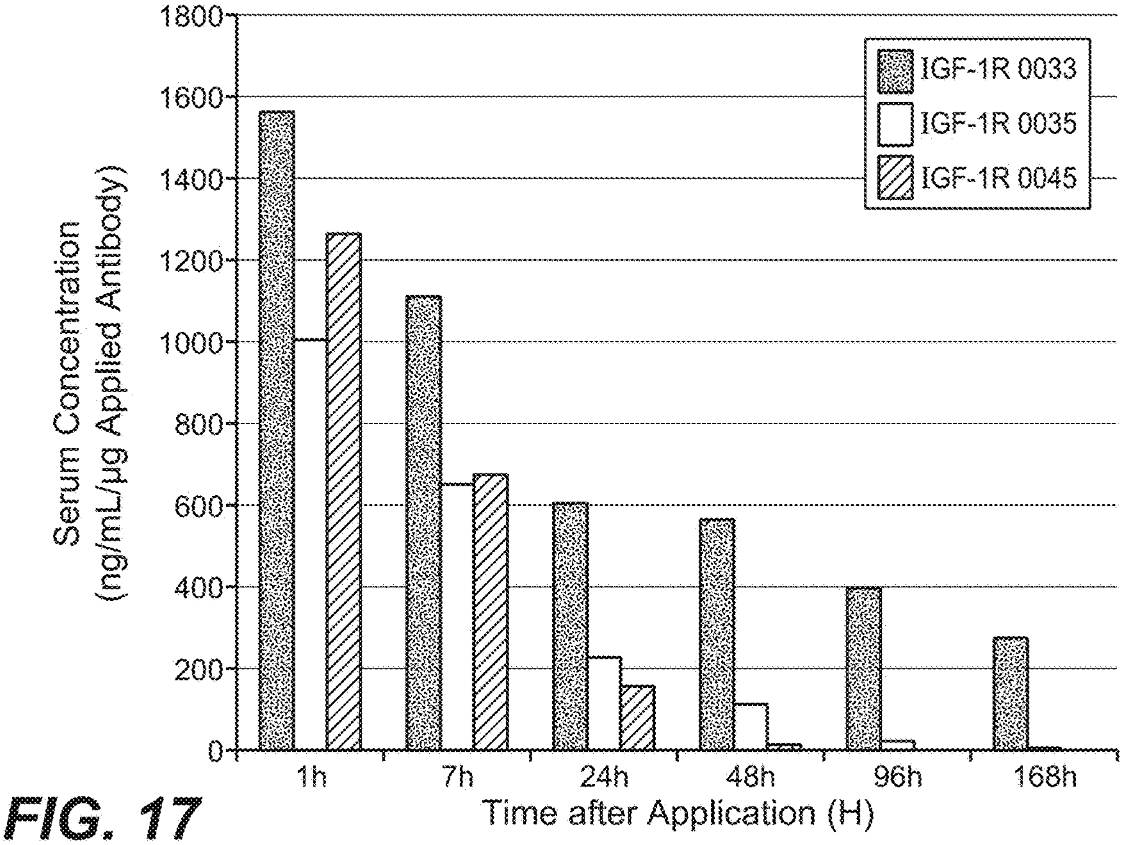
FIG. 17: Comparison of serum concentrations after intravenous application of antibodies IGF-1R 0033, 0035 and 0045.

Results for serum concentrations are shown in the following Tables and FIG. 17.

TABLE

IGF-1R 0033 (without HHY-AAA mutation): Comparison of serum concentrations after intravitreal and intravenous application (n.d. = not determined)

| ID | serum concentration after intravitreal application average conc. [μg/mL] | serum concentration after intravenous application average conc. [μg/mL] |
|---|---|---|
| 1 h | n.d. | 34.7 |
| 2 h | 5.9 | n.d. |
| 7 h | 11.1 | 24.7 |
| 24 h | 4.4 | 13.6 |
| 48 h | 7.8 | 12.6 |
| 96 h | 2.1 | 8.9 |
| 168 h | 2.9 | 6.2 |

TABLE

IGF-1R 0035 (with HHY-AAA mutation in one Fc-region polypeptide): Comparison of serum concentrations after intravitreal and intravenous application

| ID | serum concentration after intravitreal application average conc. [μg/mL] | serum concentration after intravenous application average conc. [μg/mL] |
|---|---|---|
| 1 h | n.d. | 24.5 |
| 2 h | 7.3 | n.d. |
| 7 h | 7.9 | 16.1 |
| 24 h | 2.3 | 5.7 |
| 48 h | 1.7 | 2.9 |
| 96 h | 0.3 | 0.6 |
| 168 h | 0.1 | 0.2 |

TABLE

IGF-1R 0045 (with HHY-AAA mutation in both Fc-region polypeptides): Comparison of serum concentrations after intravitreal and intravenous application (BLQ = below limit of quantitation)

| ID | serum concentration after intravitreal application average conc. [μg/mL] | serum concentration after intravenous application average conc. [μg/mL] |
|---|---|---|
| 1 h | n.d. | 40.5 |
| 2 h | 13.2 | n.d. |
| 7 h | 9.6 | 21.7 |
| 24 h | 2.2 | 5.1 |
| 48 h | 0.9 | 0.7 |
| 96 h | 0.05 | 0.03 |
| 168 h | 0.01 | BLQ |

TABLE

Comparison of serum concentrations after intravenous application of antibodies IGF-1R 0033, 0035 and 0045 normalized to 1 μg applied antibody

| ID | IGF-1R 0033 | IGF-1R 0035 | IGF-1R 0045 |
|---|---|---|---|
| | average conc. [ng/mL/μg applied antibody] | | |
| 1 h | 1564 | 1006 | 1266 |
| 7 h | 1114 | 659 | 679 |
| 24 h | 613 | 234 | 160 |
| 48 h | 569 | 118 | 21 |
| 96 h | 399 | 26 | 1 |
| 168 h | 280 | 7 | 0 |

Results

B) Concentrations in Eye-Lysates of Left and Right Eyes

Figure 18:
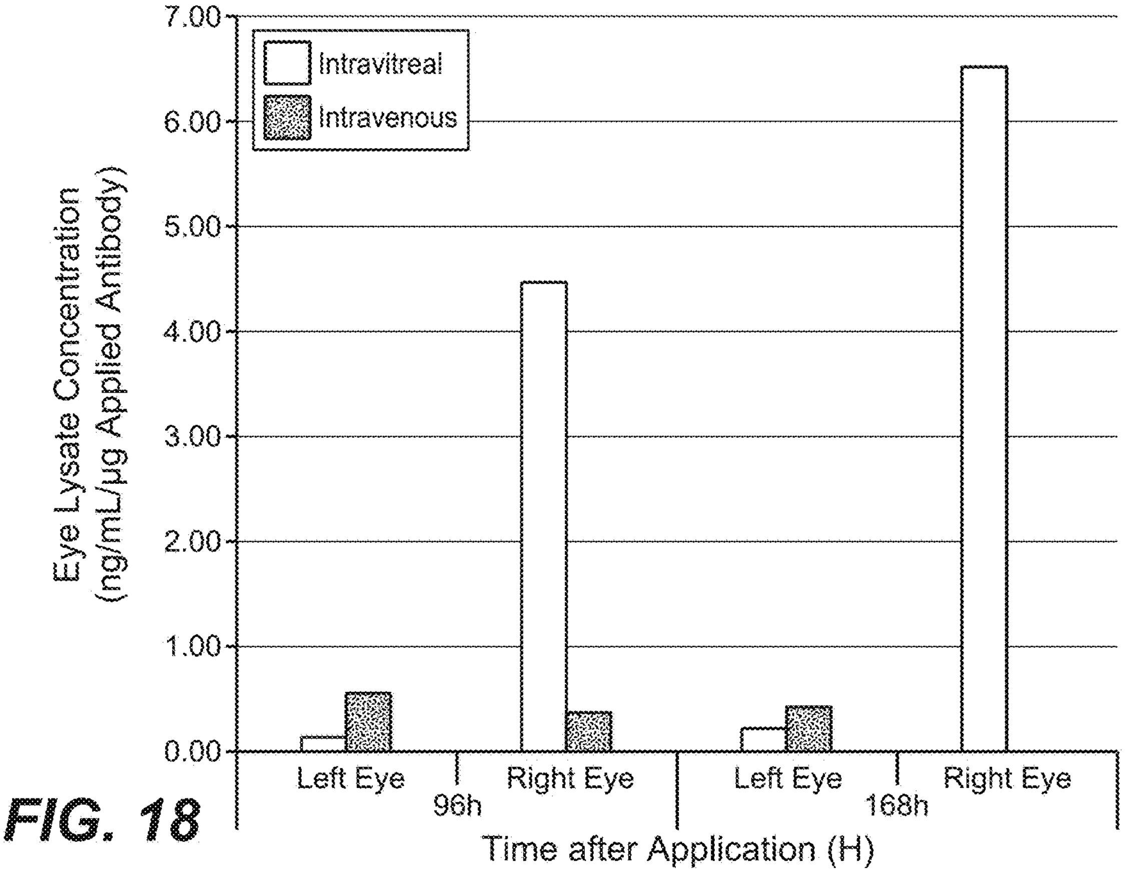
FIG. 18: Comparison of eye lysate concentration after intravitreal and intravenous application of antibody IGF-1R 0033.
Figure 19:
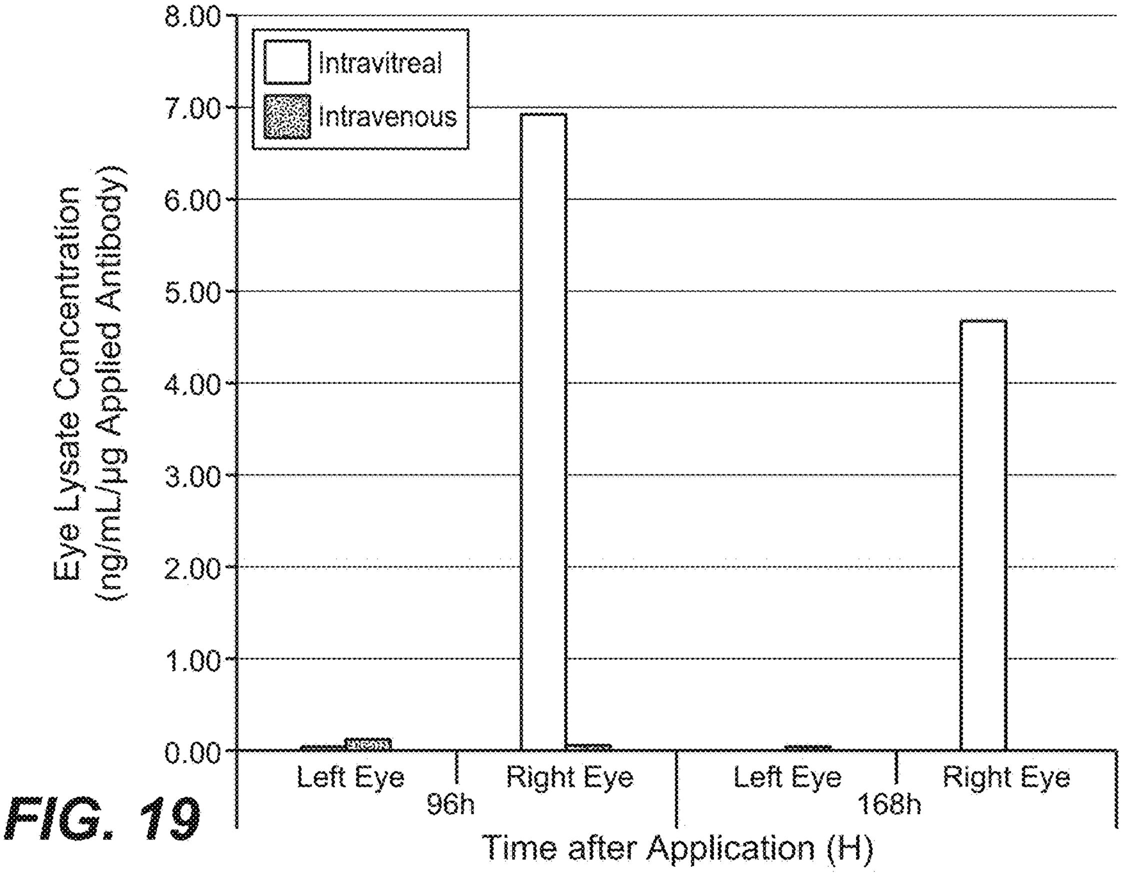
FIG. 19: Comparison of eye lysate concentration after intravitreal and intravenous application of antibody IGF-1R 0035.
Figure 20:
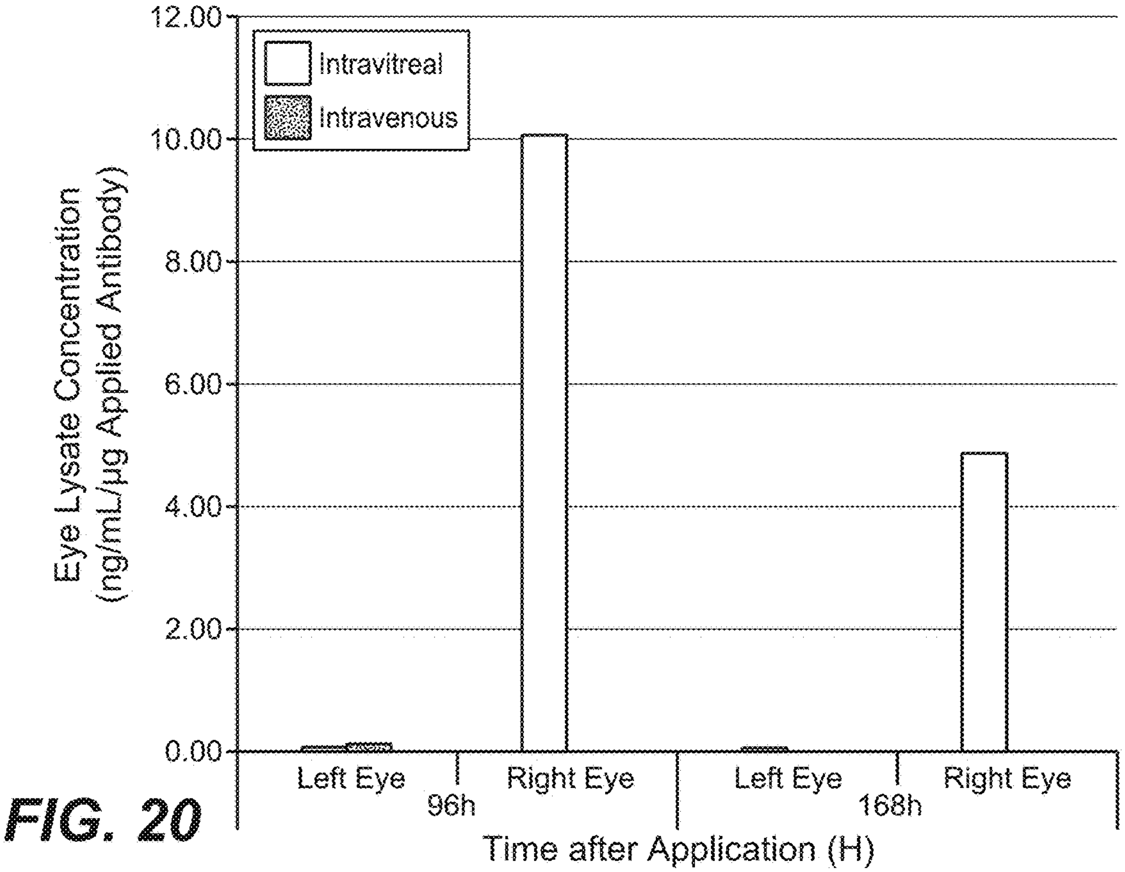
FIG. 20: Comparison of eye lysate concentration after intravitreal and intravenous application of antibody IGF-1R 0045.

Results for concentrations in eye lysates are shown in the following Tables and FIGS. 18 to 20.

TABLE

Concentrations of IGF-1R 0033 (without HHY-AAA mutation) in eye lysates after intravitreal application into the right eye mean conc. values from n = 7 (96 h) and n = 6 (196 h) mice

| ID | | mean conc. [ng/mL] |
|---|---|---|
| 96 h | left eye | 3.3 |
| | right eye | 99.5 |
| 168 h | left eye | 5.2 |
| | right eye | 144.9 |

TABLE

Concentrations of IGF-1R 0033 (without HHY-AAA mutation) in eye lysates after intravenous application (BLQ = below limit of quantitation) mean conc. values from n = 5 (96 h) and n = 6 (196 h) mice

| ID | | mean conc. [ng/mL] |
|---|---|---|
| 96 h | left eye | 12.7 |
| | right eye | 8.5 |
| 168 h | left eye | 9.7 |
| | right eye | BLQ |

TABLE

Concentrations of IGF-1R 0035 (with the HHY-AAA mutation in one Fc-region polypeptide) in eye lysates after intravitreal application into the right eye mean conc. values from n = 6 mice

| ID | | mean conc. [ng/mL] |
|---|---|---|
| 96 h | left eye | 1.1 |
| | right eye | 169.2 |
| 168 h | left eye | 0.3 |
| | right eye | 114.7 |

TABLE

Concentrations of IGF-1R 0035 (with the HHY-AAA mutation in one Fc-region polypeptide) in eye lysates after intravenous application (BLQ = below limit of quantitation) mean conc. values from n = 6 mice

| ID | | mean conc. [ng/mL] |
|---|---|---|
| 96 h | left eye | 3.7 |
| | right eye | 1.7 |
| 168 h | left eye | 1.4 |
| | right eye | 0.3 |

TABLE

Concentrations of IGF-1R 0045 (with the HHY-AAA mutation in both Fc-region polypeptides) in eye lysates after intravitreal application into the right eye mean conc. values from n = 6 mice

| ID | | mean conc. [ng/mL] |
|---|---|---|
| 96 h | left eye | 1.4 |
| | right eye | 322.6 |
| 168 h | left eye | 1.4 |
| | right eye | 156.8 |

TABLE

Concentrations of IGF-1R 0045 (with the HHY-AAA mutation in both Fc-region polypeptides) in eye lysates after intravenous application (BLQ = below limit of quantitation) mean conc. values from n = 6 (96 h) and n = 5 (196 h) mice

| ID | | mean conc. [ng/mL] |
|---|---|---|
| 96 h | left eye | 3.6 |
| | right eye | 1.3 |
| 168 h | left eye | 0.8 |
| | right eye | 0.4 |

TABLE

Concentrations of IGF-1R 0033, 0035 and 0045 in eye lysates after intravitreal application into the right eye normalized to 1 μg applied antibody

| ID | | IGF-1R 0033 | IGF-1R 0035 | IGF-1R 0045 |
|---|---|---|---|---|
| | | mean conc. [ng/mL] | | |
| 96 h | left eye | 0.15 | 0.05 | 0.04 |
| | right eye | 4.48 | 6.93 | 10.08 |
| 168 h | left eye | 0.24 | 0.01 | 0.04 |
| | right eye | 6.53 | 4.70 | 4.90 |

Summary of Results:

After intravitreal application the anti-IGF-1R antibodies 0035 and 0045 as reported herein (with one sided or both sided HHY-AAA mutation) shows similar concentrations (after 96 and 168 hours) in the eye lysates as compared to the anti-IGF-1R antibody without HHY-AAA mutation (IGF-1R 0033).

Also after intravitreal application the anti-IGF-1R antibodies 0035 and 0045 as reported herein (with one sided or both sided HHY-AAA mutation) shows in addition a faster clearance and shorter half-life in the serum as compared to the anti-IGF-1R antibody without HHY-AAA mutation (IGF-1R 0033).

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An antibody, comprising a first polypeptide and a second polypeptide each comprising in N-terminal to C-terminal direction at least a portion of an immunoglobulin hinge region, which comprises one or more cysteine residues, an immunoglobulin CH2-domain and an immunoglobulin CH3-domain, wherein:

—the first polypeptide has mutations consisting of I253A, H310A and H435A and the second polypeptide has mutations consisting of H310A, H433A and Y436A, or the first polypeptide has mutations consisting of H310A, H433A and Y436A and the second polypeptide has mutations consisting of L251D, L314D and L432D, or the first polypeptide has mutations consisting of H310A, H433A and Y436A and the second polypeptide has mutations consisting of L251S, L314S and L432S, and wherein the numbering is according to Kabat.

2. The antibody according to claim 1, wherein the antibody is a monoclonal antibody.

3. The antibody according to claim 1, wherein the antibody is a human, humanized or chimeric antibody.

4. The antibody according to claim 1, wherein the antibody is a bispecific antibody.

5. The antibody according to claim 1, wherein the antibody is a bivalent antibody.

6. The antibody according to claim 1, wherein the antibody has the same binding to *Staphylococcus* protein A as an antibody with a wild-type human IgG1 or IgG4 class Fc-region.

7. A nucleic acid encoding the antibody according to claim 1.

8. A cell comprising the nucleic acid according to claim 7.

9. A method of producing the antibody according to claim 1 comprising the steps of culturing a host cell comprising a nucleic acid encoding the antibody according to claim 1, and recovering the antibody from the cell or the cultivation medium.

10. A pharmaceutical formulation comprising the antibody according to claim 1.

11. A pharmaceutical formulation comprising the antibody according to claim 1 for the treatment of ocular vascular diseases.

* * * * *

SEQUENCE LISTING

```
<160> NUMBER OF SEQ ID NOS: 112

<210> SEQ ID NO 1
<211> LENGTH: 448
<212> TYPE: PRT
<213> ORGANISM: Homo sapiens

<400> SEQUENCE: 1

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335
```

Ile Ser Lys Ala Lys Gly Gln Pro Arg Glu Pro Gln Val Tyr Thr Leu
340 345 350

Pro Pro Ser Arg Asp Glu Leu Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly Lys
435 440 445

<210> SEQ ID NO 2
<211> LENGTH: 448
<212> TYPE: PRT
<213> ORGANISM: Homo sapiens

<400> SEQUENCE: 2

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Met
35 40 45

Ala Ile Ile Trp Phe Asp Gly Ser Ser Lys Tyr Tyr Gly Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Asp Asp Thr Ala Val Tyr Tyr Cys
85 90 95

Ala Arg Glu Leu Gly Arg Arg Tyr Phe Asp Leu Trp Gly Arg Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Ala Ala Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Gly Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Asp Glu Leu Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly Lys
435 440 445

<210> SEQ ID NO 3
<211> LENGTH: 215
<212> TYPE: PRT
<213> ORGANISM: Homo sapiens

<400> SEQUENCE: 3

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Lys Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Lys Trp Pro Pro
85 90 95

Trp Thr Phe Gly Gln Gly Thr Lys Val Glu Ser Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys 195 200 205

Ser Phe Asn Arg Gly Glu Cys
210 215

<210> SEQ ID NO 4
<211> LENGTH: 215
<212> TYPE: PRT
<213> ORGANISM: Homo sapiens

<400> SEQUENCE: 4

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Lys Trp Pro Pro
85 90 95

Trp Thr Phe Gly Gln Gly Thr Lys Val Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 5
<211> LENGTH: 118
<212> TYPE: PRT
<213> ORGANISM: Homo sapiens

<400> SEQUENCE: 5

Gln Val Glu Leu Val Glu Ser Gly Gly Gly Val Val Gln Pro Gly Arg
1 5 10 15

Ser Gln Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Ile Ile Trp Phe Asp Gly Ser Ser Thr Tyr Tyr Ala Asp Ser Val
50 55 60

Arg Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Phe Cys

```
                85                  90                  95

Ala Arg Glu Leu Gly Arg Arg Tyr Phe Asp Leu Trp Gly Arg Gly Thr
            100                 105                 110

Leu Val Ser Val Ser Ser
        115


<210> SEQ ID NO 6
<211> LENGTH: 118
<212> TYPE: PRT
<213> ORGANISM: Homo sapiens

<400> SEQUENCE: 6

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Met
        35                  40                  45

Ala Ile Ile Trp Phe Asp Gly Ser Ser Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Glu Leu Gly Arg Arg Tyr Phe Asp Leu Trp Gly Arg Gly Thr
            100                 105                 110

Leu Val Thr Val Ser Ser
        115


<210> SEQ ID NO 7
<211> LENGTH: 108
<212> TYPE: PRT
<213> ORGANISM: Homo sapiens

<400> SEQUENCE: 7

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ser Lys
            100                 105


<210> SEQ ID NO 8
<211> LENGTH: 108
<212> TYPE: PRT
<213> ORGANISM: Homo sapiens

<400> SEQUENCE: 8

Glu Ile Val Leu Thr Gln Ser Pro Ala Thr Leu Ser Leu Ser Pro Gly
1               5                   10                  15
```

```
Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ile Lys
            100                 105


<210> SEQ ID NO 9
<211> LENGTH: 107
<212> TYPE: PRT
<213> ORGANISM: Homo sapiens

<400> SEQUENCE: 9

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Trp Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Glu Ser Thr Tyr Arg Trp Ser Val Leu Thr Val Leu His Gln Asp Trp
65                  70                  75                  80

Leu Asn Gly Lys Glu Tyr Lys Cys Lys Val Ser Asn Lys Ala Leu Pro
                85                  90                  95

Ala Pro Ile Glu Lys Thr Ile Ser Lys Ala Lys
            100                 105


<210> SEQ ID NO 10
<211> LENGTH: 106
<212> TYPE: PRT
<213> ORGANISM: Homo sapiens

<400> SEQUENCE: 10

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105


<210> SEQ ID NO 11
```

<211> LENGTH: 1337
<212> TYPE: PRT
<213> ORGANISM: Homo sapiens

<400> SEQUENCE: 11

```
Glu Ile Cys Gly Pro Gly Ile Asp Ile Arg Asn Asp Tyr Gln Gln Leu
1               5                   10                  15

Lys Arg Leu Glu Asn Cys Thr Val Ile Glu Gly Tyr Leu His Ile Leu
            20                  25                  30

Leu Ile Ser Lys Ala Glu Asp Tyr Arg Ser Tyr Arg Phe Pro Lys Leu
        35                  40                  45

Thr Val Ile Thr Glu Tyr Leu Leu Leu Phe Arg Val Ala Gly Leu Glu
    50                  55                  60

Ser Leu Gly Asp Leu Phe Pro Asn Leu Thr Val Ile Arg Gly Trp Lys
65                  70                  75                  80

Leu Phe Tyr Asn Tyr Ala Leu Val Ile Phe Glu Met Thr Asn Leu Lys
                85                  90                  95

Asp Ile Gly Leu Tyr Asn Leu Arg Asn Ile Thr Arg Gly Ala Ile Arg
            100                 105                 110

Ile Glu Lys Asn Ala Asp Leu Cys Tyr Leu Ser Thr Val Asp Trp Ser
        115                 120                 125

Leu Ile Leu Asp Ala Val Ser Asn Asn Tyr Ile Val Gly Asn Lys Pro
    130                 135                 140

Pro Lys Glu Cys Gly Asp Leu Cys Pro Gly Thr Met Glu Glu Lys Pro
145                 150                 155                 160

Met Cys Glu Lys Thr Thr Ile Asn Asn Glu Tyr Asn Tyr Arg Cys Trp
                165                 170                 175

Thr Thr Asn Arg Cys Gln Lys Met Cys Pro Ser Thr Cys Gly Lys Arg
            180                 185                 190

Ala Cys Thr Glu Asn Asn Glu Cys Cys His Pro Glu Cys Leu Gly Ser
        195                 200                 205

Cys Ser Ala Pro Asp Asn Asp Thr Ala Cys Val Ala Cys Arg His Tyr
    210                 215                 220

Tyr Tyr Ala Gly Val Cys Val Pro Ala Cys Pro Pro Asn Thr Tyr Arg
225                 230                 235                 240

Phe Glu Gly Trp Arg Cys Val Asp Arg Asp Phe Cys Ala Asn Ile Leu
                245                 250                 255

Ser Ala Glu Ser Ser Asp Ser Glu Gly Phe Val Ile His Asp Gly Glu
            260                 265                 270

Cys Met Gln Glu Cys Pro Ser Gly Phe Ile Arg Asn Gly Ser Gln Ser
        275                 280                 285

Met Tyr Cys Ile Pro Cys Glu Gly Pro Cys Pro Lys Val Cys Glu Glu
    290                 295                 300

Glu Lys Lys Thr Lys Thr Ile Asp Ser Val Thr Ser Ala Gln Met Leu
305                 310                 315                 320

Gln Gly Cys Thr Ile Phe Lys Gly Asn Leu Leu Ile Asn Ile Arg Arg
                325                 330                 335

Gly Asn Asn Ile Ala Ser Glu Leu Glu Asn Phe Met Gly Leu Ile Glu
            340                 345                 350

Val Val Thr Gly Tyr Val Lys Ile Arg His Ser His Ala Leu Val Ser
        355                 360                 365

Leu Ser Phe Leu Lys Asn Leu Arg Leu Ile Leu Gly Glu Glu Gln Leu
    370                 375                 380

Glu Gly Asn Tyr Ser Phe Tyr Val Leu Asp Asn Gln Asn Leu Gln Gln
```

```
385                 390                 395                 400

Leu Trp Asp Trp Asp His Arg Asn Leu Thr Ile Lys Ala Gly Lys Met
                405                 410                 415

Tyr Phe Ala Phe Asn Pro Lys Leu Cys Val Ser Glu Ile Tyr Arg Met
            420                 425                 430

Glu Glu Val Thr Gly Thr Lys Gly Arg Gln Ser Lys Gly Asp Ile Asn
        435                 440                 445

Thr Arg Asn Asn Gly Glu Arg Ala Ser Cys Glu Ser Asp Val Leu His
    450                 455                 460

Phe Thr Ser Thr Thr Thr Ser Lys Asn Arg Ile Ile Ile Thr Trp His
465                 470                 475                 480

Arg Tyr Arg Pro Pro Asp Tyr Arg Asp Leu Ile Ser Phe Thr Val Tyr
                485                 490                 495

Tyr Lys Glu Ala Pro Phe Lys Asn Val Thr Glu Tyr Asp Gly Gln Asp
            500                 505                 510

Ala Cys Gly Ser Asn Ser Trp Asn Met Val Asp Val Asp Leu Pro Pro
        515                 520                 525

Asn Lys Asp Val Glu Pro Gly Ile Leu Leu His Gly Leu Lys Pro Trp
    530                 535                 540

Thr Gln Tyr Ala Val Tyr Val Lys Ala Val Thr Leu Thr Met Val Glu
545                 550                 555                 560

Asn Asp His Ile Arg Gly Ala Lys Ser Glu Ile Leu Tyr Ile Arg Thr
                565                 570                 575

Asn Ala Ser Val Pro Ser Ile Pro Leu Asp Val Leu Ser Ala Ser Asn
            580                 585                 590

Ser Ser Ser Gln Leu Ile Val Lys Trp Asn Pro Pro Ser Leu Pro Asn
        595                 600                 605

Gly Asn Leu Ser Tyr Tyr Ile Val Arg Trp Gln Arg Gln Pro Gln Asp
    610                 615                 620

Gly Tyr Leu Tyr Arg His Asn Tyr Cys Ser Lys Asp Lys Ile Pro Ile
625                 630                 635                 640

Arg Lys Tyr Ala Asp Gly Thr Ile Asp Ile Glu Glu Val Thr Glu Asn
                645                 650                 655

Pro Lys Thr Glu Val Cys Gly Gly Glu Lys Gly Pro Cys Cys Ala Cys
            660                 665                 670

Pro Lys Thr Glu Ala Glu Lys Gln Ala Glu Lys Glu Glu Ala Glu Tyr
        675                 680                 685

Arg Lys Val Phe Glu Asn Phe Leu His Asn Ser Ile Phe Val Pro Arg
    690                 695                 700

Pro Glu Arg Lys Arg Arg Asp Val Met Gln Val Ala Asn Thr Thr Met
705                 710                 715                 720

Ser Ser Arg Ser Arg Asn Thr Thr Ala Ala Asp Thr Tyr Asn Ile Thr
                725                 730                 735

Asp Pro Glu Glu Leu Glu Thr Glu Tyr Pro Phe Phe Glu Ser Arg Val
            740                 745                 750

Asp Asn Lys Glu Arg Thr Val Ile Ser Asn Leu Arg Pro Phe Thr Leu
        755                 760                 765

Tyr Arg Ile Asp Ile His Ser Cys Asn His Glu Ala Glu Lys Leu Gly
    770                 775                 780

Cys Ser Ala Ser Asn Phe Val Phe Ala Arg Thr Met Pro Ala Glu Gly
785                 790                 795                 800

Ala Asp Asp Ile Pro Gly Pro Val Thr Trp Glu Pro Arg Pro Glu Asn
                805                 810                 815
```

Ser Ile Phe Leu Lys Trp Pro Glu Pro Glu Asn Pro Asn Gly Leu Ile
820 825 830

Leu Met Tyr Glu Ile Lys Tyr Gly Ser Gln Val Glu Asp Gln Arg Glu
835 840 845

Cys Val Ser Arg Gln Glu Tyr Arg Lys Tyr Gly Gly Ala Lys Leu Asn
850 855 860

Arg Leu Asn Pro Gly Asn Tyr Thr Ala Arg Ile Gln Ala Thr Ser Leu
865 870 875 880

Ser Gly Asn Gly Ser Trp Thr Asp Pro Val Phe Phe Tyr Val Gln Ala
885 890 895

Lys Thr Gly Tyr Glu Asn Phe Ile His Leu Ile Ile Ala Leu Pro Val
900 905 910

Ala Val Leu Leu Ile Val Gly Gly Leu Val Ile Met Leu Tyr Val Phe
915 920 925

His Arg Lys Arg Asn Asn Ser Arg Leu Gly Asn Gly Val Leu Tyr Ala
930 935 940

Ser Val Asn Pro Glu Tyr Phe Ser Ala Ala Asp Val Tyr Val Pro Asp
945 950 955 960

Glu Trp Glu Val Ala Arg Glu Lys Ile Thr Met Ser Arg Glu Leu Gly
965 970 975

Gln Gly Ser Phe Gly Met Val Tyr Glu Gly Val Ala Lys Gly Val Val
980 985 990

Lys Asp Glu Pro Glu Thr Arg Val Ala Ile Lys Thr Val Asn Glu Ala
995 1000 1005

Ala Ser Met Arg Glu Arg Ile Glu Phe Leu Asn Glu Ala Ser Val
1010 1015 1020

Met Lys Glu Phe Asn Cys His His Val Val Arg Leu Leu Gly Val
1025 1030 1035

Val Ser Gln Gly Gln Pro Thr Leu Val Ile Met Glu Leu Met Thr
1040 1045 1050

Arg Gly Asp Leu Lys Ser Tyr Leu Arg Ser Leu Arg Pro Glu Met
1055 1060 1065

Glu Asn Asn Pro Val Leu Ala Pro Pro Ser Leu Ser Lys Met Ile
1070 1075 1080

Gln Met Ala Gly Glu Ile Ala Asp Gly Met Ala Tyr Leu Asn Ala
1085 1090 1095

Asn Lys Phe Val His Arg Asp Leu Ala Ala Arg Asn Cys Met Val
1100 1105 1110

Ala Glu Asp Phe Thr Val Lys Ile Gly Asp Phe Gly Met Thr Arg
1115 1120 1125

Asp Ile Tyr Glu Thr Asp Tyr Tyr Arg Lys Gly Gly Lys Gly Leu
1130 1135 1140

Leu Pro Val Arg Trp Met Ser Pro Glu Ser Leu Lys Asp Gly Val
1145 1150 1155

Phe Thr Thr Tyr Ser Asp Val Trp Ser Phe Gly Val Val Leu Trp
1160 1165 1170

Glu Ile Ala Thr Leu Ala Glu Gln Pro Tyr Gln Gly Leu Ser Asn
1175 1180 1185

Glu Gln Val Leu Arg Phe Val Met Glu Gly Gly Leu Leu Asp Lys
1190 1195 1200

Pro Asp Asn Cys Pro Asp Met Leu Phe Glu Leu Met Arg Met Cys
1205 1210 1215

```
Trp Gln  Tyr Asn Pro Lys Met  Arg Pro Ser Phe Leu  Glu Ile Ile
    1220                 1225                 1230

Ser Ser  Ile Lys Glu Glu Met  Glu Pro Gly Phe Arg  Glu Val Ser
    1235                 1240                 1245

Phe Tyr  Tyr Ser Glu Glu Asn  Lys Leu Pro Glu Pro  Glu Glu Leu
    1250                 1255                 1260

Asp Leu  Glu Pro Glu Asn Met  Glu Ser Val Pro Leu  Asp Pro Ser
    1265                 1270                 1275

Ala Ser  Ser Ser Ser Leu Pro  Leu Pro Asp Arg His  Ser Gly His
    1280                 1285                 1290

Lys Ala  Glu Asn Gly Pro Gly  Pro Gly Val Leu Val  Leu Arg Ala
    1295                 1300                 1305

Ser Phe  Asp Glu Arg Gln Pro  Tyr Ala His Met Asn  Gly Gly Arg
    1310                 1315                 1320

Lys Asn  Glu Arg Ala Leu Pro  Leu Pro Gln Ser Ser  Thr Cys
    1325                 1330                 1335


<210> SEQ ID NO 12
<211> LENGTH: 330
<212> TYPE: PRT
<213> ORGANISM: Homo sapiens

<400> SEQUENCE: 12

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330


<210> SEQ ID NO 13
<211> LENGTH: 327
<212> TYPE: PRT
<213> ORGANISM: Homo sapiens

<400> SEQUENCE: 13

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
```

290 295 300

Cys Ser Val Met His Glu Ala Leu His Asn His Tyr Thr Gln Lys Ser
305 310 315 320

Leu Ser Leu Ser Leu Gly Lys
325

<210> SEQ ID NO 14
<211> LENGTH: 14
<212> TYPE: PRT
<213> ORGANISM: Artificial
<220> FEATURE:
<223> OTHER INFORMATION: heavy chain CDR3H, <VEGF>ranibizumab

<400> SEQUENCE: 14

Tyr Pro Tyr Tyr Tyr Gly Thr Ser His Trp Tyr Phe Asp Val
1 5 10

<210> SEQ ID NO 15
<211> LENGTH: 17
<212> TYPE: PRT
<213> ORGANISM: Artificial
<220> FEATURE:
<223> OTHER INFORMATION: heavy chain CDR2H, <VEGF>ranibizumab

<400> SEQUENCE: 15

Trp Ile Asn Thr Tyr Thr Gly Glu Pro Thr Tyr Ala Ala Asp Phe Lys
1 5 10 15

Arg

<210> SEQ ID NO 16
<211> LENGTH: 5
<212> TYPE: PRT
<213> ORGANISM: Artificial
<220> FEATURE:
<223> OTHER INFORMATION: heavy chain CDR1H, <VEGF>ranibizumab

<400> SEQUENCE: 16

His Tyr Gly Met Asn
1 5

<210> SEQ ID NO 17
<211> LENGTH: 9
<212> TYPE: PRT
<213> ORGANISM: Artificial
<220> FEATURE:
<223> OTHER INFORMATION: light chain CDR3L, <VEGF>ranibizumab

<400> SEQUENCE: 17

Gln Gln Tyr Ser Thr Val Pro Trp Thr
1 5

<210> SEQ ID NO 18
<211> LENGTH: 7
<212> TYPE: PRT
<213> ORGANISM: Artificial
<220> FEATURE:
<223> OTHER INFORMATION: light chain CDR2L, <VEGF>ranibizumab

<400> SEQUENCE: 18

Phe Thr Ser Ser Leu His Ser
1 5

<210> SEQ ID NO 19
<211> LENGTH: 11
<212> TYPE: PRT

```
<213> ORGANISM: Artificial
<220> FEATURE:
<223> OTHER INFORMATION: light chain CDR1L,  <VEGF>ranibizumab

<400> SEQUENCE: 19

Ser Ala Ser Gln Asp Ile Ser Asn Tyr Leu Asn
1               5                   10


<210> SEQ ID NO 20
<211> LENGTH: 123
<212> TYPE: PRT
<213> ORGANISM: Artificial
<220> FEATURE:
<223> OTHER INFORMATION: heavy chain variable domain VH,
      <VEGF>ranibizumab

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser
        115                 120


<210> SEQ ID NO 21
<211> LENGTH: 107
<212> TYPE: PRT
<213> ORGANISM: Artificial
<220> FEATURE:
<223> OTHER INFORMATION: light chain variable domain VL,
      <VEGF>ranibizumab

<400> SEQUENCE: 21

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
            100                 105


<210> SEQ ID NO 22
<211> LENGTH: 20
```

```
<212> TYPE: PRT
<213> ORGANISM: Artificial
<220> FEATURE:
<223> OTHER INFORMATION: heavy chain CDR3H, <ANG-2> Ang2i_LC10 variant

<400> SEQUENCE: 22

Ser Pro Asn Pro Tyr Tyr Tyr Asp Ser Ser Gly Tyr Tyr Tyr Pro Gly
1               5                   10                  15

Ala Phe Asp Ile
            20


<210> SEQ ID NO 23
<211> LENGTH: 17
<212> TYPE: PRT
<213> ORGANISM: Artificial
<220> FEATURE:
<223> OTHER INFORMATION: heavy chain CDR2H, <ANG-2> Ang2i_LC10 variant

<400> SEQUENCE: 23

Trp Ile Asn Pro Asn Ser Gly Gly Thr Asn Tyr Ala Gln Lys Phe Gln
1               5                   10                  15

Gly


<210> SEQ ID NO 24
<211> LENGTH: 5
<212> TYPE: PRT
<213> ORGANISM: Artificial
<220> FEATURE:
<223> OTHER INFORMATION: heavy chain CDR1H, <ANG-2> Ang2i_LC10 variant

<400> SEQUENCE: 24

Gly Tyr Tyr Met His
1               5


<210> SEQ ID NO 25
<211> LENGTH: 11
<212> TYPE: PRT
<213> ORGANISM: Artificial
<220> FEATURE:
<223> OTHER INFORMATION: light chain CDR3L, <ANG-2> Ang2i_LC10 variant

<400> SEQUENCE: 25

Gln Val Trp Asp Ser Ser Ser Asp His Trp Val
1               5                   10


<210> SEQ ID NO 26
<211> LENGTH: 7
<212> TYPE: PRT
<213> ORGANISM: Artificial
<220> FEATURE:
<223> OTHER INFORMATION: light chain CDR2L, <ANG-2> Ang2i_LC10 variant

<400> SEQUENCE: 26

Asp Asp Ser Asp Arg Pro Ser
1               5


<210> SEQ ID NO 27
<211> LENGTH: 11
<212> TYPE: PRT
<213> ORGANISM: Artificial
<220> FEATURE:
<223> OTHER INFORMATION: light chain CDR1L, <ANG-2> Ang2i_LC10 variant

<400> SEQUENCE: 27

Gly Gly Asn Asn Ile Gly Ser Lys Ser Val His
1               5                   10
```

<210> SEQ ID NO 28
<211> LENGTH: 129
<212> TYPE: PRT
<213> ORGANISM: Artificial
<220> FEATURE:
<223> OTHER INFORMATION: heavy chain variable domain VH, <ANG-2>
Ang2i_LC10 variant

<400> SEQUENCE: 28

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser
```

<210> SEQ ID NO 29
<211> LENGTH: 110
<212> TYPE: PRT
<213> ORGANISM: Artificial
<220> FEATURE:
<223> OTHER INFORMATION: light chain variable domain VL, <ANG-2>
Ang2i_LC10 variant

<400> SEQUENCE: 29

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Gly Gln
            100                 105                 110
```

<210> SEQ ID NO 30
<211> LENGTH: 191
<212> TYPE: PRT
<213> ORGANISM: Homo sapiens

<400> SEQUENCE: 30

```
Met Asn Phe Leu Leu Ser Trp Val His Trp Ser Leu Ala Leu Leu Leu
```

```
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190


<210> SEQ ID NO 31
<211> LENGTH: 496
<212> TYPE: PRT
<213> ORGANISM: Homo sapiens

<400> SEQUENCE: 31

Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Ser Pro Tyr Val Ser Asn Ala
    50                  55                  60

Val Gln Arg Asp Ala Pro Leu Glu Tyr Asp Asp Ser Val Gln Arg Leu
65                  70                  75                  80

Gln Val Leu Glu Asn Ile Met Glu Asn Asn Thr Gln Trp Leu Met Lys
                85                  90                  95

Leu Glu Asn Tyr Ile Gln Asp Asn Met Lys Lys Glu Met Val Glu Ile
            100                 105                 110

Gln Gln Asn Ala Val Gln Asn Gln Thr Ala Val Met Ile Glu Ile Gly
        115                 120                 125

Thr Asn Leu Leu Asn Gln Thr Ala Glu Gln Thr Arg Lys Leu Thr Asp
    130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190
```

```
Lys Lys Val Leu Ala Met Glu Asp Lys His Ile Ile Gln Leu Gln Ser
        195                 200                 205

Ile Lys Glu Glu Lys Asp Gln Leu Gln Val Leu Val Ser Lys Gln Asn
    210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
                245                 250                 255

Asn Leu Leu Thr Met Met Ser Thr Ser Asn Ser Ala Lys Asp Pro Thr
            260                 265                 270

Val Ala Lys Glu Glu Gln Ile Ser Phe Arg Asp Cys Ala Glu Val Phe
        275                 280                 285

Lys Ser Gly His Thr Thr Asn Gly Ile Tyr Thr Leu Thr Phe Pro Asn
    290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
            340                 345                 350

Tyr Trp Leu Gly Asn Glu Phe Val Ser Gln Leu Thr Asn Gln Gln Arg
        355                 360                 365

Tyr Val Leu Lys Ile His Leu Lys Asp Trp Glu Gly Asn Glu Ala Tyr
    370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
            420                 425                 430

Cys Ile Cys Lys Cys Ser Gln Met Leu Thr Gly Gly Trp Trp Phe Asp
        435                 440                 445

Ala Cys Gly Pro Ser Asn Leu Asn Gly Met Tyr Tyr Pro Gln Arg Gln
    450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495


<210> SEQ ID NO 32
<211> LENGTH: 498
<212> TYPE: PRT
<213> ORGANISM: Homo sapiens

<400> SEQUENCE: 32

Met Thr Val Phe Leu Ser Phe Ala Phe Leu Ala Ala Ile Leu Thr His
1               5                   10                  15

Ile Gly Cys Ser Asn Gln Arg Arg Ser Pro Glu Asn Ser Gly Arg Arg
            20                  25                  30

Tyr Asn Arg Ile Gln His Gly Gln Cys Ala Tyr Thr Phe Ile Leu Pro
        35                  40                  45

Glu His Asp Gly Asn Cys Arg Glu Ser Thr Thr Asp Gln Tyr Asn Thr
    50                  55                  60

Asn Ala Leu Gln Arg Asp Ala Pro His Val Glu Pro Asp Phe Ser Ser
65                  70                  75                  80
```

```
Gln Lys Leu Gln His Leu Glu His Val Met Glu Asn Tyr Thr Gln Trp
                85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
        115                 120                 125

Glu Ile Gly Thr Ser Leu Leu Ser Gln Thr Ala Glu Gln Thr Arg Lys
    130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
            180                 185                 190

Leu Leu Glu His Lys Ile Leu Glu Met Glu Gly Lys His Lys Glu Glu
        195                 200                 205

Leu Asp Thr Leu Lys Glu Glu Lys Glu Asn Leu Gln Gly Leu Val Thr
    210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
                245                 250                 255

Thr Val His Asn Leu Val Asn Leu Cys Thr Lys Glu Gly Val Leu Leu
            260                 265                 270

Lys Gly Gly Lys Arg Glu Glu Glu Lys Pro Phe Arg Asp Cys Ala Asp
        275                 280                 285

Val Tyr Gln Ala Gly Phe Asn Lys Ser Gly Ile Tyr Thr Ile Tyr Ile
    290                 295                 300

Asn Asn Met Pro Glu Pro Lys Lys Val Phe Cys Asn Met Asp Val Asn
305                 310                 315                 320

Gly Gly Gly Trp Thr Val Ile Gln His Arg Glu Asp Gly Ser Leu Asp
                325                 330                 335

Phe Gln Arg Gly Trp Lys Glu Tyr Lys Met Gly Phe Gly Asn Pro Ser
            340                 345                 350

Gly Glu Tyr Trp Leu Gly Asn Glu Phe Ile Phe Ala Ile Thr Ser Gln
        355                 360                 365

Arg Gln Tyr Met Leu Arg Ile Glu Leu Met Asp Trp Glu Gly Asn Arg
    370                 375                 380

Ala Tyr Ser Gln Tyr Asp Arg Phe His Ile Gly Asn Glu Lys Gln Asn
385                 390                 395                 400

Tyr Arg Leu Tyr Leu Lys Gly His Thr Gly Thr Ala Gly Lys Gln Ser
                405                 410                 415

Ser Leu Ile Leu His Gly Ala Asp Phe Ser Thr Lys Asp Ala Asp Asn
            420                 425                 430

Asp Asn Cys Met Cys Lys Cys Ala Leu Met Leu Thr Gly Gly Trp Trp
        435                 440                 445

Phe Asp Ala Cys Gly Pro Ser Asn Leu Asn Gly Met Phe Tyr Thr Ala
    450                 455                 460

Gly Gln Asn His Gly Lys Leu Asn Gly Ile Lys Trp His Tyr Phe Lys
465                 470                 475                 480

Gly Pro Ser Tyr Ser Leu Arg Ser Thr Thr Met Met Ile Arg Pro Leu
                485                 490                 495
```

Asp Phe

<210> SEQ ID NO 33
<211> LENGTH: 1124
<212> TYPE: PRT
<213> ORGANISM: Homo sapiens

<400> SEQUENCE: 33

Met Asp Ser Leu Ala Ser Leu Val Leu Cys Gly Val Ser Leu Leu Leu
1 5 10 15

Ser Gly Thr Val Glu Gly Ala Met Asp Leu Ile Leu Ile Asn Ser Leu
20 25 30

Pro Leu Val Ser Asp Ala Glu Thr Ser Leu Thr Cys Ile Ala Ser Gly
35 40 45

Trp Arg Pro His Glu Pro Ile Thr Ile Gly Arg Asp Phe Glu Ala Leu
50 55 60

Met Asn Gln His Gln Asp Pro Leu Glu Val Thr Gln Asp Val Thr Arg
65 70 75 80

Glu Trp Ala Lys Lys Val Val Trp Lys Arg Glu Lys Ala Ser Lys Ile
85 90 95

Asn Gly Ala Tyr Phe Cys Glu Gly Arg Val Arg Gly Glu Ala Ile Arg
100 105 110

Ile Arg Thr Met Lys Met Arg Gln Gln Ala Ser Phe Leu Pro Ala Thr
115 120 125

Leu Thr Met Thr Val Asp Lys Gly Asp Asn Val Asn Ile Ser Phe Lys
130 135 140

Lys Val Leu Ile Lys Glu Glu Asp Ala Val Ile Tyr Lys Asn Gly Ser
145 150 155 160

Phe Ile His Ser Val Pro Arg His Glu Val Pro Asp Ile Leu Glu Val
165 170 175

His Leu Pro His Ala Gln Pro Gln Asp Ala Gly Val Tyr Ser Ala Arg
180 185 190

Tyr Ile Gly Gly Asn Leu Phe Thr Ser Ala Phe Thr Arg Leu Ile Val
195 200 205

Arg Arg Cys Glu Ala Gln Lys Trp Gly Pro Glu Cys Asn His Leu Cys
210 215 220

Thr Ala Cys Met Asn Asn Gly Val Cys His Glu Asp Thr Gly Glu Cys
225 230 235 240

Ile Cys Pro Pro Gly Phe Met Gly Arg Thr Cys Glu Lys Ala Cys Glu
245 250 255

Leu His Thr Phe Gly Arg Thr Cys Lys Glu Arg Cys Ser Gly Gln Glu
260 265 270

Gly Cys Lys Ser Tyr Val Phe Cys Leu Pro Asp Pro Tyr Gly Cys Ser
275 280 285

Cys Ala Thr Gly Trp Lys Gly Leu Gln Cys Asn Glu Ala Cys His Pro
290 295 300

Gly Phe Tyr Gly Pro Asp Cys Lys Leu Arg Cys Ser Cys Asn Asn Gly
305 310 315 320

Glu Met Cys Asp Arg Phe Gln Gly Cys Leu Cys Ser Pro Gly Trp Gln
325 330 335

Gly Leu Gln Cys Glu Arg Glu Gly Ile Pro Arg Met Thr Pro Lys Ile
340 345 350

Val Asp Leu Pro Asp His Ile Glu Val Asn Ser Gly Lys Phe Asn Pro
355 360 365

```
Ile Cys Lys Ala Ser Gly Trp Pro Leu Pro Thr Asn Glu Glu Met Thr
    370                 375                 380

Leu Val Lys Pro Asp Gly Thr Val Leu His Pro Lys Asp Phe Asn His
385                 390                 395                 400

Thr Asp His Phe Ser Val Ala Ile Phe Thr Ile His Arg Ile Leu Pro
                405                 410                 415

Pro Asp Ser Gly Val Trp Val Cys Ser Val Asn Thr Val Ala Gly Met
            420                 425                 430

Val Glu Lys Pro Phe Asn Ile Ser Val Lys Val Leu Pro Lys Pro Leu
        435                 440                 445

Asn Ala Pro Asn Val Ile Asp Thr Gly His Asn Phe Ala Val Ile Asn
    450                 455                 460

Ile Ser Ser Glu Pro Tyr Phe Gly Asp Gly Pro Ile Lys Ser Lys Lys
465                 470                 475                 480

Leu Leu Tyr Lys Pro Val Asn His Tyr Glu Ala Trp Gln His Ile Gln
                485                 490                 495

Val Thr Asn Glu Ile Val Thr Leu Asn Tyr Leu Glu Pro Arg Thr Glu
            500                 505                 510

Tyr Glu Leu Cys Val Gln Leu Val Arg Arg Gly Glu Gly Gly Glu Gly
        515                 520                 525

His Pro Gly Pro Val Arg Arg Phe Thr Thr Ala Ser Ile Gly Leu Pro
    530                 535                 540

Pro Pro Arg Gly Leu Asn Leu Leu Pro Lys Ser Gln Thr Thr Leu Asn
545                 550                 555                 560

Leu Thr Trp Gln Pro Ile Phe Pro Ser Ser Glu Asp Asp Phe Tyr Val
                565                 570                 575

Glu Val Glu Arg Arg Ser Val Gln Lys Ser Asp Gln Gln Asn Ile Lys
            580                 585                 590

Val Pro Gly Asn Leu Thr Ser Val Leu Leu Asn Asn Leu His Pro Arg
        595                 600                 605

Glu Gln Tyr Val Val Arg Ala Arg Val Asn Thr Lys Ala Gln Gly Glu
    610                 615                 620

Trp Ser Glu Asp Leu Thr Ala Trp Thr Leu Ser Asp Ile Leu Pro Pro
625                 630                 635                 640

Gln Pro Glu Asn Ile Lys Ile Ser Asn Ile Thr His Ser Ser Ala Val
                645                 650                 655

Ile Ser Trp Thr Ile Leu Asp Gly Tyr Ser Ile Ser Ser Ile Thr Ile
            660                 665                 670

Arg Tyr Lys Val Gln Gly Lys Asn Glu Asp Gln His Val Asp Val Lys
        675                 680                 685

Ile Lys Asn Ala Thr Ile Thr Gln Tyr Gln Leu Lys Gly Leu Glu Pro
    690                 695                 700

Glu Thr Ala Tyr Gln Val Asp Ile Phe Ala Glu Asn Asn Ile Gly Ser
705                 710                 715                 720

Ser Asn Pro Ala Phe Ser His Glu Leu Val Thr Leu Pro Glu Ser Gln
                725                 730                 735

Ala Pro Ala Asp Leu Gly Gly Gly Lys Met Leu Leu Ile Ala Ile Leu
            740                 745                 750

Gly Ser Ala Gly Met Thr Cys Leu Thr Val Leu Leu Ala Phe Leu Ile
        755                 760                 765

Ile Leu Gln Leu Lys Arg Ala Asn Val Gln Arg Arg Met Ala Gln Ala
    770                 775                 780

Phe Gln Asn Val Arg Glu Glu Pro Ala Val Gln Phe Asn Ser Gly Thr
```

785 790 795 800

Leu Ala Leu Asn Arg Lys Val Lys Asn Asn Pro Asp Pro Thr Ile Tyr
805 810 815

Pro Val Leu Asp Trp Asn Asp Ile Lys Phe Gln Asp Val Ile Gly Glu
820 825 830

Gly Asn Phe Gly Gln Val Leu Lys Ala Arg Ile Lys Lys Asp Gly Leu
835 840 845

Arg Met Asp Ala Ala Ile Lys Arg Met Lys Glu Tyr Ala Ser Lys Asp
850 855 860

Asp His Arg Asp Phe Ala Gly Glu Leu Glu Val Leu Cys Lys Leu Gly
865 870 875 880

His His Pro Asn Ile Ile Asn Leu Leu Gly Ala Cys Glu His Arg Gly
885 890 895

Tyr Leu Tyr Leu Ala Ile Glu Tyr Ala Pro His Gly Asn Leu Leu Asp
900 905 910

Phe Leu Arg Lys Ser Arg Val Leu Glu Thr Asp Pro Ala Phe Ala Ile
915 920 925

Ala Asn Ser Thr Ala Ser Thr Leu Ser Ser Gln Gln Leu Leu His Phe
930 935 940

Ala Ala Asp Val Ala Arg Gly Met Asp Tyr Leu Ser Gln Lys Gln Phe
945 950 955 960

Ile His Arg Asp Leu Ala Ala Arg Asn Ile Leu Val Gly Glu Asn Tyr
965 970 975

Val Ala Lys Ile Ala Asp Phe Gly Leu Ser Arg Gly Gln Glu Val Tyr
980 985 990

Val Lys Lys Thr Met Gly Arg Leu Pro Val Arg Trp Met Ala Ile Glu
995 1000 1005

Ser Leu Asn Tyr Ser Val Tyr Thr Thr Asn Ser Asp Val Trp Ser
1010 1015 1020

Tyr Gly Val Leu Leu Trp Glu Ile Val Ser Leu Gly Gly Thr Pro
1025 1030 1035

Tyr Cys Gly Met Thr Cys Ala Glu Leu Tyr Glu Lys Leu Pro Gln
1040 1045 1050

Gly Tyr Arg Leu Glu Lys Pro Leu Asn Cys Asp Asp Glu Val Tyr
1055 1060 1065

Asp Leu Met Arg Gln Cys Trp Arg Glu Lys Pro Tyr Glu Arg Pro
1070 1075 1080

Ser Phe Ala Gln Ile Leu Val Ser Leu Asn Arg Met Leu Glu Glu
1085 1090 1095

Arg Lys Thr Tyr Val Asn Thr Thr Leu Tyr Glu Lys Phe Thr Tyr
1100 1105 1110

Ala Gly Ile Asp Cys Ser Ala Glu Glu Ala Ala
1115 1120

<210> SEQ ID NO 34
<211> LENGTH: 453
<212> TYPE: PRT
<213> ORGANISM: Artificial
<220> FEATURE:
<223> OTHER INFORMATION: Heavy chain 1 of <VEGF-ANG-2> CrossMAb IgG1
with AAA mutations (VEGFang2-0012)

<400> SEQUENCE: 34

Glu Val Gln Leu Val Glu Ser Gly Gly Gly Leu Val Gln Pro Gly Gly
1 5 10 15

-continued

```
Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ala Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu Ala Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Cys Arg Asp Glu Leu Thr Lys Asn Gln
        355                 360                 365

Val Ser Leu Trp Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn Ala Tyr Thr Gln Lys Ser Leu Ser
```

```
        435                 440                 445

Leu Ser Pro Gly Lys
    450


<210> SEQ ID NO 35
<211> LENGTH: 463
<212> TYPE: PRT
<213> ORGANISM: Artificial
<220> FEATURE:
<223> OTHER INFORMATION: Heavy chain 2 of <VEGF-ANG-2> CrossMAb IgG1
      with AAA mutations (VEGFang2-0012)

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ala Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu Ala Gln Asp Trp Leu Asn Gly Lys Glu Tyr Lys
                325                 330                 335
```

```
Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Cys Thr Leu Pro
        355                 360                 365

Pro Ser Arg Asp Glu Leu Thr Lys Asn Gln Val Ser Leu Ser Cys Ala
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn Ala Tyr Thr Gln Lys Ser Leu Ser Leu Ser Pro Gly Lys
    450                 455                 460


<210> SEQ ID NO 36
<211> LENGTH: 214
<212> TYPE: PRT
<213> ORGANISM: Artificial
<220> FEATURE:
<223> OTHER INFORMATION: Light chain 1 of <VEGF-ANG-2> CrossMAb IgG1
      with AAA mutations (VEGFang2-0012)

<400> SEQUENCE: 36

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 37
```

<211> LENGTH: 213
<212> TYPE: PRT
<213> ORGANISM: Artificial
<220> FEATURE:
<223> OTHER INFORMATION: Light chain 2 of <VEGF-ANG-2> CrossMAb IgG1 with AAA mutations (VEGF-Ang2-0012)

<400> SEQUENCE: 37

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys
    210
```

<210> SEQ ID NO 38
<211> LENGTH: 453
<212> TYPE: PRT
<213> ORGANISM: Artificial
<220> FEATURE:
<223> OTHER INFORMATION: Heavy chain 1 of <VEGF-ANG-2> CrossMAb IgG1 with AAA mutations and P329G LALA mutations (VEGFang2-0016)

<400> SEQUENCE: 38

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95
```

```
Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ala Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu Ala Gln Asp Trp Leu
305                 310                 315                 320

Asn Gly Lys Glu Tyr Lys Cys Lys Val Ser Asn Lys Ala Leu Gly Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Cys Arg Asp Glu Leu Thr Lys Asn Gln
        355                 360                 365

Val Ser Leu Trp Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn Ala Tyr Thr Gln Lys Ser Leu Ser
        435                 440                 445

Leu Ser Pro Gly Lys
    450
```

```
<210> SEQ ID NO 39
<211> LENGTH: 463
<212> TYPE: PRT
<213> ORGANISM: Artificial
<220> FEATURE:
<223> OTHER INFORMATION: Heavy chain 2 of  <VEGF-ANG-2> CrossMAb IgG1
      with AAA mutations and P329G LALA mutations (VEGFang2-0016)
```

<400> SEQUENCE: 39

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Ala Ala Gly Gly Pro Ser Val
                245                 250                 255

Phe Leu Phe Pro Pro Lys Pro Lys Asp Thr Leu Met Ala Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu Ala Gln Asp Trp Leu Asn Gly Lys Glu Tyr Lys
                325                 330                 335

Cys Lys Val Ser Asn Lys Ala Leu Gly Ala Pro Ile Glu Lys Thr Ile
            340                 345                 350

Ser Lys Ala Lys Gly Gln Pro Arg Glu Pro Gln Val Cys Thr Leu Pro
        355                 360                 365

Pro Ser Arg Asp Glu Leu Thr Lys Asn Gln Val Ser Leu Ser Cys Ala
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415
```

```
Asp Gly Ser Phe Phe Leu Val Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn Ala Tyr Thr Gln Lys Ser Leu Ser Leu Ser Pro Gly Lys
    450                 455                 460


<210> SEQ ID NO 40
<211> LENGTH: 214
<212> TYPE: PRT
<213> ORGANISM: Artificial
<220> FEATURE:
<223> OTHER INFORMATION: Light chain 1 of  <VEGF-ANG-2> CrossMAb IgG1
      with AAA mutations and P329G LALA mutations (VEGFang2-0016)

<400> SEQUENCE: 40

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 41
<211> LENGTH: 213
<212> TYPE: PRT
<213> ORGANISM: Artificial
<220> FEATURE:
<223> OTHER INFORMATION: Light chain 2 of  <VEGF-ANG-2> CrossMAb IgG1
      with AAA mutations and P329G LALA mutations (VEGFang2-0016)

<400> SEQUENCE: 41

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30
```

```
His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys
    210


<210> SEQ ID NO 42
<211> LENGTH: 450
<212> TYPE: PRT
<213> ORGANISM: Artificial
<220> FEATURE:
<223> OTHER INFORMATION: Heavy chain 1 of <VEGF-ANG-2> CrossMAb IgG4
      with AAA mutations and with SPLE mutations

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
```

```
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Glu Gly Gly
225                 230                 235                 240

Pro Ser Val Phe Leu Phe Pro Pro Lys Pro Lys Asp Thr Leu Met Ala
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu Ala Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Cys
            340                 345                 350

Thr Leu Pro Pro Ser Gln Glu Glu Met Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn Ala Tyr Thr Gln Lys Ser Leu Ser Leu Ser Leu
        435                 440                 445

Gly Lys
    450


<210> SEQ ID NO 43
<211> LENGTH: 460
<212> TYPE: PRT
<213> ORGANISM: Artificial
<220> FEATURE:
<223> OTHER INFORMATION: Heavy chain 2 of <VEGF-ANG-2> CrossMAb IgG4
      with AAA mutations and with SPLE mutations

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60
```

```
Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Pro Pro Cys Pro
225                 230                 235                 240

Pro Cys Pro Ala Pro Glu Phe Glu Gly Gly Pro Ser Val Phe Leu Phe
                245                 250                 255

Pro Pro Lys Pro Lys Asp Thr Leu Met Ala Ser Arg Thr Pro Glu Val
            260                 265                 270

Thr Cys Val Val Val Asp Val Ser Gln Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Tyr Arg Val Val Ser Val Leu Thr
305                 310                 315                 320

Val Leu Ala Gln Asp Trp Leu Asn Gly Lys Glu Tyr Lys Cys Lys Val
                325                 330                 335

Ser Asn Lys Gly Leu Pro Ser Ser Ile Glu Lys Thr Ile Ser Lys Ala
            340                 345                 350

Lys Gly Gln Pro Arg Glu Pro Gln Val Tyr Thr Leu Pro Pro Cys Gln
        355                 360                 365

Glu Glu Met Thr Lys Asn Gln Val Ser Leu Trp Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Arg Leu Thr Val Asp Lys Ser Arg Trp Gln Glu
            420                 425                 430

Gly Asn Val Phe Ser Cys Ser Val Met His Glu Ala Leu His Asn Ala
        435                 440                 445

Tyr Thr Gln Lys Ser Leu Ser Leu Ser Leu Gly Lys
    450                 455                 460
```

<210> SEQ ID NO 44
<211> LENGTH: 214
<212> TYPE: PRT

<213> ORGANISM: Artificial
<220> FEATURE:
<223> OTHER INFORMATION: Light chain 1 of <VEGF-ANG-2> CrossMAb IgG4
with AAA mutations and with SPLE mutations

<400> SEQUENCE: 44

Asp Ile Gln Leu Thr Gln Ser Pro Ser Ser Leu Ser Ala Ser Val Gly
1 5 10 15

Asp Arg Val Thr Ile Thr Cys Ser Ala Ser Gln Asp Ile Ser Asn Tyr
20 25 30

Leu Asn Trp Tyr Gln Gln Lys Pro Gly Lys Ala Pro Lys Val Leu Ile
35 40 45

Tyr Phe Thr Ser Ser Leu His Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Ser Thr Val Pro Trp
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 45
<211> LENGTH: 213
<212> TYPE: PRT
<213> ORGANISM: Artificial
<220> FEATURE:
<223> OTHER INFORMATION: Light chain 2 of <VEGF-ANG-2> CrossMAb IgG4
with AAA mutations and with SPLE mutations

<400> SEQUENCE: 45

Ser Tyr Val Leu Thr Gln Pro Pro Ser Val Ser Val Ala Pro Gly Gln
1 5 10 15

Thr Ala Arg Ile Thr Cys Gly Gly Asn Asn Ile Gly Ser Lys Ser Val
20 25 30

His Trp Tyr Gln Gln Lys Pro Gly Gln Ala Pro Val Leu Val Val Tyr
35 40 45

Asp Asp Ser Asp Arg Pro Ser Gly Ile Pro Glu Arg Phe Ser Gly Ser
50 55 60

Asn Ser Gly Asn Thr Ala Thr Leu Thr Ile Ser Arg Val Glu Ala Gly
65 70 75 80

Asp Glu Ala Asp Tyr Tyr Cys Gln Val Trp Asp Ser Ser Ser Asp His
85 90 95

Trp Val Phe Gly Gly Gly Thr Lys Leu Thr Val Leu Ser Ser Ala Ser

```
            100                 105                 110

Thr Lys Gly Pro Ser Val Phe Pro Leu Ala Pro Cys Ser Arg Ser Thr
        115                 120                 125

Ser Glu Ser Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Lys Thr Tyr Thr
            180                 185                 190

Cys Asn Val Asp His Lys Pro Ser Asn Thr Lys Val Asp Lys Arg Val
        195                 200                 205

Glu Ser Lys Tyr Gly
    210


<210> SEQ ID NO 46
<211> LENGTH: 453
<212> TYPE: PRT
<213> ORGANISM: Artificial
<220> FEATURE:
<223> OTHER INFORMATION: Heavy chain 1 of <VEGF-ANG-2> OAscFab IgG1 with
      AAA mutations

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240
```

Leu Gly Gly Pro Ser Val Phe Leu Phe Pro Pro Lys Pro Lys Asp Thr
245 250 255

Leu Met Ala Ser Arg Thr Pro Glu Val Thr Cys Val Val Val Asp Val
260 265 270

Ser His Glu Asp Pro Glu Val Lys Phe Asn Trp Tyr Val Asp Gly Val
275 280 285

Glu Val His Asn Ala Lys Thr Lys Pro Arg Glu Glu Gln Tyr Asn Ser
290 295 300

Thr Tyr Arg Val Val Ser Val Leu Thr Val Leu Ala Gln Asp Trp Leu
305 310 315 320

Asn Gly Lys Glu Tyr Lys Cys Lys Val Ser Asn Lys Ala Leu Pro Ala
325 330 335

Pro Ile Glu Lys Thr Ile Ser Lys Ala Lys Gly Gln Pro Arg Glu Pro
340 345 350

Gln Val Cys Thr Leu Pro Pro Ser Arg Asp Glu Leu Thr Lys Asn Gln
355 360 365

Val Ser Leu Ser Cys Ala Val Lys Gly Phe Tyr Pro Ser Asp Ile Ala
370 375 380

Val Glu Trp Glu Ser Asn Gly Gln Pro Glu Asn Asn Tyr Lys Thr Thr
385 390 395 400

Pro Pro Val Leu Asp Ser Asp Gly Ser Phe Phe Leu Val Ser Lys Leu
405 410 415

Thr Val Asp Lys Ser Arg Trp Gln Gln Gly Asn Val Phe Ser Cys Ser
420 425 430

Val Met His Glu Ala Leu His Asn Ala Tyr Thr Gln Lys Ser Leu Ser
435 440 445

Leu Ser Pro Gly Lys
450

<210> SEQ ID NO 47
<211> LENGTH: 705
<212> TYPE: PRT
<213> ORGANISM: Artificial
<220> FEATURE:
<223> OTHER INFORMATION: Heavy chain 2 of <VEGF-ANG-2> OAscFab IgG1 with AAA mutations

<400> SEQUENCE: 47

Ser Tyr Val Leu Thr Gln Pro Pro Ser Val Ser Val Ala Pro Gly Gln
1 5 10 15

Thr Ala Arg Ile Thr Cys Gly Gly Asn Asn Ile Gly Ser Lys Ser Val
20 25 30

His Trp Tyr Gln Gln Lys Pro Gly Gln Ala Pro Val Leu Val Val Tyr
35 40 45

Asp Asp Ser Asp Arg Pro Ser Gly Ile Pro Glu Arg Phe Ser Gly Ser
50 55 60

Asn Ser Gly Asn Thr Ala Thr Leu Thr Ile Ser Arg Val Glu Ala Gly
65 70 75 80

Asp Glu Ala Asp Tyr Tyr Cys Gln Val Trp Asp Ser Ser Ser Asp His
85 90 95

Trp Val Phe Gly Gly Gly Thr Lys Leu Thr Val Leu Gly Gln Pro Lys
100 105 110

Ala Ala Pro Ser Val Thr Leu Phe Pro Pro Ser Ser Glu Glu Leu Gln
115 120 125

Ala Asn Lys Ala Thr Leu Val Cys Leu Ile Ser Asp Phe Tyr Pro Gly
130 135 140

```
Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser Gly Gly Gly Gly Ser Gly Gly Gly Gly Ser
    210                 215                 220

Gly Gly Gly Gly Ser Gly Gly Gly Gly Ser Gly Gly Gly Gly Ser Gly
225                 230                 235                 240

Gly Gly Gly Ser Gly Gly Gln Val Gln Leu Val Glu Ser Gly Ala Glu
                245                 250                 255

Val Lys Lys Pro Gly Ala Ser Val Lys Val Ser Cys Lys Ala Ser Gly
            260                 265                 270

Tyr Thr Phe Thr Gly Tyr Tyr Met His Trp Val Arg Gln Ala Pro Gly
        275                 280                 285

Gln Gly Leu Glu Trp Met Gly Trp Ile Asn Pro Asn Ser Gly Gly Thr
    290                 295                 300

Asn Tyr Ala Gln Lys Phe Gln Gly Arg Val Thr Met Thr Arg Asp Thr
305                 310                 315                 320

Ser Ile Ser Thr Ala Tyr Met Glu Leu Ser Arg Leu Arg Ser Asp Asp
                325                 330                 335

Thr Ala Val Tyr Tyr Cys Ala Arg Ser Pro Asn Pro Tyr Tyr Tyr Asp
            340                 345                 350

Ser Ser Gly Tyr Tyr Tyr Pro Gly Ala Phe Asp Ile Trp Gly Gln Gly
        355                 360                 365

Thr Met Val Thr Val Ser Ser Ala Ser Thr Lys Gly Pro Ser Val Phe
    370                 375                 380

Pro Leu Ala Pro Ser Ser Lys Ser Thr Ser Gly Gly Thr Ala Ala Leu
385                 390                 395                 400

Gly Cys Leu Val Lys Asp Tyr Phe Pro Glu Pro Val Thr Val Ser Trp
                405                 410                 415

Asn Ser Gly Ala Leu Thr Ser Gly Val His Thr Phe Pro Ala Val Leu
            420                 425                 430

Gln Ser Ser Gly Leu Tyr Ser Leu Ser Ser Val Val Thr Val Pro Ser
        435                 440                 445

Ser Ser Leu Gly Thr Gln Thr Tyr Ile Cys Asn Val Asn His Lys Pro
    450                 455                 460

Ser Asn Thr Lys Val Asp Lys Lys Val Glu Pro Lys Ser Cys Asp Lys
465                 470                 475                 480

Thr His Thr Cys Pro Pro Cys Pro Ala Pro Glu Leu Leu Gly Gly Pro
                485                 490                 495

Ser Val Phe Leu Phe Pro Pro Lys Pro Lys Asp Thr Leu Met Ala Ser
            500                 505                 510

Arg Thr Pro Glu Val Thr Cys Val Val Val Asp Val Ser His Glu Asp
        515                 520                 525

Pro Glu Val Lys Phe Asn Trp Tyr Val Asp Gly Val Glu Val His Asn
    530                 535                 540

Ala Lys Thr Lys Pro Arg Glu Glu Gln Tyr Asn Ser Thr Tyr Arg Val
545                 550                 555                 560
```

```
Val Ser Val Leu Thr Val Leu Ala Gln Asp Trp Leu Asn Gly Lys Glu
                565                 570                 575

Tyr Lys Cys Lys Val Ser Asn Lys Ala Leu Pro Ala Pro Ile Glu Lys
            580                 585                 590

Thr Ile Ser Lys Ala Lys Gly Gln Pro Arg Glu Pro Gln Val Tyr Thr
        595                 600                 605

Leu Pro Pro Cys Arg Asp Glu Leu Thr Lys Asn Gln Val Ser Leu Trp
    610                 615                 620

Cys Leu Val Lys Gly Phe Tyr Pro Ser Asp Ile Ala Val Glu Trp Glu
625                 630                 635                 640

Ser Asn Gly Gln Pro Glu Asn Asn Tyr Lys Thr Thr Pro Pro Val Leu
                645                 650                 655

Asp Ser Asp Gly Ser Phe Phe Leu Tyr Ser Lys Leu Thr Val Asp Lys
            660                 665                 670

Ser Arg Trp Gln Gln Gly Asn Val Phe Ser Cys Ser Val Met His Glu
        675                 680                 685

Ala Leu His Asn Ala Tyr Thr Gln Lys Ser Leu Ser Leu Ser Pro Gly
    690                 695                 700

Lys
705


<210> SEQ ID NO 48
<211> LENGTH: 214
<212> TYPE: PRT
<213> ORGANISM: Artificial
<220> FEATURE:
<223> OTHER INFORMATION: Light chain 1 of <VEGF-ANG-2> OAscFab IgG1 with
      AAA mutations

<400> SEQUENCE: 48

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 49
<211> LENGTH: 450
<212> TYPE: PRT
<213> ORGANISM: Artificial
<220> FEATURE:
<223> OTHER INFORMATION: Heavy chain 1 of <VEGF-ANG-2> OAscFab IgG4 with AAA mutations and with SPLE mutations

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Glu Gly Gly
225                 230                 235                 240

Pro Ser Val Phe Leu Phe Pro Pro Lys Pro Lys Asp Thr Leu Met Ala
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu Ala Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Cys

```
            340                 345                 350

Thr Leu Pro Pro Ser Gln Glu Glu Met Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn Ala Tyr Thr Gln Lys Ser Leu Ser Leu Ser Leu
        435                 440                 445

Gly Lys
    450


<210> SEQ ID NO 50
<211> LENGTH: 702
<212> TYPE: PRT
<213> ORGANISM: Artificial
<220> FEATURE:
<223> OTHER INFORMATION: Heavy chain 2 of <VEGF-ANG-2> OAscFab IgG4 with
      AAA mutations and with SPLE mutations

<400> SEQUENCE: 50

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser Gly Gly Gly Gly Ser Gly Gly Gly Gly Ser
    210                 215                 220

Gly Gly Gly Gly Ser Gly Gly Gly Gly Ser Gly Gly Gly Gly Ser Gly
225                 230                 235                 240
```

```
Gly Gly Gly Ser Gly Gly Gln Val Gln Leu Val Glu Ser Gly Ala Glu
                245                 250                 255

Val Lys Lys Pro Gly Ala Ser Val Lys Val Ser Cys Lys Ala Ser Gly
            260                 265                 270

Tyr Thr Phe Thr Gly Tyr Tyr Met His Trp Val Arg Gln Ala Pro Gly
        275                 280                 285

Gln Gly Leu Glu Trp Met Gly Trp Ile Asn Pro Asn Ser Gly Gly Thr
    290                 295                 300

Asn Tyr Ala Gln Lys Phe Gln Gly Arg Val Thr Met Thr Arg Asp Thr
305                 310                 315                 320

Ser Ile Ser Thr Ala Tyr Met Glu Leu Ser Arg Leu Arg Ser Asp Asp
                325                 330                 335

Thr Ala Val Tyr Tyr Cys Ala Arg Ser Pro Asn Pro Tyr Tyr Tyr Asp
            340                 345                 350

Ser Ser Gly Tyr Tyr Tyr Pro Gly Ala Phe Asp Ile Trp Gly Gln Gly
        355                 360                 365

Thr Met Val Thr Val Ser Ser Ala Ser Thr Lys Gly Pro Ser Val Phe
    370                 375                 380

Pro Leu Ala Pro Cys Ser Arg Ser Thr Ser Glu Ser Thr Ala Ala Leu
385                 390                 395                 400

Gly Cys Leu Val Lys Asp Tyr Phe Pro Glu Pro Val Thr Val Ser Trp
                405                 410                 415

Asn Ser Gly Ala Leu Thr Ser Gly Val His Thr Phe Pro Ala Val Leu
            420                 425                 430

Gln Ser Ser Gly Leu Tyr Ser Leu Ser Ser Val Val Thr Val Pro Ser
        435                 440                 445

Ser Ser Leu Gly Thr Lys Thr Tyr Thr Cys Asn Val Asp His Lys Pro
    450                 455                 460

Ser Asn Thr Lys Val Asp Lys Arg Val Glu Ser Lys Tyr Gly Pro Pro
465                 470                 475                 480

Cys Pro Pro Cys Pro Ala Pro Glu Phe Glu Gly Gly Pro Ser Val Phe
                485                 490                 495

Leu Phe Pro Pro Lys Pro Lys Asp Thr Leu Met Ala Ser Arg Thr Pro
            500                 505                 510

Glu Val Thr Cys Val Val Val Asp Val Ser Gln Glu Asp Pro Glu Val
        515                 520                 525

Gln Phe Asn Trp Tyr Val Asp Gly Val Glu Val His Asn Ala Lys Thr
    530                 535                 540

Lys Pro Arg Glu Glu Gln Phe Asn Ser Thr Tyr Arg Val Val Ser Val
545                 550                 555                 560

Leu Thr Val Leu Ala Gln Asp Trp Leu Asn Gly Lys Glu Tyr Lys Cys
                565                 570                 575

Lys Val Ser Asn Lys Gly Leu Pro Ser Ser Ile Glu Lys Thr Ile Ser
            580                 585                 590

Lys Ala Lys Gly Gln Pro Arg Glu Pro Gln Val Tyr Thr Leu Pro Pro
        595                 600                 605

Cys Gln Glu Glu Met Thr Lys Asn Gln Val Ser Leu Trp Cys Leu Val
    610                 615                 620

Lys Gly Phe Tyr Pro Ser Asp Ile Ala Val Glu Trp Glu Ser Asn Gly
625                 630                 635                 640

Gln Pro Glu Asn Asn Tyr Lys Thr Thr Pro Pro Val Leu Asp Ser Asp
                645                 650                 655

Gly Ser Phe Phe Leu Tyr Ser Arg Leu Thr Val Asp Lys Ser Arg Trp
```

660 665 670

Gln Glu Gly Asn Val Phe Ser Cys Ser Val Met His Glu Ala Leu His
675 680 685

Asn Ala Tyr Thr Gln Lys Ser Leu Ser Leu Ser Leu Gly Lys
690 695 700

<210> SEQ ID NO 51
<211> LENGTH: 214
<212> TYPE: PRT
<213> ORGANISM: Artificial
<220> FEATURE:
<223> OTHER INFORMATION: Light chain 1 of <VEGF-ANG-2> OAscFab IgG4 with AAA mutations and with SPLE mutations

<400> SEQUENCE: 51

Asp Ile Gln Leu Thr Gln Ser Pro Ser Ser Leu Ser Ala Ser Val Gly
1 5 10 15

Asp Arg Val Thr Ile Thr Cys Ser Ala Ser Gln Asp Ile Ser Asn Tyr
20 25 30

Leu Asn Trp Tyr Gln Gln Lys Pro Gly Lys Ala Pro Lys Val Leu Ile
35 40 45

Tyr Phe Thr Ser Ser Leu His Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Ser Thr Val Pro Trp
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 52
<211> LENGTH: 453
<212> TYPE: PRT
<213> ORGANISM: Artificial
<220> FEATURE:
<223> OTHER INFORMATION: Heavy chain 1 of <VEGF-ANG-2> CrossMAb IgG1 wild type (without AAA mutations) (VEGFang2-0201)

<400> SEQUENCE: 52

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Asp Phe Thr His Tyr
20 25 30

Gly Met Asn Trp Val Arg Gln Ala Pro Gly Lys Gly Leu Glu Trp Val

```
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Cys Arg Asp Glu Leu Thr Lys Asn Gln
        355                 360                 365

Val Ser Leu Trp Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 53
<211> LENGTH: 463
<212> TYPE: PRT
<213> ORGANISM: Artificial
<220> FEATURE:
<223> OTHER INFORMATION: Heavy chain 2 of <VEGF-ANG-2> CrossMAb IgG1 wild type (without AAA mutations) (VEGFang2-0201)

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Cys Thr Leu Pro

```
        355                 360                 365

Pro Ser Arg Asp Glu Leu Thr Lys Asn Gln Val Ser Leu Ser Cys Ala
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460


<210> SEQ ID NO 54
<211> LENGTH: 214
<212> TYPE: PRT
<213> ORGANISM: Artificial
<220> FEATURE:
<223> OTHER INFORMATION: Light chain 1 of <VEGF-ANG-2> CrossMAb IgG1
      wild type ( without AAA mutations) (VEGFang2-0201)

<400> SEQUENCE: 54

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 55
<211> LENGTH: 213
<212> TYPE: PRT
<213> ORGANISM: Artificial
<220> FEATURE:
```

<223> OTHER INFORMATION: Light chain 2 of <VEGF-ANG-2> CrossMAb IgG1
      wild type (without AAA mutations) (VEGFang2-0201)

<400> SEQUENCE: 55

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys
    210
```

<210> SEQ ID NO 56
<211> LENGTH: 453
<212> TYPE: PRT
<213> ORGANISM: Artificial
<220> FEATURE:
<223> OTHER INFORMATION: Heavy chain 1 of <VEGF-ANG-2> CrossMAb IgG1
      with P329G LALA mutations only (without AAA mutations)
      (VEGFang2-0015)

<400> SEQUENCE: 56

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110
```

```
Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Gly Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Cys Arg Asp Glu Leu Thr Lys Asn Gln
        355                 360                 365

Val Ser Leu Trp Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 57
<211> LENGTH: 463
<212> TYPE: PRT
<213> ORGANISM: Artificial
<220> FEATURE:
<223> OTHER INFORMATION: Heavy chain 2 of <VEGF-ANG-2> CrossMAb IgG1 with P329G LALA mutations only (without AAA mutations) (VEGFang2-0015)

<400> SEQUENCE: 57

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Ala Ala Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Gly Ala Pro Ile Glu Lys Thr Ile
            340                 345                 350

Ser Lys Ala Lys Gly Gln Pro Arg Glu Pro Gln Val Cys Thr Leu Pro
        355                 360                 365

Pro Ser Arg Asp Glu Leu Thr Lys Asn Gln Val Ser Leu Ser Cys Ala
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
```

```
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460


<210> SEQ ID NO 58
<211> LENGTH: 214
<212> TYPE: PRT
<213> ORGANISM: Artificial
<220> FEATURE:
<223> OTHER INFORMATION: Light chain 1 of <VEGF-ANG-2> CrossMAb IgG1
      with P329G LALA mutations only (without AAA mutations)
      (VEGFang2-0015)

<400> SEQUENCE: 58

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 59
<211> LENGTH: 213
<212> TYPE: PRT
<213> ORGANISM: Artificial
<220> FEATURE:
<223> OTHER INFORMATION: Light chain 2 of <VEGF-ANG-2> CrossMAb IgG1
      with P329G LALA mutations only (without AAA mutations)
      (VEGFang2-0015)

<400> SEQUENCE: 59

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30
```

```
His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys
    210


<210> SEQ ID NO 60
<211> LENGTH: 227
<212> TYPE: PRT
<213> ORGANISM: Homo sapiens

<400> SEQUENCE: 60

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
```

```
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 61
<211> LENGTH: 326
<212> TYPE: PRT
<213> ORGANISM: Homo sapiens

<400> SEQUENCE: 61

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320
```

```
Ser Leu Ser Pro Gly Lys
                325


<210> SEQ ID NO 62
<211> LENGTH: 377
<212> TYPE: PRT
<213> ORGANISM: Homo sapiens

<400> SEQUENCE: 62

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365
```

Lys Ser Leu Ser Leu Ser Pro Gly Lys
370 375

<210> SEQ ID NO 63
<211> LENGTH: 229
<212> TYPE: PRT
<213> ORGANISM: Homo sapiens

<400> SEQUENCE: 63

Glu Ser Lys Tyr Gly Pro Pro Cys Pro Ser Cys Pro Ala Pro Glu Phe
1 5 10 15

Leu Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Thr Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Lys
225

<210> SEQ ID NO 64
<211> LENGTH: 227
<212> TYPE: PRT
<213> ORGANISM: Artificial Sequence
<220> FEATURE:
<223> OTHER INFORMATION: human IgG1 Fc-region derived Fc-region polypeptide with the mutations L234A, L235A

<400> SEQUENCE: 64

Asp Lys Thr His Thr Cys Pro Pro Cys Pro Ala Pro Glu Ala Ala Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

```
His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 65
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with Y349C, T366S, L368A and Y407V mutations

<400> SEQUENCE: 65

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
```

```
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 66
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with S354C, T366W mutations

<400> SEQUENCE: 66

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 67
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with L234A, L235A mutations and Y349C, T366S, L368A,
      Y407V mutations

<400> SEQUENCE: 67
```

Asp Lys Thr His Thr Cys Pro Pro Cys Pro Ala Pro Glu Ala Ala Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Gln Val
115 120 125

Cys Thr Leu Pro Pro Ser Arg Asp Glu Leu Thr Lys Asn Gln Val Ser
130 135 140

Leu Ser Cys Ala Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Phe Leu Val Ser Lys Leu Thr Val
180 185 190

Asp Lys Ser Arg Trp Gln Gln Gly Asn Val Phe Ser Cys Ser Val Met
195 200 205

His Glu Ala Leu His Asn His Tyr Thr Gln Lys Ser Leu Ser Leu Ser
210 215 220

Pro Gly Lys
225

<210> SEQ ID NO 68
<211> LENGTH: 227
<212> TYPE: PRT
<213> ORGANISM: Artificial Sequence
<220> FEATURE:
<223> OTHER INFORMATION: human IgG1 Fc-region derived Fc-region polypeptide with a L234A, L235A and S354C, T366W mutations

<400> SEQUENCE: 68

Asp Lys Thr His Thr Cys Pro Pro Cys Pro Ala Pro Glu Ala Ala Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Gln Val
115 120 125

```
Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 69
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with a P329G mutation

<400> SEQUENCE: 69

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

```
<210> SEQ ID NO 70
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with L234A, L235A mutations and P329G mutation

<400> SEQUENCE: 70

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 71
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with a P239G mutation and Y349C, T366S, L368A, Y407V
      mutations

<400> SEQUENCE: 71

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60
```

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Gly Ala Pro Ile
100 105 110

Glu Lys Thr Ile Ser Lys Ala Lys Gly Gln Pro Arg Glu Pro Gln Val
115 120 125

Cys Thr Leu Pro Pro Ser Arg Asp Glu Leu Thr Lys Asn Gln Val Ser
130 135 140

Leu Ser Cys Ala Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Phe Leu Val Ser Lys Leu Thr Val
180 185 190

Asp Lys Ser Arg Trp Gln Gln Gly Asn Val Phe Ser Cys Ser Val Met
195 200 205

His Glu Ala Leu His Asn His Tyr Thr Gln Lys Ser Leu Ser Leu Ser
210 215 220

Pro Gly Lys
225

<210> SEQ ID NO 72
<211> LENGTH: 227
<212> TYPE: PRT
<213> ORGANISM: Artificial Sequence
<220> FEATURE:
<223> OTHER INFORMATION: human IgG1 Fc-region derived Fc-region polypeptide with a P329G mutation and S354C, T366W mutation

<400> SEQUENCE: 72

Asp Lys Thr His Thr Cys Pro Pro Cys Pro Ala Pro Glu Leu Leu Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Gly Ala Pro Ile
100 105 110

Glu Lys Thr Ile Ser Lys Ala Lys Gly Gln Pro Arg Glu Pro Gln Val
115 120 125

Tyr Thr Leu Pro Pro Cys Arg Asp Glu Leu Thr Lys Asn Gln Val Ser
130 135 140

Leu Trp Cys Leu Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Phe Leu Tyr Ser Lys Leu Thr Val
180 185 190

Asp Lys Ser Arg Trp Gln Gln Gly Asn Val Phe Ser Cys Ser Val Met
195 200 205

His Glu Ala Leu His Asn His Tyr Thr Gln Lys Ser Leu Ser Leu Ser
210 215 220

Pro Gly Lys
225

<210> SEQ ID NO 73
<211> LENGTH: 227
<212> TYPE: PRT
<213> ORGANISM: Artificial Sequence
<220> FEATURE:
<223> OTHER INFORMATION: human IgG1 Fc-region derived Fc-region polypeptide with L234A, L235A, P329G and Y349C, T366S, L368A, Y407V mutations

<400> SEQUENCE: 73

Asp Lys Thr His Thr Cys Pro Pro Cys Pro Ala Pro Glu Ala Ala Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Gly Ala Pro Ile
100 105 110

Glu Lys Thr Ile Ser Lys Ala Lys Gly Gln Pro Arg Glu Pro Gln Val
115 120 125

Cys Thr Leu Pro Pro Ser Arg Asp Glu Leu Thr Lys Asn Gln Val Ser
130 135 140

Leu Ser Cys Ala Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Phe Leu Val Ser Lys Leu Thr Val
180 185 190

Asp Lys Ser Arg Trp Gln Gln Gly Asn Val Phe Ser Cys Ser Val Met
195 200 205

His Glu Ala Leu His Asn His Tyr Thr Gln Lys Ser Leu Ser Leu Ser
210 215 220

Pro Gly Lys
225

<210> SEQ ID NO 74
<211> LENGTH: 227
<212> TYPE: PRT
<213> ORGANISM: Artificial Sequence
<220> FEATURE:
<223> OTHER INFORMATION: human IgG1 Fc-region derived Fc-region polypeptide with L234A, L235A, P329G mutations and S354C, T366W mutations

<400> SEQUENCE: 74

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 75
<211> LENGTH: 229
<212> TYPE: PRT
<213> ORGANISM: Artificial Sequence
<220> FEATURE:
<223> OTHER INFORMATION: human IgG4 Fc-region derived Fc-region polypeptide with S228P and L235E mutations

<400> SEQUENCE: 75

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

```
Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 76
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with S228P, L235E mutations and P329G mutation

<400> SEQUENCE: 76

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

```
<210> SEQ ID NO 77
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with S354C, T366W mutations

<400> SEQUENCE: 77

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Cys Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 78
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with Y349C, T366S, L368A, Y407V mutations

<400> SEQUENCE: 78

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
```

65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Cys Thr Leu Pro Pro Ser Gln Glu Glu Met Thr Lys Asn Gln
130 135 140

Val Ser Leu Ser Cys Ala Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Val Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Lys
225

<210> SEQ ID NO 79
<211> LENGTH: 229
<212> TYPE: PRT
<213> ORGANISM: Artificial Sequence
<220> FEATURE:
<223> OTHER INFORMATION: human IgG4 Fc-region derived Fc-region polypeptide with a S228P, L235E and S354C, T366W mutations

<400> SEQUENCE: 79

Glu Ser Lys Tyr Gly Pro Pro Cys Pro Pro Cys Pro Ala Pro Glu Phe
1 5 10 15

Glu Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Cys Gln Glu Glu Met Thr Lys Asn Gln
130 135 140

Val Ser Leu Trp Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

```
Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 80
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a S228P, L235E and Y349C, T366S, L368A, Y407V
      mutations

<400> SEQUENCE: 80

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Cys Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 81
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a P329G mutation

<400> SEQUENCE: 81

Glu Ser Lys Tyr Gly Pro Pro Cys Pro Ser Cys Pro Ala Pro Glu Phe
1               5                   10                  15
```

Leu Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Gly Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Thr Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Lys
225

<210> SEQ ID NO 82
<211> LENGTH: 229
<212> TYPE: PRT
<213> ORGANISM: Artificial Sequence
<220> FEATURE:
<223> OTHER INFORMATION: human IgG4 Fc-region derived Fc-region polypeptide with a P239G and Y349C, T366S, L368A, Y407V mutations

<400> SEQUENCE: 82

Glu Ser Lys Tyr Gly Pro Pro Cys Pro Ser Cys Pro Ala Pro Glu Phe
1 5 10 15

Leu Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Gly Ser
100 105 110

Ser Ile Glu Lys Thr Ile Ser Lys Ala Lys Gly Gln Pro Arg Glu Pro
115 120 125

Gln Val Cys Thr Leu Pro Pro Ser Gln Glu Glu Met Thr Lys Asn Gln

```
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 83
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a P329G and S354C, T366W mutations

<400> SEQUENCE: 83

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Cys Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 84
<211> LENGTH: 229
```

<212> TYPE: PRT
<213> ORGANISM: Artificial Sequence
<220> FEATURE:
<223> OTHER INFORMATION: human IgG4 Fc-region derived Fc-region polypeptide with a S228P, L235E, P329G and Y349C, T366S, L368A, Y407V mutations

<400> SEQUENCE: 84

```
Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Cys Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 85
<211> LENGTH: 229
<212> TYPE: PRT
<213> ORGANISM: Artificial Sequence
<220> FEATURE:
<223> OTHER INFORMATION: human IgG4 Fc-region derived Fc-region polypeptide with a S228P, L235E, P329G and S354C, T366W mutations

<400> SEQUENCE: 85

```
Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80
```

```
Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Cys Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 86
<211> LENGTH: 105
<212> TYPE: PRT
<213> ORGANISM: homo sapiens

<400> SEQUENCE: 86

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105


<210> SEQ ID NO 87
<211> LENGTH: 107
<212> TYPE: PRT
<213> ORGANISM: Homo sapiens

<400> SEQUENCE: 87

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60
```

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 88
<211> LENGTH: 215
<212> TYPE: PRT
<213> ORGANISM: Artificial Sequence
<220> FEATURE:
<223> OTHER INFORMATION: IGF-1R LC

<400> SEQUENCE: 88

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Lys Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Lys Trp Pro Pro
85 90 95

Trp Thr Phe Gly Gln Gly Thr Lys Val Glu Ser Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 89
<211> LENGTH: 447
<212> TYPE: PRT
<213> ORGANISM: Artificial Sequence
<220> FEATURE:
<223> OTHER INFORMATION: IGF-1R wt

<400> SEQUENCE: 89

Gln Val Glu Leu Val Glu Ser Gly Gly Gly Val Val Gln Pro Gly Arg
1 5 10 15

Ser Gln Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val

```
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445
```

<210> SEQ ID NO 90

<211> LENGTH: 447
<212> TYPE: PRT
<213> ORGANISM: Artificial Sequence
<220> FEATURE:
<223> OTHER INFORMATION: IGF-1R AAA

<400> SEQUENCE: 90

Gln Val Glu Leu Val Glu Ser Gly Gly Gly Val Val Gln Pro Gly Arg
1 5 10 15

Ser Gln Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Ile Ile Trp Phe Asp Gly Ser Ser Thr Tyr Tyr Ala Asp Ser Val
50 55 60

Arg Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Phe Cys
85 90 95

Ala Arg Glu Leu Gly Arg Arg Tyr Phe Asp Leu Trp Gly Arg Gly Thr
100 105 110

Leu Val Ser Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Leu Leu Gly Gly Pro Ser
225 230 235 240

Val Phe Leu Phe Pro Pro Lys Pro Lys Asp Thr Leu Met Ala Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu Ala Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Asp Glu Leu Thr Lys Asn Gln Val Ser Leu Thr Cys
355 360 365

Leu Val Lys Gly Phe Tyr Pro Ser Asp Ile Ala Val Glu Trp Glu Ser
370 375 380

```
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn Ala Tyr Thr Gln Lys Ser Leu Ser Leu Ser Pro Gly
        435                 440                 445


<210> SEQ ID NO 91
<211> LENGTH: 447
<212> TYPE: PRT
<213> ORGANISM: Artificial Sequence
<220> FEATURE:
<223> OTHER INFORMATION: IGF-1R YTE

<400> SEQUENCE: 91

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Tyr Ile Thr Arg
                245                 250                 255

Glu Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300
```

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Asp Glu Leu Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly
435 440 445

<210> SEQ ID NO 92
<211> LENGTH: 448
<212> TYPE: PRT
<213> ORGANISM: Artificial Sequence
<220> FEATURE:
<223> OTHER INFORMATION: IgG1 wtKiH

<400> SEQUENCE: 92

Gln Val Glu Leu Val Glu Ser Gly Gly Gly Val Val Gln Pro Gly Arg
1 5 10 15

Ser Gln Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Ile Ile Trp Phe Asp Gly Ser Ser Thr Tyr Tyr Ala Asp Ser Val
50 55 60

Arg Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Phe Cys
85 90 95

Ala Arg Glu Leu Gly Arg Arg Tyr Phe Asp Leu Trp Gly Arg Gly Thr
100 105 110

Leu Val Ser Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Leu Leu Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Cys Arg Asp Glu Leu Thr Lys Asn Gln Val Ser Leu Trp Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly Lys
435 440 445

<210> SEQ ID NO 93
<211> LENGTH: 448
<212> TYPE: PRT
<213> ORGANISM: Artificial Sequence
<220> FEATURE:
<223> OTHER INFORMATION: VH-IGG1-FCSSHOLE

<400> SEQUENCE: 93

Gln Val Glu Leu Val Glu Ser Gly Gly Gly Val Val Gln Pro Gly Arg
1 5 10 15

Ser Gln Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Ile Ile Trp Phe Asp Gly Ser Ser Thr Tyr Tyr Ala Asp Ser Val
50 55 60

Arg Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Phe Cys
85 90 95

Ala Arg Glu Leu Gly Arg Arg Tyr Phe Asp Leu Trp Gly Arg Gly Thr
100 105 110

Leu Val Ser Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

```
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 94
<211> LENGTH: 448
<212> TYPE: PRT
<213> ORGANISM: Artificial Sequence
<220> FEATURE:
<223> OTHER INFORMATION: I253A, H310A, H435A

<400> SEQUENCE: 94

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60
```

Arg Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Phe Cys
85 90 95

Ala Arg Glu Leu Gly Arg Arg Tyr Phe Asp Leu Trp Gly Arg Gly Thr
100 105 110

Leu Val Ser Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Leu Leu Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Cys Arg Asp Glu Leu Thr Lys Asn Gln Val Ser Leu Trp Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly Lys
435 440 445

<210> SEQ ID NO 95
<211> LENGTH: 448
<212> TYPE: PRT
<213> ORGANISM: Artificial Sequence
<220> FEATURE:

<223> OTHER INFORMATION: VH-AK18-IGG1-FCSSHOLE-AAA1

<400> SEQUENCE: 95

```
Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ala Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu Ala Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400
```

```
Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn Ala Tyr Thr Gln Lys Ser Leu Ser Leu Ser Pro Gly Lys
        435                 440                 445


<210> SEQ ID NO 96
<211> LENGTH: 448
<212> TYPE: PRT
<213> ORGANISM: Artificial Sequence
<220> FEATURE:
<223> OTHER INFORMATION: H310A, H433A, Y436A

<400> SEQUENCE: 96

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320
```

```
Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Asp Glu Leu Thr Lys Asn Gln Val Ser Leu Trp Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 97
<211> LENGTH: 448
<212> TYPE: PRT
<213> ORGANISM: Artificial Sequence
<220> FEATURE:
<223> OTHER INFORMATION: VH-IGG1-FCSSHOLE-AAA2

<400> SEQUENCE: 97

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240
```

```
Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu Ala Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu Ala Asn His Ala Thr Gln Lys Ser Leu Ser Leu Ser Pro Gly Lys
        435                 440                 445


<210> SEQ ID NO 98
<211> LENGTH: 448
<212> TYPE: PRT
<213> ORGANISM: Artificial Sequence
<220> FEATURE:
<223> OTHER INFORMATION: M252Y, S254T, T256E

<400> SEQUENCE: 98

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160
```

```
Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Asp Glu Leu Thr Lys Asn Gln Val Ser Leu Trp Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 99
<211> LENGTH: 448
<212> TYPE: PRT
<213> ORGANISM: Artificial Sequence
<220> FEATURE:
<223> OTHER INFORMATION: VH-IGG1-FCSSHOLE-YTE

<400> SEQUENCE: 99

```
Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Tyr Ile Thr Arg
                245                 250                 255

Glu Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 100
<211> LENGTH: 448
<212> TYPE: PRT
<213> ORGANISM: Artificial Sequence
<220> FEATURE:
<223> OTHER INFORMATION: DDD

<400> SEQUENCE: 100

```
Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Asp Glu Leu Thr Lys Asn Gln Val Ser Leu Trp Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
```

```
            420                 425                 430

Leu His Asn His Tyr Thr Gln Lys Ser Leu Ser Leu Ser Pro Gly Lys
        435                 440                 445


<210> SEQ ID NO 101
<211> LENGTH: 448
<212> TYPE: PRT
<213> ORGANISM: Artificial Sequence
<220> FEATURE:
<223> OTHER INFORMATION: VH-IGG1-FCSSHOLE-DDD

<400> SEQUENCE: 101

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Asp Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Asp Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Cys Thr Leu
```

```
            340                 345                 350

Pro Pro Ser Arg Asp Glu Leu Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Asp His Asn His Tyr Thr Gln Lys Ser Leu Ser Leu Ser Pro Gly Lys
        435                 440                 445


<210> SEQ ID NO 102
<211> LENGTH: 453
<212> TYPE: PRT
<213> ORGANISM: Artificial
<220> FEATURE:
<223> OTHER INFORMATION: Heavy chain 1 of <VEGF-ANG-2> CrossMAb IgG1
      wild type (without AAA mutations) (VEGFang2-0201)

<400> SEQUENCE: 102

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255
```

Leu Met Ile Ser Arg Thr Pro Glu Val Thr Cys Val Val Val Asp Val
260 265 270

Ser His Glu Asp Pro Glu Val Lys Phe Asn Trp Tyr Val Asp Gly Val
275 280 285

Glu Val His Asn Ala Lys Thr Lys Pro Arg Glu Glu Gln Tyr Asn Ser
290 295 300

Thr Tyr Arg Val Val Ser Val Leu Thr Val Leu Ala Gln Asp Trp Leu
305 310 315 320

Asn Gly Lys Glu Tyr Lys Cys Lys Val Ser Asn Lys Ala Leu Pro Ala
325 330 335

Pro Ile Glu Lys Thr Ile Ser Lys Ala Lys Gly Gln Pro Arg Glu Pro
340 345 350

Gln Val Tyr Thr Leu Pro Pro Cys Arg Asp Glu Leu Thr Lys Asn Gln
355 360 365

Val Ser Leu Trp Cys Leu Val Lys Gly Phe Tyr Pro Ser Asp Ile Ala
370 375 380

Val Glu Trp Glu Ser Asn Gly Gln Pro Glu Asn Asn Tyr Lys Thr Thr
385 390 395 400

Pro Pro Val Leu Asp Ser Asp Gly Ser Phe Phe Leu Tyr Ser Lys Leu
405 410 415

Thr Val Asp Lys Ser Arg Trp Gln Gln Gly Asn Val Phe Ser Cys Ser
420 425 430

Val Met His Glu Ala Leu Ala Asn His Ala Thr Gln Lys Ser Leu Ser
435 440 445

Leu Ser Pro Gly Lys
450

<210> SEQ ID NO 103
<211> LENGTH: 463
<212> TYPE: PRT
<213> ORGANISM: Artificial
<220> FEATURE:
<223> OTHER INFORMATION: Heavy chain 2 of <VEGF-ANG-2> CrossMAb IgG1 wild type (without AAA mutations) (VEGFang2-0201)

<400> SEQUENCE: 103

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Ser Pro Asn Pro Tyr Tyr Tyr Asp Ser Ser Gly Tyr Tyr Tyr
100 105 110

Pro Gly Ala Phe Asp Ile Trp Gly Gln Gly Thr Met Val Thr Val Ser
115 120 125

Ser Ala Ser Val Ala Ala Pro Ser Val Phe Ile Phe Pro Pro Ser Asp
130 135 140

Glu Gln Leu Lys Ser Gly Thr Ala Ser Val Val Cys Leu Leu Asn Asn
145 150 155 160

```
Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu Ala Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Cys Thr Leu Pro
        355                 360                 365

Pro Ser Arg Asp Glu Leu Thr Lys Asn Gln Val Ser Leu Ser Cys Ala
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
            420                 425                 430

Trp Gln Gln Gly Asn Val Phe Ser Cys Ser Val Met His Glu Ala Leu
        435                 440                 445

Ala Asn His Ala Thr Gln Lys Ser Leu Ser Leu Ser Pro Gly Lys
    450                 455                 460
```

<210> SEQ ID NO 104
<211> LENGTH: 453
<212> TYPE: PRT
<213> ORGANISM: Artificial
<220> FEATURE:
<223> OTHER INFORMATION: Heavy chain 1 of <VEGF-ANG-2> CrossMAb IgG1 wild type (without AAA mutations) (VEGFang2-0201)

<400> SEQUENCE: 104

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
```

```
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu Ala Gln Asp Trp Leu
305                 310                 315                 320

Asn Gly Lys Glu Tyr Lys Cys Lys Val Ser Asn Lys Ala Leu Gly Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Cys Arg Asp Glu Leu Thr Lys Asn Gln
        355                 360                 365

Val Ser Leu Trp Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu Ala Asn His Ala Thr Gln Lys Ser Leu Ser
        435                 440                 445

Leu Ser Pro Gly Lys
    450
```

<210> SEQ ID NO 105

```
<211> LENGTH: 463
<212> TYPE: PRT
<213> ORGANISM: Artificial
<220> FEATURE:
<223> OTHER INFORMATION: Heavy chain 2 of <VEGF-ANG-2> CrossMAb IgG1
      wild type (without AAA mutations) (VEGFang2-0201)

<400> SEQUENCE: 105

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Ala Ala Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu Ala Gln Asp Trp Leu Asn Gly Lys Glu Tyr Lys
                325                 330                 335

Cys Lys Val Ser Asn Lys Ala Leu Gly Ala Pro Ile Glu Lys Thr Ile
            340                 345                 350

Ser Lys Ala Lys Gly Gln Pro Arg Glu Pro Gln Val Cys Thr Leu Pro
        355                 360                 365

Pro Ser Arg Asp Glu Leu Thr Lys Asn Gln Val Ser Leu Ser Cys Ala
```

```
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
            420                 425                 430

Trp Gln Gln Gly Asn Val Phe Ser Cys Ser Val Met His Glu Ala Leu
        435                 440                 445

Ala Asn His Ala Thr Gln Lys Ser Leu Ser Leu Ser Pro Gly Lys
    450                 455                 460


<210> SEQ ID NO 106
<211> LENGTH: 450
<212> TYPE: PRT
<213> ORGANISM: Artificial
<220> FEATURE:
<223> OTHER INFORMATION: Heavy chain 1 of <VEGF-ANG-2> CrossMAb IgG4
      with AAA mutations and with SPLE mutations

<400> SEQUENCE: 106

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Glu Gly Gly
225                 230                 235                 240

Pro Ser Val Phe Leu Phe Pro Pro Lys Pro Lys Asp Thr Leu Met Ala
                245                 250                 255

Ser Arg Thr Pro Glu Val Thr Cys Val Val Val Asp Val Ser Gln Glu
            260                 265                 270
```

```
Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu Ala Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Cys
            340                 345                 350

Thr Leu Pro Pro Ser Gln Glu Glu Met Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Arg Leu Thr Val Asp
                405                 410                 415

Lys Ser Arg Trp Gln Glu Gly Asn Val Phe Ser Cys Ser Val Met His
            420                 425                 430

Glu Ala Leu Ala Asn His Ala Thr Gln Lys Ser Leu Ser Leu Ser Leu
        435                 440                 445

Gly Lys
    450


<210> SEQ ID NO 107
<211> LENGTH: 460
<212> TYPE: PRT
<213> ORGANISM: Artificial
<220> FEATURE:
<223> OTHER INFORMATION: Heavy chain 2 of <VEGF-ANG-2> CrossMAb IgG4
      with AAA mutations and with SPLE mutations

<400> SEQUENCE: 107

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175
```

Gln Ser Gly Asn Ser Gln Glu Ser Val Thr Glu Gln Asp Ser Lys Asp
180 185 190

Ser Thr Tyr Ser Leu Ser Ser Thr Leu Thr Leu Ser Lys Ala Asp Tyr
195 200 205

Glu Lys His Lys Val Tyr Ala Cys Glu Val Thr His Gln Gly Leu Ser
210 215 220

Ser Pro Val Thr Lys Ser Phe Asn Arg Gly Glu Cys Pro Pro Cys Pro
225 230 235 240

Pro Cys Pro Ala Pro Glu Phe Glu Gly Gly Pro Ser Val Phe Leu Phe
245 250 255

Pro Pro Lys Pro Lys Asp Thr Leu Met Ile Ser Arg Thr Pro Glu Val
260 265 270

Thr Cys Val Val Val Asp Val Ser Gln Glu Asp Pro Glu Val Gln Phe
275 280 285

Asn Trp Tyr Val Asp Gly Val Glu Val His Asn Ala Lys Thr Lys Pro
290 295 300

Arg Glu Glu Gln Phe Asn Ser Thr Tyr Arg Val Val Ser Val Leu Thr
305 310 315 320

Val Leu Ala Gln Asp Trp Leu Asn Gly Lys Glu Tyr Lys Cys Lys Val
325 330 335

Ser Asn Lys Gly Leu Pro Ser Ser Ile Glu Lys Thr Ile Ser Lys Ala
340 345 350

Lys Gly Gln Pro Arg Glu Pro Gln Val Tyr Thr Leu Pro Pro Cys Gln
355 360 365

Glu Glu Met Thr Lys Asn Gln Val Ser Leu Trp Cys Leu Val Lys Gly
370 375 380

Phe Tyr Pro Ser Asp Ile Ala Val Glu Trp Glu Ser Asn Gly Gln Pro
385 390 395 400

Glu Asn Asn Tyr Lys Thr Thr Pro Pro Val Leu Asp Ser Asp Gly Ser
405 410 415

Phe Phe Leu Tyr Ser Arg Leu Thr Val Asp Lys Ser Arg Trp Gln Glu
420 425 430

Gly Asn Val Phe Ser Cys Ser Val Met His Glu Ala Leu Ala Asn His
435 440 445

Ala Thr Gln Lys Ser Leu Ser Leu Ser Leu Gly Lys
450 455 460

<210> SEQ ID NO 108
<211> LENGTH: 453
<212> TYPE: PRT
<213> ORGANISM: Artificial
<220> FEATURE:
<223> OTHER INFORMATION: Heavy chain 1 of <VEGF-ANG-2> OAscFab IgG1 with AAA mutations

<400> SEQUENCE: 108

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Asp Phe Thr His Tyr
20 25 30

Gly Met Asn Trp Val Arg Gln Ala Pro Gly Lys Gly Leu Glu Trp Val
35 40 45

Gly Trp Ile Asn Thr Tyr Thr Gly Glu Pro Thr Tyr Ala Ala Asp Phe
50 55 60

Lys Arg Arg Phe Thr Phe Ser Leu Asp Thr Ser Lys Ser Thr Ala Tyr

```
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Ile Ala Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu Ala Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Cys Thr Leu Pro Pro Ser Arg Asp Glu Leu Thr Lys Asn Gln
        355                 360                 365

Val Ser Leu Ser Cys Ala Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Val Ser Lys Leu
                405                 410                 415

Thr Val Asp Lys Ser Arg Trp Gln Gln Gly Asn Val Phe Ser Cys Ser
            420                 425                 430

Val Met His Glu Ala Leu Ala Asn His Ala Thr Gln Lys Ser Leu Ser
        435                 440                 445

Leu Ser Pro Gly Lys
    450
```

<210> SEQ ID NO 109
<211> LENGTH: 705
<212> TYPE: PRT
<213> ORGANISM: Artificial
<220> FEATURE:
<223> OTHER INFORMATION: Heavy chain 2 of <VEGF-ANG-2> OAscFab IgG1 with AAA mutations

<400> SEQUENCE: 109

Ser Tyr Val Leu Thr Gln Pro Pro Ser Val Ser Val Ala Pro Gly Gln
1 5 10 15

Thr Ala Arg Ile Thr Cys Gly Gly Asn Asn Ile Gly Ser Lys Ser Val
20 25 30

His Trp Tyr Gln Gln Lys Pro Gly Gln Ala Pro Val Leu Val Val Tyr
35 40 45

Asp Asp Ser Asp Arg Pro Ser Gly Ile Pro Glu Arg Phe Ser Gly Ser
50 55 60

Asn Ser Gly Asn Thr Ala Thr Leu Thr Ile Ser Arg Val Glu Ala Gly
65 70 75 80

Asp Glu Ala Asp Tyr Tyr Cys Gln Val Trp Asp Ser Ser Ser Asp His
85 90 95

Trp Val Phe Gly Gly Gly Thr Lys Leu Thr Val Leu Gly Gln Pro Lys
100 105 110

Ala Ala Pro Ser Val Thr Leu Phe Pro Pro Ser Ser Glu Glu Leu Gln
115 120 125

Ala Asn Lys Ala Thr Leu Val Cys Leu Ile Ser Asp Phe Tyr Pro Gly
130 135 140

Ala Val Thr Val Ala Trp Lys Ala Asp Ser Ser Pro Val Lys Ala Gly
145 150 155 160

Val Glu Thr Thr Thr Pro Ser Lys Gln Ser Asn Asn Lys Tyr Ala Ala
165 170 175

Ser Ser Tyr Leu Ser Leu Thr Pro Glu Gln Trp Lys Ser His Arg Ser
180 185 190

Tyr Ser Cys Gln Val Thr His Glu Gly Ser Thr Val Glu Lys Thr Val
195 200 205

Ala Pro Thr Glu Cys Ser Gly Gly Gly Gly Ser Gly Gly Gly Gly Ser
210 215 220

Gly Gly Gly Gly Ser Gly Gly Gly Gly Ser Gly Gly Gly Gly Ser Gly
225 230 235 240

Gly Gly Gly Ser Gly Gly Gln Val Gln Leu Val Glu Ser Gly Ala Glu
245 250 255

Val Lys Lys Pro Gly Ala Ser Val Lys Val Ser Cys Lys Ala Ser Gly
260 265 270

Tyr Thr Phe Thr Gly Tyr Tyr Met His Trp Val Arg Gln Ala Pro Gly
275 280 285

Gln Gly Leu Glu Trp Met Gly Trp Ile Asn Pro Asn Ser Gly Gly Thr
290 295 300

Asn Tyr Ala Gln Lys Phe Gln Gly Arg Val Thr Met Thr Arg Asp Thr
305 310 315 320

Ser Ile Ser Thr Ala Tyr Met Glu Leu Ser Arg Leu Arg Ser Asp Asp
325 330 335

Thr Ala Val Tyr Tyr Cys Ala Arg Ser Pro Asn Pro Tyr Tyr Tyr Asp
340 345 350

Ser Ser Gly Tyr Tyr Tyr Pro Gly Ala Phe Asp Ile Trp Gly Gln Gly
355 360 365

Thr Met Val Thr Val Ser Ser Ala Ser Thr Lys Gly Pro Ser Val Phe
370 375 380

Pro Leu Ala Pro Ser Ser Lys Ser Thr Ser Gly Gly Thr Ala Ala Leu 385 390 395 400

Gly Cys Leu Val Lys Asp Tyr Phe Pro Glu Pro Val Thr Val Ser Trp
405 410 415

Asn Ser Gly Ala Leu Thr Ser Gly Val His Thr Phe Pro Ala Val Leu
420 425 430

Gln Ser Ser Gly Leu Tyr Ser Leu Ser Ser Val Val Thr Val Pro Ser
435 440 445

Ser Ser Leu Gly Thr Gln Thr Tyr Ile Cys Asn Val Asn His Lys Pro
450 455 460

Ser Asn Thr Lys Val Asp Lys Lys Val Glu Pro Lys Ser Cys Asp Lys
465 470 475 480

Thr His Thr Cys Pro Pro Cys Pro Ala Pro Glu Leu Leu Gly Gly Pro
485 490 495

Ser Val Phe Leu Phe Pro Pro Lys Pro Lys Asp Thr Leu Met Ile Ser
500 505 510

Arg Thr Pro Glu Val Thr Cys Val Val Val Asp Val Ser His Glu Asp
515 520 525

Pro Glu Val Lys Phe Asn Trp Tyr Val Asp Gly Val Glu Val His Asn
530 535 540

Ala Lys Thr Lys Pro Arg Glu Glu Gln Tyr Asn Ser Thr Tyr Arg Val
545 550 555 560

Val Ser Val Leu Thr Val Leu Ala Gln Asp Trp Leu Asn Gly Lys Glu
565 570 575

Tyr Lys Cys Lys Val Ser Asn Lys Ala Leu Pro Ala Pro Ile Glu Lys
580 585 590

Thr Ile Ser Lys Ala Lys Gly Gln Pro Arg Glu Pro Gln Val Tyr Thr
595 600 605

Leu Pro Pro Cys Arg Asp Glu Leu Thr Lys Asn Gln Val Ser Leu Trp
610 615 620

Cys Leu Val Lys Gly Phe Tyr Pro Ser Asp Ile Ala Val Glu Trp Glu
625 630 635 640

Ser Asn Gly Gln Pro Glu Asn Asn Tyr Lys Thr Thr Pro Pro Val Leu
645 650 655

Asp Ser Asp Gly Ser Phe Phe Leu Tyr Ser Lys Leu Thr Val Asp Lys
660 665 670

Ser Arg Trp Gln Gln Gly Asn Val Phe Ser Cys Ser Val Met His Glu
675 680 685

Ala Leu Ala Asn His Ala Thr Gln Lys Ser Leu Ser Leu Ser Pro Gly
690 695 700

Lys
705

<210> SEQ ID NO 110
<211> LENGTH: 450
<212> TYPE: PRT
<213> ORGANISM: Artificial
<220> FEATURE:
<223> OTHER INFORMATION: Heavy chain 1 of <VEGF-ANG-2> OAscFab IgG4 with
AAA mutations and with SPLE mutations

<400> SEQUENCE: 110

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Asp Phe Thr His Tyr
20 25 30

```
Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Glu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu Ala Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Cys
            340                 345                 350

Thr Leu Pro Pro Ser Gln Glu Glu Met Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Arg Leu Thr Val Asp
                405                 410                 415

Lys Ser Arg Trp Gln Glu Gly Asn Val Phe Ser Cys Ser Val Met His
            420                 425                 430

Glu Ala Leu Ala Asn His Ala Thr Gln Lys Ser Leu Ser Leu Ser Leu
        435                 440                 445

Gly Lys
```

450

<210> SEQ ID NO 111
<211> LENGTH: 702
<212> TYPE: PRT
<213> ORGANISM: Artificial
<220> FEATURE:
<223> OTHER INFORMATION: Heavy chain 2 of <VEGF-ANG-2> OAscFab IgG4 with AAA mutations and with SPLE mutations

<400> SEQUENCE: 111

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser Gly Gly Gly Gly Ser Gly Gly Gly Gly Ser
    210                 215                 220

Gly Gly Gly Gly Ser Gly Gly Gly Gly Ser Gly Gly Gly Gly Ser Gly
225                 230                 235                 240

Gly Gly Gly Ser Gly Gly Gln Val Gln Leu Val Glu Ser Gly Ala Glu
                245                 250                 255

Val Lys Lys Pro Gly Ala Ser Val Lys Val Ser Cys Lys Ala Ser Gly
            260                 265                 270

Tyr Thr Phe Thr Gly Tyr Tyr Met His Trp Val Arg Gln Ala Pro Gly
        275                 280                 285

Gln Gly Leu Glu Trp Met Gly Trp Ile Asn Pro Asn Ser Gly Gly Thr
    290                 295                 300

Asn Tyr Ala Gln Lys Phe Gln Gly Arg Val Thr Met Thr Arg Asp Thr
305                 310                 315                 320

Ser Ile Ser Thr Ala Tyr Met Glu Leu Ser Arg Leu Arg Ser Asp Asp
                325                 330                 335

Thr Ala Val Tyr Tyr Cys Ala Arg Ser Pro Asn Pro Tyr Tyr Tyr Asp
            340                 345                 350

```
Ser Ser Gly Tyr Tyr Tyr Pro Gly Ala Phe Asp Ile Trp Gly Gln Gly
        355                 360                 365

Thr Met Val Thr Val Ser Ser Ala Ser Thr Lys Gly Pro Ser Val Phe
    370                 375                 380

Pro Leu Ala Pro Cys Ser Arg Ser Thr Ser Glu Ser Thr Ala Ala Leu
385                 390                 395                 400

Gly Cys Leu Val Lys Asp Tyr Phe Pro Glu Pro Val Thr Val Ser Trp
                405                 410                 415

Asn Ser Gly Ala Leu Thr Ser Gly Val His Thr Phe Pro Ala Val Leu
            420                 425                 430

Gln Ser Ser Gly Leu Tyr Ser Leu Ser Ser Val Val Thr Val Pro Ser
        435                 440                 445

Ser Ser Leu Gly Thr Lys Thr Tyr Thr Cys Asn Val Asp His Lys Pro
    450                 455                 460

Ser Asn Thr Lys Val Asp Lys Arg Val Glu Ser Lys Tyr Gly Pro Pro
465                 470                 475                 480

Cys Pro Pro Cys Pro Ala Pro Glu Phe Glu Gly Gly Pro Ser Val Phe
                485                 490                 495

Leu Phe Pro Pro Lys Pro Lys Asp Thr Leu Met Ile Ser Arg Thr Pro
            500                 505                 510

Glu Val Thr Cys Val Val Val Asp Val Ser Gln Glu Asp Pro Glu Val
        515                 520                 525

Gln Phe Asn Trp Tyr Val Asp Gly Val Glu Val His Asn Ala Lys Thr
    530                 535                 540

Lys Pro Arg Glu Glu Gln Phe Asn Ser Thr Tyr Arg Val Val Ser Val
545                 550                 555                 560

Leu Thr Val Leu Ala Gln Asp Trp Leu Asn Gly Lys Glu Tyr Lys Cys
                565                 570                 575

Lys Val Ser Asn Lys Gly Leu Pro Ser Ser Ile Glu Lys Thr Ile Ser
            580                 585                 590

Lys Ala Lys Gly Gln Pro Arg Glu Pro Gln Val Tyr Thr Leu Pro Pro
        595                 600                 605

Cys Gln Glu Glu Met Thr Lys Asn Gln Val Ser Leu Trp Cys Leu Val
    610                 615                 620

Lys Gly Phe Tyr Pro Ser Asp Ile Ala Val Glu Trp Glu Ser Asn Gly
625                 630                 635                 640

Gln Pro Glu Asn Asn Tyr Lys Thr Thr Pro Pro Val Leu Asp Ser Asp
                645                 650                 655

Gly Ser Phe Phe Leu Tyr Ser Arg Leu Thr Val Asp Lys Ser Arg Trp
            660                 665                 670

Gln Glu Gly Asn Val Phe Ser Cys Ser Val Met His Glu Ala Leu Ala
        675                 680                 685

Asn His Ala Thr Gln Lys Ser Leu Ser Leu Ser Leu Gly Lys
    690                 695                 700


<210> SEQ ID NO 112
<211> LENGTH: 447
<212> TYPE: PRT
<213> ORGANISM: Artificial Sequence
<220> FEATURE:
<223> OTHER INFORMATION: IGF-1R wt

<400> SEQUENCE: 112

Gln Val Glu Leu Val Glu Ser Gly Gly Gly Val Val Gln Pro Gly Arg
1               5                   10                  15
```

```
Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu Ala Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430
```

-continued

```
Leu Ala Asn His Ala Thr Gln Lys Ser Leu Ser Leu Ser Pro Gly
        435                 440                 445
```